United States Patent
Chappel et al.

(10) Patent No.: US 10,793,637 B2
(45) Date of Patent: Oct. 6, 2020

(54) ANTIBODIES THAT BIND CD39 AND USES THEREOF

(71) Applicant: Surface Oncology, Inc., Cambridge, MA (US)

(72) Inventors: Scott Chappel, Milton, MA (US); Andrew Lake, Westwood, MA (US); Michael Warren, North Chelmsford, MA (US); Austin Dulak, Reading, MA (US); Erik Devereaux, Hanover, MA (US); Pamela M. Holland, Belmont, MA (US); Tauqeer Zaidi, Sharon, MA (US); Matthew Rausch, Cambridge, MA (US); Bianka Prinz, Lebanon, NH (US); Nels P. Nielson, Lebanon, NH (US); Sonia Das, Cambridge, MA (US)

(73) Assignee: Surface Oncology, Inc., Cambridge, MA (US)

( * ) Notice: Subject to any disclaimer, the term of this patent is extended or adjusted under 35 U.S.C. 154(b) by 0 days.

(21) Appl. No.: 15/931,469

(22) Filed: May 13, 2020

(65) Prior Publication Data
US 2020/0277394 A1 Sep. 3, 2020

Related U.S. Application Data

(62) Division of application No. 16/352,589, filed on Mar. 13, 2019.

(60) Provisional application No. 62/803,235, filed on Feb. 8, 2019, provisional application No. 62/642,938, filed on Mar. 14, 2018.

(51) Int. Cl.
| | | |
|---|---|---|
| *A61K 39/395* | (2006.01) | |
| *A61P 35/00* | (2006.01) | |
| *C07K 16/28* | (2006.01) | |
| *C12N 15/85* | (2006.01) | |
| *A61K 45/06* | (2006.01) | |

(52) U.S. Cl.
CPC .......... *C07K 16/2896* (2013.01); *A61P 35/00* (2018.01); *C12N 15/85* (2013.01); *A61K 45/06* (2013.01); *C07K 2317/52* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 3,773,919 A | 11/1973 | Boswell et al. |
| 4,676,980 A | 6/1987 | Segal et al. |
| 4,863,457 A | 9/1989 | Lee |
| 5,223,409 A | 6/1993 | Ladner et al. |
| 5,403,484 A | 4/1995 | Ladner et al. |
| 5,427,908 A | 6/1995 | Dower et al. |
| 5,501,856 A | 3/1996 | Ohtori et al. |
| 5,516,637 A | 5/1996 | Huang et al. |
| 5,571,698 A | 11/1996 | Ladner et al. |
| 5,580,717 A | 12/1996 | Dower et al. |
| 5,624,821 A | 4/1997 | Winter et al. |
| 5,648,260 A | 7/1997 | Winter et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,858,358 A | 1/1999 | June et al. |
| 5,883,223 A | 3/1999 | Gray |
| 5,969,108 A | 10/1999 | McCafferty et al. |
| 6,001,329 A | 12/1999 | Buchsbaum et al. |
| 6,005,079 A | 12/1999 | Casterman et al. |
| 6,194,551 B1 | 2/2001 | Idusogie et al. |
| 6,300,064 B1 | 10/2001 | Knappik et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,933,368 B2 | 8/2005 | Co et al. |
| 6,984,720 B1 | 1/2006 | Korman et al. |
| 6,995,259 B1 | 2/2006 | Vargeese et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |

(Continued)

FOREIGN PATENT DOCUMENTS

| | | |
|---|---|---|
| EP | 0133988 A2 | 3/1985 |
| EP | 0058481 B1 | 10/1986 |

(Continued)

OTHER PUBLICATIONS

Abal et al., "Taxanes: microtubule and centrosome targets, and cell cycle dependent mechanisms of action" (2003) Curr Cancer Drug Targets 3(3):193-203.
Allard et al., "CD73-adenosine: a next-generation target in immuno-oncology" (2016) Immunotherapy 8:145-163.
Allard et al., "Immunosuppressive activities of adenosine in cancer" (2016) Curr Opin Pharmacol 29:7-16.

(Continued)

*Primary Examiner* — Christine J Saoud
*Assistant Examiner* — Jon M Lockard
(74) *Attorney, Agent, or Firm* — McNeill Baur PLLC

(57) ABSTRACT

The present disclosure relates to anti-CD39 antibodies, and antigen binding portions thereof and their use in treating cancer.

20 Claims, 13 Drawing Sheets
Specification includes a Sequence Listing.

(56) References Cited

U.S. PATENT DOCUMENTS

| | | |
|---|---|---|
| 7,411,057 B2 | 8/2008 | Hanson et al. |
| 7,595,048 B2 | 9/2009 | Honjo et al. |
| 7,943,743 B2 | 5/2011 | Korman et al. |
| 8,008,449 B2 | 8/2011 | Korman et al. |
| 8,114,845 B2 | 2/2012 | Langermann et al. |
| 8,354,509 B2 | 1/2013 | Carven et al. |
| 8,728,474 B2 | 5/2014 | Honjo et al. |
| 8,779,105 B2 | 7/2014 | Korman et al. |
| 8,796,284 B2 | 8/2014 | Gomez et al. |
| 8,900,587 B2 | 12/2014 | Carven et al. |
| 8,952,136 B2 | 2/2015 | Carven et al. |
| 9,029,393 B2 | 5/2015 | Schann et al. |
| 9,067,999 B1 | 6/2015 | Honjo et al. |
| 9,073,994 B2 | 7/2015 | Honjo et al. |
| 9,133,197 B2 | 9/2015 | Cabri et al. |
| 2005/0158280 A1 | 7/2005 | Robson et al. |
| 2006/0121005 A1 | 6/2006 | Berenson et al. |
| 2008/0241223 A1 | 10/2008 | Nivaggioli et al. |
| 2011/0287002 A1 | 11/2011 | Bukhalid et al. |
| 2016/0129108 A1 | 5/2016 | Sachsenmeier et al. |
| 2016/0185861 A1 | 6/2016 | Bedoya et al. |
| 2017/0015758 A1 | 1/2017 | Hammond et al. |
| 2017/0335007 A1 | 11/2017 | Chen et al. |
| 2018/0009899 A1 | 1/2018 | Griffin et al. |
| 2019/0284295 A1 | 9/2019 | Chappel et al. |

FOREIGN PATENT DOCUMENTS

| | | |
|---|---|---|
| EP | 0088046 B1 | 12/1987 |
| EP | 0143949 B1 | 10/1988 |
| EP | 0036676 B2 | 9/1990 |
| EP | 0488401 A1 | 6/1992 |
| EP | 0430539 B1 | 10/1994 |
| EP | 0404097 B1 | 9/1996 |
| EP | 1537878 A4 | 11/2006 |
| EP | 2170959 A1 | 4/2010 |
| EP | 2161336 B1 | 7/2013 |
| EP | 2654789 B1 | 5/2018 |
| WO | 1990002809 A1 | 3/1990 |
| WO | 1991010737 A1 | 7/1991 |
| WO | 1992001047 A1 | 1/1992 |
| WO | 1992018619 A1 | 10/1992 |
| WO | 1993001161 A1 | 1/1993 |
| WO | 1993011236 A1 | 6/1993 |
| WO | 1993015722 A1 | 8/1993 |
| WO | 1994004678 A1 | 3/1994 |
| WO | 1994020069 A1 | 9/1994 |
| WO | 1994025591 A1 | 11/1994 |
| WO | 1994029351 A2 | 12/1994 |
| WO | 1995015982 A2 | 6/1995 |
| WO | 1995020401 A1 | 8/1995 |
| WO | 1996027011 A1 | 9/1996 |
| WO | 1999051642 A1 | 10/1999 |
| WO | 2008024188 | 7/2008 |
| WO | 2009036379 A2 | 3/2009 |
| WO | 2007024715 A9 | 4/2009 |
| WO | 2009095478 A1 | 8/2009 |
| WO | 2009156737 A1 | 12/2009 |
| WO | 2010027827 A2 | 3/2010 |
| WO | 2010077634 A1 | 7/2010 |
| WO | 2010105256 A1 | 9/2010 |
| WO | 2011066342 A3 | 7/2011 |
| WO | 2011095625 A1 | 8/2011 |
| WO | 2012009568 A2 | 1/2012 |
| WO | 2012085132 A1 | 6/2012 |
| WO | 2013079174 A1 | 6/2013 |
| WO | 2013173223 A1 | 11/2013 |
| WO | 2015103072 A1 | 7/2015 |
| WO | 2016106159 A1 | 6/2016 |
| WO | 2017025918 A1 | 2/2017 |
| WO | 2017152102 A2 | 9/2017 |
| WO | 2019178269 | 9/2019 |

OTHER PUBLICATIONS

Altschul et al., "Basic local alignment search tool" J. Mol. Biol. 215:403-410 (1990).

Ames et al. "Conversion of murine Fabs isolated from a combinatorial phage display library to full length immunoglobulins" (1995) J Immunol Methods 184:177-186.

Antonioli et al., "Immunity, inflammation and cancer: a leading role for adenosine" (2013) Nat Rev Cancer 13:842-857.

Azuma M. et al., "B70 antigen is a second ligand for CTLA-4 and CD28" 1993, Nature 366: 76.

Baldridge et al. "Monophosphoryl lipid A (MPL) formulations for the next generation of vaccines" (1999) Methods 19:103-107.

Berge et al. "Pharmaceutical salts" (1977) J Pharm Sci 66:1-19.

Bieg et al. "GAD65 and insulin B chain peptide (9-23) are not primary autoantigens in the type 1 diabetes syndrome of the BB rat" (1999) Autoimmunity 31(1):15-24.

Blank et al. "Interaction of PD-L1 on tumor cells with PD-1 on tumor-specific T cells as a mechanism of immune evasion: implications for tumor immunotherapy" (2005) Cancer Immunol. Immunother. 54:307-314.

Blank, C. et al. "Contribution of the PD-L1/PD-1 pathway to T-cell exhaustion: an update on implications for chronic infections and tumor evasion" (Epub Dec. 29, 2006) Immunol. Immunother. 56(5):739-745).

Boder et al. "Yeast surface display for directed evolution of protein expression, affinity, and stability" (2000) Methods Enzymology 328:430-444.

Brennan et al., "Preparation of bispecific antibodies by chemical recombination of monoclonal immunoglobulin G1 fragments" (1985) Science 229:81.

Brinkman et al. "Phage display of disulfide-stabilized Fv fragments" (1995) J Immunol Methods 182:41-50.

Burton et al. "Human antibodies from combinatorial libraries" (1994) Advances in Immunology 57:191-280.

Burton et al. "Human antibody effector function" (1992) Adv Immun 51:1-18.

Carrillo et al., "5-Fluorouracil derivatives: a patent review" (2012) Expert Opin Ther Pat 22(2):107-123.

Chasteen et al., "Eliminating helper phage from phage display" (2006) Nucleic Acids Res 34(21):e145.

Cheung et al., "Epitope-specific antibody response to the surface antigen of duck hepatitis B virus in infected ducks" Virology 176:546 (1990).

Co et al. "Genetically engineered deglycosylation of the variable domain increases the affinity of an anti-CD33 monoclonal antibody" (1993) Mol Immunol 30:1361.

Cornelis "Expressing genes in different *Escherichia coli* compartments" (2000) Curr Opin Biotechnol 11:450-454.

Di Niro et al. "Characterizing monoclonal antibody epitopes by filtered gene fragment phage display" (2005) Biochem J 388(Pt 3):889-894.

Dong et al. "B7-H1 pathway and its role in the evasion of tumor immunity" (2003) J. Mol. Med. 81:281-7.

Dong et al., "Protect the killer: CTLs need defenses against the tumor" (2002) Nat Med 8:787-789.

Dong et al., "Tumor-associated B7-H1 promotes T-cell apoptosis: a potential mechanism of immune evasion" (2002) Nat Med 8(8):793-800.

Engberg et al. "Phage-display libraries of murine and human antibody Fab fragments" (1995) Methods Mol Biol 51:355-376.

Epitope Mapping Protocols in Methods in Molecular Biology, vol. 66, G. E. Morris, Ed. (1996).

Fan et al., "Identification of CD4+ T-cell-derived CD161+ CD39+ and CD39+CD73+ microparticles as new biomarkers for rheumatoid arthritis" (2017) Biomark Med 11:107-116.

GenBank Accession No. AAC51773.

GenBank Accession No. Q9NZQ7.

Grabherr et al. "The baculovirus expression system as a tool for generating diversity by viral surface display" (2001) Comb Chem High Throughput Screen 4:185-192.

Gruber et al., "Efficient tumor cell lysis mediated by a bispecific single chain antibody expressed in *Escherichia coli*" (1994) J. Immunol. 152:5368.

(56) References Cited

OTHER PUBLICATIONS

Gupta et al. "Adjuvants for human vaccines—current status, problems and future prospects" (1995) Vaccine 13(14): 1263-1276.
Harding & Lonberg, "Class switching in human immunoglobulin transgenic mice" (1995) Ann. N.Y. Acad. Sci. 764:536-546.
Hodgson et al., "Characterization of the potent and highly selective A2A receptor antagonists preladenant and SCH 412348 [7-[2-[4-2,4-difluorophenyl]-1-piperazinyl]ethyl]-2-(2-furanyl)-7H-pyrazolo[4,3-e][1,2,4]triazolo[1,5-c]pyrimidin-5-amine] in rodent models of movement disorders and depression" (2009) J Pharmacol Exp Ther 330(1):294-303.
Hoogenboom "Designing and optimizing library selection strategies for generating high-affinity antibodies" (1997) Trends in Biotechnology 15:62-70.
Hou et al. "Expression of active thrombopoietin and identification of its key residues responsible for receptor binding" (1998) Cytokine 10:319-30.
Houdebine "Antibody manufacture in transgenic animals and comparisons with other systems" (2002) Curr Opin Biotechnol 13(6):625-629.
Hudson and Kortt, "High avidity scFv multimers; diabodies and triabodies" (1999) J. Immunol. Methods 231(1):177-189.
Johnson et al. "3-O-Desacyl monophosphoryl lipid A derivatives: synthesis and immunostimulant activitiesLodmell et al. "DNA vaccination of mice against rabies virus: effects of the route of vaccination and the adjuvant monophosphoryl lipid A (MPL)" (2000) Vaccine 18:1059-1066" (1999) J Med Chem 42:4640-4649.
Kaszubska et al. "Expression, purification, and characterization of human recombinant thrombopoietin in Chinese hamster ovary cells" (2000) Protein Expression and Purification 18:213-220.
Kettleborough et al. "Isolation of tumor cell-specific single-chain Fv from immunized mice using phage-antibody libraries and the re-construction of whole antibodies from these antibody fragments" (1994) Eur J Immunol 24:952-958.
Khakh et al., "P2X receptors as cell-surface ATP sensors in health and disease" (2006) Nature 442:527-532.
Kimura et al., "Treatment of malignant lymphomas with bleomycin" (1972) Cancer 29(1):58-60.
Kinstler et al. "Kinstler et al. (2002) Advanced Drug Deliveries Reviews 54:477-485" (2002) Advanced Drug Deliveries Reviews 54:477-485.
Kirkland et al., "Analysis of the tine specificity and cross-reactivity of monoclonal anti-lipid A antibodies" J. Immunol. 137:3614 (1986).
Kostelny et al., "Formation of a bispecific antibody by the use of leucine zippers" (1992) J. Immunol. 148(5):1547-1553.
Langer et al., "Biocompatibility of polymeric delivery systems for macromolecules" J. Biomed. Mater. Res., 15: 167-277 (1981).
Lee et al. "Prolonged circulating lives of single-chain Fv proteins conjugated with polyethylene glycol: a comparison of conjugation chemistries and compounds" (1999) Bioconjug Chem 10(6): 973-8.
Mandapathil et al. "Targeting human inducible regulatory T-Cell (Tr1) in patients with cancer: blocking of adenosine-prostaglandin E2 cooperation" Expert Opin Biol Ther. 11(9):1203-1214 (2011).
Mandapathil, et al., "Generation and Accumulation of Immunosuppressive Adenosine by Human CD4+CD25highFoxP3+ Regulatory T Cells" (2010) 285(10):7176-7186.
Marcus et al., "The Endothelial Cell Ecto-ADPase Responsible for Inhibition of Platelet Function is CD39" (1997) Journal of Clinical Inestigation 99(6):1351-1360.
Martins et al., "Molecular mechanisms of ATP secretion during immunogenic cell death" (2014) Cell Death Differ 21 (1):79-91.
Mascanfroni, et al., "Interleukin-27 acts on dendritic cells to suppress the T-cell response and autoimmunity by inducing the expression of ENTPD1 (CD39)" (2013) 14(10):1054-1063.
McGlasson and Fritsma, "Whole Blood Platelet Aggregometry and Platelet Function Testing" (2009) Seminars in Thrombosis and Hemostasis 35(2):168-180.
Meyer et al. "Expression of CD39 and CD73 as means of Evading Antitumor immune responses in Lung Cancer" J. of Immunology 184 (2010).
Moncrieffe, et al., "High Expression of the Ectonucleotidase CD39 on T Cells from the Inflamed Site Identifies Two Distinct Populations, One Regulatory and One Memory T Cell Population" (2010) J Immunol 185(1):134-143.
Mulligan and Berg "Selection for animal cells that express the *Escherichia coli* gene coding for xanthine-guanine phosphoribosyltransferase" (1981) Proc Natl Acad Sci USA 78:2072.
Nikolova, et al., "CD39/Adenosine Pathway Is Involved in AIDS Progression" (2011), PLoS Pathogens 7(7).
Ohigashi et al., "Clinical significance of programmed death-1 ligand-1 and programmed death-1 ligand-2 expression in human esophageal cancer" (2005) Clin Cancer Res 11:2947-2953.
Ohta et al. "A2A Adenosine Receptor Protects Tumors from Antitumor T-Cells" PNAS 103(35):13132-13137 (2006).
Ohtsuka et al., "An alternative approach to deoxyoligonucleotides as hybridization probes by insertion of deoxyinosine at ambiguous codon positions" Biol. Chem. 260:2605-2608, 1985.
Orru, et al., "Genetic Variants Regulating Immune Cell Levels in Health and Disease" (2013) Cell 155:242-256.
Pearson & Lipman, "Improved tools for biological sequence comparison" Proc. Nat'l. Acad. Sci. USA 85:2444 (1988).
Poljak, "Production and structure of diabodies" (1994) Structure 2(12):1121-1123.
Pollock et al. "Transgenic milk as a method for the production of recombinant antibodies" (1999) J Immunol Methods 231(1-2)147-157.
Pommier et al., "DNA topoisomerases and their poisoning by anticancer and antibacterial drugs" (2010) Chem Biol 17 (5):421-433.
Pulte et al. "CD39 activity correlates with stage and inhibits platelet reactivity in chronic lymphocytic leukemia" J. Translational Medicine 5(23):1-10 (2007).
Pulte et al., "CD39 expression on T lymphocytes correlates with severity of disease in patients with chronic lymphocytic leukemia" (2011) Clin Lymphoma Myeloma Leuk 11:367-372.
Pulte et al., "CD39/NTPDase-1 Activity and Expression in Normal Leukocytes" (2007) Thromb Res. 121(3):309-317.
Ramot and Nyska, "Drug-Induced Thrombosis—Experimental, Clinical and Mechanistic Considerations" (2007) Toxicologic Pathology 35:208-225.
Rawstron et al. "Chronic Lymphocytic Leukaemia (CLL) and CLL-Type Monoclonal B-Cell Lymphocytosis (MBL) show differential Expression of Molecules Involved in Lymphoid Tissue Homing" Cytometry 78B:S42-S46 (2010).
Robson et al. "The E-NTPDase family of ectonuckeotidases: Structure function relationships and Pathophysiological significance" Purinergic Signalling 2:409-430 (2006).
Rogers et al. "Localization of iodine-125-mIP-Des-Met14-bombesin (7-13)NH2 in ovarian carcinoma induced to express the gastrin releasing peptide receptor by adenoviral vector-mediated gene transfer" (1997) J Nucl Med 38:1221-1229.
Sarver et al. "Transformation and replication in mouse cells of a bovine papillomavirus—pML2 plasmid vector that can be rescued in bacteria" (1982) Proc Natl Acad Sci USA, 79:7147.
Schoonbroodt et al. "Oligonucleotide-assisted cleavage and ligation: a novel directional DNA cloning technology to capture cDNAs. Application in the construction of a human immune antibody phage-display library." (2005) Nucleic Acids Res 33(9):e81.
Schuetz et al. "Molecular classification of renal tumors by gene expression profiling" J. of Molecular Diagnostics 7(2): 206-218 (2005).
Schulze zur Wiesch, et al., "Comprehensive Analysis of Frequencey and Phenotype of T Regulatory Cells in HIV Infection: CD39 Expression of FoxP3+ T Regulatory Cells Correlates with Progressive Disease" (2011) J of Virology 85 (3):1287-1297.
Shalaby et al., J. Exp. Med. "Development of humanized bispecific antibodies reactive with cytotoxic lymphocytes and tumor cells overexpressing the HER2 protooncogene" (1992) 175:217-225.
Shi et al. "Prevalence of the Mercurial-Sensitive EctoATPase in Human Small Cell Lung Carcinoma: Characterization and Partial Purification" Arch. Biochem. Biophys. 315(1):177-184 (1994).

(56) References Cited

OTHER PUBLICATIONS

Shimauchi et al., "Augmented expression of programmed death-1 in both neoplastic and non-neoplastic CD4+ T-cells in adult T-cell leukemia/lymphoma" (2007) Int J Cancer 121:2585-2590.
Sitkovsky et al. "Adenosine A2A receptor antagonists: blockade of adenosinergic effects and T regulatory cells" British J. of Pharmacology 153:S457-S464 (2008).
Sitkovsky et al., "Hostile, hypoxia-A2-adenosinergic tumor biology as the next barrier to overcome for tumor immunologists" (2014) Cancer Immunol Res) 2:598-605.
Sitkovsky et al., "Hypoxia-adenosinergic immunosuppression: tumor protection by T regulatory cells and cancerous tissue hypoxia" (2008) Clin Cancer Res 14:5947-5952.
Smith & Waterman, "Comparison of biosequences" Adv. Appl. Math. 2:482 (1981).
Songsivilai & Lachmann, "Bispecific antibody: a tool for diagnosis and treatment of disease" (1990) Clin. Exp. Immunol. 79:315-321.
Stagg et al. "Extracellular adenosine triphosphate and adenosine in cancer" Oncogene 29:5346-5358 (2010).
Sun et al. "CD39/ENTPD1 Expression by CD4+Foxp3+ Regulatory T-Cells Promotes Hepatic Metastatic Tumor Growth in Mice" Gastroenterology 139:1030-1040 (2010).
Takenaka, Robson and Quintana, "Regulation of the T Cell Response by CD39" (2016) Trends in Immunology 37 (7):427-439.
Trabanelli, et al., "Extracellular ATP Exerts Opposite Effects on Activated and Regulatory CD4+ T Cells via Purinergic P2 Receptor Activation" (2012) J Immunol 189:1303-1310.
Traverso et al. "Analysis of Regulatory T-Cells in Patients affected by Renal Cell Carcinome" J. of Urology 183(4) (2010).
Van der Weyden, et al., "Genome-wide in vivo screen identifies novel host regulators of metastatic colonization" (2017) Nature.
Van Gurp et al. "Phase 1 dose-escalation study of CP-690 550 in stable renal allograft recipients: preliminary findings of safety, tolerability, effects on lymphocyte subsets and pharmacokinetics" (2008) Am J Transplantation 8 (8):1711-1718.
Vidarsson et al. "IgG subclasses and allotypes: from structure to effector functions" Front Immunol. (2014), 5: 520.
Virgilio "Purines, purinergic receptors, and cancer" (2012) Cancer Res 72(21):5441-5447.
Virgilio and Adinolfi "Extracellular purines, purinergic receptors and tumor growth" (2017) Oncogene 36:293-303.
Wang and Guidotti, "CD39 Is an Ecto-(CA2+,Mg2+)-apyrase" (1996) Journal of Biological Chemistry 271 (17):9898-9901.
Wang, Ou and Guidotti, "The Transmembrane Domains of Extoapyrase (CD39) Affect Its Enzymatic Activity and Quaternary Structure" (1998) Journal of Biological Chemistry 273(38):24814-24821.
Warren, M. C. et al. "The fully human antibody SRF617 is potent enzymatic inhibitor of CD39 with strong immunomodulatory activity", Presented at SITC2019 on Nov. 9, 2019, Poster P652.
Allard, et al., "The ectonucleotidases CD39 and CD73: novel checkpoint inhibitor targets" (2017) Immunol Rev. 276 (1):121-144.
Altschul et al., "Gapped BLAST and PSI-BLAST: a new generation of protein database search programs" (1997) Nucleic Acids Res. 25(17):3389-3402.
Antonioli et al., "CD39 and CD73 in immunity and inflammation" (2013) Trends Mol Med 19:355-367.
Augier et al., "Preclinical development of a humanized blocking antibody targeting the CD39 immune checkpoint for cancer immunotherapy" (2016) AACR Poster.
Bai, et al., "CD39 and CD161 Modulate Th17 Responses in Chrohn's Disease" (2014) J Immunol 193:3366-3377.
Banz, et al., "CD39 is incorporated into plasma microparticles where it maintains functional properties and impacts endothelial activation" (2008) Br J Haematol 142(2):627-637.
Bastid et al. "ENTPD1/CD39 is a promising therapeutic target in oncology" Oncogene 32:1743-1751 (2013).
Bastid et al. "Inhibition of CD39 Enzymatic Function at the Surface of Tumor Cells Alleviates their Immunosuppressive Activity" Cancer Immunology Res. 3(3):254-265 (2014).
Batzer et al., "Enhanced evolutionary PCR using oligonucleotides with inosine at the 3'-terminus" Nucleic Acid Res. 19:5081, 1991.
Biological Deposit Receipt for CNCM I-3889.
Biological Deposit Receipt for CNCM I-4171.
Blay et al., "The extracellular fluid of solid carcinomas contains immunosuppressive concentrations of adenosine" 1997, Cancer Research 57:2602-2605 at Materials and Methods.
Bonnefoy, et al., "CD39: A complementary target to immune checkpoints to counteract tumor-mediated immunosuppression" (2015) OncoImmunology 4(5):e1003015-1-e1003015-3.
Bono, et al., "CD73 and CD39 ectonucleotidases in T cell differentiation: Beyond immunosuppression" (2015) FEBS Letters 589:3454-3460.
Borsellino et al., "Expression of ectonucleotidase CD39 by Foxp3+ Treg cells: hydrolysis of extracellular ATP and immune suppression" (2007) Blood 110:1225-1232.
Bours et al., "P2 receptors and extracellular ATP: a novel homeostatic pathway in inflammation" (2011) Front Biosci (Schol Ed) 3:1443-1456.
Brown et al. "Blockade of programmed death-1 ligands on dendritic cells enhances T cell activation and cytokine production" (2003) J. Immunol. 170:1257-66).
Buffon et al. "NTPDase and 5' ecto-nucleotidase expression profiles and the pattern of extracellular ATP metabolism in the Walker 256 turner" Biochimica et Biophysica Acta 1770:1259-1265 (2007).
Bulavina, L, "Roles of E-NTPDase1 and 5'-eNT in the Regulation of Microglial Phagocytosis" (2013) Doctoral Dissertation, Universitatsmedizen Berlin.
Cai, et al., "High expression of CD39 in gastric cancer reduces patient outcome following radical resection" (2016) Oncology Letters 12:4080-4086.
Cai, et al., "Overexpression of CD39 in hepatocellular carcinoma is an independent indicator of poor outcome after radical resection" (2016) Medicine 95:40.
Canale, et al., "CD39 Expression Defines Cell Exhaustion in Tumor-Infiltrating CD8+ T Cells" (2017) Cancer Res 78 (1):115-128.
Canfield et al. "The binding affinity of human IgG for its high affinity Fc receptor is determined by multiple amino acids in the CH2 domain and is modulated by the hinge region" (1991) J Exp Med 173:1483-1491.
Caron et al. "Engineered humanized dimeric forms of IgG are more effective antibodies" (1992) J Exp Med 176:1191-1195.
Clayton et al. "Cancer Exosomes Express CD39 and CD73, Which Suppresses T-Cells through Adenosine Production" J. of Immunology 187(2):676-683 (2011).
Coppi and Guidotti, "Inracellular Localization of Na,K-ATPase ?2 Subunit Mutants" (1997) Archives of Biochemistry and Biophysics 346(2):312-321.
Corriden, et al., "Ecto-nucleoside Triphosphate Diphosphohydrolase 1 (E-NTPDase1/CD39) Regulates Neutrophil Chemotaxis by Hydrolyzing Released ATP to Adenosine" (2008) Journal of Biological Chemistry (2008) 283 (42):28480-28486.
Covarrubias et al., "Role of the CD39/CD73 Purinergic Pathway in Modulating Arterial Thrombosis in Mice" Arterioscler Thromb Vasc Biol 36:1809-1820.
D'Almeida, et al., "The ecto-ATPDase CD39 is involved in the acquisition of the immunoregulatory phenotype by M-CSF-macrophages and ovarian cancer tumor-associated macrophages: Regulatory role of IL-27" (2016) OncoImmunology.
Deaglio et al. "Adenosine generation catalyzed by CD39 and CD73 expressed on regulatory T-Cells mediates immune suppression" JEM 204(6):1257-1265 (2007).
Deaglio et al., "Adenosine generation catalyzed by CD39 and CD73 expressed on regulatory T cells mediates immune suppression" (2007) J Exp Med 204:1257-1265.
Deans et al. "Expression of an immunoglobulin heavy chain gene transfected into lymphocytes" (1984) Proc Natl Acad Sci USA 81:1292.
Dulphy, et al., "Contribution of CD39 to the immunosuppressive microenvironment of acute myeloid lukaemia at diagnosis" (2014) British Journal of Haematology.

(56) References Cited

OTHER PUBLICATIONS

Dunleavy "Double-hit lymphomas: current paradigms and novel treatment approaches" (2014) Hematology Am Soc Hematol Educ Program 2014(1):107-112.
Dwyer et al. "CD39 and control of cellular immune responses" Purinergic Signalling 3:171-180 (2007).
Dwyer, et al., "Thromboregulatory manifestations in human CD39 transgenic mice and the implications for thrombotic disease and transplantation"(2004) Journal of Clinical Investigation 113(10):1440-1446.
Dzhandzhugazyan et al. "Ecto-ATP Diphosphohydrolase/CD39 is Overexpressed in Differentiated Human Melanomas" FEBS Letters 430(3):227-230 (1998).
Elliot et al., "Nucleotides released by apoptotic cells act as a find-me signal to romot phagocytic clearance" (2009) Nature 461:282-287.
Eltzschig et al., "Purinergic signaling during inflammation" (2012) N Engl J Med 367:2322-2333.
Engel, P. et al."The B7-2 (B70) costimulatory molecule expressed by monocytes and activated B lymphocytes is the CD86 differentiation antigen" 1994, Blood 84: 1402.
Enjyoji et al., "Targetd disruption of cd39/ATP diphosphohydrolase results in disordered hemosasis and thromboregulation" (1999) Nature Medicine 5(9):1010-1017.
Eppstein et al, "Biological activity of liposome-encapsulated murine interferon gamma is mediated by a cell membrane receptor" Proc. Natl. Acad. Sci. USA, 82:3688-3692 (1985).
Estep et al. "High throughput solution-based measurement of antibody-antigen affinity and epitope binning" (2013) Mabs 5(2):270-278.
Etz et al. "Bacterial phage receptors, versatile tools for display of polypeptides on the cell surface" (2001) J Bacteriol 183:6924-6935.
Fang, et al., "Expression of CD39 on Activated T Cells Impairs their Survival in Older Individuals" (2016) Cell Reports 14:1218-1231.
Fredholm "Adenosine, an endogenous distress signal, modulates tissue damage and repair" Cell Death and Differentiation 14:1315-1523 (2007).
Fujarewicz et al. "A Multi-gene Approach to differentiate papillary Thyriod Carcinoma from benign lesions: Gene selection using support vector machines with bootstrapping" Endocrine-Related Cancer 14:809-826 (2007).
Fulmer, "A gut feeling for CD39" Science-Business eXchange (2009) 2(40).
Gao et al., "Overexpression of PD-L1 significantly associates with tumor aggressiveness and postoperative recurrence in human hepatocellular carcinoma" (2009) Clin Cancer Res 15:971-979.
Gebremeskel and Johnston "Concepts and mechanisms underlying chemotherapy induced immunogenic cell death: impact on clinical studies and considerations for combined therapies" (2015) 6(39):41600-41619.
Whiteside "Disarming suppressor cells to improve immunotherapy" Cancer Immunol Immunother 61:283-288 (2012).
Whiteside et al. "The role of the adenosinergic pathway in immunosuppression mediated by human regulatory T cells (Treg)" Current Medicinal Chem. 18(34):5217-5223 (2011).
Wright et al. "Antibody variable region glycosylation: position effects on antigen binding and carbohydrate structure" (1991) EMBO J 10(10):2717-2723.
Xu et al, "Addressing polyspecificity of antibodies selected from an in vitro yeast presentation system: a FACS-based, high-throughput selection and analytical tool." PEDS 26.10, 663-70 (2013).
Yang et al., "PD-L1: PD-1 interaction contributes to the functional suppression of T-cell responses to human uveal melanoma cells in vitro" (2008) Invest Ophthalmol Vis Sci 49(6):2518-2525.
Zhang "CD73: A Novel Target for Cancer Immunotherapy" Cancer Res. 70(16):6407-6411 (2010).
Zhao et al., "What Else Can CD39 Tell Us?" (2017) Front Immunol 8:727.
Zhong and Guidotti, "A Yeast Golgi E-type ATPase with an Unusual Membrane Topology" (1999) Journal of Biological Chemistry 274(46):32704-32711.
Zhong, et al., "Mammalian Plasma Membrane Ecto-nucleoside Triphosphate Diphosphohydrolase 1, CD39, Is Not Active Intracellularly" (2001) Journal of Biological Chemistry 276(44):41518-41525.
Zimmerman, H, "Two novel families of ectonucleoidases: molecular structures, catalytic properties and a search for function" (1999) TiPS 20:231-236.
Ghebeh et al., "The B7-H1 (PD-L1) T lymphocyte-inhibitory molecule is expressed in breast cancer patients with infiltrating ductal carcinoma: correlation with important high-risk prognostic factors" (2006) Neoplasia 8:190-198.
Gourdin, et al., "Autocrine Adenosine regulates tumor polyfunctional CD73+CD4+ effector T cells devoid of immune checkpoints" (2018) Cancer Research.
Gouttefangeas "Biochemcial Analysis and Epitope mapping of mAb desining CD39 . . . " Proceedings pf the 5th International Workshop; Abstract T17 (1995).
Grinthal and Guidoti, "Bilayer mechanical properties regulate transmembrane helix mobility and enzymatic state of CD39" (2007) Biochemistry 46(1):279-290.
Guesdon, J.-L. et al., "The use of avidin-biotin interaction in immunoenzymatic techniques" 1979, J. Histochem. Cytochem. 27: 1131-1139.
Gupta, et al., "CD39 Expression Identifies Terminally Exhausted CD8+ T Cells" (2015) Plos Pathogens 11(10).
Hamanishi et al., "Programmed cell death 1 ligand 1 and tumor-infiltrating CD8+ T lymphocytes are prognostic factors of human ovarian cancer" (2007) Proc Nat Acad Sci USA 104:3360-3365.
Hanouska et al. "Phase 1b dose escalation study of erlotinib in combination with infusional 5-Fluorouracil, leucovorin, and oxaliplatin in patients with advanced solid tumors" (2007) Clin Cancer Res 13(2, part 1):523-531.
Häusler et al. "CD39 Wird in vivo und in vitro von Ovarialkarzinomzellen expirmiert und inhitiert die lytische Aktivitat von NK-Zellen" Geburtshilfe Frauenheilkunded 69:p. 106 (2009) German.
Häusler et al. "CD39 Wird in vivo und in vitro von Ovarialkarzinomzellen expirmiert und inhitiert die lytische Aktivitat von NK-Zellen" Geburtshilfe Frauenheilkunded 69:p. 106 (2009) English.
Häusler et al. "Ectonucleotidases CD39 and CD73 on OvCA cells are potent adenosine-generating enzymes responsible for adenosine receptor 2A-dependent suppression of T cell function and NK cell cytotoxicity" Cancer Immunol Immunother 60:1405-1417 (2011).
Häusler et al. Geburtshilfe Frauenheilkd (2009) 69-A042 (Abstract for XXI. Akademische Tagung deutsch sprechender ochschullehrer in der Gynakologie und Geburtshilfe-Innsbruck) German.
Häusler et al. Geburtshilfe Frauenheilkd (2009) 69-A042 (Abstract for XXI. Akademische Tagung deutsch sprechender ochschullehrer in der Gynakologie und Geburtshilfe-Innsbruck) English.
Häusler et al., poster"CD39 wird von humanen Ovarialkarzinomzellinien exprimiert und hemmt die immunologishe Tumorabwehr" ( date: 2008) English Translation.
Häusler et al., poster: "CD39 wird in vivo und in vitro von Ovarialkarzinomzellen exprimiert und inhibiert die lytische Aktivitiit von NK-Zellen" ( date: 2009) English Translation.
Häusler Geburtshilfe Frauenheilkd (2008) 68: SI-S194 (68:PO-Onko_04.33) (Abstract for Kongress der Deutschen Gesellschaft fur Gynakologie und Geburtshilfe-Hamburg) German.
Häusler Geburtshilfe Frauenheilkd (2008) 68: SI-S194 (68:PO-Onko_04.33) (Abstract for Kongress der Deutschen Gesellschaft fur Gynakologie und Geburtshilfe-Hamburg) English Translation.
Hetherington et al. "Phase I dose escalation study to evaluate the safety and pharmacokinetic profile of tefibazumab in subjects with end-stage renal disease requiring hemodialysis" (2006) Antimicrobial Agents and Chemotherapy 50(10): 3499-3500.
Hino et al., "Tumor cell expression of programmed cell death-1 ligand 1 is a prognostic factor for malignant melanoma" (2010) Cancer 116(7):1757-1766).
Holland, P. "Targeting the Adenosine Axis to Treat Cancer" Brisbane Immunotherapy Conference May 2019, poster.
Hollinger et al., ""Diabodies": small bivalent and bispecific antibody fragments" (1993) Proc. Natl. Acad. Sci. USA 90:6444-6448.

(56) References Cited

OTHER PUBLICATIONS

Horenstein, et al., "A CD38/CD203a/CD73 ectoenzymatic pathway independent of CD39 drives a novel adenosinergic loop in human T lymphocytes" (2013) OncoImmunology 2(9):e26246-1-e26246-14.
Hoskin et al. "Inhibition of T-Cell and Natural Killer cell function by Adenosine and its Contribution to Immune Evasion by Tumor Cells" International Journal of Oncology 32:527-535 (2008).
Hotson/Luke et al., Oral presentation at Society for Immunotherapy of Cancer (SITC) 32nd Annual Meeting (2017) [retrieved on Mar. 13, 2019]. Retrieved from the Internet.
Hou "Comparison of Multiple Comparison methods for Identifying Differential Gene Expression in simulated and Real Papillary Thyroid Cancer Microarry Data" Presented to the Faculty of the Univeristy of Texas School of Public Health (2009).
Huang et al., "Role of A2a extracellular adenosine receptor-mediated signaling in adenosine-mediated inhibition of T-cell activation and expansion" (1997) Blood 90-1600-1610.
Hudson et al., "Engineered antibodies" Nat. Med. 9:129-134 (2003).
Idzko et al., "Nucleotide signalling during inflammation" (2014) Nature 509:310-317.
Inman et al., "PD-L1 (B7-H1) expression by urothelial carcinoma of the bladder and BCG-induced granulomata: associations with localized stage progression" (2007) Cancer 109:1499-1505.
Innate Pharma. Targeting CD39 and CD73 to Improve Anti-Tumour Immune Responses, Nov. 15, 2017, pp. 17-18 [online]. [Retrieved May 29, 2019). Retrieved from the internet: . Especially PDF p. 17-18.
International Search Report and Written Opinion issued in PCT/US2019/022108 dated Sep. 3, 2019.
Ishida, Y. et al. "Induced expression of PD-1, a novel member of the immunoglobulin gene superfamily, upon programmed cell death" (1992) EMBO J. 11:3887-3895.
Iwai et al. "Involvement of PD-L1 on tumor cells in the escape from host immune system and tumor immunotherapy by PD-L1 blockade" (2002) Proc. Nat'l. Acad. Sci. USA 99:12293-7.
Jin et al. "CD73 on Tumor Cells Impairs Antitumor T-Cell Responses: A Novel Mechanism of Tumor-Induced Immune Suppression" Cancer Research 70(6):2245-2255 (2010).
Kanthi, et al., "Flow-dependent expression of ectonucleotide tri(di) phosphohydrolase-1 and suppression of atherosclerosis" (2015) Journal of Clinical Investigation 125(8) 3021-3036.
Kieke et al. "Isolation of anti-T cell receptor scFv mutants by yeast surface display" (1997) Protein Eng 10:1303-1310.
Kishore et al. "Expression of NTPDase1 and NTPDase2 in murine kidney: relevance to regulation of P2 receptor signaling" Am. J. Physiol. Renal Physiol 288:F1032-F1043 (2005).
Kitano et al., "Tumour-infiltrating lymphocytes are correlated with higher expression levels of PD-1 and PD-L1 in early breast cancer" (2017) ESMO Open 2(2):e000150.
Kleffel et al., "Melanoma Cell-Intrinsic PD-1 Receptor Functions Promote Tumor Growth" (2015) Cell 162(6):1242-1256.
Klemm et al. "Fimbrial surface display systems in bacteria: from vaccines to random libraries" (2000) Microbiology 146:3025-3032.
Kondo et al. "Expression of CD73 and its ecto-5'-nucleotidase activity are elevated in papillary thyroid carcinomas" Histopathology 48:612-614 (2006).
Konishi et al. "B7-H1 expression on non-small cell lung cancer cells and its relationship with tumor-infiltrating lymphocytes and their PD-1 expression" (2004) Clin. Cancer Res. 10:5094-100.
Kunzli et al. "Upregulation of CD39/NTPDases and P2 receptors in himan pancreatic disease" Am. J. Gastrointest Liver Physiol 292:G223-G230 (2007).
Lapierre, et al., "Disruption of the CD39 immune checkpoint pathway increases the efficacy of various anticancer therapies in syngeneic mouse tumor models" (2016) AACR Poster.
Leoni et al., "Bendamustine (Treanda) displays a distinct pattern of cytotoxicity and unique mechanistic features compared with other alkylating agents" (2008) Clin Cancer Res 14(1):309-317.

LeWitt et al., "Adenosine A2A receptor antagonist istradefylline (KW-6002) reduces "off" time in Parkinson's disease: a double-blind, randomized, multicenter clinical trial (6002-US-005)" (2008) Ann Neurol 63(3):295-302.
Liao et al., "cAMP/CREB-mediated Transcriptional Regulaton of Ectonucleoside Triphosphate Diphosphyhydrolase 1 (CD39) Expression" (2010) Journal of Biological Chemistry 285(19):14791-14805.
Lokshin et al., "Adenosine-mediated inhibition of the cytotoxic activity and cytokine production by activated natural killer cells" (2006) Cancer Res 66:7758-7765.
Maliszewski et al., "The CD39 lymphoid cell activation antigen. Molecular cloning and structural characterization" (1994) Journal of Immunology 153:3574-3583.
Mandapathil et al. "Increased Ectonucleotidase Expression and Activity in Regulatory T-Cells of Patients with Head and Neck Cancer" Clin Cancer Res. 15(20):6348-6357 (2009).
Lodmell et al. "DNA vaccination of mice against rabies virus: effects of the route of vaccination and the adjuvant monophosphoryl lipid A (MPL)" (2000) Vaccine 18:1059-1066.
Lonberg "Human antibodies from transgenic animals" (2005) Nature Biotech. 23(9):1117-1125.
Lonberg & Huszar, "Human antibodies from transgenic mice" (1995) Intern. Rev. Immunol. 13:65-93.
Lonberg et al., "Antigen-specific human antibodies from mice comprising four distinct genetic modifications" (1994) Nature 368(6474):856-859.
Marcus et al., "Role of CD39 (NTPDAse-1) in Thromboregulation, Cerebroprotection, and Cardioprotection" (2005) Seminars in Thrombosis and Hemostasis 31(2):234-246.
Merz et al. (1995) "Generating a phage display antibody library against an identified neuron" J Neurosci Methods 62 (1-2):213-9.
Meyers and Miller "Optimal alignments in linear space" CABIOS, 4:11-17 (1989).
Minotti et al., "Anthracyclines: molecular advances and pharmacologic developments in antitumor activity and cardiotoxicity" (2004) Pharmacol Rev 56(2):185-229.
Moldenhauer et al., "Identity of HML-1 antigen on intestinal intraepithelial T cells and of B-Iy7 antigen on hairy cell leukaemia" Scand. J. Immunol. 32:77 (1990).
Morel et al., "Monoclonal antibodies to bovine serum albumin: affinity and specificity determinations" Mol. Immunol. 25 (1):7 (1988).
Mueller et al. "Humanized porcine VCAM-specific monoclonal antibodies with chimeric IgG2/G4 constant regions block human leukocyte binding to porcine endothelial cells" (1997) Mol Immunol 34(6):441-452.
Muller-Haegele et al., "Immunoregulatory activity of adenosine and its role in human cancer progression" (2014) Expert Rev Clin Immunol 10:897-914.
Muyldermans et al., "Recognition of antigens by single-domain antibody fragments: the superfluous luxury of paired domains" (2001) Trends Biochem. Sci. 26:230-235.
Nakanishi et al., "Overexpression of B7-H1 (PD-L1) significantly associates with tumor grade and postoperative prognosis in human urothelial cancers" (2007) Cancer Immunol Immunother 56:1173-1182.
Needleman and Wunsch "A general method applicable to the search for similarities in the amino acid sequence of two proteins" J. Mol. Biol. (48):444-453 (1970).
Newman et al. "Modification of the Fc region of a primatized IgG antibody to human CD4 retains its ability to modulate CD4 receptors but does not deplete CD4(+) T cells in chimpanzees" Clinical Immunol. (2001) 98(2): 164-174.
Nozawa Y. et al., "A novel monoclonal antibody (FUN-1) identifies an activation antigen in cells of the B-cell lineage and Reed-Sternberg cells" 1993, J. Pathology 169: 309.
Nuttall et al., "Immunoglobulin VH domains and beyond: design and selection of single-domain binding and targeting reagents" (2000) Curr. Pharm. Biotech. 1:253-263.
Ohta et al., "Role of G-protein-coupled adenosine receptors in downregulation of inflammation and protection from tissue damage" (2001) Nature 414:916-920.

(56) References Cited

OTHER PUBLICATIONS

Pavisić et al. "Recombinant human granulocyte colony stimulating factor pre-screening and screening of stabilizing carbohydrates and polyols" (2010) Int J Pharm 387(1-2):110-119.
Persic et al. "An integrated vector system for the eukaryotic expression of antibodies or their fragments after selection from phage display libraries" (1997) Gene 187:9-18.
Plunkett et al., "Gemcitabine: metabolism, mechanisms of action, and self-potentiation" (1995) Semin Oncol 22(4 Suppl 11):3-10.
Reichmann et al., "Single domain antibodies: comparison of camel VH and camelised human VH domains" (1999) J. Immunol. Meth. 231:25-38.
Roberts et al. "Chemistry for peptide and protein PEGylation" (2002) Advanced Drug Delivery Reviews 54:459-476.
Rondon and Marasco, "Intracellular antibodies (intrabodies) for gene therapy of infectious disease" (1997) Annu. Rev. Microbiol. 51:257-283.
Rossolini et al, "Use of deoxyinosine-containing primers vs degenerate primers for polymerase chain reaction based on ambiguous sequence information" Mol. Cell. Probes 8:91-98, 1994.
Schaflitzel et al. "Ribosome display: an in vitro method for selection and evolution of antibodies from libraries" (1999) J Immunol Methods 231:119-135.
Shi et al. "De novo selection of high-affinity antibodies from synthetic fab libraries displayed on phage as pIX fusion proteins" (2010) JMB 397:385-396.
Shiraishi et al. "Short-step chemical synthesis of DNA by use of MMTrS group for protection of 5'-hydroxyl group" (2007) Nucleic Acids Symposium Series 51(1):129-130.
Shopes "A genetically engineered human IgG mutant with enhanced cytolytic activity" (1992) Immunol 148:2918-2922.
Sidman et al., "Controlled release of macromolecules and pharmaceuticals from synthetic polypeptides based on glutamic acid" Biopolymers, 22:547-556 (1983).
Siegel et al, "High efficiency recovery and epitope-specific sorting of an scFv yeast display library." J Immunol Methods 286(1-2), 141-153 (2004).
Stagg and Smith "Extracellular adenosine triphosphate and adenosine in cancer" (2010) Oncogene 29:5346-5358.
Stahli et al., "Distinction of epitopes by monoclonal antibodies" Methods in Enzymology 92:242 (1983).
Suresh et al., "Bispecific monoclonal antibodies from hybrid hybridomas" (1986) Methods Enzymol. 121:210.
Thompson et al., "Significance of B7-H1 overexpression in kidney cancer" (2006) Clin Genitourin Cancer 5:206-211.
Todorovska et al., "Design and application of diabodies, triabodies and tetrabodies for cancer targeting" (2001) J. Immunol. Methods 248(1):47-66.
Trautmann "Extracellular ATP in the immune system: more than just a danger signal". (2009) Sci Signal 2(56):pe6.
Tutt et al. "Trispecific F(ab')3 derivatives that use cooperative signaling via the TCR/CD3 complex and CD2 to activate and redirect resting cytotoxic T cells" (1991) J Immunol 147:60.
Van Kuik-Romeijn et al. "Expression of a functional mouse-human chimeric anti-CD19 antibody in the milk of transgenic mice" (2000) Transgenic Res 9(2):155-159.
Vijayan et al., "Targeting immunosuppressive adenosine in cancer" (2017) Nat Rev Cancer 17:709-724.
Welch and Redvanly (2003) "Handbook of Radiopharmaceuticals: Radiochemistry and Applications," John Wiley and Sons.
Wigler et al. "Transformation of mammalian cells with genes from procaryotes and eucaryotes" (1979) Cell 16:777-85.
Yeung et al. "Quantitative screening of yeast surface-displayed polypeptide libraries by magnetic bead capture" (2002) Biotechnol Prog 18:212-220.
Zapata et al. "Engineering linear F(ab')2 fragments for efficient production in *Escherichia coli* and enhanced antiproliferative activity" (1995) Protein Eng. 8(10):1057-1062.
Zhan et al., "From monoclonal antibodies to small molecules: the development of inhibitors targeting the PD-1/PD-L1 pathway" (2016) Drug Discov Today 21(6):1027-1036.
Notice of allowance issued in U.S. Appl. No. 16/352,589 dated Jun. 10, 2020.

| Antibody | IgG $K_D$ Human CD39-His (M) Monovalent | MSD equilibrium $K_D$ (M) Biotinylated Human CD39-His incubated with Fab |
|---|---|---|
| SRF360-C | 7.72E-10 | 4.40E-11 |
| SRF365-C | 5.56E-10 | 5.10E-11 |
| SRF367-C | 1.57E-09 | 2.40E-10 |
| SRF370-C | 2.59E-09 | N.M. |
| SRF399-C | 2.94E-09 | 5.30E-11 |

Fig. 7

ANTIBODIES THAT BIND CD39 AND USES THEREOF

This application is a divisional of U.S. application Ser. No. 16/352,589, filed on Mar. 13, 2019, which claims the benefit of priority to U.S. Provisional Application No. 62/642,938, filed on Mar. 14, 2018, and U.S. Provisional Application No. 62/803,235, filed on Feb. 8, 2019, all of which are incorporated by reference in their entirety.

SEQUENCE LISTING

The instant application contains a Sequence Listing which has been submitted electronically in ASCII format and is hereby incorporated by reference in its entirety. Said ASCII copy, created on May 13, 2020, is named 2020-05-13_01219-0003-01US_P4P_ST25.txt and is 180,224 bytes in size.

BACKGROUND

Cancers are able to grow by subverting immune suppressive pathways, to prevent the malignant cells as being recognized as dangerous or foreign. This mechanism prevents the cancer from being eliminated by the immune system and allows disease to progress from a very early stage to a lethal state. Immunotherapies are newly developing interventions that modify the patient's immune system to fight cancer, by either directly stimulating rejection-type processes or blocking suppressive pathways. Extracellular adenosine generated by the ectonucleotidases CD39 and CD73 is a newly recognized "immune checkpoint mediator" that interferes with anti-tumor immune responses. Adenosine is an immunomodulatory metabolite within the tumor microenvironment (TME). In some cancers, extracellular adenosine accumulates and subsequently inhibits the function of immune cells, including T cells, dendritic cells (DC), and NK cells, thereby contributing to anti-tumor immune suppression and supporting tumor growth.

The ectonucleotidase CD39 hydrolyzes extracellular adenosine triphosphate (ATP) and adenosine diphosphate (ADP) to generate adenosine, which binds to adenosine receptors and inhibits immune cells such as T-cells and natural killer (NK)-cells, thereby suppressing the immune system. Overexpression of CD39 is associated with poor prognosis in patients with certain types of cancer. Within the TME, the adenosine pathway refers to the extracellular conversion of ATP to adenosine and the signaling of adenosine through the A2A/A2B adenosine receptors on immune cells. Under normal conditions, CD39 works to maintain the balance of extracellular levels of immunosuppressive adenosine and immunostimulatory ATP. In healthy tissues, ATP is barely detectable in the extracellular environment because ATP is rapidly broken down by CD39 to generate adenosine monophosphate, or AMP, which is then converted to adenosine by CD73. Under conditions of cellular stress, including cancer, extracellular ATP levels rise significantly, but because ATP is rapidly broken down, leading to low levels of ATP coupled with high levels of adenosine, recognition of the tumor by the immune system, and thus the immune response against the tumor, is hindered.

There continues to be an unmet need for the development of novel cancer therapies. Novel combinations with existing therapies and therapeutic regimens are also needed to more effectively combat various cancers.

SUMMARY OF THE DISCLOSURE

Disclosed herein are antibodies, or antigen binding portions thereof, that bind to and antagonize human CD39 (Cluster of Differentiation 39) with high affinity and specificity. The anti-CD39 antibodies disclosed are non-competitive, allosteric inhibitors of CD39. In some embodiments, the anti-CD39 antibodies allow substrate (ATP) binding, but prohibit its conversion to ADP and/or adenosine, thus maintaining or enhancing levels of ATP in the tumor microenvironment (TME) and/or preventing undesirable levels of adenosine in the TME. Nucleic acid molecules encoding the antibody molecules, expression vectors, host cells and methods for making the antibody molecules are also provided. Pharmaceutical compositions comprising the antibody molecules are also provided. The anti-CD39 antibodies, or antigen binding portions thereof, disclosed herein can be used (alone or in combination with other therapeutic agents or procedures) to treat, prevent and/or diagnose disorders, including immune disorders and cancer. Thus, compositions and methods for treating and/or diagnosing various disorders, including cancer and immune disorders, using the anti-CD39 antibody molecules are disclosed herein.

In one aspect, the disclosure provides anti-CD39 antibodies, including antibodies, that bind to and antagonize human CD39, or an antigen binding portion thereof, wherein the antibody or antigen binding portion thereof exhibits one or more of the following properties:
 (a) binds to recombinant human CD39 and/or to membrane-bound human CD39;
 (b) binds to human CD39 with an equilibrium dissociation constant ($K_D$) of less than 10 nM;
 (c) inhibits or reduces an enzymatic activity of human CD39;
 (d) inhibits or reduces conversion by human CD39 of extracellular adenosine triphosphate (eATP) or extracellular adenosine diphosphate (eADP) to extracellular adenosine monophosphate (eAMP);
 (e) increases or enhances a level of eATP;
 decreases or reduces a level of extracellular adenosine;
 (g) maintains, increases or enhances an immunostimulatory level of eATP;
 (h) increases or enhances proliferation of a lymphocyte;
 (i) increases or enhances expression of one or more dendritic cell activation markers;
 (j) increases or enhances secretion of one or more cytokines from dendritic cells;
 (k) increases or enhances macrophage infiltration in tumors;
 (l) increases or enhances secretion of macrophage attracting chemokines;
 (m) antagonizes human CD39 in a tumor microenvironment of a tissue;
 (n) cross-reacts with cynomolgus CD39; and
 (o) a combination of any one of (a)-(n).

In some embodiments, an isolated anti-CD39 antibody is provided comprising, consisting, or consisting essentially of:
 i) heavy chain CDR1, CDR2 and CDR3 sequences comprising SEQ ID NOs: 1, 2 and 3, respectively, and light chain CDR1, CDR2 and CDR3 sequences comprising SEQ ID NOs: 11, 12, and 13, respectively; or
 ii) heavy chain CDR1, CDR2 and CDR3 sequences comprising SEQ ID NOs: 4, 5, and 6, respectively, and light chain CDR1, CDR2 and CDR3 sequences comprising SEQ ID NOs: 15, 16, and 17, respectively; or
 iii) a variable heavy chain at least 90%, 91%, 92%, 93%, 94%, 95%, 96%, 97%, 98%, 99%, or 100% identical to the amino acid sequence of SEQ ID NO: 7, and a variable light chain at least 90%, 91%, 92%, 93%, 94%, 95%, 96%, 97%, 98%, 99%, or 100% identical to the amino acid sequence of SEQ ID NO: 7; or iv) a heavy chain at least 90%, 91%, 92%, 93%, 94%, 95%, 96%, 97%, 98%, 99%, or 100% identical to the amino acid sequence of SEQ ID NO: 9, and a light chain at least 90%, 91%, 92%, 93%, 94%, 95%, 96%, 97%, 98%, 99%, or 100% identical to the amino acid sequence of SEQ ID NO: 19; or v) a heavy chain at least 90%, 91%, 92%, 93%, 94%, 95%, 96%, 97%, 98%, 99%, or 100% identical to the amino acid sequence of SEQ ID NO: 21, and a light chain at least 90%, 91%, 92%, 93%, 94%, 95%, 96%, 97%, 98%, 99%, or 100% identical to the amino acid sequence of SEQ ID NO: 19; or vi) a heavy chain at least 90%, 91%, 92%, 93%, 94%, 95%, 96%, 97%, 98%, 99%, or 100% identical to the amino acid sequence of SEQ ID NO: 23, and a light chain at least 90%, 91%, 92%, 93%, 94%, 95%, 96%, 97%, 98%, 99%, or 100% identical to the amino acid sequence of SEQ ID NO: 19; or vii) a heavy chain at least 90%, 91%, 92%, 93%, 94%, 95%, 96%, 97%, 98%, 99%, or 100% identical to the amino acid sequence of SEQ ID NO: 25, and a light chain at least 90%, 91%, 92%, 93%, 94%, 95%, 96%, 97%, 98%, 99%, or 100% identical to the amino acid sequence of SEQ ID NO: 19; or viii) heavy chain CDR1, CDR2 and CDR3 sequences comprising SEQ ID NOs: 27, 28, and 29, respectively, and light chain CDR1, CDR2 and CDR3 sequences comprising SEQ ID NOs: 37, 38, and 39, respectively; or ix) heavy chain CDR1, CDR2 and CDR3 sequences comprising SEQ ID NOs: 30, 31, and 32, respectively, and light chain CDR1, CDR2 and CDR3 sequences comprising SEQ ID NOs: 40, 41, and 42, respectively; or x) a variable heavy chain at least 90%, 91%, 92%, 93%, 94%, 95%, 96%, 97%, 98%, 99%, or 100% identical to the amino acid sequence of SEQ ID NO: 33, and a variable light chain at least 90%, 91%, 92%, 93%, 94%, 95%, 96%, 97%, 98%, 99%, or 100% identical to the amino acid sequence of SEQ ID NO: 43; or xi) a heavy chain at least 90%, 91%, 92%, 93%, 94%, 95%, 96%, 97%, 98%, 99%, or 100% identical to the amino acid sequence of SEQ ID NO: 35, and a light chain at least 90%, 91%, 92%, 93%, 94%, 95%, 96%, 97%, 98%, 99%, or 100% identical to the amino acid sequence of SEQ ID NO: 45; or xii) a heavy chain at least 90%, 91%, 92%, 93%, 94%, 95%, 96%, 97%, 98%, 99%, or 100% identical to the amino acid sequence of SEQ ID NO: 47, and a light chain at least 90%, 91%, 92%, 93%, 94%, 95%, 96%, 97%, 98%, 99%, or 100% identical to the amino acid sequence of SEQ ID NO: 45; or xiii) a heavy chain at least 90%, 91%, 92%, 93%, 94%, 95%, 96%, 97%, 98%, 99%, or 100% identical to the amino acid sequence of SEQ ID NO: 49, and a light chain at least 90%, 91%, 92%, 93%, 94%, 95%, 96%, 97%, 98%, 99%, or 100% identical to the amino acid sequence of SEQ ID NO: 45; or xiv) a heavy chain at least 90%, 91%, 92%, 93%, 94%, 95%, 96%, 97%, 98%, 99%, or 100% identical to the amino acid sequence of SEQ ID NO: 51, and a light chain at least 90%, 91%, 92%, 93%, 94%, 95%, 96%, 97%, 98%, 99%, or 100% identical to the amino acid sequence of SEQ ID NO: 45; or xv) heavy chain CDR1, CDR2 and CDR3 sequences comprising SEQ ID NOs: 53, 54, and 55, respectively, and light chain CDR1, CDR2 and CDR3 sequences comprising SEQ ID NOs: 63, 64, and 65, respectively; or xvi) heavy chain CDR1, CDR2 and CDR3 sequences comprising SEQ ID NOs: 56, 57, and 58, respectively, and light chain CDR1, CDR2 and CDR3 sequences comprising SEQ ID NOs: 66, 67, and 68, respectively; or xvii) a variable heavy chain at least 90%, 91%, 92%, 93%, 94%, 95%, 96%, 97%, 98%, 99%, or 100% identical to the amino acid sequence of SEQ ID NO: 59, and a variable light chain at least 90%, 91%, 92%, 93%, 94%, 95%, 96%, 97%, 98%, 99%, or 100% identical to the amino acid sequence of SEQ ID NO: 69; or xviii) a heavy chain at least 90%, 91%, 92%, 93%, 94%, 95%, 96%, 97%, 98%, 99%, or 100% identical to the amino acid sequence of SEQ ID NO: 61, and a light chain at least 90%, 91%, 92%, 93%, 94%, 95%, 96%, 97%, 98%, 99%, or 100% identical to the amino acid sequence of SEQ ID NO: 71; or xix) a heavy chain at least 90%, 91%, 92%, 93%, 94%, 95%, 96%, 97%, 98%, 99%, or 100% identical to the amino acid sequence of SEQ ID NO: 73, and a light chain at least 90%, 91%, 92%, 93%, 94%, 95%, 96%, 97%, 98%, 99%, or 100% identical to the amino acid sequence of SEQ ID NO: 71; or xx) a heavy chain at least 90%, 91%, 92%, 93%, 94%, 95%, 96%, 97%, 98%, 99%, or 100% identical to the amino acid sequence of SEQ ID NO: 75, and a light chain at least 90%, 91%, 92%, 93%, 94%, 95%, 96%, 97%, 98%, 99%, or 100% identical to the amino acid sequence of SEQ ID NO: 71; or xxi) a heavy chain at least 90%, 91%, 92%, 93%, 94%, 95%, 96%, 97%, 98%, 99%, or 100% identical to the amino acid sequence of SEQ ID NO: 77, and a light chain at least 90%, 91%, 92%, 93%, 94%, 95%, 96%, 97%, 98%, 99%, or 100% identical to the amino acid sequence of SEQ ID NO: 71; or xxii) heavy chain CDR1, CDR2 and CDR3 sequences comprising SEQ ID NOs: 79, 80, and 81, respectively, and light chain CDR1, CDR2 and CDR3 sequences comprising SEQ ID NOs: 89, 90, and 91, respectively; or xxiii) heavy chain CDR1, CDR2 and CDR3 sequences comprising SEQ ID NOs: 82, 83, and 84, respectively, and light chain CDR1, CDR2 and CDR3 sequences comprising SEQ ID NOs: 92, 93, and 94, respectively; or xxiv) a variable heavy chain at least 90%, 91%, 92%, 93%, 94%, 95%, 96%, 97%, 98%, 99%, or 100% identical to the amino acid sequence of SEQ ID NO: 85, and a variable light chain at least 90%, 91%, 92%, 93%, 94%, 95%, 96%, 97%, 98%, 99%, or 100% identical to the amino acid sequence of SEQ ID NO: 95; or xxv) a heavy chain at least 90%, 91%, 92%, 93%, 94%, 95%, 96%, 97%, 98%, 99%, or 100% identical to the amino acid sequence of SEQ ID NO: 87, and a light chain at least 90%, 91%, 92%, 93%, 94%, 95%, 96%, 97%, 98%, 99%, or 100% identical to the amino acid sequence of SEQ ID NO: 97; or xxvi) a heavy chain at least 90%, 91%, 92%, 93%, 94%, 95%, 96%, 97%, 98%, 99%, or 100% identical to the amino acid sequence of SEQ ID NO: 99, and a light chain at least 90%, 91%, 92%, 93%, 94%, 95%, 96%, 97%, 98%, 99%, or 100% identical to the amino acid sequence of SEQ ID NO: 97; or xxvii) a heavy chain at least 90%, 91%, 92%, 93%, 94%, 95%, 96%, 97%, 98%, 99%, or 100% identical to the amino acid sequence of SEQ ID NO: 101, and a light chain at least 90%, 91%, 92%, 93%, 94%, 95%, 96%, 97%, 98%, 99%, or 100% identical to the amino acid sequence of SEQ ID NO: 97; or xxviii) a heavy chain at least 90%, 91%, 92%, 93%, 94%, 95%, 96%, 97%, 98%, 99%, or 100% identical to the amino acid sequence of SEQ ID NO: 103, and a light chain at least 90%, 91%, 92%, 93%, 94%, 95%, 96%, 97%, 98%, 99%, or 100% identical to the amino acid sequence of SEQ ID NO: 97; or xxix) heavy chain CDR1, CDR2 and CDR3 sequences comprising SEQ ID NOs: 105, 106, and 107, respectively, and light chain CDR1, CDR2 and CDR3 sequences comprising SEQ ID NOs: 115, 116, and 117, respectively; or xxx) heavy chain CDR1, CDR2 and CDR3 sequences comprising SEQ ID NOs: 108, 109, 110, respectively, and light chain CDR1, CDR2 and CDR3 sequences comprising SEQ ID NOs: 118, 119, and 120, respectively; or xxxi) a variable heavy chain at least 90%, 91%, 92%, 93%, 94%, 95%, 96%, 97%, 98%, 99%, or 100% identical to the amino acid sequence of SEQ ID NO: 111, and a variable light chain at least 90%, 91%, 92%, 93%, 94%, 95%, 96%, 97%, 98%, 99%, or 100% identical to the amino acid sequence of SEQ ID NO: 121; or xxxii) a heavy chain at least 90%, 91%, 92%, 93%, 94%, 95%, 96%, 97%, 98%, 99%, or 100% identical to the amino acid sequence of SEQ ID NO: 113, and a light chain at least 90%, 91%, 92%, 93%, 94%, 95%, 96%, 97%, 98%, 99%, or 100% identical to the amino acid sequence of SEQ ID NO: 123; or xxxiii) a heavy chain at least 90%, 91%, 92%, 93%, 94%, 95%, 96%, 97%, 98%, 99%, or 100% identical to the amino acid sequence of SEQ ID NO: 125, and a light chain at least 90%, 91%, 92%, 93%, 94%, 95%, 96%, 97%, 98%, 99%, or 100% identical to the amino acid sequence of SEQ ID NO: 123; or xxxiv) a heavy chain at least 90%, 91%, 92%, 93%, 94%, 95%, 96%, 97%, 98%, 99%, or 100% identical to the amino acid sequence of SEQ ID NO: 127, and a light chain at least 90%, 91%, 92%, 93%, 94%, 95%, 96%, 97%, 98%, 99%, or 100% identical to the amino acid sequence of SEQ ID NO: 123; or xxxv) a heavy chain at least 90%, 91%, 92%, 93%, 94%, 95%, 96%, 97%, 98%, 99%, or 100% identical to the amino acid sequence of SEQ ID NO: 129, and a light chain at least 90%, 91%, 92%, 93%, 94%, 95%, 96%, 97%, 98%, 99%, or 100% identical to the amino acid sequence of SEQ ID NO: 123.

In some embodiments, the anti-CD39 antibody comprises the structural features described in i) through xxxv) above and one or more of the functional features described in (a) through (o) above. In some embodiments, the anti-CD39 antibody, or antigen binding fragment thereof, binds to substantially the same epitope as a reference antibody described in (a) through (o) above or i) through xxxv) above.

In some embodiments, the disclosure provides an anti-CD39 antibody, or antigen binding portion thereof, comprising or consisting of heavy chain CDR1, CDR2 and CDR3 sequences comprising SEQ ID NOs: 27, 28, and 29, respectively, and light chain CDR1, CDR2 and CDR3 sequences comprising SEQ ID NOs: 37, 38, and 39, respectively.

In some embodiments, the disclosure provides an anti-CD39 antibody, or antigen binding portion thereof, comprising or consisting of heavy chain CDR1, CDR2 and CDR3 sequences comprising SEQ ID NOs: 30, 31, and 32, respectively, and light chain CDR1, CDR2 and CDR3 sequences comprising SEQ ID NOs: 40, 41, and 42, respectively.

In some embodiments, the disclosure provides an anti-CD39 antibody, or antigen binding portion thereof, comprising or consisting of a variable heavy chain at least 90%, 91%, 92%, 93%, 94%, 95%, 96%, 97%, 98%, 99%, or 100% identical to the amino acid sequence of SEQ ID NO: 33, and a variable light chain at least 90%, 91%, 92%, 93%, 94%, 95%, 96%, 97%, 98%, 99%, or 100% identical to the amino acid sequence of SEQ ID NO: 43.

In some embodiments, the disclosure provides an anti-CD39 antibody, or antigen binding portion thereof, comprising or consisting of a heavy chain at least 90%, 91%, 92%, 93%, 94%, 95%, 96%, 97%, 98%, 99%, or 100% identical to the amino acid sequence of SEQ ID NO: 49, and a light chain at least 90%, 91%, 92%, 93%, 94%, 95%, 96%, 97%, 98%, 99%, or 100% identical to the amino acid sequence of SEQ ID NO: 45.

In some embodiments, the disclosure provides an anti-CD39 antibody that binds to and antagonizes human CD39 comprising or consisting of heavy chain CDR1, CDR2 and CDR3 sequences comprising SEQ ID NOs: 27, 28, and 29, respectively, and light chain CDR1, CDR2 and CDR3 sequences comprising SEQ ID NOs: 37, 38, and 39, respectively; or heavy chain CDR1, CDR2 and CDR3 sequences comprising SEQ ID NOs: 4, 5, and 6, respectively, and light chain CDR1, CDR2 and CDR3 sequences comprising SEQ ID NOs: 15, 16, and 17, respectively, wherein the antibody:

a. increases proliferation of a lymphocyte, optionally wherein the lymphocyte is a tumor-infiltrating lymphocyte, or CD4+ T cell, and/or b. enhances expression of one or more dendritic cell activation markers, optionally wherein the dendritic cell activation marker is CD86, HLA-DR, or a both CD86 and HLA-DR; and/or c. enhances secretion of one or more cytokines from dendritic cells, optionally wherein the cytokine is IL-16, IL-12/IL-23p40, VEGFA, or any combination thereof; and/or d. wherein the antagonism of human CD39 occurs in a tumor microenvironment, optionally wherein the antagonism is non-competitive and/or allosteric; and/or e. wherein the antibody or antigen binding portion thereof cross-reacts with cynomolgus CD39.

In some embodiments, the anti-CD39 antibody, or antigen binding portion thereof, comprises an IgG1, an IgG2, an IgG3, an IgG4, an IgM, an IgA1, an IgA2, ad IgD, or an IgE antibody.

In some embodiments, the anti-CD39 antibody, or antigen binding portion thereof, comprises a wild type or mutant IgG1 or IgG4 antibody. In some embodiments, the anti-CD39 antibody, or antigen binding portion thereof, comprises a mutant IgG4 heavy chain constant region, wherein the mutation i) reduces the ability of the IgG4 to form half-molecules; and/or ii) minimizes binding to Fc receptors.

In some embodiments, the anti-CD39 antibody, or antigen binding portion thereof, comprises a mutant IgG4 heavy chain constant region comprising an S228P mutation. In some embodiments, the anti-CD39 antibody, or antigen binding portion thereof, comprises a mutant IgG4 heavy chain constant region comprising S228P and L235E mutations.

In some embodiments, the anti-CD39 antibody, or antigen binding portion thereof, comprises the heavy chain CDR3 sequence set forth in SEQ ID NO: 3. In some embodiments, the anti-CD39 antibody, or antigen binding portion thereof, binds to substantially the same epitope as a reference antibody or antigen binding portion thereof comprising the heavy chain CDR3 sequence set forth in SEQ ID NO: 3.

It has previously been described that CD39 is increased in subjects resistant to anti-PD1/anti-PD-L1 therapy. See, e.g., Hotson/Luke et al., Oral presentation at Society for Immunotherapy of Cancer (SITC) 32nd Annual Meeting (2017) [retrieved on 2019-03-13]. Retrieved from the Internet: <URL: https://www.corvuspharma.com/file.cfm/23/docs/SITC 2017 Slides.pdf>. In some embodiments, a method of treating human subjects that are resistant to anti-PD1 or anti-PD-L1 therapy is provided comprising administering any one of the anti-CD39 antibodies described herein. Subjects who are resistant to anti-PD1 or anti-PD-L1 include subject whose benefit from the anti-PD1 or anti-PD-L1 therapy remained diminished by at least one standard deviation as compared to a non-resistant control for greater than three months.

In one aspect, the disclosure provides an antibody or antigen binding portion thereof that binds to human recombinant CD39 and/or membrane-bound human CD39. In one aspect, the disclosure provides an antibody or antigen binding portion thereof that binds to human CD39 with an equilibrium dissociation constant ($K_D$) of less than 10 nM. In one aspect, the disclosure provides an antibody or antigen binding portion thereof that inhibits or reduces an enzymatic activity of human CD39. In one aspect, the disclosure provides an antibody or antigen binding portion thereof that binds to human recombinant CD39 and/or membrane-bound human CD39 with an equilibrium dissociation constant ($K_D$) of less than 10 nM and inhibits or reduces an enzymatic activity of human CD39. In some aspects, the enzymatic activity of human CD39 is the hydrolysis of eATP or eADP.

In some aspects, the antibody or antigen binding portion of the disclosure inhibits or reduces the conversion of eATP or eADP to eAMP. In some aspects, the antibody or antigen binding portion thereof binds to human recombinant CD39 and/or membrane-bound human CD39 with an equilibrium dissociation constant ($K_D$) of less than 10 nM, and inhibits or reduces the conversion of eATP or eADP to eAMP.

In some aspects, the antibody or antigen binding portion of the disclosure increases or enhances a level eATP. In some aspects, the antibody or antigen binding portion thereof binds to human recombinant CD39 and/or membrane-bound human CD39 with an equilibrium dissociation constant ($K_D$) of less than 10 nM, and increases or enhances a level eATP.

In some aspects, the antibody or antigen binding portion of the disclosure decreases or reduces a level of extracellular adenosine. In some aspects, the antibody or antigen binding portion thereof binds to human recombinant CD39 and/or membrane-bound human CD39 with an equilibrium dissociation constant ($K_D$) of less than 10 nM, and decreases or reduces a level of extracellular adenosine. Methods for assessing adenosine levels are known in the art, for example, in Blay et al., 1997, Cancer Research 57:2602-2605 at Materials and Methods, incorporated herein by reference in its entirety.

In some aspects, the antibody or antigen binding portion of the disclosure maintains, increases or enhances an immunostimulatory level of eATP. In some aspects, the antibody or antigen binding portion thereof binds to human recombinant CD39 and/or membrane-bound human CD39 with an equilibrium dissociation constant ($K_D$) of less than 10 nM, and maintains, increases or enhances an immunostimulatory level of eATP.

In some aspects, the antibody or antigen binding portion of the disclosure increases proliferation of a lymphocyte. In some aspects, the antibody or antigen binding portion thereof binds to human recombinant CD39 and/or membrane-bound human CD39 with an equilibrium dissociation constant ($K_D$) of less than 10 nM, and increases proliferation of a lymphocyte. In some aspects, the antibody or antigen binding portion thereof binds to human recombinant CD39 and/or membrane-bound human CD39 with an equilibrium dissociation constant ($K_D$) of less than 10 nM, inhibits or reduces an enzymatic activity of human CD39, and increases proliferation of a lymphocyte. In some aspects, the antibody or antigen binding portion thereof binds to human recombinant CD39 and/or membrane-bound human CD39 with an equilibrium dissociation constant ($K_D$) of less than 10 nM, maintains, increases or enhances a level eATP, and increases proliferation of a lymphocyte. In some aspects, the antibody or antigen binding portion thereof binds to human recombinant CD39 and/or membrane-bound human CD39 with an equilibrium dissociation constant ($K_D$) of less than 10 nM, maintains, increases or enhances a level eATP, and/or decreases or reduces a level of adenosine, and increases proliferation of a lymphocyte. In some aspects, the lymphocyte is a tumor-infiltrating lymphocyte. In some aspects, the lymphocyte is T cell. In some aspects, the T cell is a CD4+ T cell.

In some aspects, the antibody or antigen binding portion of the disclosure increases or enhances expression of one or more dendritic cell activation markers and/or increases or enhances secretion of one or more cytokines from dendritic cells. In some aspects, the antibody or antigen binding portion thereof binds to human recombinant CD39 and/or membrane-bound human CD39 with an equilibrium dissociation constant ($K_D$) of less than 10 nM, and increases or enhances expression of one or more dendritic cell activation markers and/or increases or enhances secretion of one or more cytokines from dendritic cells. In some aspects, the antibody or antigen binding portion thereof binds to human recombinant CD39 and/or membrane-bound human CD39 with an equilibrium dissociation constant ($K_D$) of less than 10 nM, inhibits or reduces an enzymatic activity of human CD39, and increases or enhances expression of one or more dendritic cell activation markers and/or increases or enhances secretion of one or more cytokines from dendritic cells. In some aspects, the antibody or antigen binding portion thereof binds to human recombinant CD39 and/or membrane-bound human CD39 with an equilibrium dissociation constant ($K_D$) of less than 10 nM, maintains, increases or enhances a level eATP, and increases or enhances expression of one or more dendritic cell activation markers and/or increases or enhances secretion of one or more cytokines from dendritic cells. In some aspects, the antibody or antigen binding portion thereof binds to human recombinant CD39 and/or membrane-bound human CD39 with an equilibrium dissociation constant ($K_D$) of less than 10 nM, maintains, increases or enhances a level eATP, and/or decreases or reduces a level of adenosine, and increases or enhances expression of one or more dendritic cell activation markers and/or increases or enhances secretion of one or more cytokines from dendritic cells. In some aspects, the one or more dendritic cell activation markers is CD86, HLA-DR, or a combination thereof. In some aspects, the one or more cytokines is IL-16, IL-12/IL-23p40, VEGFA, or any combination thereof.

In some aspects, the antibody or antigen binding portion of the disclosure causes antagonism of human CD39 in a tumor microenvironment of a tissue.

In some aspects, the antibody or antigen binding portion of the disclosure cross-reacts with cynomolgus CD39 and/or mouse CD39.

In some aspects, the antibody or antigen binding portion of the disclosure is selected from an IgG1, an IgG2, and IgG3, an IgG4, and IgM, and IgA1, and IgA2, and IgD, and an IgE antibody. In some aspects, the antibody or antigen binding portion of the disclosure is an IgG1 antibody or an IgG4 antibody. In some aspects, the antibody or antigen binding portion of the disclosure comprises a wild type IgG1 heavy chain constant region. In some aspects, the antibody or antigen binding portion of the disclosure comprises a wild type IgG4 heavy chain constant region. In some aspects, the antibody or antigen binding portion of the disclosure comprises an Fc domain comprising at least one mutation. In some aspects, the antibody or antigen binding portion of the disclosure comprises a mutant IgG1 heavy chain constant region. In some aspects, the antibody or antigen binding portion of the disclosure comprises a mutant IgG4 heavy chain constant region. In some aspects, the antibody or antigen binding portion of the disclosure comprises a mutant IgG4 heavy chain constant region, wherein the mutant IgG4 heavy chain constant region comprises any one of the substitutions S228P, L235E, L235A, or a combination thereof, according to EU numbering. In some aspects, the antibody or antigen binding portion of the disclosure comprises a mutant IgG4 heavy chain constant region, wherein the mutant IgG4 heavy chain constant region comprises a S228P substitution. In some aspects, the antibody or antigen binding portion of the disclosure comprises a mutant IgG4 heavy chain constant region, wherein the mutant IgG4 heavy chain constant region comprises S228P and L235E substitutions. In some aspects, the antibody or antigen binding portion of the disclosure comprises a mutant IgG4 heavy chain constant region, wherein the mutant IgG4 heavy chain constant region comprises S228P and L235A substitutions.

In some aspects, the antibody or antigen binding portion of the disclosure comprises the heavy chain CDR3 sequence set forth in SEQ ID NO: 3. In some aspects, the antibody or antigen binding portion of the disclosure binds to substantially the same epitope as a reference antibody or antigen binding portion thereof comprising the heavy chain CDR3 sequence set forth in SEQ ID NO: 3. In some aspects, the antibody or antigen binding portion of the disclosure binds to at least one of the amino acid residues bound by a reference antibody or antigen binding portion thereof comprising the heavy chain CDR3 sequence set forth in SEQ ID NOs: 3. In some aspects, the antibody or antigen binding portion of the disclosure, wherein a mutation of the epitope bound by the antibody inhibits, reduces, or blocks binding to both the antibody and to a reference antibody or antigen binding portion thereof comprising the heavy chain CDR3 sequence set forth in SEQ ID NOs: 3.

In some aspects, the antibody or antigen binding portion of the disclosure binds to substantially the same epitope as a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively. In some aspects, the antibody or antigen binding portion of the disclosure binds to at least one of the amino acid residues bound by a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively. In some embodiments, a mutation of the epitope bound by the antibody or antigen binding portion of the disclosure inhibits, reduces, or blocks binding to both the antibody and to a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively.

In some embodiments, the antibody or antigen binding portion thereof of the disclosure binds to substantially the same epitope as a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

In some embodiments, the antibody or antigen binding portion thereof of the disclosure binds to at least one of the amino acid residues bound by a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

In some embodiments, a mutation of the epitope bound by the antibody or antigen binding portion thereof of the disclosure inhibits, reduces, or blocks binding to both the antibody or antigen binding portion thereof and to a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

In some aspects, the antibody or antigen binding portion of the disclosure binds to and antagonizes human CD39 and comprises heavy and light chain CDRs selected from the group consisting of:

(i) heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively;

(ii) heavy chain CDR1, CDR2 and CDR3 sequences set forth in SEQ ID NOs: 1, 2 and 3, respectively, and light chain CDR1, CDR2 and CDR3 sequences set forth in SEQ ID NOs: 11, 12 and 13, respectively;

(iii) heavy chain CDR1, CDR2 and CDR3 sequences set forth in SEQ ID NOs: 53, 54 and 55, respectively, and light chain CDR1, CDR2 and CDR3 sequences set forth in SEQ ID NOs: 63, 64 and 65, respectively;

(iv) heavy chain CDR1, CDR2 and CDR3 sequences set forth in SEQ ID NOs: 79, 80 and 81, respectively, and light chain CDR1, CDR2 and CDR3 sequences set forth in SEQ ID NOs: 89, 90 and 91, respectively; and (v) heavy chain CDR1, CDR2 and CDR3 sequences set forth in SEQ ID NOs: 105, 106 and 107, respectively, and light chain CDR1, CDR2 and CDR3 sequences set forth in SEQ ID NOs: 115, 116 and 117, respectively.

In some embodiments, the antibody or antigen binding portion thereof of the disclosure binds to and antagonizes human CD39 and comprises heavy and light chain CDRs, wherein the heavy chain CDR1, CDR2 and CDR3 sequences are set forth in SEQ ID NOs: 27, 28 and 29, respectively, and the light chain CDR1, CDR2 and CDR3 sequences are set forth in SEQ ID NOs: 37, 38 and 39, respectively.

In some embodiments, the antibody or antigen binding portion thereof of the disclosure binds to and antagonizes human CD39 and comprises heavy and light chain CDRs selected from the group consisting of:

(i) heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively;

(ii) heavy chain CDR1, CDR2 and CDR3 sequences set forth in SEQ ID NOs: 4, 5 and 6, respectively, and light chain CDR1, CDR2 and CDR3 sequences set forth in SEQ ID NOs: 14, 15 and 16, respectively;

(iii) heavy chain CDR1, CDR2 and CDR3 sequences set forth in SEQ ID NOs: 56, 57 and 58, respectively, and light chain CDR1, CDR2 and CDR3 sequences set forth in SEQ ID NOs: 66, 67 and 68, respectively;

(iv) heavy chain CDR1, CDR2 and CDR3 sequences set forth in SEQ ID NOs: 82, 83 and 84, respectively, and light chain CDR1, CDR2 and CDR3 sequences set forth in SEQ ID NOs: 92, 93 and 94, respectively; and (v) heavy chain CDR1, CDR2 and CDR3 sequences set forth in SEQ ID NOs: 108, 109 and 110, respectively, and light chain CDR1, CDR2 and CDR3 sequences set forth in SEQ ID NOs: 118, 119 and 120, respectively.

In some embodiments, the antibody or antigen binding portion thereof of the disclosure binds to and antagonizes human CD39 and comprises heavy and light chain CDRs, wherein the heavy chain CDR1, CDR2 and CDR3 sequences are set forth in SEQ ID NOs: 30, 31 and 32, respectively, and the light chain CDR1, CDR2 and CDR3 sequences are set forth in SEQ ID NOs: 40, 41 and 42, respectively;

In some aspects, the antibody or antigen binding portion of the disclosure binds to and antagonizes human CD39 and comprises heavy and light chain variable regions, wherein the heavy chain variable region comprises an amino acid sequence selected from the group consisting of SEQ ID NOs: 33, 7, 59, 85 and 111; and wherein the light chain variable region comprises an amino acid sequence selected from the group consisting of SEQ ID NOs: 43, 17, 69, 95 and 121.

In some aspects, the antibody or antigen binding portion thereof of the disclosure binds to an antagonizes human CD39 and comprises heavy and light chain variable regions comprising amino acid sequences selected from the group consisting of:

(i) SEQ ID NO: 33 and 43, respectively;
(ii) SEQ ID NO: 7 and 17, respectively;
(iii) SEQ ID NO: 59 and 69, respectively;
(iv) SEQ ID NO: 85 and 95, respectively; and
(v) SEQ ID NO: 111 and 121, respectively.

In some aspects, the antibody or antigen binding portion thereof of the disclosure binds to and antagonizes human CD39 and comprises heavy and light chain variable regions comprising amino acid sequences set forth in SEQ ID NO: 33 and 43, respectively.

In some aspects, the antibody or antigen binding portion of the disclosure binds to and antagonizes human CD39 and comprises heavy and light chain variable regions, wherein the heavy chain variable region comprises an amino acid sequence which is at least 90%, at least 95%, at least 97%, at least 98%, at least 99% identical to the amino acid sequence selected from the group consisting of SEQ ID NOs: 33, 7, 59, 85 and 111; and wherein the light chain variable region comprises an amino acid sequence which is at least 90%, at least 95%, at least 97%, at least 98%, at least 99% identical to the amino acid sequence selected from the group consisting of SEQ ID NOs: 43, 17, 69, 95 and 121.

In some aspects, the antibody or antigen binding portion of the disclosure binds to an antagonizes human CD39 and comprises heavy and light chain variable regions comprising amino acid sequences at least 90%, at least 95%, at least 97%, at least 98%, at least 99% identical to the amino acid sequences selected from the group consisting of:

(i) SEQ ID NO: 33 and 43, respectively;
(ii) SEQ ID NO: 7 and 17, respectively;
(iii) SEQ ID NO: 59 and 69, respectively;
(iv) SEQ ID NO: 85 and 95, respectively; and
(v) SEQ ID NO: 111 and 121, respectively.

In some aspects, the antibody or antigen binding portion thereof of the disclosure binds to and antagonizes human CD39 and comprises heavy and light chain variable regions comprising amino acid sequences at least 90%, at least 95%, at least 97%, at least 98%, at least 99% identical to the amino acid sequences set forth in SEQ ID NO: 33 and 43, respectively.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 35, 9, 61, 87 and 113; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 35, 9, 61, 87 and 113; and wherein the light chain comprises an amino acid sequence which is at least 90%, at least 95%, at least 97%, at least 98%, at least 99% to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 47, 21, 73, 99, and 125; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 47, 21, 73, 99 and 125; and wherein the light chain comprises an amino acid sequence which is at least 90%, at least 95%, at least 97%, at least 98%, at least 99% identical to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 49, 23, 75, 101 and 127; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 49, 23, 75, 101 and 127; and wherein the light chain comprises an amino acid sequence which is at least 90%, at least 95%, at least 97%, at least 98%, at least 99% identical to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 51, 25, 77, 103 and 129; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 51, 25, 77, 103 and 129; and wherein the light chain comprises an amino acid sequence which is at least 90%, at least 95%, at least 97%, at least 98%, at least 99% identical to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 35 and 45, respectively;
  (ii) SEQ ID NO: 9 and 19, respectively;
  (iii) SEQ ID NO: 61 and 71, respectively;
  (iv) SEQ ID NO: 87 and 97, respectively; and
  (v) SEQ ID NO: 113 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 35 and 45, respectively;
  (ii) SEQ ID NO: 9 and 19, respectively;
  (iii) SEQ ID NO: 61 and 71, respectively;
  (iv) SEQ ID NO: 87 and 97, respectively; and
  (v) SEQ ID NO: 113 and 123, respectively.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 47 and 45, respectively;
  (ii) SEQ ID NO: 21 and 19, respectively;
  (iii) SEQ ID NO: 73 and 71, respectively;
  (iv) SEQ ID NO: 99 and 97, respectively; and
  (v) SEQ ID NO: 125 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 47 and 45, respectively;
  (ii) SEQ ID NO: 21 and 19, respectively;
  (iii) SEQ ID NO: 73 and 71, respectively;
  (iv) SEQ ID NO: 99 and 97, respectively; and
  (v) SEQ ID NO: 125 and 123, respectively.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 49 and 45, respectively;
  (ii) SEQ ID NO: 23 and 19, respectively;
  (iii) SEQ ID NO: 75 and 71, respectively;
  (iv) SEQ ID NO: 101 and 97, respectively; and
  (v) SEQ ID NO: 127 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 49 and 45, respectively;
  (ii) SEQ ID NO: 23 and 19, respectively;
  (iii) SEQ ID NO: 75 and 71, respectively;
  (iv) SEQ ID NO: 101 and 97, respectively; and
  (v) SEQ ID NO: 127 and 123, respectively.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 51 and 45, respectively;
  (ii) SEQ ID NO: 25 and 19, respectively;
  (iii) SEQ ID NO: 77 and 71, respectively;
  (iv) SEQ ID NO: 103 and 97, respectively; and
  (v) SEQ ID NO: 129 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 51 and 45, respectively;
  (ii) SEQ ID NO: 25 and 19, respectively;
  (iii) SEQ ID NO: 77 and 71, respectively;
  (iv) SEQ ID NO: 103 and 97, respectively; and
  (v) SEQ ID NO: 129 and 123, respectively.

In some embodiments, the antibody or antigen binding portion thereof of the disclosure binds to and antagonizes human CD39 and comprises a heavy chain and a light chain comprising amino acid sequences set forth in SEQ ID NO: 35 and 45, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 35 and 45, respectively.

In some embodiments, the antibody or antigen binding portion thereof of the disclosure binds to and antagonizes human CD39 and comprises a heavy chain and a light chain comprising amino acid sequences set forth in SEQ ID NO: 47 and 45, respectively, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 47 and 45, respectively.

In some embodiments, the antibody or antigen binding portion thereof of the disclosure binds to and antagonizes human CD39 and comprises a heavy chain and a light chain comprising amino acid sequences set forth in SEQ ID NO: 49 and 45, respectively, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 49 and 45, respectively.

In some embodiments, the antibody or antigen binding portion thereof of the disclosure binds to and antagonizes human CD39 and comprises a heavy chain and a light chain comprising amino acid sequences set forth in SEQ ID NO: 51 and 45, respectively, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 51 and 45, respectively.

In some aspects, the disclosure provides a pharmaceutical composition comprising an isolated anti-CD39 antibody or antigen binding portion thereof of the disclosure, and a pharmaceutically acceptable carrier.

In some aspects, the disclosure provides a nucleic acid comprising a nucleotide sequence encoding the light chain, heavy chain, or both light and heavy chains of the isolated antibody, or antigen binding portion thereof, of the disclosure. In some aspects, the disclosure provides an expression vector comprising the nucleic acid of the disclosure. In some aspects, the disclosure provides a cell transformed with an expression vector of the disclosure.

In some aspects, the disclosure provides a method for producing an antibody that binds human CD39, or an antigen binding portion thereof, the method comprising maintaining a cell according to the disclosure under conditions permitting expression of the antibody or antigen binding portion thereof. In some aspects, the method further comprises obtaining the antibody or antigen binding portion thereof.

In some embodiments, the disclosure provides a method of stimulating an immune response in a subject, the method comprising administering to the subject an effective amount of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier.

In some embodiments, the disclosure provides a method of treating a cancer in a subject, the method comprising administering to the subject an effective amount an isolated antibody, or antigen binding portion thereof, that binds to and antagonizes CD39, provided by the disclosure, or a pharmaceutical composition comprising the antibody or antigen binding portion thereof, and a pharmaceutically acceptable carrier.

In some embodiments, the disclosure provides a method of treating a cancer in a subject, the method comprising administering to the subject an effective amount an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or pharmaceutical composition inhibits or reduces the enzymatic activity of human CD39 in a tumor microenvironment, thereby treating the cancer.

In some embodiments, the disclosure provides a method of treating a cancer in a subject, the method comprising administering to the subject an effective amount an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of CD39 inhibits or reduces the conversion of extracellular adenosine triphosphate (eATP) or extracellular adenosine diphosphate (eADP) to extracellular adenosine monophosphate (AMP) in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of CD39 increases or enhances a level of extracellular adenosine triphosphate (eATP) in a tumor microenvironment, thereby treating the cancer.

In some embodiments, the anti-CD39 antibody is monoclonal.

In some embodiments, the disclosure provides a method of treating a cancer in a subject, the method comprising administering to the subject an effective amount of an isolated anti-CD39 antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of CD39 decreases or reduces a level of extracellular adenosine in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of human CD39 increases or enhances a level of extracellular adenosine triphosphate (eATP) and decreases or reduces a level of extracellular adenosine in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of human CD39 maintains, increases or enhances an immunostimulatory level of extracellular adenosine triphosphate (eATP) in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of human CD39 increases or enhances the proliferation of a lymphocyte in the tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of human CD39 enhances expression of one or more dendritic cell activation markers.

In some embodiments, the disclosure provides a method of treating a cancer in a subject, the method comprising administering to the subject an effective amount of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of human CD39, wherein the inhibition or reduction of the enzymatic activity of human CD39 enhances secretion of one or more cytokines from dendritic cells.

In some embodiments, the disclosure provides methods of treating cancer in a subject, wherein the cancer is selected from the group consisting of: lung cancer (e.g., non-small cell lung cancer), ovarian cancer, kidney cancer, testicular cancer, pancreas cancer, breast cancer (e.g., triple-negative breast cancer), melanoma, head and neck cancer (e.g., squamous head and neck cancer), colorectal cancer, bladder cancer, endometrial cancer, prostate cancer, thyroid cancer, hepatocellular carcinoma, gastric cancer, brain cancer, lymphoma or renal cancer (e.g., renal cell carcinoma).

In some aspects, the disclosure provides use of an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, in stimulating an immune response in a subject or treating cancer in a subject, optionally in combination with one or more additional therapeutic agents or procedure.

In some aspects, the disclosure provides a kit comprising an isolated antibody, or antigen binding portion thereof, that binds to and antagonizes human CD39, provided by the disclosure, or a pharmaceutical composition comprising the antibody or antigen binding portion thereof, and a pharmaceutically acceptable carrier, and instructions for use in stimulating an immune response in a subject or treating cancer in a subject, optionally with instructions for use in combination with one or more additional therapeutic agents or procedure.

In some embodiments, the disclosure provides a method of treating cancer in a subject, the method comprising administering to the subject an effective amount of an isolated antibody, or antigen binding portion thereof, that binds to and antagonizes CD39, provided by the disclosure, in combination with one or more additional therapeutic agents or procedure. In some aspects, the second therapeutic agent or procedure is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

In some embodiments, the one or more additional therapeutic agents is a PD-1 antagonist, an adenosine A2AR antagonist, a CD73 inhibitor, a CTLA-4 inhibitor, a TIM-3 inhibitor, a LAG-3 inhibitor, chimeric antigen receptor (CAR) cell therapy, or a combination thereof.

In some embodiments, the one or more additional therapeutic agents is a combination of a CD73 inhibitor and an A2AR antagonist. In some embodiments, the one or more additional therapeutic agents is a combination of a PD-1 antagonist and an adenosine A2AR antagonist. In some embodiments, the one or more additional therapeutic agents is a PD-1 antagonist.

In some embodiments, the PD-1 antagonist is selected from the group consisting of: PDR001, nivolumab, pembrolizumab, pidilizumab, MEDI0680, REGN2810, TSR-042, PF-06801591, and AMP-224. In some embodiments, the PD-1 antagonist is selected from the group consisting of: FAZ053, Atezolizumab, Avelumab, Durvalumab, and BMS-936559.

In some embodiments, the one or more additional therapeutic agents is an adenosine A2AR antagonist. In some embodiments, the adenosine A2AR antagonist is selected from the group consisting of: NIR178, CPI-444, AZD4635, Vipadenant, GBV-2034, and AB928. In some embodiments, the adenosine A2AR antagonist is CPI-444.

In some embodiments, the one or more additional therapeutic agents is a CD73 inhibitor. In some embodiments, the CD73 inhibitor is selected from the group consisting of: AB421, MEDI9447, and BMS-986179.

In some embodiments, the one or more additional therapeutic agents is a CTLA-4 inhibitor. In some embodiments, the CTLA-4 inhibitor is Ipilimumab or Tremelimumab.

In some embodiments, the one or more additional therapeutic agents is a TIM-3 inhibitor. In some embodiments, the TIM-3 inhibitor is MGB453 or TSR-022.

In some embodiments, the one or more additional therapeutic agents is a LAG-3 inhibitor. In some embodiments, the LAG-3 inhibitor is selected from the group consisting of LAG525, BMS-986016, and TSR-033.

In some embodiments, the one or more additional therapeutic agents is a chimeric antigen receptor (CAR) cell therapy. In some embodiments, the CAR cell therapy is CTL019.

In some embodiments, the one or more additional therapeutic agents is an anthracycline. In some embodiments, the anthracycline is selected from doxorubicin, daunorubicin, epirubicin, idarubicin, and valrubicin. In some embodiments, the anthracycline is doxorubicin.

In some embodiments, the disclosure provides a method of detecting CD39 in a biological sample or in a subject, comprising (i) contacting the sample or the subject (and optionally, a reference sample or subject) with any antibody in Table 1 under conditions that allow interaction of the antibody molecule and CD39 to occur, and (ii) detecting formation of a complex between the antibody molecule and the sample or the subject (and optionally, the reference sample or subject).

The following embodiments are provided and are non-limiting:

Embodiment 1

An isolated monoclonal antibody that specifically binds to and antagonizes human CD39, or an antigen binding portion thereof, wherein the antibody or antigen binding portion thereof exhibits at least one or more of the following properties:
  (i) binds to recombinant human CD39 and/or to membrane-bound human CD39;
  (ii) binds to human CD39 with an equilibrium dissociation constant ($K_D$) of less than 10 nM;
  (iii) inhibits or reduces an enzymatic activity of human CD39;
  (iv) inhibits or reduces conversion by human CD39 of extracellular adenosine triphosphate (eATP) or extracellular adenosine diphosphate (eADP) to extracellular adenosine monophosphate (eAMP);
  (v) increases or enhances a level of eATP;
  (vi) decreases or reduces a level extracellular adenosine;
  (vii) maintains, increases or enhances an immunostimulatory level of eATP;
  (viii) increases or enhances proliferation of a lymphocyte;
  (ix) increases or enhances expression of one or more dendritic cell activation markers;
  (x) increases or enhances secretion of one or more cytokines from dendritic cells;
  (xi) increases or enhances macrophage infiltration in tumors;
  (xii) increases or enhances secretion of macrophage attracting chemokines;
  (xiii) antagonizes human CD39 in a tumor microenvironment of a tissue;
  (xiv) cross-reacts with cynomolgus CD39 and/or mouse CD39; or
  (xv) a combination of any one of (i)-(xiv).

Embodiment 2

The isolated monoclonal antibody, or antigen binding portion thereof, of embodiment 1, wherein the antibody or antigen binding portion thereof binds to human recombinant CD39 and/or membrane-bound human CD39.

Embodiment 3

The isolated monoclonal antibody, or antigen binding portion thereof, of embodiment 1 or 2, wherein the antibody or antigen binding portion thereof binds to human CD39 with an equilibrium dissociation constant ($K_D$) of less than 10 nM.

Embodiment 4

The isolated monoclonal antibody, or antigen binding portion thereof, of any one of embodiments 1-3, wherein the antibody or antigen binding portion thereof inhibits or reduces an enzymatic activity of human CD39.

Embodiment 5

The isolated monoclonal antibody, or antigen binding portion thereof, of embodiment 4, wherein the enzymatic activity of human CD39 is the hydrolysis of eATP or eADP.

Embodiment 6

The isolated monoclonal antibody, or antigen binding portion thereof, of any one of embodiments 1-5, wherein the antibody or antigen binding portion thereof inhibits or reduces the conversion of eATP or eADP to eAMP.

Embodiment 7

The isolated monoclonal antibody, or antigen binding portion thereof, of any one of embodiments 1-6, wherein the antibody or antigen binding portion thereof increases or enhances a level of eATP.

Embodiment 8

The isolated monoclonal antibody, or antigen binding portion thereof, of any one of embodiments 1-7, wherein the antibody or antigen binding portion thereof decreases or reduces a level of extracellular adenosine.

Embodiment 9

The isolated monoclonal antibody, or antigen binding portion thereof, of any one of embodiments 1-8, wherein the antibody or antigen binding portion thereof maintains, increases or enhances an immunostimulatory level of eATP.

Embodiment 10

The isolated monoclonal antibody, or antigen binding portion thereof, of any one of embodiments 1-9, wherein the antibody or antigen binding portion thereof increases proliferation of a lymphocyte.

Embodiment 11

The isolated monoclonal antibody, or antigen binding portion thereof, of embodiment 10, wherein the lymphocyte is a tumor-infiltrating lymphocyte.

Embodiment 12

The isolated monoclonal antibody, or antigen binding portion thereof, of embodiment 10 or 11, wherein the lymphocyte is T cell.

Embodiment 13

The isolated monoclonal antibody, or antigen binding portion thereof, of embodiment 12, wherein the T cell is a CD4+ T cell.

Embodiment 14

The isolated monoclonal antibody, or antigen binding portion thereof, of any one of embodiments 1-13, wherein the antibody or antigen binding portion thereof enhances expression of one or more dendritic cell activation markers.

Embodiment 15

The isolated monoclonal antibody, or antigen binding portion thereof, of embodiment 14, wherein the one or more dendritic cell activation markers is CD86, HLA-DR, or a combination thereof.

Embodiment 16

The isolated monoclonal antibody, or antigen binding portion thereof of any one of embodiments 1-15, wherein the antibody or antigen binding portion thereof enhances secretion of one or more cytokines from dendritic cells.

Embodiment 17

The isolated monoclonal antibody, or antigen binding portion thereof, of embodiment 16, wherein the one or more cytokines is IL-16, IL-12/IL-23p40, VEGFA, or any combination thereof.

Embodiment 18

The isolated monoclonal antibody, or antigen binding portion thereof, of any one of embodiments 1-17, wherein the antagonism of human CD39 occurs in a tumor microenvironment of a tissue.

Embodiment 19

The isolated monoclonal antibody, or antigen binding portion thereof, of any one of embodiments 1-18, wherein the antibody or antigen binding portion thereof cross-reacts with cynomolgus CD39 and/or mouse CD39.

Embodiment 20

The isolated monoclonal antibody, or antigen binding portion thereof, of any one of embodiments 1-19, wherein the antibody is selected from the group consisting of an IgG1, an IgG2, and IgG3, an IgG4, and IgM, and IgA1, and IgA2, and IgD, and an IgE antibody.

Embodiment 21

The isolated monoclonal antibody, or antigen binding portion thereof, according to embodiment 20, wherein the antibody is an IgG1 antibody or an IgG4 antibody.

Embodiment 22

The isolated monoclonal antibody, or antigen binding portion thereof, according to embodiment 20 or 21, wherein the antibody comprises a wild type IgG1 heavy chain constant region.

Embodiment 23

The isolated monoclonal antibody, or antigen binding portion thereof, of embodiment 20 or 21, wherein the antibody comprises a wild type IgG4 heavy chain constant region.

Embodiment 24

The isolated monoclonal antibody, or antigen binding portion thereof, of any one of embodiments 1-21, wherein the antibody comprises an Fc domain comprising at least one mutation.

Embodiment 25

The isolated monoclonal antibody, or antigen binding portion thereof, of embodiment 24, wherein the antibody comprises a mutant IgG1 heavy chain constant region.

Embodiment 26

The isolated monoclonal antibody, or antigen binding portion thereof, of embodiment 24, wherein the antibody comprises a mutant IgG4 heavy chain constant region.

Embodiment 27

The isolated monoclonal antibody, or antigen binding portion thereof, of embodiment 26 wherein the mutant IgG4 heavy chain constant region comprises any one of the substitutions S228P, L235E, L235A, or a combination thereof, according to EU numbering.

Embodiment 28

The isolated monoclonal antibody, or antigen binding portion thereof, of any one of embodiments 1-27, wherein the antibody or antigen binding portion thereof comprises the heavy chain CDR3 sequence set forth in SEQ ID NO: 3.

Embodiment 29

The isolated monoclonal antibody, or antigen binding portion thereof, of any one of embodiments 1-28, wherein the antibody or antigen binding portion thereof binds to substantially the same epitope as a reference antibody or antigen binding portion thereof comprising the heavy chain CDR3 sequence set forth in SEQ ID NO: 3.

Embodiment 30

The isolated monoclonal antibody, or antigen binding portion thereof, of any one of embodiments 1-29, wherein the antibody or antigen binding portion thereof binds to at least one of the amino acid residues bound by a reference antibody or antigen binding portion thereof comprising the heavy chain CDR3 sequence set forth in SEQ ID NOs: 3.

Embodiment 31

The isolated monoclonal antibody, or antigen binding portion thereof, of any one of embodiments 1-30, wherein a mutation of the epitope bound by the antibody inhibits, reduces, or blocks binding to both the antibody and to a reference antibody or antigen binding portion thereof comprising the heavy chain CDR3 sequence set forth in SEQ ID NOs: 3.

Embodiment 32

The isolated monoclonal antibody, or antigen binding portion thereof, of any one of embodiments 1-31, wherein the antibody or antigen binding portion thereof binds to substantially the same epitope as a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively.

Embodiment 33

The isolated monoclonal antibody, or antigen binding portion thereof, of any one of embodiments 1-32, wherein the antibody or antigen binding portion thereof binds to at least one of the amino acid residues bound by a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively.

Embodiment 34

The isolated monoclonal antibody, or antigen binding portion thereof, of any one of embodiments 1-33, wherein a mutation of the epitope bound by the antibody inhibits, reduces, or blocks binding to both the antibody and to a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively.

Embodiment 35

The isolated monoclonal antibody, or antigen binding portion thereof, of any one of embodiments 1-31, wherein the antibody or antigen binding portion thereof binds to substantially the same epitope as a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

Embodiment 36

The isolated monoclonal antibody, or antigen binding portion thereof, of any one of embodiments 1-31 and 35, wherein the antibody or antigen binding portion thereof binds to at least one of the amino acid residues bound by a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

Embodiment 37

The isolated monoclonal antibody, or antigen binding portion thereof, of any one of embodiments 1-31, 35, and 36, wherein a mutation of the epitope bound by the antibody inhibits, reduces, or blocks binding to both the antibody and to a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

Embodiment 38

An isolated monoclonal antibody that specifically binds to and antagonizes human CD39, or antigen binding portion thereof, wherein the antibody or antigen binding portion thereof comprises heavy and light chain CDRs selected from the group consisting of:
 (i) heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively;
 (ii) heavy chain CDR1, CDR2 and CDR3 sequences set forth in SEQ ID NOs: 1, 2 and 3, respectively, and light chain CDR1, CDR2 and CDR3 sequences set forth in SEQ ID NOs: 11, 12 and 13, respectively;
 (iii) heavy chain CDR1, CDR2 and CDR3 sequences set forth in SEQ ID NOs: 53, 54 and 55, respectively, and light chain CDR1, CDR2 and CDR3 sequences set forth in SEQ ID NOs: 63, 64 and 65, respectively;
 (iv) heavy chain CDR1, CDR2 and CDR3 sequences set forth in SEQ ID NOs: 79, 80 and 81, respectively, and light chain CDR1, CDR2 and CDR3 sequences set forth in SEQ ID NOs: 89, 90 and 91, respectively; and
 (v) heavy chain CDR1, CDR2 and CDR3 sequences set forth in SEQ ID NOs: 105, 106 and 107, respectively, and light chain CDR1, CDR2 and CDR3 sequences set forth in SEQ ID NOs: 115, 116 and 117, respectively.

Embodiment 39

An isolated monoclonal antibody that specifically binds to and antagonizes human CD39, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 27, 28 and 29, respectively, and the light chain CDR1, CDR2 and CDR3 sequences are set forth in SEQ ID NOs: 37, 38 and 39, respectively.

Embodiment 40

An isolated monoclonal antibody that specifically binds to and antagonizes human CD39, or antigen binding portion thereof, wherein the antibody or antigen binding portion thereof comprises heavy and light chain CDRs selected from the group consisting of:

(i) heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively;
(ii) heavy chain CDR1, CDR2 and CDR3 sequences set forth in SEQ ID NOs: 4, 5 and 6, respectively, and light chain CDR1, CDR2 and CDR3 sequences set forth in SEQ ID NOs: 14, 15 and 16, respectively;
(iii) heavy chain CDR1, CDR2 and CDR3 sequences set forth in SEQ ID NOs: 56, 57 and 58, respectively, and light chain CDR1, CDR2 and CDR3 sequences set forth in SEQ ID NOs: 66, 67 and 68, respectively;
(iv) heavy chain CDR1, CDR2 and CDR3 sequences set forth in SEQ ID NOs: 82, 83 and 84, respectively, and light chain CDR1, CDR2 and CDR3 sequences set forth in SEQ ID NOs: 92, 93 and 94, respectively; and
(v) heavy chain CDR1, CDR2 and CDR3 sequences set forth in SEQ ID NOs: 108, 109 and 110, respectively, and light chain CDR1, CDR2 and CDR3 sequences set forth in SEQ ID NOs: 118, 119 and 120, respectively.

Embodiment 41

An isolated monoclonal antibody that specifically binds to and antagonizes human CD39, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 30, 31 and 32, respectively, and the light chain CDR1, CDR2 and CDR3 sequences are set forth in SEQ ID NOs: 40, 41 and 42, respectively.

Embodiment 42

An isolated monoclonal antibody that specifically binds to and antagonizes human CD39, or antigen binding portion thereof, wherein the antibody or antigen binding portion thereof comprises heavy and light chain variable regions, wherein the heavy chain variable region comprises an amino acid sequence selected from the group consisting of SEQ ID NOs: 33, 7, 59, 85 and 111; and wherein the light chain variable region comprises an amino acid sequence selected from the group consisting of SEQ ID NOs: 43, 17, 69, 95 and 121.

Embodiment 43

An isolated monoclonal antibody that specifically binds to and antagonizes human CD39, or antigen binding portion thereof, wherein the antibody or antigen binding portion thereof comprises heavy and light chain variable regions comprising amino acid sequences selected from the group consisting of:
(i) SEQ ID NO: 33 and 43, respectively;
(ii) SEQ ID NO: 7 and 17, respectively;
(iii) SEQ ID NO: 59 and 69, respectively;
(iv) SEQ ID NO: 85 and 95, respectively; and
(v) SEQ ID NO: 111 and 121, respectively.

Embodiment 44

An isolated monoclonal antibody that specifically binds to and antagonizes human CD39, or antigen binding portion thereof, wherein the antibody or antigen binding portion thereof comprises heavy and light chain variable regions comprising amino acid sequences set forth in SEQ ID NO: 33 and 43, respectively.

Embodiment 45

An isolated monoclonal antibody that specifically binds to and antagonizes human CD39, or antigen binding portion thereof, wherein the antibody or antigen binding portion thereof comprises heavy and light chain variable regions, wherein the heavy chain variable region comprises an amino acid sequence which is at least 90% identical to the amino acid sequence selected from the group consisting of SEQ ID NOs: 33, 7, 59, 85 and 111; and wherein the light chain variable region comprises an amino acid sequence which is at least 90% identical to the amino acid sequence selected from the group consisting of SEQ ID NOs: 43, 17, 69, 95 and 121.

Embodiment 46

An isolated monoclonal antibody that specifically binds to and antagonizes human CD39, or antigen binding portion thereof, wherein the antibody or antigen binding portion thereof comprises heavy and light chain variable regions comprising amino acid sequences at least 90% identical to the amino acid sequences selected from the group consisting of:
(i) SEQ ID NO: 33 and 43, respectively;
(ii) SEQ ID NO: 7 and 17, respectively;
(iii) SEQ ID NO: 59 and 69, respectively;
(iv) SEQ ID NO: 85 and 95, respectively; and
(v) SEQ ID NO: 111 and 121, respectively.

Embodiment 47

An isolated monoclonal antibody that specifically binds to and antagonizes human CD39, or antigen binding portion thereof, wherein the antibody or antigen binding portion thereof comprises heavy and light chain variable regions comprising amino acid sequences at least 90% identical to the amino acid sequences set forth in SEQ ID NO: 33 and 43, respectively.

Embodiment 48

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence selected from the group consisting of SEQ ID NOs: 35, 9, 61, 87 and 113; and wherein the light chain comprises an amino acid sequence selected from the group consisting of SEQ ID NOs: 45, 19, 71, 97 and 123.

Embodiment 49

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence which is at least 90% identical to the amino acid sequence selected from the group consisting of SEQ ID NOs: 35, 9, 61, 87 and 113; and wherein the light chain comprises an amino acid sequence which is at least 90% identical to the amino acid sequence selected from the group consisting of SEQ ID NOs: 45, 19, 71, 97 and 123.

Embodiment 50

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence selected from the group consisting of SEQ ID NOs: 47, 21, 73, 99, and 125; and wherein the light chain comprises an amino acid sequence selected from the group consisting of SEQ ID NOs: 45, 19, 71, 97 and 123.

Embodiment 51

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence which is at least 90% identical to the amino acid sequence selected from the group consisting of SEQ ID NOs: 47, 21, 73, 99 and 125; and wherein the light chain comprises an amino acid sequence which is at least 90% identical to the amino acid sequence selected from the group consisting of SEQ ID NOs: 45, 19, 71, 97 and 123.

Embodiment 52

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence selected from the group consisting of SEQ ID NOs: 49, 23, 75, 101 and 127; and wherein the light chain comprises an amino acid sequence selected from the group consisting of SEQ ID NOs: 45, 19, 71, 97 and 123.

Embodiment 53

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence which is at least 90% identical to the amino acid sequence selected from the group consisting of SEQ ID NOs: 49, 23, 75, 101 and 127; and wherein the light chain comprises an amino acid sequence which is at least 90% identical to the amino acid sequence selected from the group consisting of SEQ ID NOs: 45, 19, 71, 97 and 123.

Embodiment 54

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence selected from the group consisting of SEQ ID NOs: 51, 25, 77, 103 and 129; and wherein the light chain comprises an amino acid sequence selected from the group consisting of SEQ ID NOs: 45, 19, 71, 97 and 123.

Embodiment 55

An isolated monoclonal antibody that specifically binds to and antagonizes human CD39, or antigen binding portion thereof, wherein the antibody or antigen binding portion thereof comprises a heavy chain and a light chain, wherein the heavy chain comprises an amino acid sequence which is at least 90% identical to the amino acid sequence selected from the group consisting of SEQ ID NOs: 51, 25, 77, 103 and 129; and wherein the light chain comprises an amino acid sequence which is at least 90% identical to the amino acid sequence selected from the group consisting of SEQ ID NOs: 45, 19, 71, 97 and 123.

Embodiment 56

An isolated monoclonal antibody that specifically binds to and antagonizes human CD39, or antigen binding portion thereof, wherein the antibody or antigen binding portion thereof comprises a heavy chain and a light chain comprising amino acid sequences selected from the group consisting of:
(i) SEQ ID NO: 35 and 45, respectively;
(ii) SEQ ID NO: 9 and 19, respectively;
(iii) SEQ ID NO: 61 and 71, respectively;
(iv) SEQ ID NO: 87 and 97, respectively; and
(v) SEQ ID NO: 113 and 123, respectively.

Embodiment 57

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences selected from the group consisting of:
(i) SEQ ID NO: 35 and 45, respectively;
(ii) SEQ ID NO: 9 and 19, respectively;
(iii) SEQ ID NO: 61 and 71, respectively;
(iv) SEQ ID NO: 87 and 97, respectively; and
(v) SEQ ID NO: 113 and 123, respectively.

Embodiment 58

An isolated monoclonal antibody that specifically binds to and antagonizes human CD39, or antigen binding portion thereof, wherein the antibody or antigen binding portion thereof comprises a heavy chain and a light chain comprising amino acid sequences selected from the group consisting of:
(i) SEQ ID NO: 47 and 45, respectively;
(ii) SEQ ID NO: 21 and 19, respectively;
(iii) SEQ ID NO: 73 and 71, respectively;
(iv) SEQ ID NO: 99 and 97, respectively; and
(v) SEQ ID NO: 125 and 123, respectively.

Embodiment 59

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences selected from the group consisting of:
(i) SEQ ID NO: 47 and 45, respectively;
(ii) SEQ ID NO: 21 and 19, respectively;
(iii) SEQ ID NO: 73 and 71, respectively;
(iv) SEQ ID NO: 99 and 97, respectively; and
(v) SEQ ID NO: 125 and 123, respectively.

Embodiment 60

An isolated monoclonal antibody that specifically binds to and antagonizes human CD39, or antigen binding portion thereof, wherein the antibody or antigen binding portion thereof comprises a heavy chain and a light chain comprising amino acid sequences selected from the group consisting of:
  (i) SEQ ID NO: 49 and 45, respectively;
  (ii) SEQ ID NO: 23 and 19, respectively;
  (iii) SEQ ID NO: 75 and 71, respectively;
  (iv) SEQ ID NO: 101 and 97, respectively; and
  (v) SEQ ID NO: 127 and 123, respectively.

Embodiment 61

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences selected from the group consisting of:
  (i) SEQ ID NO: 49 and 45, respectively;
  (ii) SEQ ID NO: 23 and 19, respectively;
  (iii) SEQ ID NO: 75 and 71, respectively;
  (iv) SEQ ID NO: 101 and 97, respectively; and
  (v) SEQ ID NO: 127 and 123, respectively.

Embodiment 62

An isolated monoclonal antibody that specifically binds to and antagonizes human CD39, or antigen binding portion thereof, wherein the antibody or antigen binding portion thereof comprises a heavy chain and a light chain comprising amino acid sequences selected from the group consisting of:
  (i) SEQ ID NO: 51 and 45, respectively;
  (ii) SEQ ID NO: 25 and 19, respectively;
  (iii) SEQ ID NO: 77 and 71, respectively;
  (iv) SEQ ID NO: 103 and 97, respectively; and
  (v) SEQ ID NO: 129 and 123, respectively.

Embodiment 63

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences selected from the group consisting of:
  (i) SEQ ID NO: 51 and 45, respectively;
  (ii) SEQ ID NO: 25 and 19, respectively;
  (iii) SEQ ID NO: 77 and 71, respectively;
  (iv) SEQ ID NO: 103 and 97, respectively; and
  (v) SEQ ID NO: 129 and 123, respectively.

Embodiment 64

An isolated monoclonal antibody that specifically binds to and antagonizes human CD39, or antigen binding portion thereof, wherein the antibody or antigen binding portion thereof comprises a heavy chain and a light chain comprising amino acid sequences set forth in SEQ ID NO: 35 and 45, respectively.

Embodiment 65

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences set forth in SEQ ID NO: 35 and 45, respectively.

Embodiment 66

An isolated monoclonal antibody that specifically binds to and antagonizes human CD39, or antigen binding portion thereof, wherein the antibody or antigen binding portion thereof comprises a heavy chain and a light chain comprising amino acid sequences set forth in SEQ ID NO: 47 and 45, respectively, respectively.

Embodiment 67

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences set forth in SEQ ID NO: 47 and 45, respectively.

Embodiment 68

An isolated monoclonal antibody that specifically binds to and antagonizes human CD39, or antigen binding portion thereof, wherein the antibody or antigen binding portion thereof comprises a heavy chain and a light chain comprising amino acid sequences set forth in SEQ ID NO: 49 and 45, respectively.

Embodiment 69

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences set forth in SEQ ID NO: 49 and 45, respectively.

Embodiment 70

An isolated monoclonal antibody that specifically binds to and antagonizes human CD39, or antigen binding portion thereof, wherein the antibody or antigen binding portion thereof comprises a heavy chain and a light chain comprising amino acid sequences set forth in SEQ ID NO: 51 and 45, respectively.

Embodiment 71

An isolated monoclonal antibody that specifically binds to and antagonizes human CD39, or antigen binding portion thereof, wherein the antibody or antigen binding portion thereof comprises a heavy chain and a light chain comprising amino acid sequences at least 90% identical to the amino acid sequences set forth in SEQ ID NO: 51 and 45, respectively.

Embodiment 72

A pharmaceutical composition comprising an isolated monoclonal antibody or antigen binding portion thereof, of any one of the preceding embodiments, and a pharmaceutically acceptable carrier.

Embodiment 73

A nucleic acid comprising a nucleotide sequence encoding the light chain, heavy chain, or both light and heavy chains of the isolated monoclonal antibody, or antigen binding portion thereof, of any one of embodiments 1-71.

Embodiment 74

An expression vector comprising the nucleic acid of embodiment 73.

Embodiment 75

A cell transformed with an expression vector of embodiment 74.

Embodiment 76

A method for producing a monoclonal antibody that specifically binds human CD39, or an antigen binding portion thereof, the method comprising maintaining a cell according to embodiment 75 under conditions permitting expression of the monoclonal antibody or antigen binding portion thereof.

Embodiment 77

The method of embodiment 76, further comprising obtaining the monoclonal antibody or antigen binding portion thereof.

Embodiment 78

A method of stimulating an immune response in a subject, the method comprising administering to the subject an effective amount of the isolated monoclonal antibody of any one embodiments 1-71 or the pharmaceutical composition of embodiment 72.

Embodiment 79

A method of treating a cancer in a subject, the method comprising administering to the subject an effective amount of the isolated monoclonal antibody of any one embodiments 1-71 or the pharmaceutical composition of embodiment 72.

Embodiment 80

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or pharmaceutical composition inhibits or reduces the enzymatic activity of human CD39 in a tumor microenvironment, thereby treating the cancer.

Embodiment 81

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 inhibits or reduces the conversion of eATP or eADP to AMP in a tumor microenvironment, thereby treating the cancer.

Embodiment 82

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 increases or enhances a level of eATP in a tumor microenvironment, thereby treating the cancer.

Embodiment 83

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 decreases or reduces a level of extracellular adenosine in a tumor microenvironment, thereby treating the cancer.

Embodiment 84

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 increases or enhances a level of eATP and decreases or reduces a level of extracellular adenosine in a tumor microenvironment, thereby treating the cancer.

Embodiment 85

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 maintains, increases or enhances an immunostimulatory level of eATP in a tumor microenvironment, thereby treating the cancer.

Embodiment 86

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 increases or enhances the proliferation of a lymphocyte in the tumor microenvironment, thereby treating the cancer.

Embodiment 87

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 enhances expression of one or more dendritic cell activation markers.

Embodiment 88

A method of treating a cancer in a subject, the method comprising administering to the subject an effective amount of the isolated monoclonal antibody, or antigen binding portion thereof, of any one of embodiments 1-71 or the pharmaceutical composition of embodiment 72, wherein the antibody, or antigen binding portion thereof, or the pharmaceutical composition inhibits or reduces the enzymatic activity of human CD39, wherein the inhibition or reduction of the enzymatic activity of human CD39 enhances secretion of one or more cytokines from dendritic cells Embodiment 89

The method of any one of embodiments 79-88, wherein the cancer is selected from the group consisting of: lung cancer (e.g., non-small cell lung cancer), ovarian cancer, kidney cancer, testicular cancer, pancreas cancer, breast cancer (e.g., triple-negative breast cancer), melanoma, head and neck cancer (e.g., squamous head and neck cancer), colorectal cancer, bladder cancer, endometrial cancer, prostate cancer, thyroid cancer, hepatocellular carcinoma, gastric cancer, brain cancer, lymphoma or renal cancer (e.g., renal cell carcinoma).

Embodiment 90

The method of any one of embodiments 79-89, wherein the isolated monoclonal antibody, or antigen binding portion thereof, is administered in combination with one or more additional therapeutic agents or procedure, wherein the second therapeutic agent or procedure is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

Embodiment 91

The method of embodiment 90, wherein the one or more additional therapeutic agents is a PD-1 antagonist, an adenosine A2AR antagonist, a CD73 inhibitor, a CTLA-4 inhibitor, a TIM-3 inhibitor, a LAG-3 inhibitor, chimeric antigen receptor (CAR) cell therapy, an anthracycline, or a combination thereof.

Embodiment 92

The method of embodiment 91, wherein the one or more additional therapeutic agents is a combination of a CD73 inhibitor and an A2AR antagonist.

Embodiment 93

The method of embodiment 91, wherein the one or more additional therapeutic agents is a combination of a PD-1 antagonist and an adenosine A2AR antagonist.

Embodiment 94

The method of embodiment 91, wherein the one or more additional therapeutic agents is a PD-1 antagonist.

Embodiment 95

The method of any one of embodiments 91, 93 or 94, wherein the PD-1 antagonist is selected from the group consisting of: PDR001, nivolumab, pembrolizumab, pidilizumab, MEDI0680, REGN2810, TSR-042, PF-06801591, AMP-224, FAZ053, Atezolizumab, Avelumab, Durvalumab, and BMS-936559.

Embodiment 96

The method of embodiments 91, wherein the one or more additional therapeutic agents is an adenosine A2AR antagonist.

Embodiment 97

The method of any one of embodiments 91-93, or 97, wherein the adenosine A2AR antagonist is selected from the group consisting of: NIR178, CPI-444, AZD4635, Vipadenant, GBV-2034, and AB928.

Embodiment 98

The method of embodiment 97, wherein the adenosine A2AR antagonist is CPI-444.

Embodiment 99

The method of embodiment 91, wherein the one or more additional therapeutic agents is a CD73 inhibitor.

Embodiment 100

The method of any one of embodiments 91, 92 or 99 wherein the CD73 inhibitor is selected from the group consisting of: AB421, MEDI9447, and BMS-986179.

Embodiment 101

The method of embodiment 91, wherein the one or more additional therapeutic agents is a CTLA-4 inhibitor.

Embodiment 102

The method of embodiment 101, wherein the CTLA-4 inhibitor is Ipilimumab or Tremelimumab.

Embodiment 103

The method of embodiment 91, wherein the one or more additional therapeutic agents is a TIM-3 inhibitor.

Embodiment 104

The method of embodiment 103, wherein the TIM-3 inhibitor is MGB453 or TSR-022.

Embodiment 105

The method of embodiment 91, wherein the one or more additional therapeutic agents is a LAG-3 inhibitor.

Embodiment 106

The method of embodiment 105, wherein the LAG-3 inhibitor is selected from the group consisting of LAG525, BMS-986016, and TSR-033.

Embodiment 107

The method of embodiment 91, wherein the one or more additional therapeutic agents is a chimeric antigen receptor (CAR) cell therapy.

Embodiment 108

The method of embodiment 107, wherein the CAR cell therapy is CTL019.

Embodiment 109

A method of detecting human CD39 in a biological sample or in a subject, comprising (i) contacting the sample or the subject (and optionally, a reference sample or subject) with any antibody in Table 1 under conditions that allow interaction of the antibody molecule and human CD39 to occur, and (ii) detecting formation of a complex between the antibody molecule and the sample or the subject (and optionally, the reference sample or subject).

Embodiment 110

Use of the isolated monoclonal antibody, or antigen binding portion thereof, of any one of embodiments 1-71 or the pharmaceutical composition of embodiment 72 for stimulating an immune response in a subject, or for treating cancer in a subject, optionally for use in in combination with one or more additional therapeutic agents or procedure.

Embodiment 111

A kit comprising the isolated monoclonal antibody, or antigen binding portion thereof, of any one of embodiments 1-71 or the pharmaceutical composition of embodiment 72 and instructions for use in stimulating an immune response in a subject, or treating cancer in a subject, optionally with instructions for use in combination with one or more additional therapeutic agents or procedure.

Embodiment 112

The use of embodiment 110 or kit of embodiment 111, wherein the second therapeutic agent or procedure is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

Embodiment 113

The use of embodiment 110 or kit of embodiment 111, wherein the one or more additional therapeutic agents is a PD-1 antagonist, an adenosine A2AR antagonist, a CD73 inhibitor, a CTLA-4 inhibitor, a TIM-3 inhibitor, a LAG-3 inhibitor, chimeric antigen receptor (CAR) cell therapy, an anthracycline, or a combination thereof.

Embodiment 114

The use of embodiment 110 or kit of embodiment 111, wherein the one or more additional therapeutic agents is a combination of a CD73 inhibitor and an A2AR antagonist.

Embodiment 115

The use of embodiment 110 or kit of embodiment 111, wherein the one or more additional therapeutic agents is a combination of a PD-1 antagonist and an adenosine A2AR antagonist.

Embodiment 116

The use of embodiment 110 or kit of embodiment 111, wherein the one or more additional therapeutic agents is a PD-1 antagonist.

Embodiment 117

The use of embodiment 116 or kit of embodiment 116, wherein the PD-1 antagonist is selected from the group consisting of: PDR001, nivolumab, pembrolizumab, pidilizumab, MEDI0680, REGN2810, TSR-042, PF-06801591, and AMP-224.

Embodiment 118

The use of embodiment 116 or kit of embodiment 116, wherein the PD-1 antagonist is selected from the group consisting of: FAZ053, Atezolizumab, Avelumab, Durvalumab, and BMS-936559.

Embodiment 119

The use of embodiment 110 or kit of embodiment 111, wherein the one or more additional therapeutic agents is an adenosine A2AR antagonist.

Embodiment 120

The use of embodiment 119 or kit of embodiment 119, wherein the adenosine A2AR antagonist is selected from the group consisting of: NIR178, CPI444, AZD4635, Vipadenant, GBV-2034, and AB928.

Embodiment 121

The use of embodiment 110 or kit of embodiment 111, wherein the one or more additional therapeutic agents is a CD73 inhibitor.

Embodiment 122

The use of embodiment 121 or kit of embodiment 121, wherein the CD73 inhibitor is selected from the group consisting of: AB421, MEDI9447, and BMS-986179.

Embodiment 123

The use of embodiment 110 or kit of embodiment 111, wherein the one or more additional therapeutic agents is a CTLA-4 inhibitor.

Embodiment 124

The use of embodiment 123 or kit of embodiment 123, wherein the CTLA-4 inhibitor is Ipilimumab or Tremelimumab.

Embodiment 125

The use of embodiment 110 or kit of embodiment 111, wherein the one or more additional therapeutic agents is a TIM-3 inhibitor.

Embodiment 126

The use of embodiment 125 or kit of embodiment 125, wherein the TIM-3 inhibitor is MGB453 or TSR-022.

Embodiment 127

The use of embodiment 110 or kit of embodiment 111, wherein the one or more additional therapeutic agents is a LAG-3 inhibitor.

Embodiment 128

The use of embodiment 127 or kit of embodiment 127, wherein the LAG-3 inhibitor is selected from the group consisting of LAG525, BMS-986016, and TSR-033.

Embodiment 129

The use of embodiment 110 or kit of embodiment 111, wherein the one or more additional therapeutic agents is a chimeric antigen receptor (CAR) cell therapy.

Embodiment 130

The use of embodiment 129 or kit of embodiment 129, wherein the CAR cell therapy is CTL019.

Embodiment 131

The method of embodiment 91, wherein the one or more additional therapeutic agents is an anthracycline.

Embodiment 132

The method of embodiment 131, wherein the anthracycline is selected from doxorubicin, daunorubicin, epirubicin, idarubicin, and valrubicin.

Embodiment 133

The method of embodiment 132, wherein the anthracycline is doxorubicin.

Embodiment 134

The use of embodiment 110 or kit of embodiment 111, wherein the one or more additional therapeutic agents is an anthracycline.

Embodiment 135

The use of embodiment 134 or kit of embodiment 134, wherein the anthracycline is selected from doxorubicin, daunorubicin, epirubicin, idarubicin, and valrubicin.

Embodiment 136

The use of embodiment 135 or kit of embodiment 135, wherein the anthracycline is doxorubicin.

BRIEF DESCRIPTION OF THE FIGURES

FIG. 7 provides a table showing affinities ($K_D$) measured by ForteBio and MSD analysis for exemplary anti-CD39 antibodies to recombinant human CD39.

DETAILED DESCRIPTION

Figure 1A:
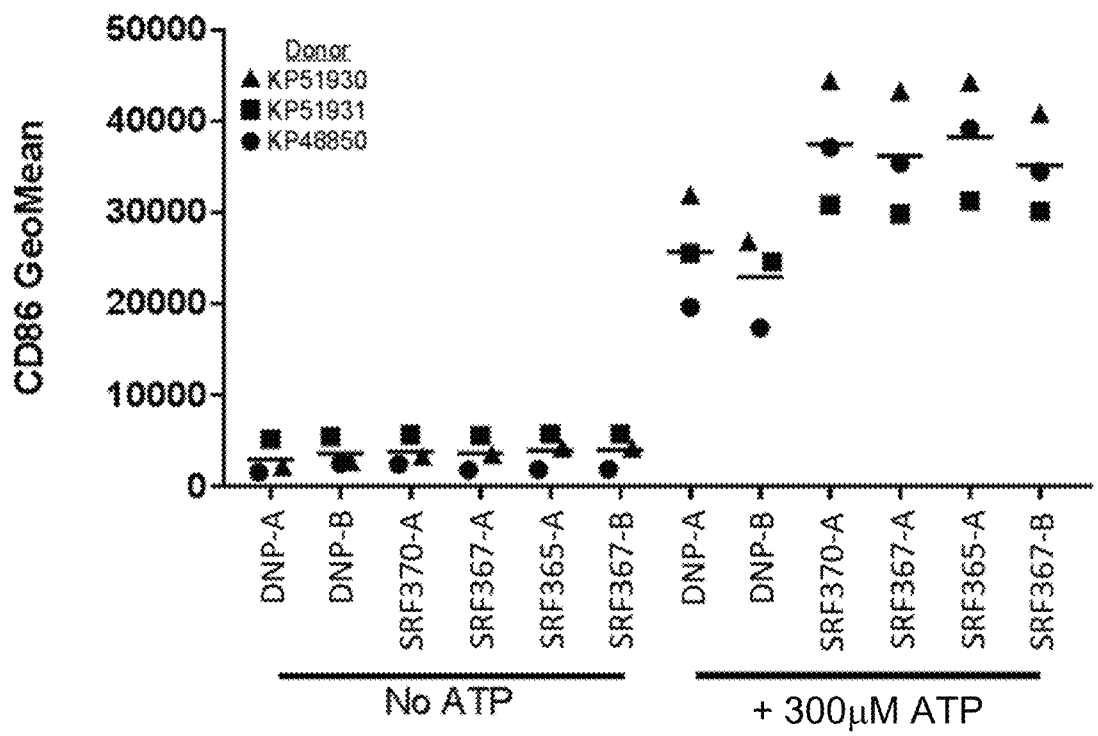
FIG. 1A provides a graph quantifying the expression of CD86 on dendritic cells treated with anti-CD39 antibodies or control antibodies, as indicated, in the presence or absence of ATP. Expression of CD86 was determined by flow cytometry analysis.

Various diseases are characterized by the development of progressive immunosuppression in a patient. The presence of an impaired immune response in patients with malignancies has been particularly well-documented. Cancer patients exhibit a variety of altered immune functions such as a decrease in delayed hypersensitivity, and decrease in lytic function and proliferation response of lymphocytes. Augmenting immune functions in cancer patients may have beneficial effects for tumor control.

In one aspect, the present disclosure provides anti-CD39 antagonist antibodies. In other aspects, the disclosure provides methods for treating a disorder associated with aberrant CD39 expression. In some embodiments, the disclosure provides an antibody which binds human CD39, or antigen binding portion thereof, and inhibits or reduces the enzymatic activity of human CD39. Without being bound by theory, it is believed that inhibition or reduction of the enzymatic activity of human CD39 maintains, increases or enhances a level of extracellular adenosine triphosphate (eATP) (e.g., an immunostimulatory level) and decreases or reduces a level of extracellular adenosine in a tumor microenvironment in a patient, thereby providing a therapeutic benefit to the patient.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

In this application, the use of "or" means "and/or" unless stated otherwise. In the context of a multiple dependent claim, the use of "or" refers back to more than one preceding independent or dependent claim in the alternative only. The terms "comprising," "including," and "having" can be used interchangeably herein. According to the present invention, an "isolated" molecule is a molecule that has been removed from its natural milieu. As such, the term "isolated" does not necessarily reflect the extent to which the molecule has been purified.

As used herein, the term "extracellular adenosine triphosphate" or "extracellular ATP" or "eATP" refers to adenosine 5'-triphosphate that is located in a tissue or tissue sample outside of cells in the tissue or tissue sample, and functions in purinergic signaling. As used herein, the term "extracellular adenosine" refers to adenosine that is located in a tissue or tissue sample outside of cells in the tissue or tissue sample, and functions in purinergic signaling. Within a tissue or tissue sample, there is a relationship between the amount, concentration, or level of extracellular ATP and the amount, concentration or level of extracellular adenosine. Under physiological (i.e., normal) conditions, the steady-state cytosolic (i.e., intracellular) concentration of ATP ranges from approximately 3 mM to approximately 10 mM, whereas the amount, concentration, or level of extracellular ATP is approximately 10 nM. The level of extracellular ATP is maintained as a result of the activities of extracellular enzymes (e.g., ectonucleotidases, CD39, CD79) that metabolize or convert extracellular ATP into extracellular adenosine 5'-diphosphate (eADP), extracellular adenosine 5'-monophosphate (eAMP), and extracellular adenosine (Trautmann (2009) Sci Signal 2(56):pe6).

Extracellular nucleosides (e.g., extracellular adenosine) and nucleotides (e.g., extracellular ATP) participate in purinergic signaling, which is involved in mediating normal physiological cellular responses including, but not limited to, stimulation (or inhibition) of cell death, cell proliferation, migration, and/or differentiation, and secretion of growth factors and/or inflammatory mediators by cells. Pathophysiological processes such as tissue homeostasis, wound healing, neurodegeneration, anti-tumor immunity, inflammation and cancer are also modulated by purinergic signaling (Bours et al., (2011) Front Biosci (Schol Ed) 3:1443-1456; Khakh et al., (2006) Nature 442:527-532; Idzko et al., (2014) 509:310-317; Antonioli et al., (2013) Rev Cancer 13:842-857). A low concentration of extracellular ATP surrounding resting cells in a tissue signals the presence of neighboring living cells. And, transient increases in extracellular ATP are associated with normal physiological signaling, for example, in the nervous and vascular systems. However, significant increases in extracellular ATP levels in a tissue (e.g., during immunogenic cell death ICD) serve as a key "danger" signal resulting in the induction of inflammatory processes and modulation of immune system responses (e.g., anti-tumor responses) (Martins et al., (2014) Cell Death Differ 21(1):79-91).

In contrast to healthy tissue, where extracellular ATP levels are relatively low (approximately 10 nM), elevated levels of extracellular ATP at sites of tissue damage, inflammation and in the tumor microenvironment (TME) can reach concentrations of greater than 100 µM (Virgilio and Adinolfi (2017) Oncogene 36:293-303). Elevated levels of extracellular ATP in a damaged tissue or the TME has been shown to result in immunomodulatory and immunostimulatory effects (Vijayan et al., (2017) Nat Rev Cancer 17:709-724). As used herein the term "immunostimulatory level of ATP" refers to an amount, quantity, concentration, abundance or level of extracellular ATP that induces, stimulates or enhances an immune response.

In some cancers, conditions within the TME can ultimately result in the accumulation of extracellular adenosine as a consequence of accelerated hydrolysis of elevated levels of extracellular ATP. In contrast to immunostimulatory effects of elevated levels of extracellular ATP, extracellular adenosine is known to induce immunosuppressive effects, for example, in the TME of some cancers (Virgilio (2012) Cancer Res 72(21):5441-5447). The enzymes primarily responsible for the conversion of extracellular ATP to extracellular adenosine in the TME are the ectonucleotidases CD39 and CD73. In the TME, the immunosuppressive effects of adenosine have been shown to be mediated, at least in part, by expansion of regulatory T cells (Tregs), inhibition of effector T cell responses, and expansion of myeloid derived suppressor cells (MDSCs) (Allard et al., (2016) Curr Opin Pharmacol 29:7-16; Allard et al., (2016) Immunotherapy 8:145-163)

As used herein, the term "alanine scanning" refers to a technique used to determine the contribution of a specific wild-type residue to the stability or function(s) (e.g., binding affinity) of given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "amount" or "level" is used in the broadest sense and refers to a quantity, concentration or abundance of a substance (e.g., a metabolite, a small molecule, a protein, an mRNA, a marker). When referring to a metabolite or small molecule (e.g. adenosine triphosphate (ATP)), the terms "amount", "level" and "concentration" are generally used interchangeably and generally refer to a detectable amount in a biological sample. "Elevated levels" or "increased levels" refers to an increase in the quantity, concentration or abundance of a substance within a sample relative to a control sample, such as from an individual or individuals who are not suffering from the disease or disorder (e.g., cancer) or an internal control. In some embodiments, the elevated level of a substance (e.g., ATP) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., malachite green assay). "Reduced levels" refers to a decrease in the quantity, concentration or abundance of a substance (e.g., ATP) in an individual relative to a control, such as from an individual or individuals who are not suffering from the disease or disorder (e.g., cancer) or an internal control. In some embodiments, a reduced level is little or no detectable quantity, concentration or abundance. In some embodiments, the reduced level of a substance (e.g., ATP) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., malachite green assay).

When referring to a protein, mRNA or a marker, such as those described herein, the terms "level of expression" or "expression level" in general are used interchangeably and generally refer to a detectable amount of a protein, mRNA, or marker in a biological sample. In some embodiments, a detectable amount or detectable level of a protein, mRNA or a marker is associated with a likelihood of a response to an agent, such as those described herein. "Expression" generally refers to the process by which information contained within a gene is converted into the structures (e.g., a protein marker, such as CD86) present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). "Elevated expression," "elevated expression levels," or "elevated levels" refers to an increased expression or increased levels of a substance within a sample relative to a control sample, such as an individual or individuals who are not suffering from the disease or disorder (e.g., cancer) or an internal control. In some embodiments, the elevated expression of a substance (e.g., a protein marker, such as CD86) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., FACS). "Reduced expression," "reduced expression levels," or "reduced levels" refers to a decrease expression or decreased levels of a substance (e.g., a protein marker) in an individual relative to a control, such as an individual or individuals who are not suffering from the disease or disorder (e.g., cancer) or an internal control. In some embodiments, reduced expression is little or no expression. In some embodiments, the reduced expression of a substance (e.g., a protein marker) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., FACS).

As used herein, the terms "antagonize," "antagonizes," or when referring to a noun "antagonist," and the like refer to partially or fully blocking, inhibiting, or neutralizing, eliminating, or removing a biological activity of a native polypeptide (including an enzyme). As used herein, an antibody that "antagonizes human CD39" is one that partially or fully blocks, inhibits, neutralizes, eliminates, or removes the enzymatic activity of the CD39 enzyme. In some embodiments, antagonizing activity is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, identifying antibodies that bind to an antagonize human CD39, such as, for example, binding assays such as enzyme-linked immuno-absorbent assay (ELISA), Forte Bio© systems, and radioimmunoassay (MA). Assays such as these can be used to determine the ability of an antibody to bind the polypeptide of interest (e.g., CD39) as well as the ability of the antibody to antagonize the polypeptide (e.g., CD39). Efficacy of an antagonist antibody can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist may be defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the term "anti-CD39 antagonist antibody" (interchangeably termed "anti-CD39 antibody") refers to an antibody described herein, for example, in Table 1. In some embodiments, an anti-CD39 antibody binds to CD39 (e.g., human CD39) and antagonizes a CD39 biological activity and/or downstream pathway(s) mediated by CD39 signaling or other CD39-mediated function, e.g., enzymatic activity. An anti-CD39 antagonist antibody encompasses antibodies that block, antagonize, suppress, inhibit, eliminate, or reduce CD39 biological activity (e.g., ligand binding, enzymatic activity), including downstream pathways mediated by CD39 signaling or function, such as receptor binding and/or elicitation of a cellular response to CD39 or its metabolites. In some embodiments, an anti-CD39 antibody specifically binds to CD39.

In some embodiments, an anti-CD39 antagonist antibody binds to CD39 and prevents or inhibits CD39 binding to its cognate or normal ligand. In some embodiments, an anti-CD39 antagonist antibody binds to CD39 and inhibits or reduces the enzymatic conversion of adenosine triphosphate (ATP) to adenosine monophosphate (AMP). In some embodiments, an anti-CD39 antagonist antibody binds to CD39 and inhibits or reduces the enzymatic conversion of adenosine diphosphate (ADP) to adenosine monophosphate (AMP). In some embodiments, an anti-CD39 antagonist antibody binds to CD39 and maintains or increases an immunostimulatory amount of ATP. In some embodiments, an anti-CD39 antagonist antibody binds to CD39 reduces or decreases adenosine levels. In some embodiments, an anti-CD39 antagonist antibody binds to CD39 and stimulates or enhances an anti-tumor response. In some embodiments, the anti-CD39 antagonist antibody binds to CD39 with an affinity of about 5 nM-20 nM. In some embodiment, the anti-CD39 antagonist antibody binds to CD39 and comprises a wild type or mutant IgG1 or a wild type or mutant IgG4 heavy chain constant region. Examples of anti-CD39 antagonist antibodies are provided herein.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be an isolated, purified or a recombinant antibody.

As used herein, the term "antibody fragment," "antigen-binding fragment," or similar terms refer to a fragment of an antibody that retains the ability to bind to a target antigen (e.g., CD39) and inhibit the activity of the target antigen, but is less than full length. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al., (2001) *J. Immunol. Methods* 248(1):47-66; Hudson and Kortt, (1999) *J. Immunol. Methods* 231(1):177-189; Poljak, (1994) *Structure* 2(12):1121-1123; Rondon and Marasco, (1997) *Annu. Rev. Microbiol.* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al., (2001) *Trends Biochem. Sci.* 26:230-235; Nuttall et al., (2000) *Curr. Pharm. Biotech.* 1:253-263; Reichmann et al., (1999) *J. Immunol. Meth.* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

In some embodiment, an antigen-binding fragment includes the variable region of a heavy chain polypeptide and the variable region of a light chain polypeptide. In some embodiments, an antigen-binding fragment described herein comprises the CDRs of the light chain and heavy chain polypeptide of an antibody.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Antibody fragments can be made by various techniques, including but not limited to proteolytic digestion of an intact antibody as well as production by recombinant host cells (e.g. *E. coli* or phage), as described herein.

The term "antigen presenting cell" or "APC" is a cell that displays foreign antigen complexed with MHC on its surface. T cells recognize this complex using T cell receptor (TCR). Examples of APCs include, but are not limited to, B cells, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "apoptosis" refers to the process of programmed cell death that occurs in multicellular organisms (e.g. humans). The highly-regulated biochemical and molecular events that result in apoptosis can lead to observable and characteristic morphological changes to a cell, including membrane blebbing, cell volume shrinkage, chromosomal DNA condensation and fragmentation, and mRNA decay. A common method to identify cells, including T cells, undergoing apoptosis is to expose cells to a fluorophore-conjugated protein (Annexin V). Annexin V is commonly used to detect apoptotic cells by its ability to bind to phosphatidylserine on the outer leaflet of the plasma membrane, which is an early indicator that the cell is undergoing the process of apoptosis.

As used herein, the term "B cell" (alternatively "B lymphocyte") refers to a type of white blood cell of the lymphocyte subtype. B cells function in the humoral immunity component of the adaptive immune system by secreting antibodies. B cells also present antigen and secrete cytokines. B cells, unlike the other two classes of lymphocytes, T cells and natural killer cells, express B cell receptors (BCRs) on their cell membrane. BCRs allow the B cell to bind to a specific antigen, against which it will initiate an antibody response.

As used herein, the term "binds to immobilized CD39," refers to the ability of an antibody of the disclosure to bind to CD39, for example, expressed on the surface of a cell or which is attached to a solid support.

As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) *J Immunol.* 148:1547-1553.

Traditionally, the recombinant production of bispecific antibodies is based on the co-expression of two immunoglobulin heavy-chain/light-chain pairs, where the two heavy chain/light-chain pairs have different specificities (Milstein and Cuello, (1983) *Nature* 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al., (1986) *Methods Enzymol.* 121:210; PCT Publication No. WO 96/27011; Brennan et al., (1985) *Science* 229:81; Shalaby et al., *J. Exp. Med.* (1992) 175:217-225; Kostelny et al., (1992) *J Immunol.* 148(5): 1547-1553; Hollinger et al., (1993) *Proc. Natl. Acad. Sci. USA* 90:6444-6448; Gruber et al., (1994) *J. Immunol.* 152: 5368; and Tutt et al., (1991) *J Immunol.* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368. Alternatively, the antibodies can be "linear antibodies" as described in, e.g., Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

Antibodies with more than two valencies (e.g., trispecific antibodies) are contemplated and described in, e.g., Tutt et al. (1991) J Immunol 147:60.

The disclosure also embraces variant forms of multispecific antibodies such as the dual variable domain immunoglobulin (DVD-Ig) molecules described in Wu et al. (2007) Nat Biotechnol 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715. In some embodiments, the bispecific antibody is a Fabs-in-Tandem immunoglobulin, in which the light chain variable region with a second specificity is fused to the heavy chain variable region of a whole antibody. Such antibodies are described in, e.g., International Patent Application Publication No. WO 2015/103072.

As used herein, "cancer antigen" or "tumor antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, the term "cancer-specific immune response" refers to the immune response induced by the presence of tumors, cancer cells, or cancer antigens. In certain embodiments, the response includes the proliferation of cancer antigen specific lymphocytes. In certain embodiments, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain embodiments, the cancer-specific immune response is a T cell response.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-CD39 antibodies described herein can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, the term "CD39" refers to the ectonucleoside triphosphate diphospholydrolase 1 polypeptide encoded in humans by the ENTPD1 gene. Other names for CD39 include ENTPD1, ATPDase, NTPDase-1, and SPG64. CD39 catalyzes the hydrolysis of γ- and β-phosphate residues of extracellular nucleoside triphosphates (NTPs; e.g., adenosine triphosphate or ATP) and nucleoside diphosphates (NDPs; e.g., adenosine diphosphate or ADP), converting these molecules to the nucleoside monophosphate (NMP; e.g., adenosine monophosphate or AMP) derivative. An exemplary amino acid sequence of CD39 is set forth in SEQ ID NO: 138, and also at NCBI Reference Sequence: NP_001767.3. The present disclosure provides antibodies that bind and antagonize human CD39.

As used herein, the term "CD86" (B70/B7-2) refers to a cell surface protein of about 75 kD, which is a second ligand for CD28 and CTLA-4 and plays an important role in co-stimulation of T cells in early immune response (Azuma M. et al., 1993, Nature 366: 76; Nozawa Y. et al., 1993, J. Pathology 169: 309; Engle, P. et al. 1994, Blood 84: 1402; Engel, P. et al., CD86 Workshop Report. In: Leukocyte Typing V. Schlossman, S. F. et al. eds., 1994, Oxford University Press; Yang, X. F. et al., 1994, Upregulation of CD86 antigen on TPA stimulated U937 cells, 1994, (abstract). American Society of Hematology, Nashville, Tenn.; Guesdon, J.-L. et al., 1979, J. Histochem. Cytochem. 27: 1131-1139).

As used herein, the term "CDR" means a complementarity-determining region. The term "hypervariable region" or "HVR" is sometimes used in place of "CDR", and both terms refer to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs/CDRs: three in the VH (H1, H2, H3), and three in the VL (L1, L2, L3).

As used herein, the term "cytotoxic T lymphocyte (CTL) response" refers to an immune response induced by cytotoxic T cells. CTL responses are mediated primarily by $CD8^+$ T cells.

As used herein, the term "chemotherapeutic agent" (alternatively "cytotoxic chemotherapeutic agent") refers to a chemical or pharmacological agent that is known to be of use in the treatment of cancer. Furthermore, as used herein, the term connotes those pharmacological agents that are generally cytotoxic, non-specific intracellular poisons, especially those that function to inhibit the process of cell division known as mitosis, and excludes pharmacological agents that more selectively target cellular components known to cause or contribute to the formation, development and/or maintenance of cancer. Chemotherapeutic agents can induce one or more cell death modalities including immunogenic cell death which can lead to ATP release.

As used herein the term "compete", when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody, such as SRF367) to a common antigen (e.g., CD39 or a fragment thereof). In some embodiments, the antibodies described herein cross compete with SRF367 (i.e., an antibody comprising the heavy and light chain variable sequences of SEQ ID NOs: 33 and 43, respectively).

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in Table 1. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in Table 1. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in Table 1. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from a sequence set forth in Table 1.

In certain embodiments, the antibodies of the disclosure are encoded by a nucleotide sequence. Nucleotide sequences of the invention can be useful for a number of applications, including cloning, gene therapy, protein expression and purification, mutation introduction, DNA vaccination of a host in need thereof, antibody generation for, e.g., passive immunization, PCR, primer and probe generation, and the like. In certain embodiments, the nucleotide sequence of the invention comprises, consists of, or consists essentially of, a nucleotide sequence selected from a sequence set forth in Table 1. In certain embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence selected from a sequence set forth in Table 1. In certain embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence selected from a sequence set forth in Table 1. In certain embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence selected from a sequence set forth in Table 1.

It will also be understood by one of ordinary skill in the art that the antibodies suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The antibodies suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term antigen "cross-presentation" refers to presentation of exogenous protein antigens to T cells via MHC class I and class II molecules on APCs.

As used herein, the term "cross-reacts" refers to the ability of an antibody of the disclosure to bind to CD39 from a different species. For example, an antibody of the present disclosure which binds human CD39 may also bind another species of CD39. As used herein, cross-reactivity is measured by detecting a specific reactivity with purified antigen in binding assays (e.g., SPR, ELISA) or binding to, or otherwise functionally interacting with, cells physiologically expressing CD39. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques.

As used herein, the term "cytotoxic T lymphocyte (CTL) response" refers to an immune response induced by cytotoxic T cells. CTL responses are mediated primarily by $CD8^+$ T cells.

As used herein, the term "dendritic cell" or "DC" refers to type of antigen-presenting cells that are bone marrow (BM)-derived leukocytes and are the most potent type of antigen-presenting cells. DCs are capture and process antigens, converting proteins to peptides that are presented on major histocompatibility complex (MHC) molecules recognized by T cells. DCs are heterogeneous, e.g. myeloid and plasmacytoid DCs; although all DCs are capable of antigen uptake, processing and presentation to naive T cells, the DC subtypes have distinct markers and differ in location, migratory pathways, detailed immunological function and dependence on infections or inflammatory stimuli for their generation. During the development of an adaptive immune response, the phenotype and function of DCs play a role in initiating tolerance, memory, and polarized T-helper 1 (Th1), Th2 and Th17 differentiation.

As used herein, the term "dendritic cell activation" refers to the transition from immature to mature dendritic cell; and the activated dendritic cells encompass mature dendritic cells and dendritic cells in the process of the transition, wherein the expression of CD80 and CD86 that induce costimulatory signals are elevated by the activating stimuli. Mature human dendritic cells are cells that are positive for the expression of CD40, CD80, CD86, and HLA-class II (e.g., HLA-DR). An immature dendritic cell can be distinguished from a mature dendritic cell, for example, based on markers selected from the group consisting of CD80 and CD86. An immature dendritic cell is weakly positive and preferably negative for these markers, while a mature dendritic cell is positive. Discrimination of mature dendritic cells is routinely performed by those skilled in the art, and the respective markers described above and methods for measuring their expression are also well known to those skilled in the art.

As used herein, the term "$EC_{50}$" refers to the concentration of an antibody or an antigen-binding portion thereof, which induces a response, either in an in vitro or an in vivo assay, which is 50% of the maximal response, i.e., halfway between the maximal response and the baseline.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a site on an antigen to which an immunoglobulin or antibody specifically binds. The term "epitope mapping" refers to a process or method of identifying the binding site, or epitope, of an antibody, or antigen binding fragment thereof, on its target protein antigen. Epitope mapping methods and techniques are provided herein. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from CD39 are tested for reactivity with the given anti-CD39 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Also encompassed by the present disclosure are antibodies that bind to an epitope on CD39 which comprises all, or a portion of an epitope recognized by the particular antibodies described herein (e.g., the same or an overlapping region or a region between or spanning the region).

Also encompassed by the present disclosure are antibodies that bind the same epitope and/or antibodies that compete for binding to human CD39 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as CD39. Numerous types of competitive binding assays are known, for example: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label MA using I-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen:antibody complexes which provides atomic resolution of the epitope and mass spectrometry combined with hydrogen/deuterium (H/D) exchange which studies the conformation and dynamics of antigen:antibody interactions. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "Fc-mediated effector functions" or "Fc effector functions" refer to the biological activities of an antibody other than the antibody's primary function and purpose. For example, the effector functions of a therapeutic agnostic antibody are the biological activities other than the activation of the target protein or pathway. Examples of antibody effect functions include C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. Many effector functions begin with Fc binding to an Fcγ receptor. In some embodiments, the tumor antigen-targeting antibody has effector function, e.g., ADCC activity. In some embodiments, a tumor antigen-targeting antibody described herein comprises a variant constant region having increased effector function (e.g. increased ability to mediate ADCC) relative to the unmodified form of the constant region.

As used herein, the term "Fc receptor" refers to a polypeptide found on the surface of immune effector cells, which is bound by the Fc region of an antibody. In some embodiments, the Fc receptor is an Fcγ receptor. There are three subclasses of Fcγ receptors, FcγRI (CD64), FcγRII (CD32) and FγcRIII (CD16). All four IgG isotypes (IgG1, IgG2, IgG3 and IgG4) bind and activate Fc receptors FcγRI, FcγRIIA and FcγRIIIA FcγRIIB is an inhibitory receptor, and therefore antibody binding to this receptor does not activate complement and cellular responses. FcγRI is a high affinity receptor that binds to IgG in monomeric form, whereas FcγRIIA and FcγRIIA are low affinity receptors that bind IgG only in multimeric form and have slightly lower affinity. The binding of an antibody to an Fc receptor and/or C1q is governed by specific residues or domains within the Fc regions. Binding also depends on residues located within the hinge region and within the CH2 portion of the antibody. In some embodiments, the agonistic and/or therapeutic activity of the antibodies described herein is dependent on binding of the Fc region to the Fc receptor (e.g., FcγR). In some embodiments, the agonistic and/or therapeutic activity of the antibodies described herein is enhanced by binding of the Fc region to the Fc receptor (e.g., FcγR).

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e. humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The terms "inducing an immune response" and "enhancing an immune response" are used interchangeably and refer the stimulation of an immune response (i.e., either passive or adaptive) to a particular antigen. The terms "induce" as used with respect to inducing CDC or ADCC refer to the stimulation of particular direct cell killing mechanisms.

As used herein, the term "immunogenic cell death" (alternatively known as "immunogenic apoptosis" refers to a cell death modality wherein contact of a tumor cell with a chemical, biological, or pharmacological agent is associated with the activation of one or more signaling pathways that induces the pre-mortem expression and emission of damaged-associated molecular pattern (DAMPs) molecules (e.g., adenosine triphosphate, ATP) from the tumor cell, resulting in the increase of immunogenicity of the tumor cell and the death of the tumor cell in an immunogenic manner (e.g., by phagocytosis). ICD is a form of cell death which induces endoplasmic reticulum (ER) stress and involves changes in the composition of the cell surface as well as the release of DAMPs that elevate the immunogenic potential of dying cells. DAMPs include calreticulin, heat-shock proteins, secreted amphoterin (HMGB1) and ATP. Following ICD induction, calreticulin is translocated to the surface of dying cell where it functions as an "eat me" signal for professional phagocytes. HSP70 and HSP90 are also translocated to the plasma membrane where they interact with antigen-presenting cell (APCs) and facilitate cross-presentation of tumor antigens with MHC class I molecules, resulting in a CD8+ T cell response. HMGB1 is released into the extracellular space where is binds Toll-like receptors on APCs and facilitates presentation of tumor antigens by dendritic cells (professional APCs) to T cells. ATP secretion recruit's monocytes to the site of cell death. Changes associated with ICD of tumor or cancer cells can induce an effective anti-tumor immune response through activation, maturation and enhanced antigen presentation of dendritic cells and activation of a specific T cell response in a subject.

As used herein, the term "immunogenic cell death-inducing agent" refers to a chemical, biological, or pharmacological agent that induces an immunogenic cell death process, pathway, or modality.

As used herein, the term "in combination," as used in connection with a therapeutic treatment, is understood to mean that two (or more) different treatments, for example, two (or more) therapeutic agents, are delivered to the subject during the course of the subject's affliction with the disorder, such that the effects of the treatments on the patient overlap at a point in time. In certain embodiments, the delivery of one treatment ends before the delivery of the other treatment begins (e.g., the first treatment is prior to a second or third (a subsequent) treatment). In certain other embodiments, the delivery of one treatment is still occurring when the delivery of the second begins, so that there is overlap in terms of administration. This is sometimes referred to herein as "simultaneous" or "concurrent delivery." In certain embodiments, the reduction of a symptom, or other parameter related to the disorder upon delivery of a combination therapy is greater than what would be observed with one treatment delivered in the absence of the other.

As used herein, the terms "inhibits" or "blocks" (e.g., referring to inhibition/blocking of human CD39-mediated conversion of a nucleoside triphosphate (e.g. adenosine triphosphate, ATP) or a nucleoside diphosphate (e.g. adenosine diphosphate, ADP) into a nucleoside monophosphate (e.g. adenosine monophosphate, AMP)) are used interchangeably and encompass both partial and complete inhibition/blocking. The inhibition/blocking of CD39 reduces or alters the normal level or type of activity that occurs without inhibition or blocking. Inhibition and blocking are also intended to include any measurable decrease in the binding affinity of CD39 when in contact with an anti-CD39 antibody as compared to CD39 not in contact with an anti-CD39 antibody, e.g., inhibits binding of CD39 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In some embodiments, the anti-CD39 antibody inhibits the conversion of nucleoside triphosphate (e.g., ATP) by at least about 70%. In some embodiments, the anti-CD39 antibody inhibits the conversion of nucleotide triphosphate (e.g. ATP) by at least 80%.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-CD39 antibody).

The term "in vivo" refers to processes that occur in a living organism.

As used herein, the term "isolated antibody" is intended to refer to an antibody which is substantially free of other antibodies having different antigenic specificities (e.g., an isolated antibody that binds to human CD39 is substantially free of antibodies that bind antigens other than CD39). An isolated antibody that binds to an epitope may, however, have cross-reactivity to other CD39 proteins from different species. However, the antibody continues to display specific binding to human CD39 in a specific binding assay as described herein. In addition, an isolated antibody is typically substantially free of other cellular material and/or chemicals. In some embodiments, a combination of "isolated" antibodies having different CD39 specificities is combined in a well-defined composition.

As used herein, the term "isolated nucleic acid molecule" refers to nucleic acids encoding antibodies or antibody portions (e.g., VH, VL, CDR3) that bind to CD39, is intended to refer to a nucleic acid molecule in which the nucleotide sequences encoding the antibody or antibody portion are free of other nucleotide sequences encoding antibodies or antibody portions that bind antigens other than CD39, which other sequences may naturally flank the nucleic acid in human genomic DNA. For example, a sequence selected from a sequence set forth in Table 1 corresponds to the nucleotide sequences comprising the heavy chain (VH) and light chain (VL) variable regions of anti-CD39 antibody antibodies described herein.

As used herein, "isotype" refers to the antibody class (e.g., IgM or IgG1) that is encoded by heavy chain constant region genes. In some embodiments, a human antibody of the disclosure is of the IgG1 isotype. In some embodiments, a human antibody of the disclosure is of the IgG2 isotype. In some embodiments, a human antibody of the disclosure is of the IgG3 isotype. In some embodiments, a human antibody of the disclosure is of the IgG4 isotype. In some embodiments, the isotype is wildtype. In some embodiments, the isotype is mutant. As used herein, an antibody having an "A" designation has an IgG4 isotype comprising a S228P mutation, according to EU numbering. As used herein, an antibody having an "B" designation has an IgG4 isotype comprising a S228P and L235E mutation, according to EU numbering. As used herein, an antibody having an "C" designation has "C" designation has a wild type IgG1 isotype. As used herein, an antibody having an "D" designation has a wild type IgG4 isotype. See, e.g., Vidarsson et al. Front Immunol. (2014), 5: 520, incorporated by reference herein in its entirety, and at page 6, col. 2, first full paragraph for discussion of S228P IgG4 mutation. See, e.g., Newman et al. Clinical Immunol. (2001) 98(2): 164-174, incorporated herein by reference in its entirety, for discussion of S228P and L235E IgG4 mutations.

As used herein, the term "isotype switching" refers to the phenomenon by which the class, or isotype, of an antibody changes from one Ig class to one of the other Ig classes.

As used herein the term "KD" or "$K_D$" refers to the equilibrium dissociation constant of a binding reaction between an antibody and an antigen. The value of $K_D$ is a numeric representation of the ratio of the antibody off-rate constant (kd) to the antibody on-rate constant (ka). The value of $K_D$ is inversely related to the binding affinity of an antibody to an antigen. The smaller the $K_D$ value the greater the affinity of the antibody for its antigen. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of an antibody from an antibody/antigen complex. The value of kd is a numeric representation of the fraction of complexes that decay or dissociate per second, and is expressed in units $sec^{-1}$.

As used herein, the term "ka" or "$k_a$" (alternatively "kon" or "$k_{on}$") is intended to refer to the on-rate constant for the association of an antibody with an antigen. The value of ka is a numeric representation of the number of antibody/antigen complexes formed per second in a 1 molar (1M) solution of antibody and antigen, and is expressed in units $M^{-1} sec^{-1}$.

As used herein, the term "leukocyte" refers to a type of white blood cell involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes).

As used herein, the term "lymphocytes" refers to a type of leukocyte or white blood cell that is involved in the immune defenses of the body. There are two main types of lymphocytes: B-cells and T-cells.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "monocyte" refers to a type of leukocyte and can differentiate into macrophages and dendritic cells to effect an immune response.

As used herein, the term "natural killer (NK) cell" refers to a type of cytotoxic lymphocyte. These are large, usually granular, non-T, non-B lymphocytes, which kill certain tumor cells and play an important in innate immunity to viruses and other intracellular pathogens, as well as in antibody-dependent cell-mediated cytotoxicity (ADCC).

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human σμ and human Σμ (δ-associated deletion). Alternative non-classical switching mechanisms, such as intertransgene and/or interchromosomal recombination, among others, may occur and effectuate isotype switching.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" is used interchangeably with "subject" and "individual" and includes human and other mammalian subjects that receive either prophylactic or therapeutic treatment.

As used herein, the term "PD-1 antagonist" refers to any chemical compound or biological molecule that inhibits the PD-1 signaling pathway or that otherwise inhibits PD-1 function in a cell (e.g. an immune cell). In some embodiments, a PD-1 antagonist blocks binding of PD-L1 to PD-1 and/or PD-L2 to PD-1. In some embodiments, the PD-1 antagonist binds PD-1. In some embodiments, the PD-1 antagonist binds PD-L1.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "Programmed Cell Death Protein 1" or "PD-1" refers to the Programmed Cell Death Protein 1 polypeptide, an immune-inhibitory receptor belonging to the CD28 family and is encoded by the PDCD1 gene in humans. Alternative names or synonyms for PD-1 include: PDCD1, PD1, CD279 and SLEB2. PD-1 is expressed predominantly on previously activated T cells, B cells, and myeloid cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773.

As used herein, the term "Programmed Death Ligand-1" or "PD-L1" is one of two cell surface glycoprotein ligands for PD-1 (the other being PD-L2) that downregulates T cell activation and cytokine secretion upon binding to PD-1. Alternative names and synonyms for PD-L1 include: PDCD1L1, PDL1, B7H1, B7-4, CD274 and B7-H. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

PD-1 is known as an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745). The interaction between PD-1 and PD-L1 can act as an immune checkpoint, which can lead to a decrease in T-cell receptor mediated proliferation (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

For several cancers, tumor survival and proliferation is sustained by tumor-mediated immune checkpoint modulation. This modulation can result in the disruption of anti-cancer immune system functions. For example, recent studies have indicated that the expression of immune checkpoint receptors ligands, such as PD-L1 or PD-L2, by tumor cells can downregulate immune system activity in the tumor microenvironment and promote cancer immune evasion. particularly by suppressing T cells. PD-L1 is abundantly expressed by a variety of human cancers (Dong et al., (2002) Nat Med 8:787-789). The receptor for PD-L1, PD-1, is expressed on lymphocytes (e.g., activated T cells) and is normally involved in down-regulating the immune system and promoting self-tolerance, particularly by suppressing T cells. However, when PD-1 receptors expressed on T cells bind to cognate PD-L1 ligands on tumor cells, the resulting T cell suppression contributes to an impaired immune response against the tumor (e.g., a decrease in tumor infiltrating lymphocytes or the establishment of immune evasion by cancer cells).

In large sample sets of e.g. ovarian, renal, colorectal, pancreatic, liver cancers and melanoma, it was shown that PD-L1 expression correlated with poor prognosis and reduced overall survival irrespective of subsequent treatment (see e.g., Dong et al., (2002) Nat Med 8(8):793-800; Yang et al., (2008) Invest Ophthalmol Vis Sci 49(6):2518-2525; Ghebeh et al., (2006) Neoplasia 8:190-198; Hamanishi et al., (2007) Proc Nat Acad Sci USA 104:3360-3365; Thompson et al., (2006) Clin Genitourin Cancer 5:206-211; Nomi et al., (2005) Clin Cancer Res 11:2947-2953; Inman et al., (2007) Cancer 109:1499-1505; Shimauchi et al., (2007) Int J Cancer 121:2585-2590; Gao et al., (2009) Clin Cancer Res 15:971-979; Nakanishi et al., (2007) Cancer Immunol Immunother 56:1173-1182; Hino et al., (2010) Cancer 116(7):1757-1766). Similarly, PD-1 expression on tumor lymphocytes was found to mark dysfunctional T cells in breast cancer (Kitano et al., (2017) ESMO Open 2(2): e000150) and melanoma (Kleffel et al., (2015) Cell 162(6): 1242-1256). PD-1 antagonists, such as those that affect the function of the PD-1/PD-L1/PD-L2 signaling axis and/or disrupt the interaction between PD-1 and PD-L1 and/or PD-L2, for example, have been developed and represent a novel class of anti-tumor inhibitors that function via modulation of immune cell-tumor cell interaction.

As used herein, the term "rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the term "reference antibody" (used interchangeably with "reference mAb") or "reference antigen-binding protein" refers to an antibody, or an antigen-binding fragment thereof, that binds to a specific epitope on CD39 and is used to establish a relationship between itself and one or more distinct antibodies, wherein the relationship is the binding of the reference antibody and the one or more distinct antibodies to the same epitope on CD39. As used herein, the term connotes an anti-CD39 antibody that is useful in a test or assay, such as those described herein, (e.g., a competitive binding assay), as a competitor, wherein the assay is useful for the discovery, identification or development, of one or more distinct antibodies that bind to the same epitope. The variable heavy (VH) and light chain (VL) amino acid sequences of an exemplary reference antibody (SRF367) are provided in Table 1 (VH, SEQ ID NO. 33; VL, SEQ ID NO. 43).

As used herein, the terms "specific binding," "selective binding," "selectively binds," and "specifically binds," refer to antibody binding to an epitope on a predetermined antigen. Typically, the antibody binds with an equilibrium dissociation constant (KD) of approximately less than $10^{-6}$ M, such as approximately less than $10^{-7}$ $10^{-8}$M, $10^{-9}$M or $10^{-10}$ M or even lower when determined by surface plasmon resonance (SPR) technology in a BIACORE 2000 instrument using recombinant human CD39 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen," and "an antibody that binds" are used interchangeably herein with the term "an antibody which binds specifically to an antigen," such as, CD39.

As used herein, the term "switch sequence" refers to those DNA sequences responsible for switch recombination. A "switch donor" sequence, typically μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and) (BLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g.,)(BLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "T cell" refers to a type of white blood cell that can be distinguished from other white blood cells by the presence of a T cell receptor on the cell surface. There are several subsets of T cells, including, but not limited to, T helper cells (a.k.a. TH cells or CD4+ T cells) and subtypes, including TH1, TH2, TH3, TH17, TH9, and TFH cells, cytotoxic T cells (a.k.a TC cells, CD8+ T cells, cytotoxic T lymphocytes, T-killer cells, killer T cells), memory T cells and subtypes, including central memory T cells (TCM cells), effector memory T cells (TEM and TEMRA cells), and resident memory T cells (TRM cells), regulatory T cells (a.k.a. Treg cells or suppressor T cells) and subtypes, including CD4+ FOXP3+ Treg cells, CD4+FOXP3− Treg cells, Tr1 cells, Th3 cells, and Treg17 cells, natural killer T cells (a.k.a. NKT cells), mucosal associated invariant T cells (MAITs), and gamma delta T cells ($\gamma\delta$ T cells), including V$\gamma$9/V$\delta$2 T cells. Any one or more of the aforementioned or unmentioned T cells may be the target cell type for a method of use of the invention.

As used herein, the term "T cell-mediated response" refers to any response mediated by T cells, including, but not limited to, effector T cells (e.g., CD8+ cells) and helper T cells (e.g., CD4+ cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., an anti-CD39 antibody or an antigen-binding fragment thereof) that will elicit the desired biological or medical response (e.g., an improvement in one or more symptoms of a cancer).

The terms "treat," "treating," and "treatment," refers to clinical intervention in an attempt to alter the natural course of the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease. In some embodiments, treatment as used herein, refer to therapeutic or preventative measures. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

As used herein, the term "unrearranged" or "germline configuration" refers to a V segment refers to the configuration wherein the V segment is not recombined so as to be immediately adjacent to a D or J segment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Anti-CD39 Antibodies and Antigen-Binding Fragments Thereof

The present disclosure provides antibodies, and antigen binding portions thereof, that bind to and antagonize CD39, in particular human CD39. Provided herein are isolated antibodies or antigen binding portion thereof that bind to human CD39, comprising heavy and light chain CDRs and variable sequences as set forth in Table 1.

The adenosine pathway is a signaling system which acts to fine-tune immune cell functions, such as cell-to-cell interactions, cytokine and chemokine secretion, surface antigen shedding, intracellular pathogen removal, and generating reactive oxygen species (ROS). ATP and ADP, play a fundamental role in inflammation, immune system regulation and tissue homeostasis through the activation of receptors (Eltzschig et al., (2012) N Engl J Med 367:2322-2333). Mediators, such as ATP and adenosine, are released into the extracellular space in response to metabolic disturbances or other types of insults, and operate both as sensory and efferent signals to shape immune responses. ATP is released either by cell lysis or by non-lytic mechanisms including: (i) exocytosis of ATP-containing vesicles, (ii) through nucleotide-permeable channels (connexin/pannexin hemichannels, maxi-anion channels, volume-regulated anion channels or P2X7 receptor channels), (iii) via transport vesicles that deliver proteins to the cell membrane, and (iv) via lysosomes. CD39 hydrolyzes extracellular adenosine triphosphate (ATP) and adenosine diphosphate (ADP) to generate adenosine.

The P1 adenosine receptor family encompasses the A1, A2A (the main adenosine receptor expressed by T cells), A2B, and A3 G-protein-coupled receptors. The adenosine-A2A receptor axis provides an immunosuppressive mechanism that dampens inflammation and protects normal tissues from immune system-mediated damage Ohta et al., (2001) Nature 414:916-920). In some cancers, this immunosuppressive pathway is aberrantly activated and provides protection for cancer cells against the immune system (Sitkovsky et al., (2014) Cancer Immunol Res) 2:598-605). Activation of this pathway and accumulation of extracellular adenosine in tumors generate an immunosuppressive and proangiogenic niche that is favorable to tumor growth (Antonioli et al., (2013) Nat Rev Cancer 13:842-857; Stagg and Smith (2010) Oncogene 29:5346-5358; Sitkovsky et al., (2008) Clin Cancer Res 14:5947-5952; Muller-Haegele et al., (2014) Expert Rev Clin Immunol 10:897-914; Antonioli et al., (2013) Trends Mol Med 19:355-367). The principal role of this pathway in promoting cancer is evidenced by the complete rejection of large immunogenic tumors in A2AR-deficient mice (Ohta et al., (2006) Proc Natl Acad Sci USA 103: 13132-13137) as well as the tumor-resistant phenotype of CD39 Sun et al., (2010) Gastroenterology 139:1030-1040).

Within the pathway, CD39 (also known as ecto-nucleoside triphosphate diphosphohydrolase 1, E-NTPDase1, and cluster of differentiation 39) and CD73 (also known as ecto-5'-nucleotidase, Ecto5'NTase, 5'-nucleotidase (5'-NT), and cluster of differentiation 73), are the major nucleotide metabolizing enzymes that regulate immunity and inflammation. The activity of CD39 and CD73 represents the primary source of extracellular adenosine. CD39 hydrolyses extracellular ATP and ADP into adenosine monophosphate (AMP) (Deaglio et al., (2007) J Exp Med 204:1257-1265; Borsellino et al., (2007) Blood 110:1225-1232). AMP is then processed into the anti-inflammatory adenosine, essentially by the ectonucleotidase CD73. Upon binding to A2A receptors on T cells, adenosine induces the accumulation of intracellular cyclic AMP, thereby preventing TCR-induced CD25 upregulation and inhibiting effector T-lymphocyte proliferation and inflammatory cytokine secretion (Huang et al., (1997) Blood 90:1600-1610; Lokshin et al., (2006) Cancer Res 66:7758-7765). Adenosine also blocks the cytotoxic activity and cytokine production of activated natural killer (NK) cells.

Accordingly, the disclosure provides an isolated antibody that binds to and antagonizes human CD39, or an antigen binding portion thereof, wherein the antibody or antigen binding portion thereof exhibits at least one or more of the following properties: (i) binds to recombinant human CD39 and/or to membrane-bound human CD39; (ii) binds to CD39 with an equilibrium dissociation constant (KD) of less than 10 nM; (iii) inhibits or reduces an enzymatic activity of CD39; (iv) inhibits or reduces conversion of extracellular adenosine triphosphate (eATP) or extracellular adenosine diphosphate (eADP) to extracellular adenosine monophosphate (eAMP); (v) increases or enhances a level of extracellular adenosine triphosphate (eATP); (vi) decreases or reduces a level extracellular adenosine; (vii) maintains, increases or enhances an immunostimulatory level of extracellular adenosine triphosphate (eATP); (viii) increases or enhances proliferation of a lymphocyte; (ix) increases or enhances expression of one or more dendritic cell activation markers; (x) increases or enhances secretion of one or more cytokines from dendritic cells; (xi) increases or enhances macrophage infiltration in tumors; (xii) increases or enhances secretion of macrophage attracting chemokines; (xiii) antagonizes human CD39 in a tumor microenvironment of a tissue; (xiv) cross-reacts with cynomolgus CD39 and/or mouse CD39; or (xv) a combination of any one of (i)-(xiv).

In some embodiments, the isolated antibody, or antigen binding portion thereof, binds to recombinant CD39 and/or membrane-bound CD39. In some embodiments, the isolated antibody, or antigen binding portion thereof, binds to recombinant human CD39 and/or membrane-bound human CD39.

In some embodiments, the isolated antibody, or antigen binding portion thereof, binds to CD39 with an equilibrium dissociation constant (KD) of less than 10 nM.

In some embodiments, the isolated antibody, or antigen binding portion thereof, inhibits or reduces an enzymatic activity of CD39.

In some embodiments, the isolated antibody, or antigen binding portion thereof, inhibits or reduces the enzymatic activity of CD39, wherein the enzymatic activity of CD39 is the hydrolysis of extracellular adenosine triphosphate (eATP) or extracellular adenosine diphosphate (eADP).

In some embodiments, the isolated antibody, or antigen binding portion thereof, inhibits or reduces the conversion of extracellular adenosine triphosphate (eATP) or extracellular adenosine diphosphate (eADP) to extracellular adenosine monophosphate (eAMP).

In some embodiments, the isolated antibody, or antigen binding portion thereof, increases or enhances a level of extracellular adenosine triphosphate (eATP).

In some embodiments, the isolated antibody, or antigen binding portion thereof, decreases or reduces a level of extracellular adenosine.

In some embodiments, the isolated antibody, or antigen binding portion thereof, increases or enhances an immunostimulatory level of extracellular adenosine triphosphate (eATP).

In some embodiments, the isolated antibody, or antigen binding portion thereof, increases proliferation of a lymphocyte. In some embodiments the lymphocyte is a tumor-infiltrating lymphocyte. In some embodiments, the lymphocyte is T cell. In some embodiments, the T cell is a CD4+ T cell.

In some embodiments, the isolated antibody, or antigen binding portion thereof, enhances expression of one or more dendritic cell activation markers. In some embodiments, the one or more dendritic cell activation markers is CD86, HLA-DR, or a combination thereof.

In some embodiments, the isolated antibody, or antigen binding portion thereof, enhances secretion of one or more cytokines from dendritic cells. In some embodiments, the one or more cytokines is IL-16, IL-12/IL-23p40, VEGFA, or any combination thereof.

In some embodiments, the isolated antibody, or antigen binding portion thereof, increases or enhances macrophage infiltration in tumors.

In some embodiments, the isolated antibody, or antigen binding portion thereof, increases or enhances secretion of macrophage attracting chemokines.

In some embodiments, the isolated antibody, or antigen binding portion thereof, antagonizes human CD39 in a tumor microenvironment.

In some embodiments, the isolated antibody, or antigen binding portion thereof, cross-reacts with cynomolgus CD39 and/or mouse CD39.

In some embodiments, the isolated antibody, or antigen binding portion thereof, is selected from the group consisting of an IgG1, an IgG2, and IgG3, an IgG4, and IgM, and IgA1, and IgA2, and IgD, and an IgE antibody.

In some embodiments, the isolated antibody, or antigen binding portion thereof, is an IgG1 antibody of IgG4 antibody.

In some embodiments, the isolated antibody, or antigen binding portion thereof, comprises a wild type IgG1 heavy chain constant region.

In some embodiments, the isolated antibody, or antigen binding portion thereof, comprises a wild type IgG4 heavy chain constant region.

In some embodiments, the isolated antibody, or antigen binding portion thereof, comprises an Fc domain comprising at least one mutation.

In some embodiments, the isolated antibody, or antigen binding portion thereof, comprises a mutant IgG1 heavy chain constant region.

In some embodiments, the isolated antibody, or antigen binding portion thereof, comprises a mutant IgG4 heavy chain constant region. In some embodiments, the mutant IgG4 heavy chain constant region comprises any one of the substitutions S228P, L235E, L235A, or a combination thereof, according to EU numbering.

In some aspects, antibody or antigen binding portion thereof the disclosure comprises the heavy chain CDR3 sequence set forth in SEQ ID NO: 3. In some aspects, the antibody or antigen binding portion of the disclosure binds to substantially the same epitope as a reference antibody or antigen binding portion thereof comprising the heavy chain CDR3 sequence set forth in SEQ ID NO: 3. In some aspects, the antibody or antigen binding portion of the disclosure binds to at least one of the amino acid residues bound by a reference antibody or antigen binding portion thereof comprising the heavy chain CDR3 sequence set forth in SEQ ID NOs: 3. In some aspects, the antibody or antigen binding portion of the disclosure, wherein a mutation of the epitope bound by the antibody inhibits, reduces, or blocks binding to both the antibody and to a reference antibody or antigen binding portion thereof comprising the heavy chain CDR3 sequence set forth in SEQ ID NOs: 3.

In some embodiments, the antibody or antigen binding portion of the disclosure binds to substantially the same epitope as a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively. In some embodiments, the antibody or antigen binding portion of the disclosure binds to at least one of the amino acid residues bound by a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively. In some embodiments, a mutation of the epitope bound by the antibody or antigen binding portion of the disclosure inhibits, reduces, or blocks binding to both the antibody and to a reference antibody or antigen binding portion thereof comprising heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively.

In some embodiments, the antibody or antigen binding portion thereof of the disclosure binds to substantially the same epitope as a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

In some embodiments, the antibody or antigen binding portion thereof of the disclosure binds to at least one of the amino acid residues bound by a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

In some embodiments, a mutation of the epitope bound by the antibody or antigen binding portion thereof of the disclosure inhibits, reduces, or blocks binding to both the antibody and to a reference antibody or antigen binding portion thereof comprising heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively.

In some aspects, the antibody or antigen binding portion of the disclosure binds to and antagonizes human CD39 and comprises heavy and light chain CDRs selected from the group consisting of:
  (i) heavy chain CDR1, CDR2 and CDR3 sequences set forth in SEQ ID NOs: 27, 28 and 29, respectively, and light chain CDR1, CDR2 and CDR3 sequences set forth in SEQ ID NOs: 37, 38 and 39, respectively;
  (ii) heavy chain CDR1, CDR2 and CDR3 sequences set forth in SEQ ID NOs: 1, 2 and 3, respectively, and light chain CDR1, CDR2 and CDR3 sequences set forth in SEQ ID NOs: 11, 12 and 13, respectively;
  (iii) heavy chain CDR1, CDR2 and CDR3 sequences set forth in SEQ ID NOs: 53, 54 and 55, respectively, and light chain CDR1, CDR2 and CDR3 sequences set forth in SEQ ID NOs: 63, 64 and 65, respectively;
  (iv) heavy chain CDR1, CDR2 and CDR3 sequences set forth in SEQ ID NOs: 79, 80 and 81, respectively, and light chain CDR1, CDR2 and CDR3 sequences set forth in SEQ ID NOs: 89, 90 and 91, respectively; and
  (v) heavy chain CDR1, CDR2 and CDR3 sequences set forth in SEQ ID NOs: 105, 106 and 107, respectively, and light chain CDR1, CDR2 and CDR3 sequences set forth in SEQ ID NOs: 115, 116 and 117, respectively.

In some embodiments, the antibody or antigen binding portion thereof of the disclosure binds to and antagonizes human CD39 and comprises heavy and light chain CDRs, wherein the heavy chain CDR1, CDR2 and CDR3 sequences are set forth in SEQ ID NOs: 27, 28 and 29, respectively, and the light chain CDR1, CDR2 and CDR3 sequences are set forth in SEQ ID NOs: 37, 38 and 39, respectively.

In some embodiments, the antibody or antigen binding portion thereof of the disclosure binds to and antagonizes human CD39 and comprises heavy and light chain CDRs selected from the group consisting of:
  (i) heavy chain CDR1, CDR2 and CDR3 sequences set forth in SEQ ID NOs: 30, 31 and 32, respectively, and light chain CDR1, CDR2 and CDR3 sequences set forth in SEQ ID NOs: 40, 41 and 42, respectively;
  (ii) heavy chain CDR1, CDR2 and CDR3 sequences set forth in SEQ ID NOs: 4, 5 and 6, respectively, and light chain CDR1, CDR2 and CDR3 sequences set forth in SEQ ID NOs: 14, 15 and 16, respectively;
  (iii) heavy chain CDR1, CDR2 and CDR3 sequences set forth in SEQ ID NOs: 56, 57 and 58, respectively, and light chain CDR1, CDR2 and CDR3 sequences set forth in SEQ ID NOs: 66, 67 and 68, respectively;
  (iv) heavy chain CDR1, CDR2 and CDR3 sequences set forth in SEQ ID NOs: 82, 83 and 84, respectively, and light chain CDR1, CDR2 and CDR3 sequences set forth in SEQ ID NOs: 92, 93 and 94, respectively; and
  (v) heavy chain CDR1, CDR2 and CDR3 sequences set forth in SEQ ID NOs: 108, 109 and 110, respectively, and light chain CDR1, CDR2 and CDR3 sequences set forth in SEQ ID NOs: 118, 119 and 120, respectively.

In some embodiments, the antibody or antigen binding portion thereof of the disclosure binds to and antagonizes human CD39 and comprises heavy and light chain CDRs, wherein the heavy chain CDR1, CDR2 and CDR3 sequences are set forth in SEQ ID NOs: 30, 31 and 32, respectively, and the light chain CDR1, CDR2 and CDR3 sequences are set forth in SEQ ID NOs: 40, 41 and 42, respectively;

In some aspects, the antibody or antigen binding portion of the disclosure binds to and antagonizes human CD39 and comprises heavy and light chain variable regions, wherein the heavy chain variable region comprises an amino acid sequence selected from the group consisting of SEQ ID NOs: 33, 7, 59, 85 and 111; and wherein the light chain variable region comprises an amino acid sequence selected from the group consisting of SEQ ID NOs: 43, 17, 69, 95 and 121.

In some embodiments, the antibody or antigen binding portion thereof of the disclosure binds to an antagonizes human CD39 and comprises heavy and light chain variable regions comprising amino acid sequences selected from the group consisting of:
  (i) SEQ ID NO: 33 and 43, respectively;
  (ii) SEQ ID NO: 7 and 17, respectively;
  (iii) SEQ ID NO: 59 and 69, respectively;
  (iv) SEQ ID NO: 85 and 95, respectively; and
  (v) SEQ ID NO: 111 and 121, respectively.

In some embodiments, the antibody or antigen binding portion thereof of the disclosure binds to and antagonizes human CD39 and comprises heavy and light chain variable regions comprising amino acid sequences set forth in SEQ ID NO: 33 and 43, respectively.

In some aspects, the antibody or antigen binding portion of the disclosure binds to and antagonizes human CD39 and comprises heavy and light chain variable regions, wherein the heavy chain variable region comprises an amino acid sequence which is at least 90%, at least 95%, at least 97%, at least 98%, at least 99% identical to the amino acid sequence selected from the group consisting of SEQ ID NOs: 33, 7, 59, 85 and 111; and wherein the light chain variable region comprises an amino acid sequence which is at least 90%, at least 95%, at least 97%, at least 98%, at least 99% identical to the amino acid sequence selected from the group consisting of SEQ ID NOs: 43, 17, 69, 95 and 121.

In some embodiments, the antibody or antigen binding portion of the disclosure binds to an antagonizes human CD39 and comprises heavy and light chain variable regions comprising amino acid sequences at least 90%, at least 95%, at least 97%, at least 98%, at least 99% identical to the amino acid sequences selected from the group consisting of:
  (i) SEQ ID NO: 33 and 43, respectively;
  (ii) SEQ ID NO: 7 and 17, respectively;
  (iii) SEQ ID NO: 59 and 69, respectively;
  (iv) SEQ ID NO: 85 and 95, respectively; and
  (v) SEQ ID NO: 111 and 121, respectively.

In some embodiments, the antibody or antigen binding portion thereof of the disclosure binds to and antagonizes human CD39 and comprises heavy and light chain variable regions comprising amino sequences at least 90%, at least 95%, at least 97%, at least 98%, at least 99% identical to the amino acid sequences set forth in SEQ ID NO: 33 and 43, respectively.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 35, 9, 61, 87 and 113; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 35, 9, 61, 87 and 113; and wherein the light chain comprises an amino acid sequence which is at least 90%, at least 95%, at least 97%, at least 98%, at least 99% to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 47, 21, 73, 99, and 125; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 47, 21, 73, 99 and 125; and wherein the light chain comprises an amino acid sequence which is at least 90%, at least 95%, at least 97%, at least 98%, at least 99% identical to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 49, 23, 75, 101 and 127; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 49, 23, 75, 101 and 127; and wherein the light chain comprises an amino acid sequence which is at least 90%, at least 95%, at least 97%, at least 98%, at least 99% identical to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence selected from the group consisting of SEQ ID NOs: 51, 25, 77, 103 and 129; and wherein the light chain comprises an amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain, wherein the heavy chain comprises an amino acid sequence which is at least 90%, at least 95%, at least 97%, at least 98%, at least 99% identical to the amino acid sequence selected from the group consisting of SEQ ID NOs: 51, 25, 77, 103 and 129; and wherein the light chain comprises an amino acid sequence which is at least 90%, at least 95%, at least 97%, at least 98%, at least 99% identical to the amino acid sequence selected from the group consisting of SEQ ID NOs: 45, 19, 71, 97 and 123.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 35 and 45, respectively;
  (ii) SEQ ID NO: 9 and 19, respectively;
  (iii) SEQ ID NO: 61 and 71, respectively;
  (iv) SEQ ID NO: 87 and 97, respectively; and
  (v) SEQ ID NO: 113 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 35 and 45, respectively;
  (ii) SEQ ID NO: 9 and 19, respectively;
  (iii) SEQ ID NO: 61 and 71, respectively;
  (iv) SEQ ID NO: 87 and 97, respectively; and
  (v) SEQ ID NO: 113 and 123, respectively.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 47 and 45, respectively;
  (ii) SEQ ID NO: 21 and 19, respectively;
  (iii) SEQ ID NO: 73 and 71, respectively;
  (iv) SEQ ID NO: 99 and 97, respectively; and
  (v) SEQ ID NO: 125 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 47 and 45, respectively;
  (ii) SEQ ID NO: 21 and 19, respectively;
  (iii) SEQ ID NO: 73 and 71, respectively;
  (iv) SEQ ID NO: 99 and 97, respectively; and
  (v) SEQ ID NO: 125 and 123, respectively.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 49 and 45, respectively;
  (ii) SEQ ID NO: 23 and 19, respectively;
  (iii) SEQ ID NO: 75 and 71, respectively;
  (iv) SEQ ID NO: 101 and 97, respectively; and
  (v) SEQ ID NO: 127 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 49 and 45, respectively;
  (ii) SEQ ID NO: 23 and 19, respectively;
  (iii) SEQ ID NO: 75 and 71, respectively;
  (iv) SEQ ID NO: 101 and 97, respectively; and
  (v) SEQ ID NO: 127 and 123, respectively.

In some embodiments, the antibody or antigen binding portion thereof of the disclosure binds to and antagonizes human CD39 and comprises a heavy chain and a light chain comprising amino acid sequences selected from the group consisting of:
  (i) SEQ ID NO: 51 and 45, respectively;
  (ii) SEQ ID NO: 25 and 19, respectively;
  (iii) SEQ ID NO: 77 and 71, respectively;
  (iv) SEQ ID NO: 103 and 97, respectively; and
  (v) SEQ ID NO: 129 and 123, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences selected from the group consisting of:
  (i) SEQ ID NO: 51 and 45, respectively;
  (ii) SEQ ID NO: 25 and 19, respectively;
  (iii) SEQ ID NO: 77 and 71, respectively;
  (iv) SEQ ID NO: 103 and 97, respectively; and
  (v) SEQ ID NO: 129 and 123, respectively.

In some embodiments, the antibody or antigen binding portion thereof of the disclosure binds to and antagonizes human CD39 and comprises a heavy chain and a light chain comprising amino acid sequences set forth in SEQ ID NO: 35 and 45, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 35 and 45, respectively.

In some embodiments, the antibody or antigen binding portion thereof of the disclosure binds to and antagonizes human CD39 and comprises a heavy chain and a light chain comprising amino acid sequences set forth in SEQ ID NO: 47 and 45, respectively, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 47 and 45, respectively.

In some embodiments, the antibody or antigen binding portion thereof of the disclosure binds to and antagonizes human CD39 and comprises a heavy chain and a light chain comprising amino acid sequences set forth in SEQ ID NO: 49 and 45, respectively, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 49 and 45, respectively.

In some embodiments, the antibody or antigen binding portion thereof of the disclosure binds to and antagonizes human CD39 and comprises a heavy chain and a light chain comprising amino acid sequences set forth in SEQ ID NO: 51 and 45, respectively, respectively.

In some embodiments, the antibody or antigen binding portion thereof of the disclosure binds to and antagonizes human CD39 and comprises a heavy chain and a light chain comprising amino acid sequences at least 90%, at least 95%, at least 97%, at least 98%, at least 99% identical to the amino acid sequences set forth in SEQ ID NO: 51 and 45, respectively.

In some embodiments, the isolated antibody, or antigen binding portion thereof, comprises a mutant IgG4 heavy chain constant region. In some embodiments, the mutant IgG4 heavy chain constant region comprises a S228P substitution. In some embodiments, the mutant IgG4 heavy chain constant region comprises a S228P substitution and an L235E substitution. In some embodiments, the mutant IgG4 heavy chain constant region comprises a S228P substitution and an L235A substitution. Numbering according to EU numbering.

Methods for Producing the Anti-CD39 Antibodies and Antigen-Binding Fragments Thereof The disclosure also features methods for producing any of the anti-CD39 antibodies or antigen-binding fragments thereof described herein. In some embodiments, methods for preparing an antibody described herein can include immunizing a subject (e.g., a non-human mammal) with an appropriate immunogen. Suitable immunogens for generating any of the antibodies described herein are set forth herein. For example, to generate an antibody that binds to CD39, a skilled artisan can immunize a suitable subject (e.g., a non-human mammal such as a rat, a mouse, a gerbil, a hamster, a dog, a cat, a pig, a goat, a horse, or a non-human primate) with a full-length CD39 polypeptide such as a full-length human CD39 polypeptide comprising the amino acid sequence depicted in SEQ ID NO: 138.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) Autoimmunity 31(1):15-24. See also, e.g., Lodmell et al. (2000) Vaccine 18:1059-1066; Johnson et al. (1999) J Med Chem 42:4640-4649; Baldridge et al. (1999) Methods 19:103-107; and Gupta et al. (1995) Vaccine 13(14): 1263-1276.

In some embodiments, the methods include preparing a hybridoma cell line that secretes a monoclonal antibody that binds to the immunogen. For example, a suitable mammal such as a laboratory mouse is immunized with a CD39 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to human CD39 and In some embodiments, a skilled artisan can identify an anti-CD39 antibody from a non-immune biased library as described in, e.g., U.S. Pat. No. 6,300,064 (to Knappik et al.; Morphosys AG) and Schoonbroodt et al. (2005) Nucleic Acids Res 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) J Bacteriol 183:6924-6935; Cornelis (2000) Curr Opin Biotechnol 11:450-454; Klemm et al. (2000) Microbiology 146:3025-3032; Kieke et al. (1997) Protein Eng 10:1303-1310; Yeung et al. (2002) Biotechnol Prog 18:212-220; Boder et al. (2000) Methods Enzymology 328:430-444; Grabherr et al. (2001) Comb Chem High Throughput Screen 4:185-192; Michael et al. (1995) Gene Ther 2:660-668; Pereboev et al. (2001) J Virol 75:7107-7113; Schaffitzel et al. (1999) J Immunol Methods 231:119-135; and Hanes et al. (2000) Nat Biotechnol 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) JMB 397:385-396. Examples of phage display methods that can be used to make the immunoglobulins, or fragments thereof, described herein include those disclosed in Brinkman et al. (1995) J Immunol Methods 182:41-50; Ames et al. (1995) J Immunol Methods 184:177-186; Kettleborough et al. (1994) Eur J Immunol 24:952-958; Persic et al. (1997) Gene 187:9-18; Burton et al. (1994) Advances in Immunology 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with CD39 polypeptide as described above. mRNA can be isolated from the cells and converted to cDNA using standard molecular biology techniques. See, e.g., Sambrook et al. (1989) "Molecular Cloning: A Laboratory Manual, 2nd Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) J Neurosci Methods 62(1-2):213-9; Di Niro et al. (2005) Biochem J 388(Pt 3):889-894; and Engberg et al. (1995) Methods Mol Biol 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) Trends in Biotechnology 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al., (2006) Nucleic Acids Res 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human CD39) using any immunological or biochemical based method known in the art. For example, specific binding of an antibody to CD39, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

It is understood that the above methods can also be used to determine if, e.g., an anti-CD39 antibody does not bind to full-length, human CD39 and/or CD39 proteins.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) Nucleic Acids Symposium Series 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some embodiments, the anti-CD39 antibodies described herein comprise an altered heavy chain constant region that has reduced (or no) effector function relative to its corresponding unaltered constant region. Effector functions involving the constant region of the anti-CD39 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

In one embodiment, the anti-CD39 antibodies described herein comprise an IgG4 heavy chain constant region. In one embodiment, the IgG4 heavy chain constant region is a wild type IgG4 heavy chain constant region. In another embodiment, the IgG4 constant region comprises a mutation, e.g., one or both of S228P and L235E or L235A, e.g., according to EU numbering (Kabat, E. A., et al., supra). Representative sequences for use in antibodies of the disclosure of wild-type and mutant IgG4 constant regions are set forth in Table 1. In one embodiment, the anti-CD39 antibodies described herein comprise an IgG1 constant region. In one embodiment, the IgG1 heavy chain constant region is a wild type IgG1 heavy chain constant region. In another embodiment, the IgG1 heavy chain constant region comprises a mutation. Representative sequences for use in antibodies of the disclosure of wild-type and mutant IgG4 constant regions are set forth in Table 1.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-CD39 antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-CD39 antibody described herein comprising an altered constant region displaying reduced ADCC and/or CDC may exhibit reduced or no ADCC and/or CDC activity.

In some embodiments, an anti-CD39 antibody described herein exhibits reduced or no effector function. In some embodiments, an anti-CD39 antibody comprises a hybrid constant region, or a portion thereof, such as a G2/G4 hybrid constant region (see e.g., Burton et al. (1992) Adv Immun 51:1-18; Canfield et al. (1991) J Exp Med 173:1483-1491; and Mueller et al. (1997) Mol Immunol 34(6):441-452). See above.

In some embodiments, an anti-CD39 antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) J Exp Med 176:1191-1195 and Shopes (1992) Immunol 148:2918-2922; PCT publication nos. WO 99/51642 and WO 94/29351; Duncan and Winter (1988) Nature 322:738-40; and U.S. Pat. Nos. 5,648,260 and 5,624,821.

Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as E. coli gpt (Mulligan and Berg (1981) Proc Natl Acad Sci USA 78:2072) or Tn5 neo (Southern and Berg (1982) Mol Appl Genet 1:327). The selectable marker gene can be either linked to the DNA gene sequences to be expressed, or introduced into the same cell by co-transfection (Wigler et al. (1979) Cell 16:77). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147), cytomegalovirus, polyoma virus (Deans et al. (1984) Proc Natl Acad Sci USA 81:1292), or SV40 virus (Lusky and Botchan (1981) Nature 293:79).

The expression vectors can be introduced into cells in a manner suitable for subsequent expression of the nucleic acid. The method of introduction is largely dictated by the targeted cell type, discussed below. Exemplary methods include CaPO4 precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as E. coli, fungi such as Saccharomyces cerevisiae and Pichia pastoris, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) Curr Opin Biotechnol 13(6):625-629; van Kuik-Romeijn et al. (2000) Transgenic Res 9(2):155-159; and Pollock et al. (1999) J Immunol Methods 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in E. coli can be refolded from inclusion bodies (see, e.g., Hou et al. (1998) Cytokine 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) Protein Expression and Purification 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3rd edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

Modification of the Antibodies or Antigen-Binding Fragments Thereof

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (FLAG (DYKDDDDK (SEQ ID NO: 135)), polyhistidine (6-His; HHHHHH (SEQ ID NO: 136), hemagglutinin (HA; YPYDVPDYA (SEQ ID NO: 137)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., 32P, 33P, 14C, 125I, 131I, 35S, and 3H. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-☐-methyl-☐(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., 125I in meta-[125I]iodophenyl-N-hydroxysuccinimide ([125I]mIPNHS) which binds to free amino groups to form meta-iodophenyl (mIP) derivatives of relevant proteins (see, e.g., Rogers et al. (1997) J Nucl Med 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NETS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radio pharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) Bioconjug Chem 10(6): 973-8; Kinstler et al. (2002) Advanced Drug Deliveries Reviews 54:477-485; and Roberts et al. (2002) Advanced Drug Delivery Reviews 54:459-476 or HESylated (Fresenius Kabi, Germany; see, e.g., Pavisić et al. (2010) Int J Pharm 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) EMBO J 10(10):2717-2723; and Co et al. (1993) Mol Immunol 30:1361.

Pharmaceutical Compositions and Formulations

In certain embodiments, the invention provides for a pharmaceutical composition comprising an anti-CD39 antibody with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol);

delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and/or rate of in vivo clearance of the anti-CD39 antibody.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an anti-CD39 antibody can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an anti-CD39 antibody can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an anti-CD39 antibody, in a pharmaceutically acceptable vehicle. In certain embodiments, a vehicle for parenteral injection is sterile distilled water in which an anti-CD39 antibody is formulated as a sterile, isotonic solution, and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an anti-CD39 antibody can be formulated as a dry powder for inhalation. In certain embodiments, an inhalation solution comprising an anti-CD39 antibody can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an anti-CD39 antibody that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an anti-CD39 antibody. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an anti-CD39 antibody in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an anti-CD39 antibody in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an anti-CD39 antibody to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an anti-CD39 antibody is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of an anti-CD39 antibody in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an anti-CD39 antibody in an ex vivo manner. In such instances, cells, tissues and/or organs that have been removed from the patient are exposed to a pharmaceutical composition comprising an anti-CD39 antibody after which the cells, tissues and/or organs are subsequently implanted back into the patient.

In certain embodiments, an anti-CD39 antibody can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Applications

The compositions described herein can be used in a number of diagnostic and therapeutic applications. For example, detectably-labeled antigen-binding molecules can be used in assays to detect the presence or amount of the target antigens in a sample (e.g., a biological sample). The compositions can be used in in vitro assays for studying inhibition of target antigen function. In some embodiments, e.g., in which the compositions bind to and inhibit a complement protein, the compositions can be used as positive controls in assays designed to identify additional novel compounds that inhibit complement activity or otherwise are useful for treating a complement-associated disorder. For example, a CD39-inhibiting composition can be used as a positive control in an assay to identify additional compounds (e.g., small molecules, aptamers, or antibodies) that reduce or abrogate CD39 production. The compositions can also be used in therapeutic methods as elaborated on below.

In some embodiments, the disclosure provides a method of detecting CD39 in a biological sample or in a subject, comprising (i) contacting the sample or the subject (and optionally, a reference sample or subject) with any antibody in Table 1 under conditions that allow interaction of the antibody molecule and CD39 to occur, and (ii) detecting formation of a complex between the antibody molecule and the sample or the subject (and optionally, the reference sample or subject).

Kits

In some embodiments, the disclosure provides a kit comprising an anti-CD39 antibody as disclosed herein, and instructions for use. In some embodiments, the disclosure provides a kit comprising an isolated antibody that binds human CD39, or antigen binding portion thereof, such as those described herein or the pharmaceutical composition comprising the antibody, or antigen binding portion thereof, and instructions for use in stimulating an immune response in a subject, or treating cancer in a subject, optionally with instructions for use in combination with one or more additional therapeutic agents or procedures. In some embodiments, the one or more additional therapeutic agents or procedures is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

In some embodiments, the kit provides instructions for use in combination with a PD-1 antagonist, an adenosine A2AR antagonist, a CD73 inhibitor, a CTLA-4 inhibitor, a TIM-3 inhibitor, a LAG-3 inhibitor, chimeric antigen receptor (CAR) cell therapy, an anthracycline, or a combination thereof.

In some embodiments, the kit provides instructions for use in combination with a combination of a CD73 inhibitor and an A2AR antagonist. In some embodiments, the kit provides instructions for use in combination with a combination of a PD-1 antagonist and an adenosine A2AR antagonist.

In some embodiments, the kit provides instruction for use in combination with a PD-1 antagonist. In some embodiments, the PD-1 antagonist is selected from the group consisting of: PDR001, nivolumab, pembrolizumab, pidilizumab, MEDI0680, REGN2810, TSR-042, PF-06801591, and AMP-224. In some embodiments, the PD-1 antagonist is selected from the group consisting of: FAZ053, Atezolizumab, Avelumab, Durvalumab, and BMS-936559.

In some embodiments, the kit provides instructions for use in combination with an adenosine A2AR antagonist. In some embodiments, the adenosine A2AR antagonist is selected from the group consisting of: NIR178, CPI-444, AZD4635, Vipadenant, GBV-2034, and AB928. In some embodiments, the adenosine A2AR antagonist is CPI-444.

In some embodiments, the kit provides instructions for use in combination with a CD73 inhibitor. In some embodiments, the CD73 inhibitor is selected from the group consisting of: AB421, MEDI9447, and BMS-986179.

In some embodiments, the kit provides instructions for use in combination with a CTLA-4 inhibitor. In some embodiments, the CTLA-4 inhibitor is Ipilimumab or Tremelimumab.

In some embodiments, the kit provides instruction for use in combination with a TIM-3 inhibitor. In some embodiments, the TIM-3 inhibitor is MGB453 or TSR-022.

In some embodiments, the kit provides instructions for use in combination with a LAG-3 inhibitor. In some embodiments, the LAG-3 inhibitor is selected from the group consisting of LAG525, BMS-986016, and TSR-033.

In some embodiments, the kit provides instructions for use in combination with a chimeric antigen receptor (CAR) cell therapy. In some embodiments, the CAR cell therapy is CTL019.

In some embodiments, the kit provides instructions for use in combination with an anthracycline. In some embodiments, anthracycline is selected from doxorubicin, daunorubicin, epirubicin, idarubicin, and valrubicin. In some embodiments, the anthracycline is doxorubicin.

A kit can include an anti-CD39 antibody as disclosed herein, and instructions for use. The kits may comprise, in a suitable container, an anti-CD39 antibody, one or more controls, and various buffers, reagents, enzymes and other standard ingredients well known in the art. In some aspects, the disclosure provides a kit comprising an anti-CD39 antibody or antigen-binding portion as disclosed herein, and instructions for use in stimulating an immune response in a subject, or treating cancer in a subject, optionally with instructions for use in combination with one or more additional therapeutic agents or procedure as disclosed herein.

The container can include at least one vial, well, test tube, flask, bottle, syringe, or other container means, into which an anti-CD39 antibody may be placed, and in some instances, suitably aliquoted. Where an additional component is provided, the kit can contain additional containers into which this component may be placed. The kits can also include a means for containing an anti-CD39 antibody and any other reagent containers in close confinement for commercial sale. Such containers may include injection or blow-molded plastic containers into which the desired vials are retained. Containers and/or kits can include labeling with instructions for use and/or warnings.

Methods of Use

The compositions of the present invention have numerous in vitro and in vivo utilities involving the detection and/or quantification of CD39 and/or the antagonism of CD39 function.

In some embodiments, the disclosure provides methods and uses of stimulating an immune response in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier.

In some embodiments, the disclosure provides methods and uses of treating a cancer in a subject, the method comprising administering to the subject an effective amount an isolated antibody, or antigen binding portion thereof, that binds to and antagonizes CD39, provided by the disclosure, or a pharmaceutical composition comprising the antibody or antigen binding portion thereof, and a pharmaceutically acceptable carrier.

In some embodiments, the disclosure provides a method of treating a cancer in a subject, the method comprising administering to the subject an effective amount an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or pharmaceutical composition inhibits or reduces the enzymatic activity of CD39 in a tumor microenvironment, thereby treating the cancer.

In some embodiments, the disclosure provides a method of treating a cancer in a subject, the method comprising administering to the subject an effective amount an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 inhibits or reduces the conversion of extracellular adenosine triphosphate (eATP) or extracellular adenosine diphosphate (eADP) to extracellular adenosine monophosphate (AMP) in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 increases or enhances a level of extracellular adenosine triphosphate (eATP) in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 decreases or reduces a level of extracellular adenosine in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 increases or enhances a level of extracellular adenosine triphosphate (eATP) and decreases or reduces a level of extracellular adenosine in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 maintains, increases or enhances an immunostimulatory level of extracellular adenosine triphosphate (eATP) in a tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 increases or enhances the proliferation of a lymphocyte in the tumor microenvironment, thereby treating the cancer.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 enhances expression of one or more dendritic cell activation markers.

In some embodiments, the disclosure provides a method of treating a cancer in a subject, the method comprising administering to the subject an effective amount of an isolated antibody, or antigen binding portion thereof, that binds to and antagonizes CD39, provided by the disclosure, or a pharmaceutical composition comprising the antibody or antigen binding portion thereof, and a pharmaceutically acceptable carrier, wherein the antibody, or antigen binding portion thereof, or the pharmaceutical composition inhibits or reduces the enzymatic activity of CD39, wherein the inhibition or reduction of the enzymatic activity of CD39 enhances secretion of one or more cytokines from dendritic cells.

In some embodiments, the disclosure provides methods of treating cancer in a subject, wherein the cancer is selected from the group consisting of: lung cancer (e.g., non-small cell lung cancer), ovarian cancer, kidney cancer, testicular cancer, pancreas cancer, breast cancer (e.g., triple-negative breast cancer), melanoma, head and neck cancer (e.g., squamous head and neck cancer), colorectal cancer, bladder cancer, endometrial cancer, prostate cancer, thyroid cancer, hepatocellular carcinoma, gastric cancer, brain cancer, lymphoma or renal cancer (e.g., renal cell carcinoma).

The above-described compositions are useful in, inter alia, methods for treating or preventing a variety of cancers in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an anti-CD39 antibody or antigen-binding fragment thereof is therapeutically delivered to a subject by way of local administration.

A suitable dose of an antibody or fragment thereof described herein, which dose is capable of treating or preventing cancer in a subject, can depend on a variety of factors including, e.g., the age, sex, and weight of a subject to be treated and the particular inhibitor compound used. For example, a different dose of a whole anti-CD39 antibody may be required to treat a subject with cancer as compared to the dose of a CD39-binding Fab' antibody fragment required to treat the same subject. Other factors affecting the dose administered to the subject include, e.g., the type or severity of the cancer. For example, a subject having metastatic melanoma may require administration of a different dosage of an anti-CD39 antibody than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse). Suitable dosages are described herein.

A pharmaceutical composition can include a therapeutically effective amount of an anti-CD39 antibody or antigen-binding fragment thereof described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., reduction in tumor growth. For example, a therapeutically effective amount of an anti-CD39 antibody can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the antibodies or fragments thereof described herein can further be evaluated in, e.g., Phase I dose escalation studies. See, e.g., van Gurp et al. (2008) Am J Transplantation 8(8):1711-1718; Hanouska et al. (2007) Clin Cancer Res 13(2, part 1):523-531; and Hetherington et al. (2006) Antimicrobial Agents and Chemotherapy 50(10): 3499-3500.

In some embodiments, the composition contains any of the antibodies or antigen-binding fragments thereof described herein and one or more (e.g., two, three, four, five, six, seven, eight, nine, 10, or 11 or more) additional therapeutic agents such that the composition as a whole is therapeutically effective. For example, a composition can contain an anti-CD39 antibody described herein and an alkylating agent, wherein the antibody and agent are each at a concentration that when combined are therapeutically effective for treating or preventing a cancer (e.g., melanoma) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. An antibody or antigen-binding fragment thereof that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the ED50 with little or no toxicity. The dosage may vary within this range depending upon the dosage form employed and the route of administration utilized. For an anti-CD39 antibody described herein, the therapeutically effective dose can be estimated initially from cell culture assays. A dose can be formulated in animal models to achieve a circulating plasma concentration range that includes the IC50 (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the compositions described herein (e.g., anti-CD39 compositions) can be used to treat a variety of cancers such as but not limited to: Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, Karposi's Sarcoma, skin cancer, stomach cancer, testicular cancer, thyroid cancer, uterine cancer, and cancer of the urinary system.

Priority indications may be selected based on a variety of protein expression patterns: 1) negligible CD39 expression on normal tissue with upregulation in tumor tissue (lung cancer, ovarian cancer, pancreatic cancer, kidney cancer, testicular cancer), 2) maintenance of CD39 expression on hematopoietic cancers (B-cell lymphomas, acute myelogenous leukemia, acute myeloid leukemia) and 3) positive CD39 expression on myeloid- or Treg-rich cancers (breast cancer, gastric cancer, head and neck cancer, esophageal cancer).

Combination Therapy

In some embodiments, an anti-CD39 antibody, or antigen binding portion thereof, provided by the disclosure, can be combined with one or more additional therapeutics or treatments, e.g., another therapeutic or treatment for a cancer. For example, the anti-CD39 antibody, or antigen binding portion thereof, can be administered to a subject (e.g., a human patient) in combination with one or more additional therapeutics, wherein the combination provides a therapeutic benefit to a subject who has, or is at risk of developing, cancer.

In some embodiments, an anti-CD39 antibody, or antigen binding portion thereof, and the one or more additional therapeutics are administered at the same time (e.g., simultaneously). In other embodiments, the anti-CD39 antibody, or antigen binding portion thereof, is administered first in time and the one or more additional therapeutics are administered second in time (e.g., sequentially). In some embodiments, the one or more additional therapeutics are administered first in time and the anti-CD39 antibody is administered second in time.

An anti-CD39 antibody or an antigen-binding fragment thereof described herein can replace or augment a previously or currently administered therapy. For example, upon treating with an anti-CD39 antibody or antigen-binding fragment thereof, administration of the one or more additional therapeutics can cease or diminish, e.g., be administered at lower levels. In some embodiments, administration of the previous therapy can be maintained. In some embodiments, a previous therapy will be maintained until the level of the anti-CD39 antibody reaches a level sufficient to provide a therapeutic effect.

In some embodiments, the disclosure provides a method of treating cancer in a subject, the method comprising administering to the subject an effective amount of an isolated anti-CD39 antibody, or antigen binding portion thereof, that binds to and antagonizes CD39, provided by the disclosure, in combination with one or more additional therapeutic agents or procedure, wherein the second therapeutic agent or procedure is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

In some embodiments, the one or more additional therapeutic agents is a PD-1 antagonist, an adenosine A2AR antagonist, a CD73 inhibitor, a CTLA-4 inhibitor, a TIM-3 inhibitor, a LAG-3 inhibitor, chimeric antigen receptor (CAR) cell therapy, an anthracycline, or a combination thereof.

In some embodiments, the one or more additional therapeutic agents is a combination of a CD73 inhibitor and an A2AR antagonist. In some embodiments, the one or more additional therapeutic agents is a combination of a PD-1 antagonist and an adenosine A2AR antagonist. In some embodiments, the one or more additional therapeutic agents is a PD-1 antagonist.

In some embodiments, the PD-1 antagonist is selected from the group consisting of: PDR001, nivolumab, pembrolizumab, pidilizumab, MEDI0680, REGN2810, TSR-042, PF-06801591, and AMP-224. In some embodiments, the PD-1 antagonist is selected from the group consisting of: FAZ053, Atezolizumab, Avelumab, Durvalumab, and BMS-936559.

In some embodiments, the one or more additional therapeutic agents is an adenosine A2AR antagonist. In some embodiments, the adenosine A2AR antagonist is selected from the group consisting of: NIR178, CPI-444, AZD4635, Vipadenant, GBV-2034, and AB928. In some embodiments, the adenosine A2AR antagonist is CPI-444.

In some embodiments, the one or more additional therapeutic agents is a CD73 inhibitor. In some embodiments, the CD73 inhibitor is selected from the group consisting of: AB421, MEDI9447, and BMS-986179.

In some embodiments, the one or more additional therapeutic agents is a CTLA-4 inhibitor. In some embodiments, the CTLA-4 inhibitor is Ipilimumab or Tremelimumab.

In some embodiments, the one or more additional therapeutic agents is a TIM-3 inhibitor. In some embodiments, the TIM-3 inhibitor is MGB453 or TSR-022.

In some embodiments, the one or more additional therapeutic agents is a LAG-3 inhibitor. In some embodiments, the LAG-3 inhibitor is selected from the group consisting of LAG525, BMS-986016, and TSR-033.

In some embodiments, the one or more additional therapeutic agents is a chimeric antigen receptor (CAR) cell therapy. In some embodiments, the CAR cell therapy is CTL019.

In some embodiments, the one or more additional therapeutic agents is an anthracycline. In some embodiments, the anthracycline is selected from doxorubicin, daunorubicin, epirubicin, idarubicin, and valrubicin. In some embodiments, the anthracycline is doxorubicin.

Combination with Chemotherapeutic Agents

In some embodiments, a chemotherapeutic agent is used in combination with an anti-CD39 antibody described herein. Exemplary chemotherapeutic agents include, but are not limited to, anthracyclines (e.g., doxorubicin, idarubicin, daunorubicin, cytarabine, epirubicin, valrubicin and mitoxantrone) (see e.g., Minotti et al., (2004) Pharmacol Rev 56(2):185-229), topoisomerase inhibitors (e.g., topotecan; Hycamtin, camptothecin, etoposide) (see e.g., Pommier et al., (2010) Chem Biol 17(5):421-433; which is incorporated herein by reference in its entirety), bleomycin (Kimura et al., (1972) Cancer 29(1):58-60), gemcitabine (Plunkett et al., (1995) Semin Oncol 22(4 Suppl 11):3-10), platins (e.g., carboplatin, cisplatin, oxaliplatin, satraplatin, picoplatin) (Kelland (2007) Nat Rev Cancer 7(8):573-584), taxanes (e.g., docetaxel, paclitaxel, abraxane) (Abal et al., (2003) Curr Cancer Drug Targets 3(3):193-203), DNA alkylating agents (eg. cyclophosphamide, bendamustine) (Leoni et al., (2008) Clin Cancer Res 14(1):309-317), CHOP (drug combination of cyclophosphamide, doxorubicin hydrochloride, vincristine and prednisone) (Dunleavy (2014) Hematology Am Soc Hematol Educ Program 2014(1):107-112), and fluorouracil and derivatives thereof (Alvarez et al., (2012) Expert Opin Ther Pat 22(2):107-123, which is incorporated herein by reference in its entirety).

Recent studies have demonstrated that therapeutic outcomes with specific chemotherapeutic agents (e.g. anthracyclines) correlate strongly with their ability to induce a process of immunogenic cell death (ICD) in cancer cells. This process generates a series of signals that stimulate the immune system to recognize and clear tumor cells. Extensive studies have revealed that chemotherapy-induced ICD occurs via the exposure/release of calreticulin (CALR), ATP, chemokine (C-X-C motif) ligand 10 (CXCL10) and high mobility group box 1 (HMGB1) (Gebremeskel and Johnston (2015) 6(39):41600-41619). In some embodiments, the chemotherapeutic agent induces immunogenic cell death (ICD). In some embodiments, the agent that induces ICD is an anthracycline. In some embodiments, the anthracycline is selected from doxorubicin, daunorubicin, epirubicin, idarubicin, and valrubicin. In some embodiments, the anthracycline is doxorubicin. In some embodiments, the agent that induces ICD is a platinum derivative. In some embodiments, the platinum derivative is selected from oxaliplatin, carboplatin, and cisplatin. In some embodiments, the platinum derivative is oxaliplatin.

Other chemotherapeutic agents suitable for combination and/or co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and anti-mitotic agents (e.g. vincristine and vinblastine) and temozolomide.

Combination with PD-1/PD-L1 Antagonists

In some embodiments, the anti-CD39 antibodies, or antigen binding portions thereof, provided by the disclosure are combined (e.g., administered in combination) with one or more PD-1 antagonist that binds to human PD-1 or PD-L1 and inhibits PD-1/PD-L1 biological activity and/or downstream pathway(s) and/or cellular processed mediated by human PD-1/PD-L1 signaling or other human PD-1/PD-L1-mediated functions.

Accordingly, provided herein are PD-1 antagonists that directly or allosterically block, antagonize, suppress, inhibit or reduce PD-1/PD-L1 biological activity, including downstream pathways and/or cellular processes mediated by PD-1/PD-L1 signaling, such as receptor binding and/or elicitation of a cellular response to PD-1/PD-L1. Also provided herein are PD-1 antagonists that reduce the quantity or amount of human PD-1 or PD-L1 produced by a cell or subject.

In some embodiments, the disclosure provides a PD-1 antagonist that binds human PD-1 and prevents, inhibits or reduces PD-L1 binding to PD-1. In some aspects, the PD-1 antagonist binds to the mRNA encoding PD-1 or PD-L1 and prevents translation. In some embodiments, the PD-1 antagonist binds to the mRNA encoding PD-1 or PD-L1 and causes degradation and/or turnover.

In some embodiments, the PD-1 antagonist inhibits PD-1 signaling or function. In some embodiments, the PD-1 antagonist blocks binding of PD-1 to PD-L1, PD-L2, or to both PD-L1 and PD-L2. In some embodiments, the PD-1 antagonist blocks binding of PD-1 to PD-L1. In some embodiments, the PD-1 antagonist blocks binding of PD-1 to PD-L2. In some embodiments, the PD-1 antagonist blocks the binding of PD-1 to PD-L1 and PD-L2. In some embodiments, the PD-1 antagonist binds PD-1. In some embodiments, the PD-1 antagonist binds PD-L1. In some embodiments, the PD-1 antagonist binds PD-L2.

In some embodiments, the PD-1 antagonist inhibits the binding of PD-1 to its cognate ligand. In some embodiments, the PD-1 antagonist inhibits the binding of PD-1 to PD-L1, PD-1 to PD-L2, or PD-1 to both PD-L1 and PD-L2. In some embodiments, the PD-1 antagonist does not inhibit the binding of PD-1 to its cognate ligand.

In some embodiments, the PD-1 antagonist is an isolated antibody (mAb), or antigen binding fragment thereof, which binds to PD-1 or PD-L1. In some embodiments, the PD-1 antagonist is an antibody or antigen binding fragment thereof that binds to human PD-1. In some embodiments, the PD-1 antagonist is an antibody or antigen binding fragment thereof that binds to human PD-L1. In some embodiments, the PD-1 antagonist is an antibody or antigen binding fragment that binds to human PD-L1 and inhibits the binding of PD-L1 to PD-1. In some embodiments, the PD-1 antagonist is an antibody or antigen binding fragment that binds to human PD-1 and inhibits the binding of PD-L1 to PD-1.

Several immune checkpoint antagonists that inhibit or disrupt the interaction between PD-1 and either one or both of its ligands PD-L1 and PD-L2 are in clinical development or are currently available to clinicians for treating cancer.

Examples of anti-human PD-1 antibodies, or antigen binding fragments thereof, that may comprise the PD-1 antagonist in any of the compositions, methods, and uses provided by the disclosure include, but are not limited to: KEYTRUDA® (pembrolizumab, MK-3475, h409A11; see U.S. Pat. Nos. 8,952,136, 8,354,509, 8,900,587, and EP2170959, all of which are included herein by reference in their entirety; Merck), OPDIVO® (nivolumab, BMS-936558, MDX-1106, ONO-4538; see U.S. Pat. Nos. 7,595,048, 8,728,474, 9,073,994, 9,067,999, EP1537878, U.S. Pat. Nos. 8,008,449, 8,779,105, and EP2161336, all of which are included herein by reference in their entirety; Bristol Myers Squibb), MEDI0680 (AMP-514), BGB-A317 and BGB-108 (BeiGene), 244C8 and 388D4 (see WO2016106159, which is incorporated herein by reference in its entirety; Enumeral Biomedical), PDR001 (Novartis), and REGN2810 (Regeneron). Accordingly, in some embodiments the PD-1 antagonist is pembrolizumab. In some embodiments, the PD-1 antagonist is nivolumab.

Examples of anti-human PD-L1 antibodies, or antigen binding fragments thereof, that may comprise the PD-1 antagonist in any of the compositions, methods, and uses provided by the disclosure include, but are not limited to: BAVENCIO® (avelumab, MSB0010718C, see WO2013/79174, which is incorporated herein by reference in its entirety; Merck/Pfizer), IMFINZI® (durvalumab, MEDI4736), TECENTRIQ® (atezolizumab, MPDL3280A, RG7446; see WO2010/077634, which is incorporated herein by reference in its entirety; Roche), MDX-1105 (BMS-936559, 12A4; see U.S. Pat. No. 7,943,743 and WO2013/173223, both of which are incorporated herein by reference in their entirety; Medarex/BMS), and FAZ053 (Novartis). Accordingly, in some embodiments the PD-1 antagonist is avelumab. In some embodiments, the PD-1 antagonist is durvalumab. In some embodiments, the PD-1 antagonist is atezolizumab.

In some embodiments, the PD-1 antagonist is an immunoadhesin that bind to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that bind to PD-1 are described in WO2010/027827 and WO2011/066342, both of which are incorporated herein by reference in their entirety. In some embodiments, the PD-1 antagonist is AMP-224 (also known as B7-DCIg), which is a PD-L2-FC fusion protein that binds to human PD-1.

It will be understood by one of ordinary skill that any PD-1 antagonist which binds to PD-1 or PD-L1 and disrupts the PD-1/PD-L1 signaling pathway, is suitable for compositions, methods, and uses disclosed herein.

In some embodiments, the PD-1/PD-L1 antagonist is a small molecule, a nucleic acid, a peptide, a peptide mimetic, a protein, a carbohydrate, a carbohydrate derivative, or a glycopolymer. Exemplary small molecule PD-1 inhibitors are described in Zhan et al., (2016) Drug Discov Today 21(6):1027-1036.

Combinations with CD73 Inhibitors

In some embodiments, an anti-CD39 antibody, or antigen binding portion thereof, provided by the disclosure is combined (e.g., administered in combination) with a CD73 inhibitor. Non-limiting examples of CD73 inhibitors include AB421 (Arcus), an antibody, or antigen binding portion thereof, that binds to CD73 such as MEDI9447 (Medimmune), BMS-986179 (Bristol Meyers Squibb), or such as described in US2018/0009899 (Corvus), which is incorporated herein by reference in its entirety.

Combinations with Adenosine A2A Receptor Antagonists

In some embodiments, an anti-CD39 antibody, or antigen binding portion thereof, provided by the disclosure is combined (e.g., administered in combination) with an adenosine A2A receptor (A2AR) antagonist. Non-limiting examples of A2AR antagonists include Preladenant/SCH 420814 (Merck/Schering, CAS Registry Number: 377727-87-2), which is described in Hodgson et al., (2009) J Pharmacol Exp Ther 330(1):294-303 and incorporated herein by reference in its entirety; ST-4206 (Leadiant Biosciences), which is described in U.S. Pat. No. 9,133,197 and incorporated herein by reference in its entirety; KW-6356 (Kyowa Hakko Kogyo), Tozadenant/SYN-115 (Acorda), Istradefylline/KW-6002 (Kyowa Hakko Kogyo, CAS Registry Number: 155270-99-8), which is described in LeWitt et al., (2008) Ann Neurol 63(3):295-302 and is incorporated herein by reference in its entirety; theophylline (CAS Registry Number: 58-55-9), NIR178 (Novartis); AB928 (Arcus Biosciences), GBV-2034 (Globavir), Vipadenant (Redox/Juno), AZD4635/HTL-1071 (AstraZeneca/Heptares), which is described in WO2011/095625 and is incorporated herein by reference in its entirety; CPI-444/V81444 (Corvus/Genentech), which is described in WO 2009/156737 and is incorporated herein by reference in its entirety; and PBF509 (Palobiofarma/Novartis), which is described in U.S. Pat. No. 8,796,284 and WO 2017/025918 and are incorporated herein by reference in their entirety. In some embodiments, an anti-CD39 antibody, or antigen binding portion thereof, provided by the disclosure is combined (e.g., administered in combination) with CPI-444.

In some embodiments, the A2AR antagonist is an A2AR antagonist described in U.S. Pat. Nos. 8,114,845, 9,029,393, US20170015758, or US20160129108, all of which are incorporated herein by reference in their entirety.

Other exemplary A2AR antagonists include ATL-444, MSX-3, SCH-58261, SCH-412,348, SCH-442,416, VER-6623, VER-6947, VER-7835, CGS-15943, or ZM-241,385.

Combinations with CTLA-4 Inhibitors

In some embodiments, an anti-CD39 antibody, or antigen binding portion thereof, provided by the disclosure is combined (e.g., administered in combination) with a CTLA-4 inhibitor. In some embodiments, the CTLA-4 inhibitor is an antibody, an antigen binding fragment thereof, an immunoadhesin, a fusion protein, or an oligopeptide. In some embodiments, the CTLA-4 inhibitor is Ipilimumab (Yervoy®, Bristol-Myers Squibb). In some embodiments, the CTLA-4 inhibitor is Tremelimumab (Pfizer). The antibody Ipilimumab and other anti-CTLA-4 antibodies are disclosed in U.S. Pat. No. 6,984,720, which is incorporated herein by reference in its entirety. The antibody Tremelimumab and other anti-CTLA-4 antibodies are disclosed in U.S. Pat. No. 7,411,057, which is incorporated herein by reference in its entirety.

Combinations with TIM-3 Inhibitors

In some embodiments, an anti-CD39 antibody, or antigen binding portion thereof, provided by the disclosure is combined (e.g., administered in combination) with a TIM-3 inhibitor. The TIM-3 inhibitor may be an antibody, an antigen binding fragment thereof, an immunoadhesin, a fusion protein, or an oligopeptide. In some embodiments, the TIM-3 inhibitor is chosen from MGB453 (Novartis), TSR-022 (Tesaro), or LY3321367 (Eli Lilly). In some embodiments, the anti-CD39 antibody, or antigen binding portion thereof, is administered in combination with MGB453. In some embodiments, the anti-CD39 antibody, or antigen binding portion thereof, is administered in combination with TSR-022.

Combinations with LAG-3 Inhibitors

In some embodiments, an anti-CD39 antibody, or antigen binding portion thereof, provided by the disclosure is combined (e.g., administered in combination) with a LAG-3 inhibitor. The LAG-3 inhibitor may be an antibody, an antigen binding fragment thereof, an immunoadhesin, a fusion protein, or oligopeptide. In some embodiments, the LAG-3 inhibitor is chosen from LAG525 (Novartis), BMS-986016 (Bristol-Myers Squibb), TSR-033 (Tesaro), MK-4280 (Merck & Co), or REGN3767 (Regeneron).

Combinations with CAR Cell Therapy

In some embodiments, an anti-CD39 antibody, or antigen binding portion thereof, is combined (e.g. administered in combination) with one or more additional therapeutics, wherein the one or more additional therapeutics comprises a cell, e.g., an immune effector cell, comprising an chimeric antigen receptor (CAR). In some embodiments, the CAR comprises an extracellular antigen binding domain, a transmembrane domain, and an intracellular signaling domain. In some embodiments, the intracellular signaling domain comprises one or both of a primary signaling domain and a costimulatory domain. In some embodiments, the CAR may further comprise a leader sequence, optionally, a hinge sequence. In some embodiments, the antigen binding domain binds to a tumor antigen.

In some embodiments, the antigen binding domain comprising the CAR can be any domain that binds to an antigen of, including but not limited, to a monoclonal antibody, a polyclonal antibody, a recombinant antibody, a human antibody, a humanized antibody, and a functional fragment or portion thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain. In some embodiments, the antigen binding domain of the CAR is a scFv antibody fragment.

In some embodiments, the CAR comprises an antigen binding domain that binds to a tumor antigen selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bD-Galp(1-4)bDG1cp(1-i)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-1 IRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDG1cp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocy tomato sis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the antigen binding domain of the CAR binds to CD19. An exemplary CAR that binds to CD19 is described in US2015/0283178 (e.g., CTL019), which is incorporated herein by reference in its entirety. In some embodiments, the CD19 CAR comprises an amino acid sequence shown in US2015/0283178 or a sequence substantially identical thereto (e.g., a sequence having at least about 85%, 90%, or 95% sequence identity thereto).

In one embodiment, the CAR comprises a transmembrane domain derived from a protein selected from the group consisting of: the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

In some embodiments, the CAR comprises an intracellular signaling domain derived from a protein selected from the group consisting of: a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CDL la/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CDL ld, ITGAE, CD103, ITGAL, CDL la, LFA-1, ITGAM, CDL lb, ITGAX, CDL lc, ITGB 1, CD29, ITGB2, CD 18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

In embodiments of any of the methods and compositions described herein, the cell comprising a CAR comprises a nucleic acid encoding the CAR. In one embodiment, the nucleic acid encoding the CAR is a lentiviral vector. In one embodiment, the nucleic acid encoding the CAR is introduced into the cells by lentiviral transduction. In one embodiment, the nucleic acid encoding the CAR is an RNA, e.g., an in vitro transcribed RNA. In one embodiment, the nucleic acid encoding the CAR is introduced into the cells by electroporation.

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 2006/0121005, incorporated herein by reference.

Examples of immune effector cells include T cells, e.g., alpha/beta T cells and gamma/delta T cells, B cells, natural killer (NK) cells, natural killer T (NKT) cells, mast cells, and myeloid-derived phagocytes.

Methods of making CAR-expressing cells are described, e.g., in US 2016/0185861, incorporated herein by reference.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, an anti-CD39 antibody or an antigen-binding fragment thereof described herein can be employed in methods of detection and/or quantification of human CD39 in a biological sample. For example, CD39 has been identified as a potential diagnostic, prognostic and progression biomarker of diseases (Pulte et al., (2011) Clin Lymphoma Myeloma Leuk 11:367-372; Fan et al., (2017) Biomark Med 11:107-116; Zhao et al., (2017) Front Immunol 8:727)

Accordingly, an anti-CD39 antibody, or an antigen-binding fragment thereof, as described herein is useful to diagnose, prognose and/or determine progression of disease (e.g., cancer) in a patient.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: Methods

Antigen Preparation

CD39 antigens (recombinant CD39; R&D systems cat #4397-EN) were biotinylated using the EZ-Link Sulfo-NHS-Biotinylation Kit from Pierce. Goat F(ab')$_2$ anti-human kappa-FITC (LC-FITC), ExtrAvidin-PE (EA-PE) and Streptavidin-AF633 (SA-633) were obtained from Southern Biotech, Sigma, and Molecular Probes, respectively. Streptavidin MicroBeads and MACS LC separation columns were purchased from Miltenyi Biotec. Goat anti-human IgG-PE (Human-PE) was obtained from Southern Biotech, Primary Discovery Eight naïve human synthetic yeast libraries each of ~$10^9$ diversity were propagated as previously described (see, e.g., Y. Xu et al, Addressing polyspecificity of antibodies selected from an in vitro yeast presentation system: a FACS-based, high-throughput selection and analytical tool. *PEDS* 26.10, 663-70 (2013); WO2009036379; WO2010105256; and WO2012009568.) For the first two rounds of selection, a magnetic bead sorting technique utilizing the Miltenyi MACS system was performed, as previously described (see, e.g., Siegel et al, High efficiency recovery and epitope-specific sorting of an scFv yeast display library." *J. Immunol Methods* 286(1-2), 141-153 (2004).) Briefly, yeast cells (~$10^{10}$ cells/library) were incubated with 5 ml of 100 nM biotinylated antigen for 30 min at 30° C. in wash buffer (phosphate-buffered saline (PBS)/0.1% bovine serum albumin (BSA)). After washing once with 40 ml ice-cold wash buffer, the cell pellet was resuspended in 20 mL wash buffer, and Streptavidinr MicroBeads (500 µl) were added to the yeast and incubated for 15 min at 4° C. Next, the yeast were pelleted, resuspended in 20 mL wash buffer, and loaded onto a Miltenyi LS column. After the 20 mL were loaded, the column was washed 3 times with 3 ml wash buffer. The column was then removed from the magnetic field, and the yeast were eluted with 5 mL of growth media and then grown overnight. The following rounds of selection were performed using flow cytometry. Approximately 2×$10^7$ yeast were pelleted; washed three times with wash buffer, and incubated at 30° C. with either decreasing concentrations of biotinylated antigen (200 to 5 nM) under equilibrium conditions, 200 nM biotinylated antigens of mouse species in order to obtain species cross-reactivity, or with a poly-specificity depletion reagent (PSR) to remove non-specific antibodies from the selection. For the PSR depletion, the libraries were incubated with a 1:10 dilution of biotinylated PSR reagent as previously described (see, e.g., Y. Xu et al, Addressing polyspecificity of antibodies selected from an in vitro yeast presentation system: a FACS-based, high-throughput selection and analytical tool. *PEDS* 26.10, 663-70 (2013)) Yeast were then washed twice with wash buffer and stained with LC-FITC (diluted 1:100) and either SA-633 (diluted 1:500) or EAPE (diluted 1:50) secondary reagents for 15 min at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Light Chain Batch Shuffle

Light chain diversification protocol was used during the primary discovery, phase for further discovery and improvement of antibodies.

Light chain batch diversification protocol: Heavy chain plasmids from a naïve selection output were extracted from the yeast via smash and grab, propagated in and subsequently purified from E. coli, and transformed into a light chain library with a diversity of 5×10$^6$. Selections were performed with one round of MACS and three rounds of FACS as described in the naïve discovery. In the different FACS rounds the libraries were looked at for PSR binding, species cross-reactivity, and affinity pressure by antigen titration. Sorting was performed in order to obtain a population with the desired characteristics.

Antibody Optimization

Optimization of antibodies was performed by introducing diversities into the heavy chain variable regions as described below.

CDRH1 and CDRH2 selection: The CDRH3 of a single antibody was recombined into a premade library with CDRH1 and CDRH2 variants of a diversity of 1×10$^8$ and selections were performed with one round of MACS and four rounds of FACS as described in the naïve discovery. In the different FACS rounds the libraries were looked at for PSR binding, species cross-reactivity, and affinity pressure by titration, and sorting vas performed in order to obtain a population with the desired characteristics.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

ForteBio K$_D$ Measurements

ForteBio affinity measurements were performed on an Octet RED3.84 generally as previously described (see, e.g., Estep et al, High throughput solution-based measurement of antibody-antigen affinity and epitope binning. Mabs 5(2), 270-278 (2013)). Briefly, ForteBio affinity measurements were performed by loading IgGs on-line onto AHC sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. All kinetics were analyzed using the 1:1 binding model.

ForteBio Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

MSD-SET Kinetic Assay

Equilibrium affinity measurements performed as previously described (Estep et al., 2013). Solution equilibrium titrations (SET) were performed in PBS+0.1% IgG-Free BSA (PBSF) with antigen held constant at 10-100 pM and incubated with 3- to 5-fold serial dilutions of antibody starting at 5-100 µM (experimental condition is sample dependent). Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the K$_D$. To improve throughput, liquid handling robots were used throughout MSD-SET experiments, including SET sample preparation.

Cell Binding Analysis

Approximately 100,000 cells overexpressing the antigen were washed with wash buffer and incubated with 100 ul 100 nM IgG for 5 minutes at room temperature. Cells were then washed twice with wash buffer and incubated with 100 ul of 1:100 Human-PE for 15 minutes on ice. Cells were then washed twice with wash buffer and analyzed on a FACS Canto II analyzer (BD Biosciences).

Example 2: Effect of Anti-CD39 Antibodies on Dendritic Cells

To determine an effect of anti-CD39 antibodies on dendritic cells, the expression level of CD86, a transmembrane protein that provides a co-stimulatory signal necessary for T cell activation and survival, was determined. Monocytes from 3 healthy donors were treated with GM-CSF (50 ng/mL) (R&D Systems) and IL-4 (10 ng/mL) (R&D Systems) for 4 days at 37 C in RPMI-1640+10% FBS+1% Penicillin-streptomycin (R10) (Life Technologies) to generate immature dendritic cells. Dendritic cells were washed and resuspended in R10 supplemented with GM-CSF (50 ng/mL) and IL-4 (10 ng/mL). 5×10$^4$ dendritic cells were added to each well of a 96-well U-bottom plate. Dendritic cells were incubated with isotype control antibody or anti-CD39 antibodies (10 ug/mL), as indicated in FIG. 1A, for 1 h at 37 C. After 1 h, R10 with or without ATP supplementation was added to the cells and further incubated for 24 h. Dendritic cells were stained with antibodies against CD86 and CD11c (Biolegend). Cells were acquired using a LSR-Fortessa X-20 (BD Biosciences) and analyzed with FlowJo software (Tree Star). Quantitation of CD86 expression (GeoMean) on dendritic cells derived from each donor is shown.

As shown in FIG. 1A, treatment of dendritic cells with anti-CD39 antibodies SRF370-A, SRF367-A, SRF365-A, and SRF367-B in the presence of ATP resulted in an increase in expression of CD86 that was higher than with treatment with isotype control antibodies DNP-A and DNP-B. These results demonstrate that treatment of dendritic cells with anti-CD39 antibodies enhances the ATP-induced expression of CD86.

To further evaluate effects of anti-CD39 antibodies on dendritic cells, the expression level of both CD86 and the human leukocyte antigen-antigen D related (HLA-DR), an MEW class II cell surface receptor, was determined essentially as described above. Dendritic cells were treated with the anti-CD39 antibody SRF367-A or an isotype control antibody (DNP-A) in the presence or absence of ATP, as indicated in FIG. 1B.

Figure 1B:
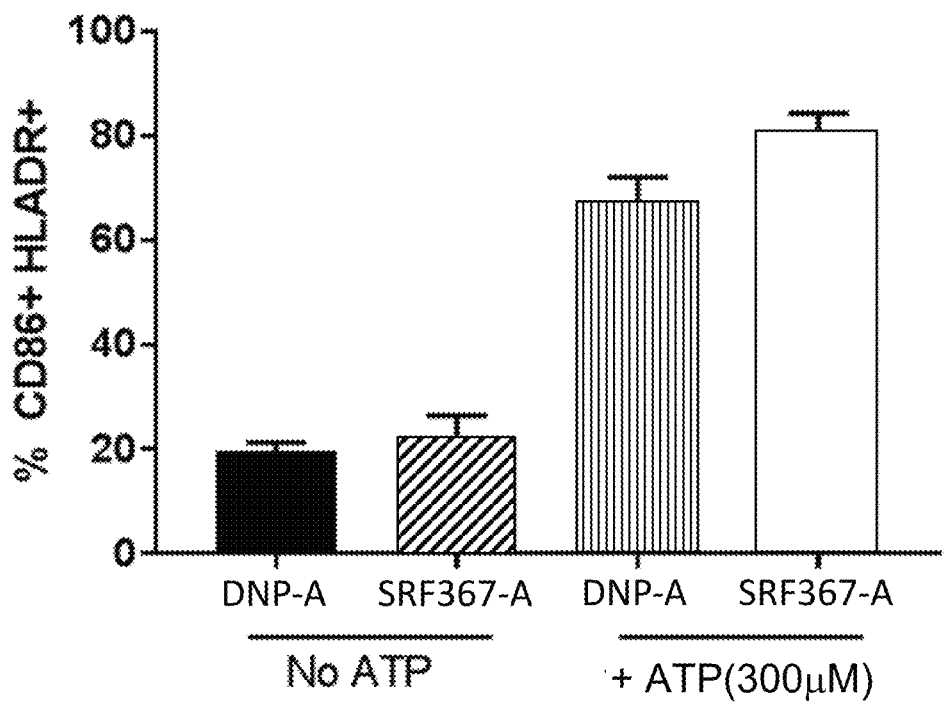
FIG. 1B provides a graph quantifying the expression of CD86 and HLA-DR on dendritic cells treated with anti-CD39 antibody or control antibody, as indicated, in the presence or absence of ATP. Expression of CD86 and HLA-DR was determined by flow cytometry analysis.

As shown in FIG. 1B, treatment of dendritic cells with the anti-CD39 antibody SRF367-A in the presence of ATP resulted in an increase in expression of HLA-DR and CD86 that was higher than with treatment with the isotype control antibody DNP-A. Consistent with the results shown in FIG. 1A, these results shown in FIG. 1B demonstrate that treatment of dendritic cells with the anti-CD39 antibody SRF367-A enhances the ATP-induced expression of CD86 and HLA-DR.

To determine the effect of anti-CD39 antibodies on cytokine secretion, the secretion of cytokines IL-16, IL-12/IL-23p40 and VEGFA from the same dendritic cells as in FIG. 1B was determined. Supernatants from treated dendritic cell cultures were diluted 1:2 and a Meso Scale Discovery (MSD) U-plex kit protocol was followed per manufacturer's instructions. Secretion of VEGF-A, IL-12/IL-23p40 and IL-16 were quantitated using MSD software according to manufacturer's instructions.

Figure 1C:
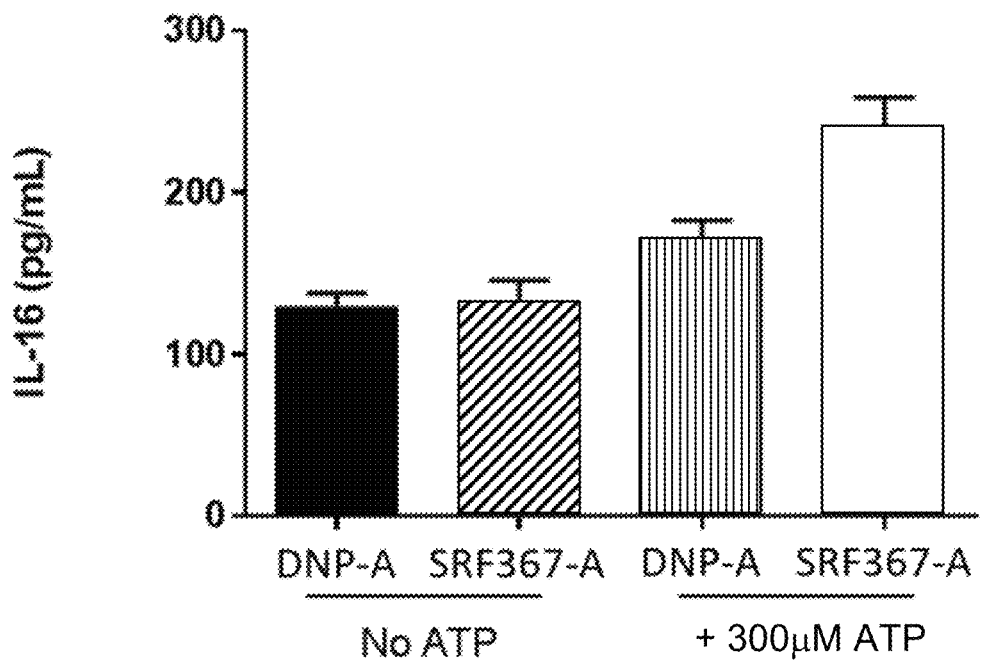
FIG. 1C provides a graph quantifying the secretion of cytokine IL-16 by dendritic cells treated with anti-CD39 antibody or control antibody, as indicated, in the presence or absence of ATP. Quantification of IL-16 was determined by MSD.
Figure 1D:
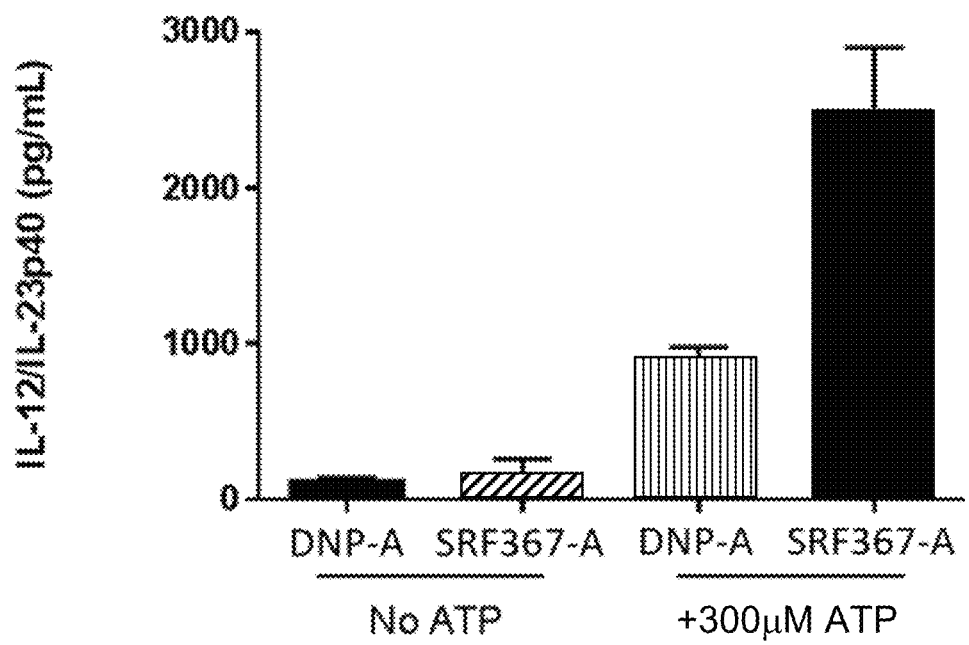
FIG. 1D provides a graph quantifying the secretion of cytokine IL-12/IL-23p40 by dendritic cells treated with anti-CD39 antibody or control antibody, as indicated, in the presence or absence of ATP. Quantification of IL-12/IL-23p40 was determined by MSD.
Figure 1E:
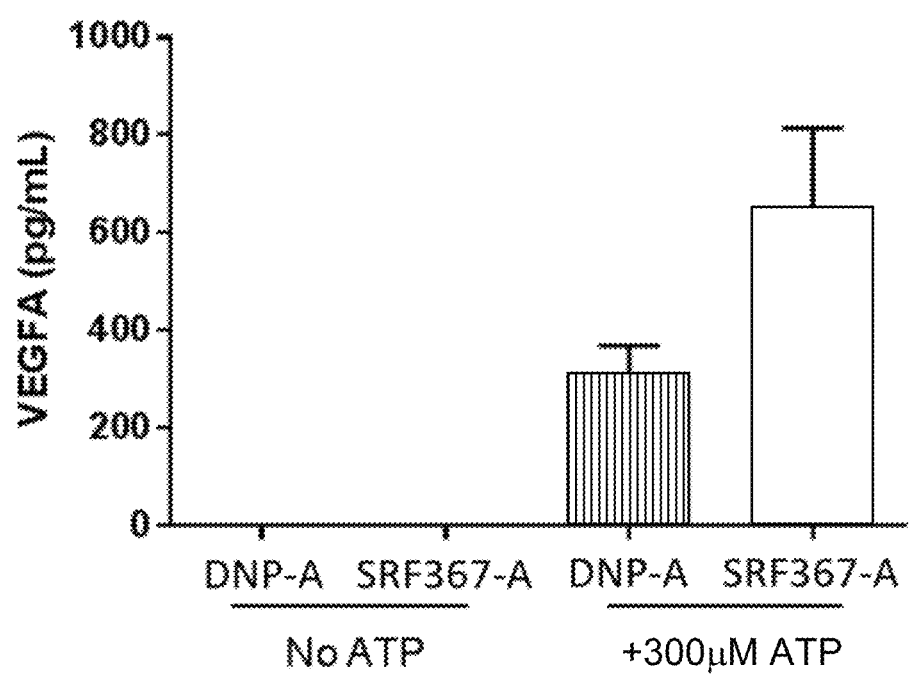
FIG. 1E provides a graph quantifying the secretion of cytokine VEGFA by dendritic cells treated with anti-CD39 antibody or control antibody, as indicated, in the presence or absence of ATP. Quantification of VEGFA was determined by MSD.

As shown in FIGS. 1C, 1D, and 1E, treatment of dendritic cells with the anti-CD39 antibody SRF367-A in the presence of ATP resulted in an increase in secretion of IL-16 (FIG. 1C), IL-12/IL-23p40 (FIG. 1D) and IL-16 (FIG. 1E) that was higher than with treatment with the isotype control antibody DNP-A. These results shown in FIGS. 1C, 1D, and 1E demonstrate that treatment of dendritic cells with the anti-CD39 antibody SRF367-A enhances the ATP-induced secretion of cytokines IL-16, IL-12/IL-23p40 and VEGFA, respectively.

Example 3: Effect of Anti-CD39 Antibodies on CD4+ T Cell Proliferation

Figure 2:
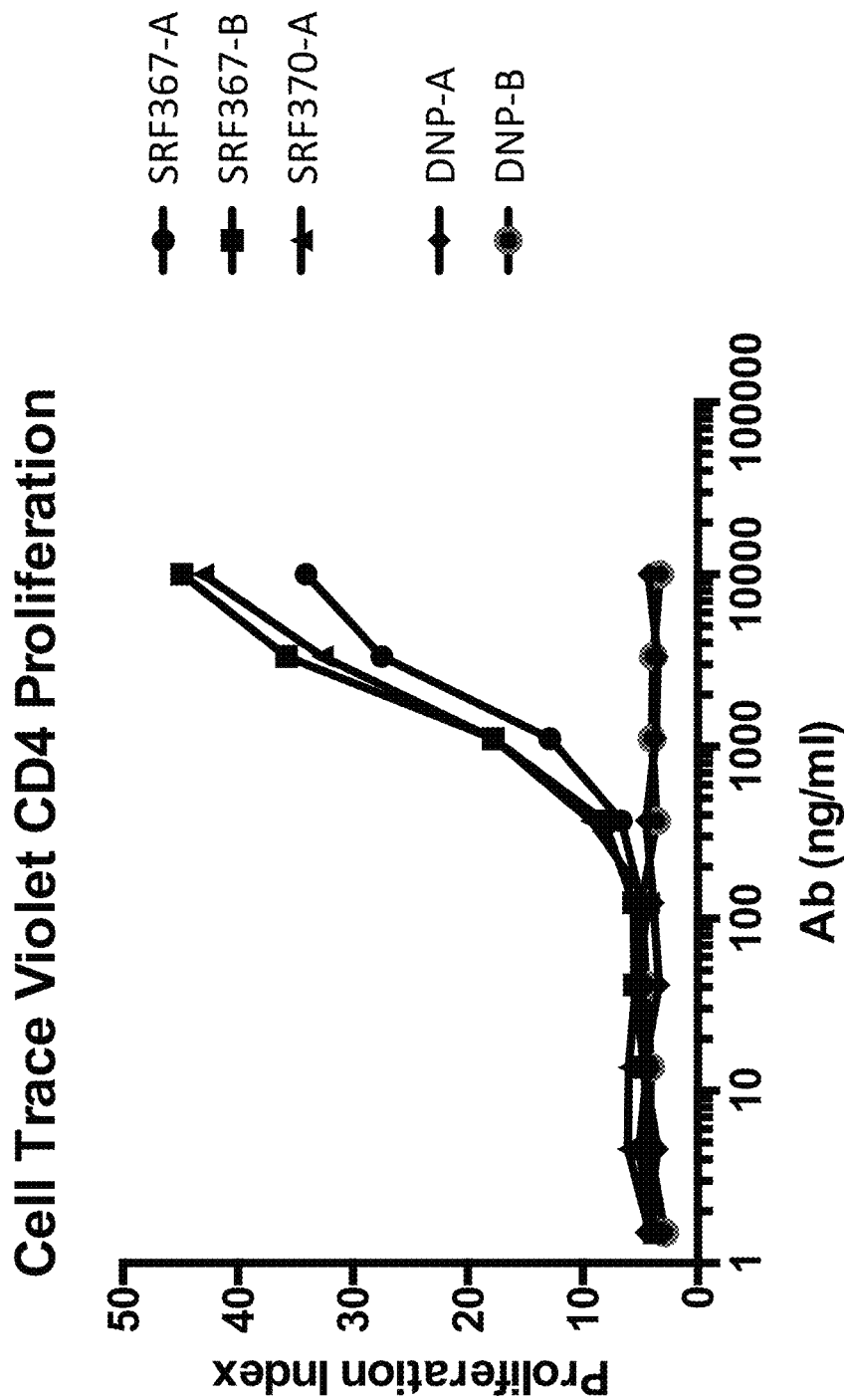
FIG. 2 provides a graph depicting the proliferation index of CD4+ T cells treated with anti-CD39 antibodies or control antibodies, as indicated, in the presence of ATP. Cells were stained with cell trace violet and proliferation was determined by flow cytometry analysis.

To determine an effect of treatment with anti-CD39 antibodies on CD4+ T cells, the amount of proliferation of CD4+ T cells in vitro in response to treatment with a range of concentrations of anti-CD39 antibodies (SRF367-A, SRF367-B, and SRF370-A) or isotype control antibodies (DNP-A and DNP-B) was determined. CD4+ cells from freshly PBMCs from human donor blood were stained with cell trace violet stain prior to seeding in 96-well plates. Cells were incubated with 250 µM ATP, anti-CD3/CD28 beads to stimulate the T-cells, and anti-CD39 or isotype control antibodies, as indicated in FIG. 2, for 3 days, and the proliferation index for each antibody treatment was quantitated by flow cytometry by measuring the amount of cell trace violet remaining in the cells. Cells were also stained for CD4 to confirm T-cell lineage. As shown in FIG. 2, the proliferation index of CD4+ T-cells in response to ATP is increased in the presence of anti-CD39 antibodies.

Example 4: Effect of Anti-CD39 Antibodies on CD39 Activity on Malignant and Immune Cells CD39 is a membrane bound ectonucleosidase that converts adenosine triphosphate (ATP) and adenosine diphosphate (ADP) to adenosine monophosphate (AMP). The ability of anti-CD39 antibodies to inhibit the enzymatic activity of CD39 on malignant cell lines and primary immune cells was measured using a malachite green phosphate assay. Briefly, cells were treated for 60 min. with anti-CD39 antibodies or control antibody and 25 µM ATP. Release of inorganic phosphate from ATP was measured using a malachite green phosphate assay kit (Enzo Life Sciences, Catalog # BML-AK111). Normalized percent inhibition (% INH) was determined using 'time zero control' to represent 100% inhibition and a 'no antibody control' to represent 0% INH. The 'time zero control' is a well with all of the reagents where the reaction is stopped immediately to mimic conditions where no phosphate is generated and CD39 is completely inhibited. The 'no antibody control' is a well where all of the reagents and cells are added but no antibodies are present. This well mimics conditions where the maximal amount of phosphate is released and there is no inhibition of CD39. To determine percent inhibition: the 'no antibody control' value is subtracted from the assay value and divided by the 'no antibody control' value subtracted from the 'time zero control' value. The resulting value is multiplied by 100 to give a percentage value. MOLP-8 (human multiple myeloma cell line), SK-MEL-28, primary human B cells (isolated from whole blood), or primary human monocytes (isolated from whole blood) were used in this assay.

Figure 3A:
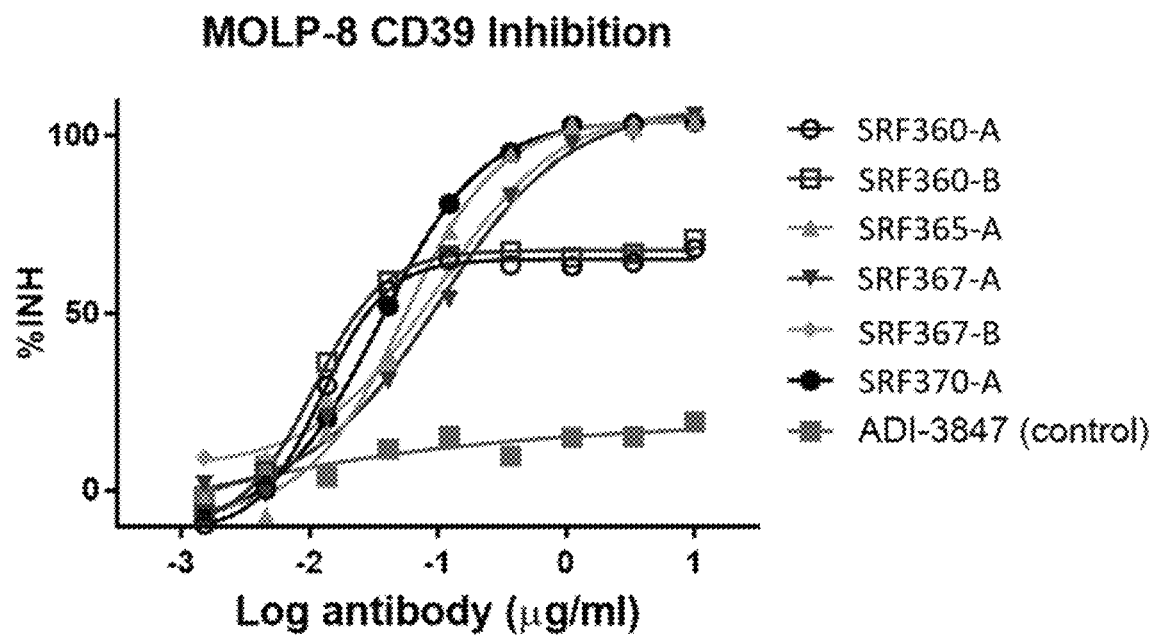
FIG. 3A provides a graph depicting the percent inhibition of CD39 activity on the surface of MOLP-8 cells treated with a range of concentrations of anti-CD39 antibodies or control antibodies, as indicated. Inhibition of ATP conversion was determined by a malachite green phosphate assay.

As shown in FIG. 3A, treatment of MOLP-8 cells (a human multiple myeloma cell line) with a range of concentrations of anti-CD39 antibodies (SRF360-A, SRF360-B, SRF365-A, SRF367-A, SRF367-B, and SRF370-A) or a control antibody, as indicated, in the presence of ATP resulted in a dose-dependent inhibition of CD39 activity by all anti-CD39 antibodies tested. Inhibition of CD39 activity was determined by the extent of inorganic phosphate released and expressed as % inhibition (% INH).

Figure 3B:
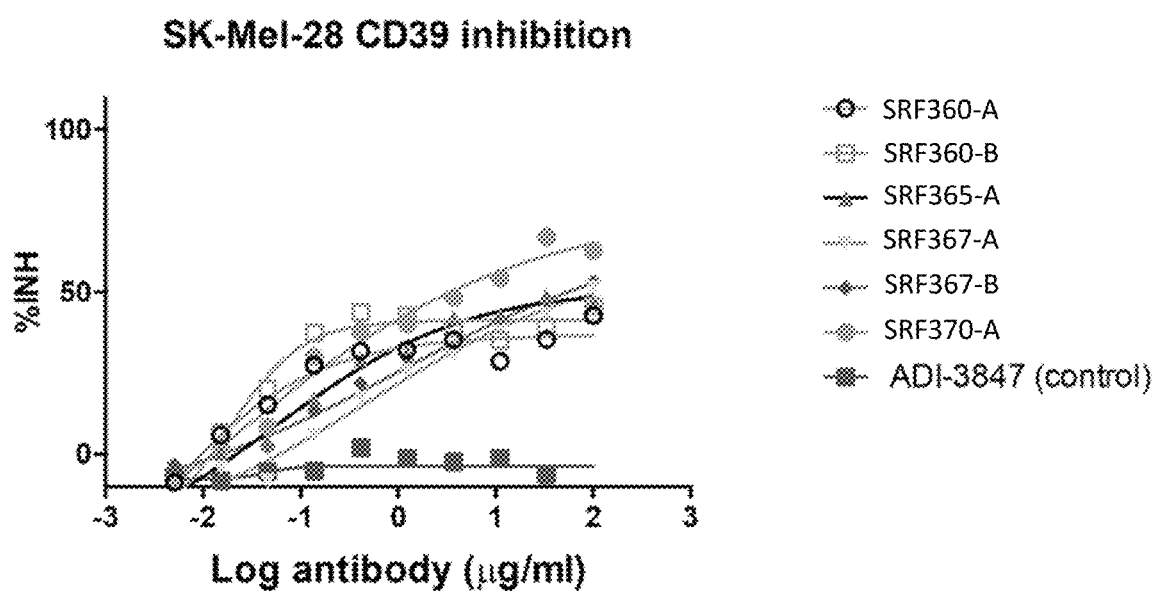
FIG. 3B provides a graph depicting the percent inhibition of CD39 activity on the surface of human SK-MEL-28 cells treated with a range of concentrations of anti-CD39 antibodies or control antibodies, as indicated. Inhibition of ATP conversion was determined by a malachite green phosphate assay.

As shown in FIG. 3B, treatment of SK-MEL-28 cells (a human melanoma cell line) with a range of concentrations of anti-CD39 antibodies (SRF360-A, SRF360-B, SRF365-A, SRF367-A, SRF367-B, and SRF370-A) or a control antibody, as indicated, in the presence of ATP resulted in a dose-dependent inhibition of CD39 activity by all anti-CD39 antibodies tested, consistent with the results shown in FIG. 3A. Inhibition of CD39 activity was determined by the extent of inorganic phosphate released and expressed as % inhibition (% INH).

Figure 3C:
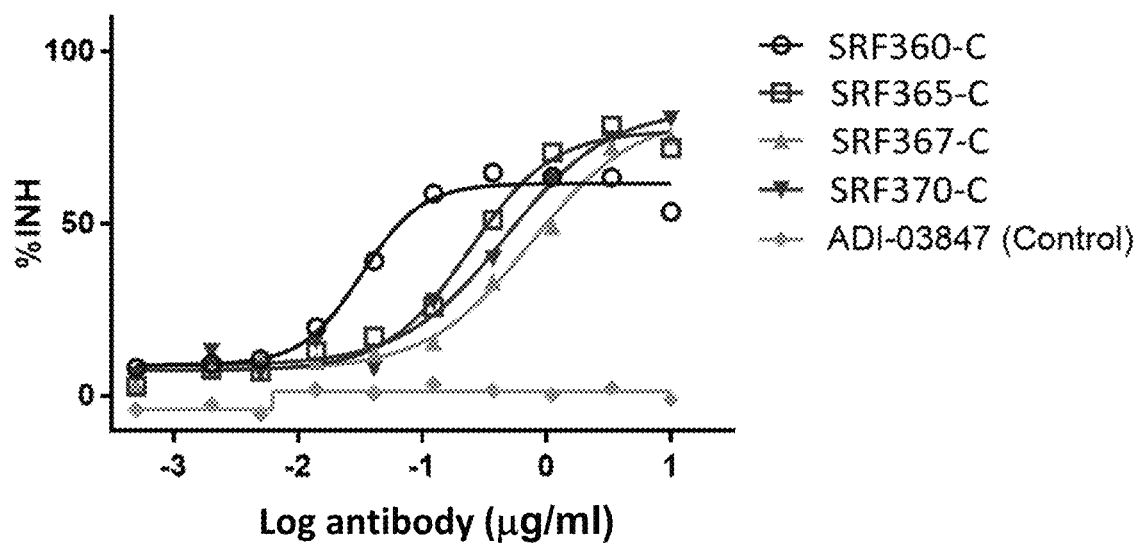
FIG. 3C provides a graph depicting the percent inhibition of CD39 activity on the surface of primary human B cells treated with a range of concentrations of anti-CD39 antibodies or control antibodies, as indicated. Inhibition of ATP conversion was determined by a malachite green phosphate assay.

As shown in FIG. 3C, treatment of primary human B cells isolated from whole blood with a range of concentrations of anti-CD39 antibodies (SRF360-C, SRF365-C, SRF367-C and SRF370-C) or a control antibody, as indicated, in the presence of ATP resulted in a dose-dependent inhibition of CD39 activity by all anti-CD39 antibodies tested, consistent with the results seen in FIGS. 3A and 3B. Inhibition of CD39 activity was determined by the extent of inorganic phosphate released and expressed as % inhibition (% INH).

Figure 3D:
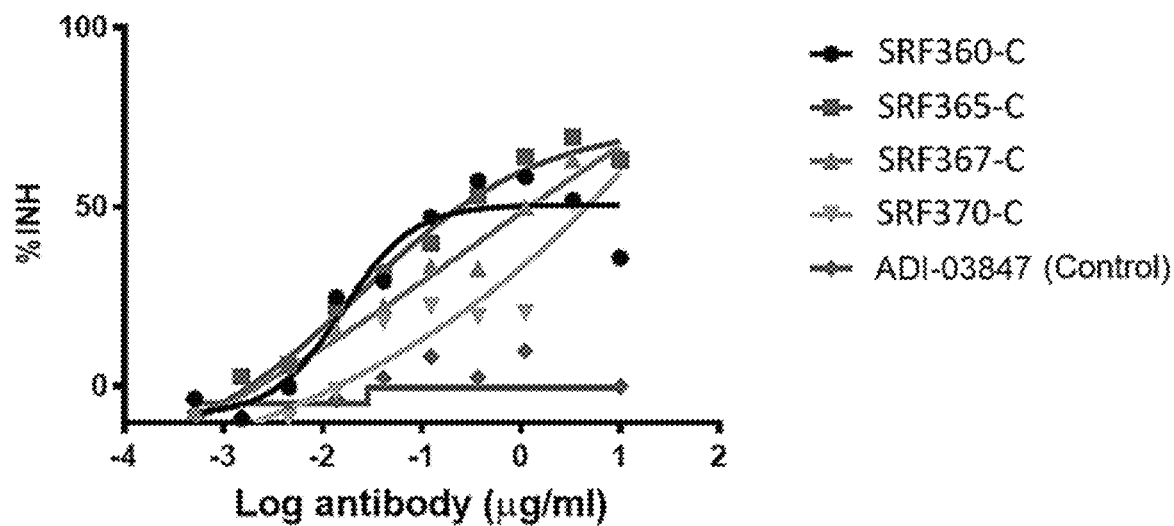
FIG. 3D provides a graph depicting the percent inhibition of CD39 activity on the surface of primary human monocytes treated with a range of concentrations of anti-CD39 antibodies or control antibodies, as indicated. Inhibition of ATP conversion was determined by a malachite green phosphate assay.

As shown in FIG. 3D, treatment of primary human monocytes isolated from whole blood with a range of concentrations of anti-CD39 antibodies (SRF360-C, SRF365-C, SRF367-C and SRF370-C) or a control antibody, as indicated, in the presence of ATP resulted in a dose-dependent inhibition of CD39 activity by all anti-CD39 antibodies tested, consistent with to results seen in FIGS. 3A and 3B. Inhibition of CD39 activity was determined by the extent of inorganic phosphate released and expressed as % inhibition (% INH).

Taken together, these results demonstrate that treatment of malignant and immune cells with anti-CD39 antibodies inhibits CD39 enzymatic activity.

Example 5: Anti-CD39 Antibodies Bind to Human Cancer Cells

Figure 4A:
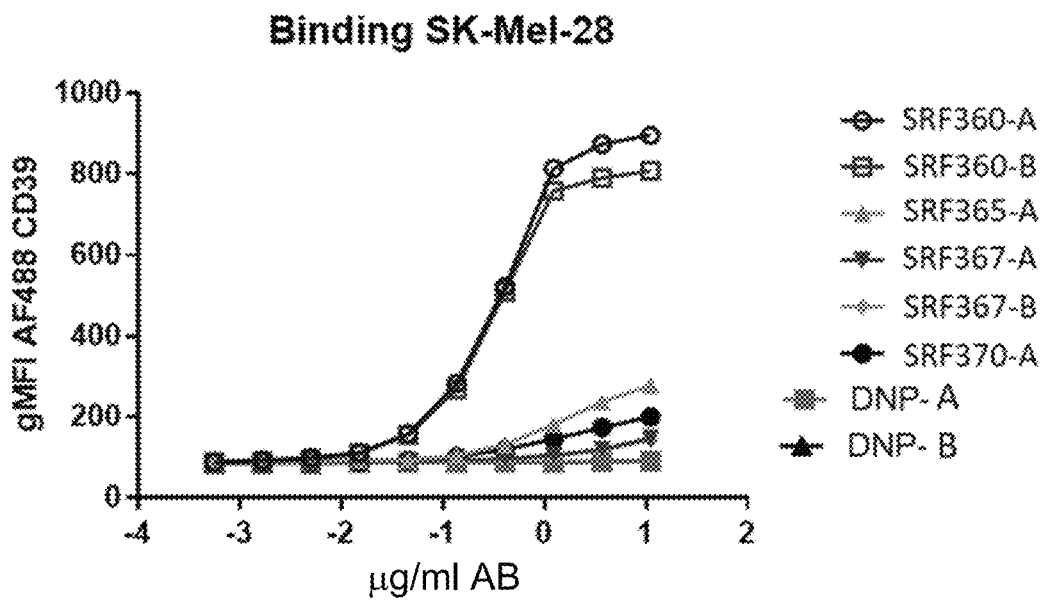
FIG. 4A provides a graph depicting the extent of anti-CD39 antibody binding or control antibody binding to the surface of SK-MEL-28 cells. Cells were treated with a range of concentrations of fluorescently-labeled anti-CD39 antibodies or control antibodies, as indicated. Extent of antibody binding was determined by flow cytometry analysis.
Figure 4B:
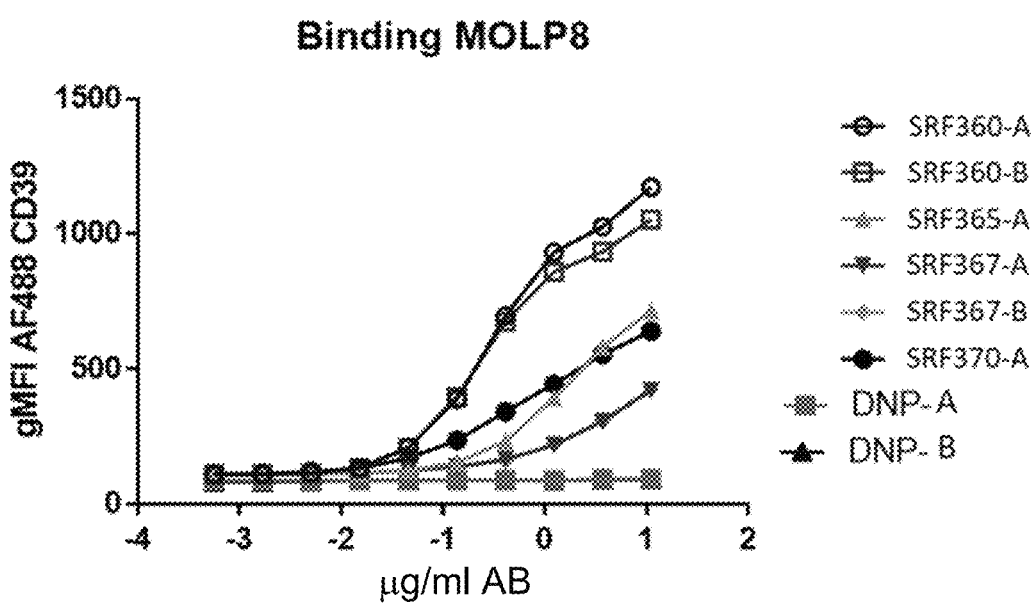
FIG. 4B provides a graph depicting the extent of anti-CD39 antibody binding or control antibody binding to the surface of MOLP-8 cells. Cells were treated with a range of concentrations of fluorescently-labeled anti-CD39 antibodies or control antibodies, as indicated. Extent of antibody binding was determined by flow cytometry analysis.

To determine the relative extent of binding of anti-CD39 antibodies to cells, MOLP-8 or SK-MEL-28 cells were treated with a range of concentrations of fluorescently-labeled anti-CD39 antibodies (SRF360-A, SRF360-B, SRF365-A, SRF367-A, SRF367-B, and SRF370-A) or isotype control antibodies (DNP-A and DNP-B), as indicated in FIGS. 4A and 4B. The extent of binding to cells was determined and expressed as mean fluorescent intensity (MFI). Cells were washed with FACS Buffer (2 mM EDTA, 2% FBS) and pelleted by centrifugation. The cells were resuspended in FACS buffer containing a dose range of anti-CD39 or isotype control antibodies directly labelled with fluorophore Alexa Fluor 488 (AF488) and incubated for 30 minutes at room temperature. Cells were then washed twice with FACS buffer followed by fixation in 4% paraformaldehyde (PFA) and resuspended in FACS buffer and analyzed on a FACS Canto II analyzer (BD Biosciences).

As shown in FIG. 4A, the anti-CD39 antibodies SRF360-A and SRF360-B bound to SK-MEL-28 cells in a dose-dependent manner. Anti-CD39 antibodies SRF365-A, SRF367-A, SRF367-B, and SRF370-A bound to SK-MEL-28 to a lesser extent relative to SRF360-A and SRF360-B, but to a greater extent relative to the isotype control antibodies. As shown in FIG. 4B, the anti-CD39 antibodies SRF360-A and SRF360-B bound to MOLP-8 cells in a dose-dependent manner. Anti-CD39 antibodies SRF365-A, SRF367-A, SRF367-B, and SRF370-A bound to SK-MEL-28 to a lesser extent relative to SRF360-A and SRF360-B, but to a greater extent relative to the isotype control antibodies, consistent with the results shown in FIG. 4A.

Example 6: Efficacy of Anti-CD39 Antibodies in Tumor-Bearing Mice

Figure 5A:
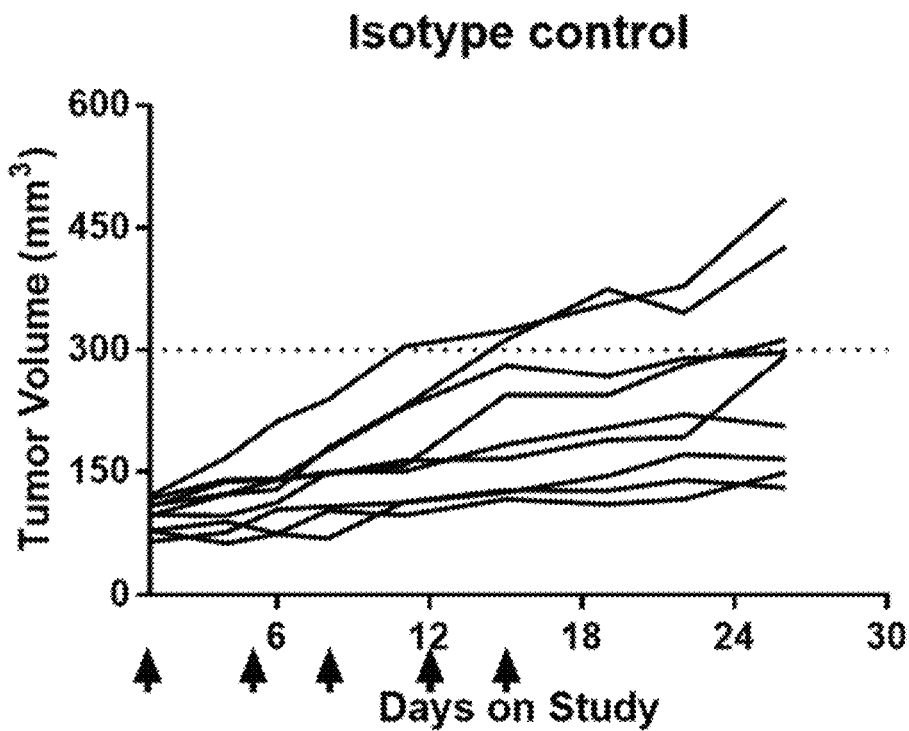
FIG. 5A provides a graph depicting tumor volume measurements in mice implanted with SK-MEL-28 cells and treated with an isotype control antibody.
Figure 5B:
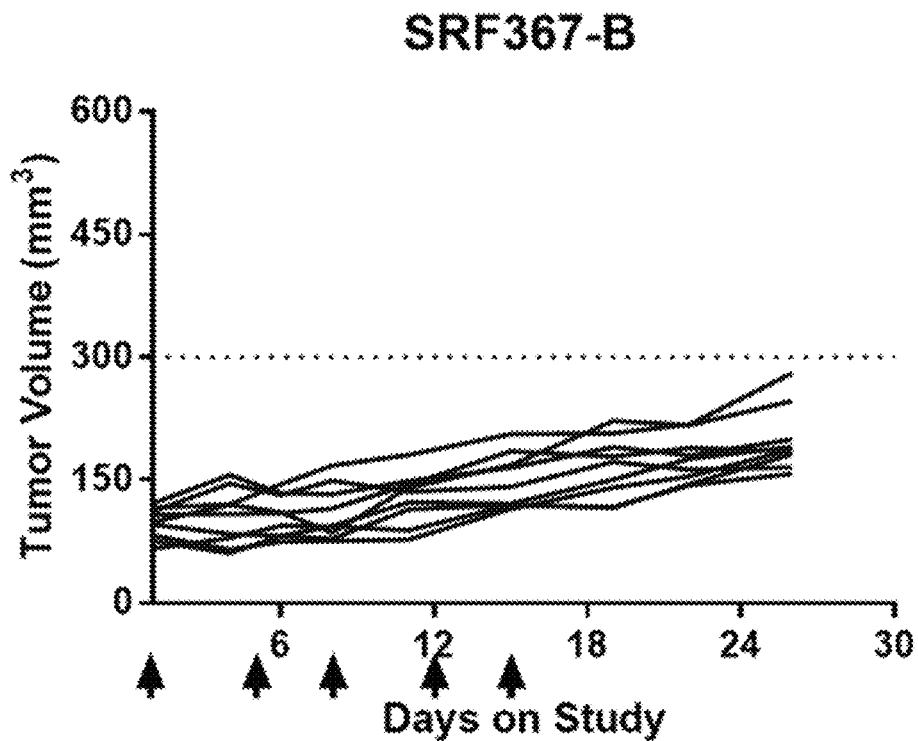
FIG. 5B provides a graph depicting tumor volume measurements in mice implanted with SK-MEL-28 cells and treated with an anti-CD39 antibody, as indicated.

Given the effects of anti-CD39 antibodies on malignant and immune cells in vitro, as shown in Examples 1-4, anti-CD39 antibodies were tested for anti-tumor activity against established tumors in vivo. Mice bearing SK-MEL-28 tumors were treated with either SRF367-B or an isotype control antibody, as indicated in FIGS. 5A and 5B, and tumor growth was measured. The SK-MEL-28 human xenograft model was chosen because it expresses high amounts of CD39. CB17SCID mice (n=9 per group) (Charles River Labs) were implanted s.c. in the right flank with 5×106 SK-MEL-28 tumor cells in 50% Matrigel (Thermo Fisher). Tumor xenografts were measured three times weekly by measuring perpendicular tumor diameters (mm) and tumor volumes were calculated using the equation V=((L×W×W)× 0.52) where V is the tumor volume (mm3), L is the long diameter, and W is the short diameter. When the SK-MEL-28 tumors reached an average size of 100 mm3 the animals were divided into two groups of 9 mice for dosing with either SRF367-B or polyclonal human IgG isotype control antibody. All antibodies were dosed intraperitoneally (i.p.) at 400 µg/mouse BIW in 100 µl of PBS for a total of 5 injections (Days 1, 5, 8, 12, and 15).

The average growth rate of SK-MEL-28 tumors from mice treated with SRF367-B (FIG. 5B) was consistently slower compared to tumors from animals treated with the isotype control (FIG. 5A). These results demonstrate treatment of tumor-bearing mice with the anti-CD39 antibody delays the growth of established CD39-expressing human xenograft tumors.

Example 7: Effect of Anti-PD-1 Antibody on CD39 Expression in Human PBMCs

Figure 6:
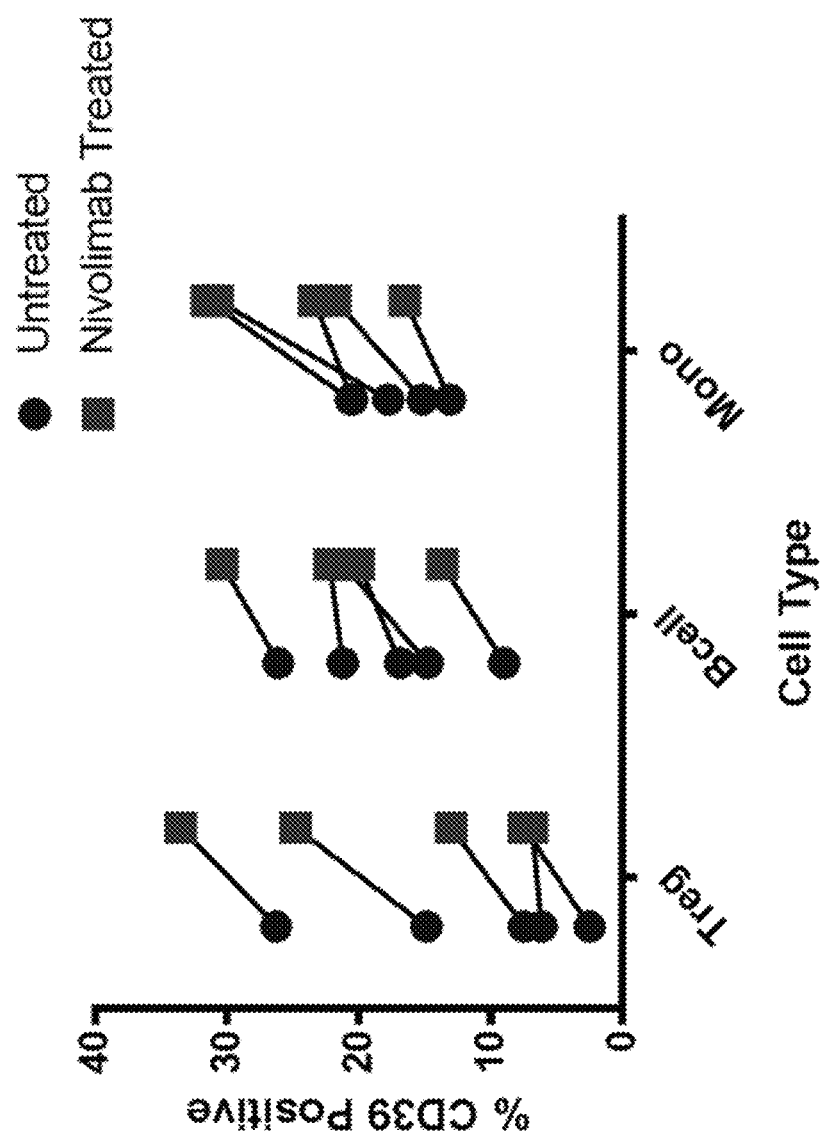
FIG. 6 provides a graph depicting the effect of Nivolumab treatment on the expression of CD39 on immune cells from 5 human donors, as determined by flow cytometry analysis. A line connects donor matched untreated to Nivolumab-treated CD39 levels in 3 different immune cell types.

To determine the effect of PD-1 inhibition on CD39 expression in PBMC derived immune cell populations, PBMCs were isolated from the whole blood of 5 separate human donors. The PBMCs were incubated in complete cell culture media (10% FBS, RPMI or complete cell culture media supplemented with 10 ug/ml anti-PD-1 antibody Nivolumab) for 96 hours. Cells were washed, stained and fixed for flow cytometry analysis to determine the percentage of CD39 positive cells. Lineage markers were used to discriminate Tregs (CD3, CD4 and FoxP3); Monocytes (CD14); and, B-cells (CD19). As shown in FIG. 6, CD39 expression increased across all cell types, across all donors in the presence of Nivolumab, indicating that treatment with an anti-PD-1 antibody increases the expression of CD39 on human cells. Thus, increased expression of CD39 in subjects treated with anti-PD1 (or anti-PD-L1) may be the mechanism by which subjects become resistant to anti-PD1 therapy. Treatment of these subjects with anti-CD39 antibodies disclosed herein is provided.

Example 8: Distribution of Binding Affinities of Anti-CD39 Antibodies

The binding affinities of anti-CD39 antibodies (SRF360, SRF365, SRF367, SRF370, SRF399) were determined by measuring their kinetic constants ($k_a$, $k_d$, $K_D$) using a ForteBio Octet RED384 (Pall Forte Bio Corporation, Menlo Park, Calif.) generally as previously described (Estep et al. (2013) Mabs 5(2):270-278, which is incorporated herein by reference in its entirety).

Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 minutes for off-rate measurement. All kinetics were analyzed using the 1:1 binding model. Carrier free human CD39-His lacking transmembrane domains was used as the antigen (R&D Systems Cat: 4397-EN-010).

Equilibrium affinity measurements performed as previously described (Estep et al., (2013) Mabs 5(2):270-278). Solution equilibrium titrations (SET) were performed in PBS+0.1% IgG-Free BSA (PBSF) with antigen held constant at 10-100 pM and incubated with 3- to 5-fold serial dilutions of antibody starting at 5-100 nM (experimental conditions are sample dependent). Antibodies (20 nM in PBS) were coated onto standard-bind MSD-ECL plates overnight at 4° C. or at room temperature for 30 minutes. Plates were then blocked for 30 min with shaking at 700 rpm, followed by three washes with wash buffer (PBSF+ 0.05% Tween 20). SET samples were applied and incubated on the plates for 150 seconds with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Graphpad Prism and fit to a quadratic equation to extract the KD. To improve throughput, liquid handling robots were used throughout MSD-SET experiments, including SET sample preparation. Carrier free human CD39-His lacking transmembrane domains was biotinylated and used as the antigen (R&D Systems Cat: 4397-EN-010). Fortebio and MSD affinity measurements for the anti-CD39 antibodies are provided in FIG. 7.

Example 9: Synergistic Effect of Anti-CD39 Antibody and Doxorubicin in a MOLP-8 Murine Model of Human Multiple Myeloma To determine the anti-tumor effect(s) of combining CD39 inhibition with an immunogenic cell death agent, the anti-CD39 antibody SRF367-A in combination with doxorubicin was evaluated in a subcutaneous xenograft MOLP-8 human multiple myeloma model in severe combined immunodeficient (SCID) mice. Briefly, 6-8 week-old SCID mice (Charles River Labs) were inoculated by subcutaneous injection into right flank with 1×107 MOLP-8 tumor cells in 0.1 mL of PBS mixed with Matrigel (1:1) and randomized into 4 treatment groups when tumors reached a mean volume of approximately 100 mm3. The groups (n=10 mice each) were treated intraperitoneally (i.p) with an isotype control antibody (DNP-A), an anti-CD39 antibody (SRF367-A) alone (400 µg or 20 mg/kg) twice a week for 3 weeks, Aldoxorubicin alone (a doxorubicin prodrug that releases free doxorubicin in the tumor environment) (200 µg or 10 mg/kg) once a week for 3 weeks or both SRF367-A and Aldoxorubicin in combination. All antibodies tested were formulated in PBS (Gibco). Aldoxorubicin stock solution (100 mg/mL) was prepared in DMSO and diluted to 1 mg/mL in PBS. Anti-tumor activity was determined, in part, by measuring tumor size (length and width) using a Vernier caliper and tumor volume was calculated using the following formula: (L*W*W)/2. Body weight (data not shown) and tumor volumes were determined twice weekly until day 19. For tumor volume analysis, a one-way Anova analysis was performed to test statistical significance for each group compared to control (p<0.005).

Figure 8A:
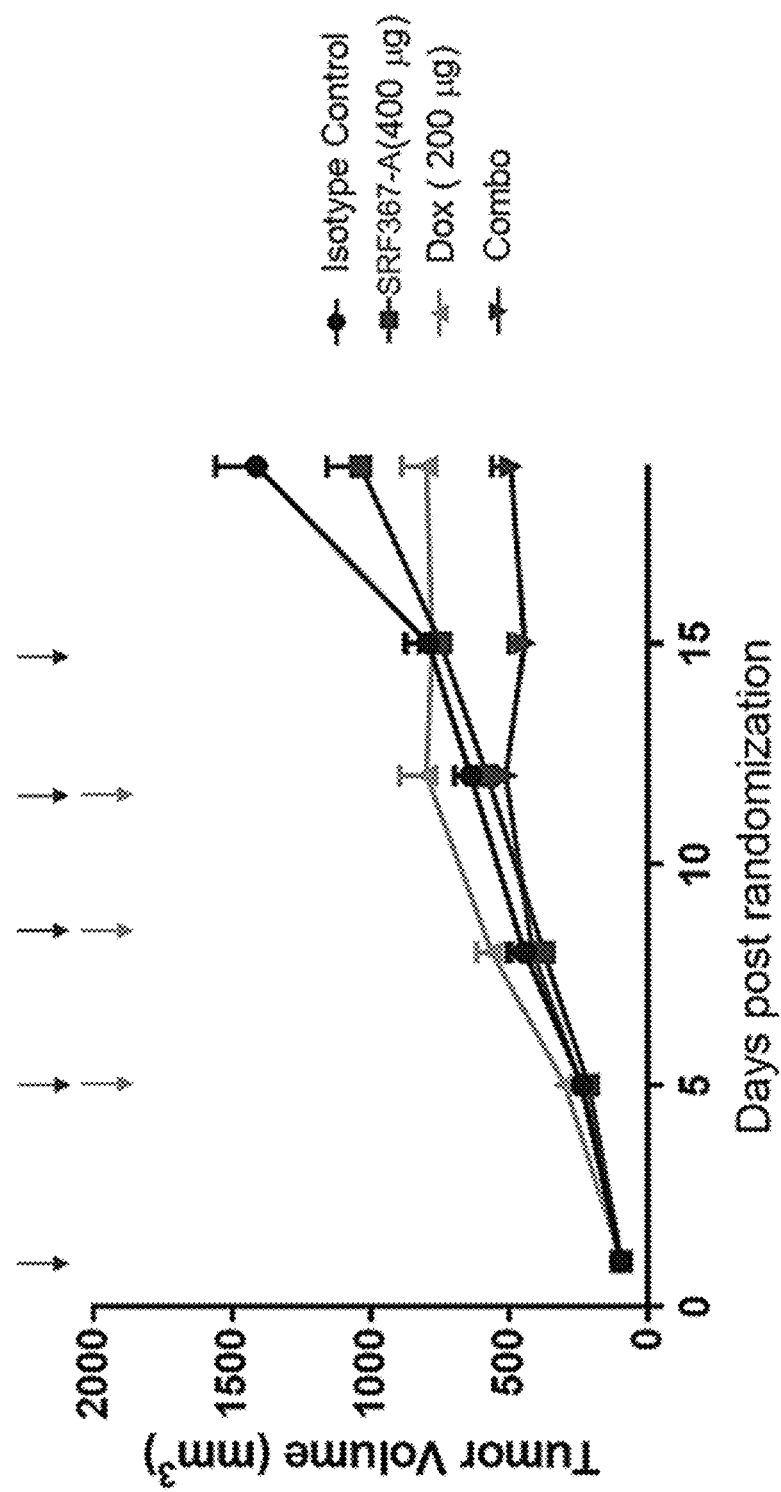
FIG. 8A provides a graph depicting tumor volume measurements over time in mice implanted with MOLP-8 human multiple myeloma cells and treated with an anti-CD39 antibody (SRF367-A) alone or in combination with the anthracycline doxorubicin (Dox), as indicated. Black arrows indicate treatment with antibody. Grey arrows indicate treatment with doxorubicin. Mice treated with an isotype control antibody or with doxorubicin alone were used as comparators.
Figure 8B:
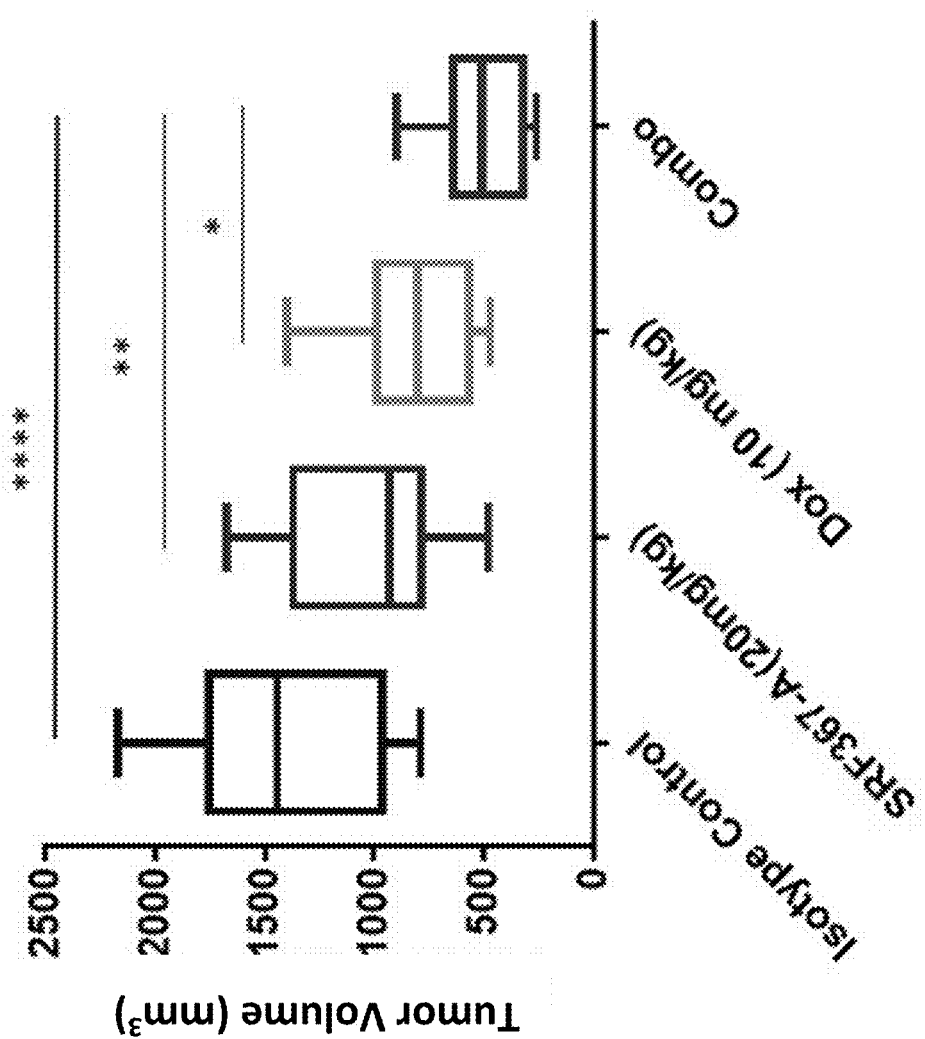
FIG. 8B provides a graph depicting mean tumor volumes of mice treated as in FIG. 8A on day 19.

FIG. 8A shows mean tumor volumes in mice over time following treatment as indicated. Black arrows indicate treatment with SRF367-A and grey arrows indicate treatment with Aldoxorubicin. FIG. 8B shows the mean tumor volumes in mice on day 19 following treatment as indicated.

Treatment with the anti-CD39 antibody SRF367-A, either alone or in combination with doxorubicin, demonstrated a statistically significant reduction in tumor volume compared to treatment with the isotype control antibody DNP-A on day 19, as shown in FIG. 8B (p<0.005). Some body weight loss was observed after 3 doses in the doxorubicin alone arm but no significant loss in body weight was observed in the combo arm compared to doxorubicin alone and anti-CD39 antibody treatment alone did not cause any loss in body weight (data not shown).

These data demonstrate that treatment with an anti-CD39 antibody in combination with doxorubicin results in a synergistic anti-tumor effect, reducing tumor volume to a greater extent when compared to treatment with either the anti-CD39 antibody or doxorubicin alone.

Example 10: Synergistic Effect of Anti-CD39 Antibody and Adenosine A2A Receptor (A2AR) Antagonist in a MOLP-8 Xenograft Model of Human Multiple Myeloma To determine the anti-tumor effect(s) of combining CD39 inhibition with another agent that blocks the adenosine pathway, the anti-tumor activity of the anti-CD39 antibody SRF367-A in combination with the A2AR antagonist CPI-444 was evaluated in a subcutaneous xenograft MOLP-8 human multiple myeloma model in severe combined immunodeficient (SCID) mice. Briefly, 6-8-week-old SCID mice (Charles River Labs) were inoculated by subcutaneous injection into right flank with 1×107 MOLP-8 tumor cells in 0.1 mL of PBS mixed with Matrigel (1:1) and randomized into 4 treatment groups when tumors reached a mean volume of approximately 100 mm3. The groups (n=8 mice each) were treated intraperitoneally (i.p) with isotype control (DNP-A), anti-CD39 antibody alone (400 µg or 20 mg/kg) twice a week for 3 weeks or in combination with CPI-444. CPI-444 was administered orally at dose of 100 mg/kg 5 days a week for 3 weeks. All antibodies tested were formulated in PBS (Gibco). CPI-444 stock solution (10 mg/ml) was prepared in 40% hydroxypropyl b-cyclodextrin in 0.1 N hydrochloric acid, mixed on a stirrer plate, and filtered through a 0.45-mm filter. The solution was adjusted with 1.0 N sodium hydroxide and 1.0 mol/L citric acid to pH 3-4. Anti-tumor activity was determined, in part, by measuring tumor size (length and width) using a Vernier caliper and tumor volume was calculated using the following formula: (L*W*W)/2. Body weight (data not shown) and tumor volumes were determined thrice weekly until day 28. For tumor volume analysis, a one-way Anova was performed to test statistical significance for each group compared to control and to the single agent alone treatment arms. (p<0.005).

Figure 9:
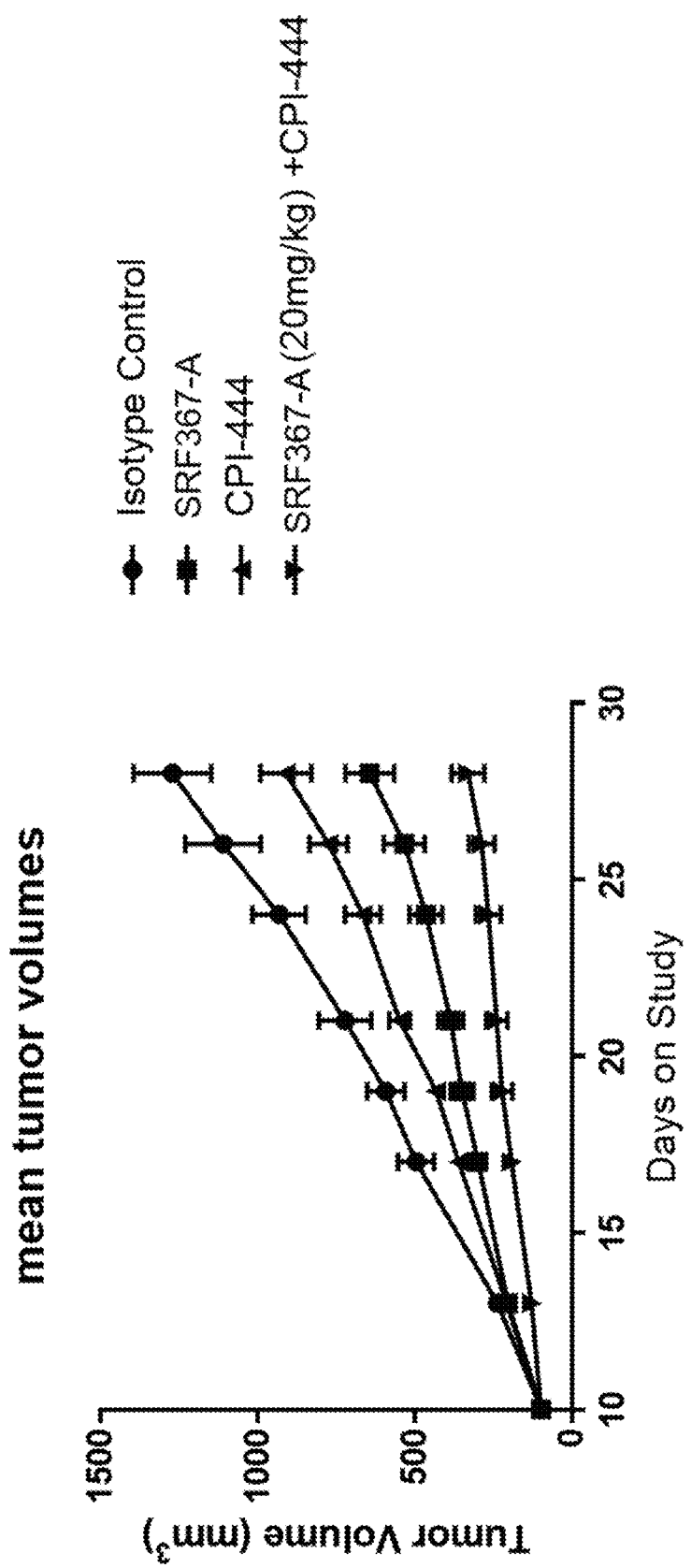
FIG. 9 provides a graph depicting tumor volume measurements over time in mice implanted with MOLP-8 human multiple myeloma cells and treated with an anti-CD39 antibody (SRF367-A) alone or in combination with an adenosine A2A receptor (A2AR) antagonist (CPI-444) as indicated. Mice treated with an isotype control antibody or with CPI-444 alone were used as comparators.

Mean tumor volumes of treated mice are shown in FIG. 9. These data indicate that treatment with an anti-CD39 antibody (SRF367-A) in combination with an A2AR antagonist (CPI-444) leads to a synergistic anti-tumor effect, reducing tumor volume when compared to treatment with either an anti-CD39 antibody or CPI-444 alone. Treatment with all test agents (anti-CD39 antibody and CPI-444), alone or in combination, demonstrated statistically significant anti-tumor efficacy compared to isotype control (p<0.005). Some body weight loss was observed after one week of dosing in the CPI-444 alone arm but no significant loss in body weight was observed in the combo arm compared to CPI-444 alone and anti-CD39 antibody treatment alone did not cause any loss in body weight (data not shown).

TABLE 1

SEQUENCE LISTING
NT = non-traditional

SRF365-C

| | | | |
|---|---|---|---|
| SEQ ID NO: 1 | HCDR1 (IMGT) | GGTFSDKA | |
| SEQ ID NO: 2 | HCDR2 (IMGT) | ILPIFGTA | |
| SEQ ID NO: 3 | HCDR3 (IMGT) | AREAGYYRYRYFDL | |
| SEQ ID NO: 4 | HCDR1 (NT) | GTFSDKAIS | |

TABLE 1-continued

SEQUENCE LISTING
NT = non-traditional

| SEQ ID NO: 5 | HCDR2 (NT) | SILPIFGTANYAQKFQG |
|---|---|---|
| SEQ ID NO: 6 | HCDR3 (NT) | AREAGYYRYRYFDL |
| SEQ ID NO: 7 | VH | QVQLVQSGAEVKKPGSSVKVSCKASGGTFSDKAISWVRQAPG QGLEWMGSILPIFGTANYAQKFQGRVTITADESTSTAYMELS SLRSEDTAVYYCAREAGYYRYRYFDLWGRGTLVTVSS |
| SEQ ID NO: 8 | DNA VH | CAGGTGCAGCTGGTGCAGTCTGGGGCTGAGGTGAAGAAGCCT GGGTCCTCGGTGAAGGTCTCCTGCAAGGCTTCTGGAGGCACC TTCAGCGATAAGGCTATCAGCTGGGTGCGACAGGCCCCTGGA CAAGGGCTTGAGTGGATGGGATCGATCCTTCCTATCTTTGGT ACAGCAAACTACGCACAGAAGTTCCAGGGCAGAGTCACGATT ACCGCGGACGAATCCACGAGCACAGCCTACATGGAGCTGAGC AGCCTGAGATCTGAGGACACGGCGGTGTACTACTGCGCCAGA GAAGCCGGATACTACCGCTACCGATACTTCGACCTATGGGGG AGAGGTACCTTGGTCACCGTCTCCTCA |
| SEQ ID NO: 9 | HEAVY CHAIN | QVQLVQSGAEVKKPGSSVKVSCKASGGTFSDKAISWVRQAPG QGLEWMGSILPIFGTANYAQKFQGRVTITADESTSTAYMELS SLRSEDTAVYYCAREAGYYRYRYFDLWGRGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSRDELTKNQVSLTCLVKGFYP SDIAVEWESNGQPENNYKTTPPVLDSDGSFFLYSKLTVDKSR WQQGNVFSCSVMHEALHNHYTQKSLSLSPGK |
| SEQ ID NO: 10 | DNA HEAVY CHAIN | CAGGTGCAGCTGGTGCAGTCTGGGGCTGAGGTGAAGAAGCCT GGGTCCTCGGTGAAGGTCTCCTGCAAGGCTTCTGGAGGCACC TTCAGCGATAAGGCTATCAGCTGGGTGCGACAGGCCCCTGGA CAAGGGCTTGAGTGGATGGGATCGATCCTTCCTATCTTTGGT ACAGCAAACTACGCACAGAAGTTCCAGGGCAGAGTCACGATT ACCGCGGACGAATCCACGAGCACAGCCTACATGGAGCTGAGC AGCCTGAGATCTGAGGACACGGCGGTGTACTACTGCGCCAGA GAAGCCGGATACTACCGCTACCGATACTTCGACCTATGGGGG AGAGGTACCTTGGTCACCGTCTCCTCAGCGAGCACCAAAGGC CCGAGCGTGTTTCCGCTGGCGCCGAGCAGCAAAAGCACCAGC GGCGGCACCGCGGCGCTGGGCTGCCTGGTGAAAGATTATTTT CCGGAACCGGTGACCGTGAGCTGGAACAGCGGCGCGCTGACC AGCGGCGTGCATACCTTTCCGGCGGTGCTGCAGAGCAGCGGC CTGTATAGCCTGAGCAGCGTGGTGACCGTGCCGAGCAGCAGC CTGGGCACCCAGACCTATATTTGCAACGTGAACCATAAACCG AGCAACACCAAAGTGGATAAAAAAGTGGAACCGAAAAGCTGC GATAAAACCCATACCTGCCCGCCGTGCCCGGCGCCGGAACTG CTGGGCGGCCCGAGCGTGTTTCTGTTTCCGCCGAAACCGAAA GATACCCTGATGATTAGCCGCACCCCGGAAGTGACCTGCGTG GTGGTGGATGTGAGCCATGAAGATCCGGAAGTGAAATTTAAC TGGTATGTGGATGGCGTGGAAGTGCATAACGCGAAAACCAAA CCGCGCGAAGAACAGTATAACAGCACCTATCGCGTGGTGAGC GTGCTGACCGTGCTGCATCAGGATTGGCTGAACGGCAAAGAA TATAAATGCAAAGTGAGCAACAAAGCGCTGCCGGCGCCGATT GAAAAAACCATTAGCAAAGCGAAAGGCCAGCCGCGCGAACCG CAGGTGTATACCCTGCCGCCGAGCCGCGATGAACTGACCAAA AACCAGGTGAGCCTGACCTGCCTGGTGAAAGGCTTTTATCCG AGCGATATTGCGGTGGAATGGGAAAGCAACGGCCAGCCGGAA AACAACTATAAAACCACCCCGCCGGTGCTGGATAGCGATGGC AGCTTTTTTCTGTATAGCAAACTGACCGTGGATAAAAGCCGC TGGCAGCAGGGCAACGTGTTTAGCTGCAGCGTGATGCATGAA GCGCTGCATAACCATTATACCCAGAAAAGCCTGAGCCTGAGC CCGGGCAAA |
| SEQ ID NO: 11 | LCDR1 (IMGT) | QSVSSN |
| SEQ ID NO: 12 | LCDR2 (IMGT) | GAS |
| SEQ ID NO: 13 | LCDR3 (IMGT) | QQHALWPLT |
| SEQ ID NO: 14 | LCDR1 (NT) | RASQSVSSNLA |
| SEQ ID NO: 15 | LCDR2 (NT) | GASTRAT |
| SEQ ID NO: 16 | LCDR3 (NT) | QQHALWPLT |
| SEQ ID NO: 17 | VL | EIVMTQSPATLSVSPGERATLSCRASQSVSSNLAWYQQKPGQ APRLLIYGASTRATGIPARFSGSGSGTEFTLTISSLQSEDFA VYYCQQHALWPLTFGGGTKVEIK |
| SEQ ID NO: 18 | DNA VL | GAAATAGTGATGACGCAGTCTCCAGCCACCCTGTCTGTGTCT CCAGGGGAAAGAGCCACCCTCTCCTGCAGGGCCAGTCAGAGT |

TABLE 1-continued

SEQUENCE LISTING
NT = non-traditional

| | | |
|---|---|---|
| | | GTTAGCAGCAACTTAGCCTGGTACCAGCAGAAACCTGGCCAG
GCTCCCAGGCTCCTCATCTATGGTGCATCCACCAGGGCCACT
GGTATCCCAGCCAGGTTCAGTGGCAGTGGGTCTGGGACAGAG
TTCACTCTCACCATCAGCAGCCTGCAGTCTGAAGATTTTGCA
GTTTATTACTGTCAGCAGCACGCCCTCTGGCCTCTCACTTTT
GGCGGAGGGACCAAGGTTGAGATCAAA |
| SEQ ID NO: 19 | LIGHT CHAIN | EIVMTQSPATLSVSPGERATLSCRASQSVSSNLAWYQQKPGQ
APRLLIYGASTRATGIPARFSGSGSGTEFTLTISSLQSEDFA
VYYCQQHALWPLTFGGGTKVEIKRTVAAPSVFIFPPSDEQLK
SGTASVVCLLNNFYPREAKVQWKVDNALQSGNSQESVTEQDS
KDSTYSLSSILTLSKADYEKHKVYACEVTHQGLSSPVTKSFN
RGEC |
| SEQ ID NO: 20 | DNA LIGHT CHAIN | GAAATAGTGATGACGCAGTCTCCAGCCACCCTGTCTGTGTCT
CCAGGGGAAAGAGCCACCCTCTCCTGCAGGGCCAGTCAGAGT
GTTAGCAGCAACTTAGCCTGGTACCAGCAGAAACCTGGCCAG
GCTCCCAGGCTCCTCATCTATGGTGCATCCACCAGGGCCACT
GGTATCCCAGCCAGGTTCAGTGGCAGTGGGTCTGGGACAGAG
TTCACTCTCACCATCAGCAGCCTGCAGTCTGAAGATTTTGCA
GTTTATTACTGTCAGCAGCACGCCCTCTGGCCTCTCACTTTT
GGCGGAGGGACCAAGGTTGAGATCAAACGTACGGTGGCCGCT
CCCTCCGTGTTCATCTTCCCACCCTCCGACGAGCAGCTGAAG
TCCGGCACCGCCTCCGTCGTGTGCCTGCTGAACAACTTCTAC
CCTCGCGAGGCCAAAGTGCAGTGGAAAGTGGACAACGCCCTG
CAGTCCGGCAACTCCCAGGAATCCGTCACCGAGCAGGACTCC
AAGGACAGCACCTACTCCCTGTCCTCCACCCTGACCCTGTCC
AAGGCCGACTACGAGAAGCACAAAGTGTACGCCTGCGAAGTG
ACCCACCAGGGCCTGTCCAGCCCCGTGACCAAGTCCTTCAAC
CGGGGCGAGTGC |

SRF365-D

| | | |
|---|---|---|
| SEQ ID NO: 21 | HEAVY CHAIN | QVQLVQSGAEVKKPGSSVKVSCKASGGTFSDKAISWVRQAPG
QGLEWMGSILPIFGTANYAQKFQGRVTITADESTSTAYMELS
SLRSEDTAVYYCAREAGYYRYRYFDLWGRGTLVTVSSASTKG
PSVFPLAPCSRSTSESTAALGCLVKDYFPEPVTVSWNSGALT
SGVHTFPAVLQSSGLYSLSSVVTVPSSSLGTKTYTCNVDHKP
SNTKVDKRVESKYGPPCPSCPAPEFLGGPSVFLFPPKPKDTL
MISRTPEVTCVVVDVSQEDPEVQFNWYVDGVEVHNAKTKPRE
EQFNSTYRVVSVLTVLHQDWLNGKEYKCKVSNKGLPSSIEKT
ISKAKGQPREPQVYTLPPSQEEMTKNQVSLTCLVKGFYPSDI
AVEWESNGQPENNYKTTPPVLDSDGSFFLYSRLTVDKSRWQE
GNVFSCSVMHEALHNHYTQKSLSLSLG |
| SEQ ID NO: 22 | DNA HEAVY CHAIN | CAGGTGCAGCTGGTGCAGTCTGGGGCTGAGGTGAAGAAGCCT
GGGTCCTCGGTGAAGGTCTCCTGCAAGGCTTCTGGAGGCACC
TTCAGCGATAAGGCTATCAGCTGGGTGCGACAGGCCCCTGGA
CAAGGGCTTGAGTGGATGGGATCGATCCTTCCTATCTTTGGT
ACAGCAAACTACGCACAGAAGTTCCAGGGCAGAGTCACGATT
ACCGCGGACGAATCCACGAGCACAGCCTACATGGAGCTGAGC
AGCCTGAGATCTGAGGACACGGCGGTGTACTACTGCGCCAGA
GAAGCCGGATACTACCGCTACCGATACTTCGACCTATGGGGG
AGAGGTACCTTGGTCACCGTCTCCTCAGCTTCCACCAAGGGC
CCCTCCGTGTTCCCTCTGGCCCCTTGCTCCCGGTCCACCTCC
GAGTCTACCGCCGCTCTGGGCTGCCTCGTGAAGGACTACTTC
CCCGAGCCCGTGACCGTGTCCTGGAACTCTGGCGCCCTGACC
TCCGGCGTGCACACCTTCCCTGCCGTGCTGCAGTCCTCCGGC
CTGTACTCCCTGTCCAGCGTCGTGACCGTGCCCTCCTCCAGC
CTGGGCACCAAGACCTACACCTGTAACGTGGACCACAAGCCC
TCCAACACCAAAGTGGACAAGCGGGTGGAATCTAAGTACGGC
CCTCCCTGCCCTTCCTGCCCTGCCCCTGAGTTCCTGGGCGGA
CCTTCCGTGTTCCTGTTCCCTCCAAAGCCCAAGGACACCCTG
ATGATCTCCCGGACCCCTGAAGTGACCTGCGTGGTGGTGGAC
GTGTCCCAGGAAGATCCCGAAGTCCAGTTCAATTGGTACGTG
GACGGCGTGGAAGTGCACAACGCCAAGACCAAGCCCAGAGAG
GAACAGTTCAACTCCACCTACCGGGTGGTGTCCGTGCTGACC
GTGCTGCACCAGGACTGGCTGAACGGCAAAGAGTACAAGTGC
AAAGTGTCCAACAAGGGCCTGCCCTCCAGCATCGAAAAGACC
ATCTCCAAGGCCAAGGGCCAGCCCCGCGAGCCCCAAGTGTAC
ACCCTGCCTCCCAGCCAGGAAGAGATGACCAAGAATCAAGTG
TCCCTGACTTGTCTGGTCAAGGGCTTCTACCCCTCCGATATC
GCCGTGGAGTGGGAGTCCAACGGCCAGCCCGAGAACAACTAC
AAGACCACCCCTCCCGTGCTGGACTCCGACGGCTCCTTCTTC
CTGTACTCTCGGCTGACCGTGGACAAGTCCCGGTGGCAGGAA
GGCAACGTCTTCTCCTGCTCCGTGATGCACGAGGCCCTGCAC
AACCACTACACCCAGAAGTCCCTGTCCCTGTCTCTGGGC |

SRF365-A

| | | |
|---|---|---|
| SEQ ID NO: 23 | HEAVY CHAIN | QVQLVQSGAEVKKPGSSVKVSCKASGGTFSDKAISWVRQAPG
QGLEWMGSILPIFGTANYAQKFQGRVTITADESTSTAYMELS |

TABLE 1-continued

SEQUENCE LISTING
NT = non-traditional

| | | |
|---|---|---|
| | | SLRSEDTAVYYCAREAGYYRYRYFDLWGRGTLVTVSSASTKG
PSVFPLAPCSRSTSESTAALGCLVKDYFPEPVTVSWNSGALT
SGVHTFPAVLQSSGLYSLSSVVTVPSSSLGTKTYTCNVDHKP
SNTKVDKRVESKYGPPCPPCPAPEFLGGPSVFLFPPKPKDTL
MISRTPEVTCVVVDVSQEDPEVQFNWYVDGVEVHNAKTKPRE
EQFNSTYRVVSVLTVLHQDWLNGKEYKCKVSNKGLPSSIEKT
ISKAKGQPREPQVYTLPPSQEEMTKNQVSLTCLVKGFYPSDI
AVEWESNGQPENNYKTTPPVLDSDGSFFLYSRLTVDKSRWQE
GNVFSCSVMHEALHNHYTQKSLSLSLG |
| SEQ ID NO: 24 | DNA HEAVY CHAIN | CAGGTGCAGCTGGTGCAGTCTGGGGCTGAGGTGAAGAAGCCT
GGGTCCTCGGTGAAGGTCTCCTGCAAGGCTTCTGGAGGCACC
TTCAGCGATAAGGCTATCAGCTGGGTGCGACAGGCCCCTGGA
CAAGGGCTTGAGTGGATGGGATCGATCCTTCCTATCTTTGGT
ACAGCAAACTACGCACAGAAGTTCCAGGGCAGAGTCACGATT
ACCGCGGACGAATCCACGAGCACAGCCTACATGGAGCTGAGC
AGCCTGAGATCTGAGGACACGGCGGTGTACTACTGCGCCAGA
GAAGCCGGATACTACCGCTACCGATACTTCGACCTATGGGGG
AGAGGTACCTTGGTCACCGTCTCCTCAGCTTCCACCAAGGGC
CCCTCCGTGTTCCCTCTGGCCCCTTGCTCCCGGTCCACCTCC
GAGTCTACCGCCGCTCTGGGCTGCCTCGTGAAGGACTACTTC
CCCGAGCCCGTGACCGTGTCCTGGAACTCTGGCGCCCTGACC
TCCGGCGTGCACACCTTCCCTGCCGTGCTGCAGTCCTCCGGC
CTGTACTCCCTGTCCAGCGTCGTGACCGTGCCCTCCTCCAGC
CTGGGCACCAAGACCTACACCTGTAACGTGGACCACAAGCCC
TCCAACACCAAAGTGGACAAGCGGGTGGAATCTAAGTACGGC
CCTCCCTGCCCTCCTTGCCCTGCCCCTGAGTTCCTGGGCGGA
CCTTCCGTGTTCCTGTTCCCTCCAAAGCCCAAGGACACCCTG
ATGATCTCCCGGACCCCTGAAGTGACCTGCGTGGTGGTGGAC
GTGTCCCAGGAAGATCCCGAAGTCCAGTTCAATTGGTACGTG
GACGGCGTGGAAGTGCACAACGCCAAGACCAAGCCCAGAGAG
GAACAGTTCAACTCCACCTACCGGGTGGTGTCCGTGCTGACC
GTGCTGCACCAGGACTGGCTGAACGGCAAAGAGTACAAGTGC
AAAGTGTCCAACAAGGGCCTGCCCTCCAGCATCGAAAAGACC
ATCTCCAAGGCCAAGGGCCAGCCCCGCGAGCCCCAAGTGTAC
ACCCTGCCTCCCAGCCAGGAAGAGATGACCAAGAATCAAGTG
TCCCTGACTTGTCTGGTCAAGGGCTTCTACCCCTCCGATATC
GCCGTGGAGTGGGAGTCCAACGGCCAGCCCGAGAACAACTAC
AAGACCACCCCTCCCGTGCTGGACTCCGACGGCTCCTTCTTC
CTGTACTCTCGGCTGACCGTGGACAAGTCCCGGTGGCAGGAA
GGCAACGTCTTCTCCTGCTCCGTGATGCACGAGGCCCTGCAC
AACCACTACACCCAGAAGTCCCTGTCCCTGTCTCTGGGC |

SRF365-B

| | | |
|---|---|---|
| SEQ ID NO: 25 | HEAVY CHAIN | QVQLVQSGAEVKKPGSSVKVSCKASGGTFSDKAISWVRQAPG
QGLEWMGSILPIFGTANYAQKFQGRVTITADESTSTAYMELS
SLRSEDTAVYYCAREAGYYRYRYFDLWGRGTLVTVSSASTKG
PSVFPLAPCSRSTSESTAALGCLVKDYFPEPVTVSWNSGALT
SGVHTFPAVLQSSGLYSLSSVVTVPSSSLGTKTYTCNVDHKP
SNTKVDKRVESKYGPPCPPCPAPEFEGGPSVFLFPPKPKDTL
MISRTPEVTCVVVDVSQEDPEVQFNWYVDGVEVHNAKTKPRE
EQFNSTYRVVSVLTVLHQDWLNGKEYKCKVSNKGLPSSIEKT
ISKAKGQPREPQVYTLPPSQEEMTKNQVSLTCLVKGFYPSDI
AVEWESNGQPENNYKTTPPVLDSDGSFFLYSRLTVDKSRWQE
GNVFSCSVMHEALHNHYTQKSLSLSLG |
| SEQ ID NO: 26 | DNA HEAVY CHAIN | CAGGTGCAGCTGGTGCAGTCTGGGGCTGAGGTGAAGAAGCCT
GGGTCCTCGGTGAAGGTCTCCTGCAAGGCTTCTGGAGGCACC
TTCAGCGATAAGGCTATCAGCTGGGTGCGACAGGCCCCTGGA
CAAGGGCTTGAGTGGATGGGATCGATCCTTCCTATCTTTGGT
ACAGCAAACTACGCACAGAAGTTCCAGGGCAGAGTCACGATT
ACCGCGGACGAATCCACGAGCACAGCCTACATGGAGCTGAGC
AGCCTGAGATCTGAGGACACGGCGGTGTACTACTGCGCCAGA
GAAGCCGGATACTACCGCTACCGATACTTCGACCTATGGGGG
AGAGGTACCTTGGTCACCGTCTCCTCAGCTTCCACCAAGGGC
CCCTCCGTGTTCCCTCTGGCCCCTTGCTCCCGGTCCACCTCC
GAGTCTACCGCCGCTCTGGGCTGCCTCGTGAAGGACTACTTC
CCCGAGCCCGTGACCGTGTCCTGGAACTCTGGCGCCCTGACC
TCCGGCGTGCACACCTTCCCTGCCGTGCTGCAGTCCTCCGGC
CTGTACTCCCTGTCCAGCGTCGTGACCGTGCCCTCCTCCAGC
CTGGGCACCAAGACCTACACCTGTAACGTGGACCACAAGCCC
TCCAACACCAAAGTGGACAAGCGGGTGGAATCTAAGTACGGC
CCTCCCTGCCCTCCTTGCCCTGCCCCTGAGTTCGAGGGCGGA
CCTTCCGTGTTCCTGTTCCCTCCAAAGCCCAAGGACACCCTG
ATGATCTCCCGGACCCCTGAAGTGACCTGCGTGGTGGTGGAC
GTGTCCCAGGAAGATCCCGAAGTCCAGTTCAATTGGTACGTG
GACGGCGTGGAAGTGCACAACGCCAAGACCAAGCCCAGAGAG
GAACAGTTCAACTCCACCTACCGGGTGGTGTCCGTGCTGACC
GTGCTGCACCAGGACTGGCTGAACGGCAAAGAGTACAAGTGC |

TABLE 1-continued

SEQUENCE LISTING
NT = non-traditional

|  |  |  |
|---|---|---|
|  |  | AAAGTGTCCAACAAGGGCCTGCCCTCCAGCATCGAAAAGACC<br>ATCTCCAAGGCCAAGGGCCAGCCCCGCGAGCCCCAAGTGTAC<br>ACCCTGCCTCCCAGCCAGGAAGAGATGACCAAGAATCAAGTG<br>TCCCTGACTTGTCTGGTCAAGGGCTTCTACCCCTCCGATATC<br>GCCGTGGAGTGGGAGTCCAACGGCCAGCCCGAGAACAACTAC<br>AAGACCACCCCTCCCGTGCTGGACTCCGACGGCTCCTTCTTC<br>CTGTACTCTCGGCTGACCGTGGACAAGTCCCGGTGGCAGGAA<br>GGCAACGTCTTCTCCTGCTCCGTGATGCACGAGGCCCTGCAC<br>AACCACTACACCCAGAAGTCCCTGTCCCTGTCTCTGGGC |
| SRF367-C |  |  |
| SEQ ID NO: 27 | HCDR1<br>(IMGT) | GGTFSSEG |
| SEQ ID NO: 28 | HCDR2<br>(IMGT) | ILPIFGTA |
| SEQ ID NO: 29 | HCDR3<br>(IMGT) | AREAGYYRYRYFDL |
| SEQ ID NO: 30 | HCDR1<br>(NT) | GTFSSEGIS |
| SEQ ID NO: 31 | HCDR2<br>(NT) | SILPIFGTANYAQKFQG |
| SEQ ID NO: 32 | HCDR3<br>(NT) | AREAGYYRYRYFDL |
| SEQ ID NO: 33 | VH | QVQLVQSGAEVKKPGSSVKVSCKASGGTFSSEGISWVRQAPG<br>QGLEWMGSILPIFGTANYAQKFQGRVTITADESTSTAYMELS<br>SLRSEDTAVYYCAREAGYYRYRYFDLWGKGTLVTVSS |
| SEQ ID NO: 34 | DNA VH | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCAGCGAGGGTATCAGCTGGGTGCGACAGGCCCCTGGA<br>CAAGGGCTTGAGTGGATGGGAAGTATCTTGCCTATCTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GAAGCCGGATACTACCGCTACCGATACTTCGACCTATGGGGG<br>AAAGGTACCTTGGTCACCGTCTCCTCA |
| SEQ ID NO: 35 | HEAVY<br>CHAIN | QVQLVQSGAEVKKPGSSVKVSCKASGGTFSSEGISWVRQAPG<br>QGLEWMGSILPIFGTANYAQKFQGRVTITADESTSTAYMELS<br>SLRSEDTAVYYCAREAGYYRYRYFDLWGKGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKKVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPI<br>EKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVMHEALHNHYTQKSLSLSPGK |
| SEQ ID NO: 36 | DNA<br>HEAVY<br>CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCAGCGAGGGTATCAGCTGGGTGCGACAGGCCCCTGGA<br>CAAGGGCTTGAGTGGATGGGAAGTATCTTGCCTATCTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GAAGCCGGATACTACCGCTACCGATACTTCGACCTATGGGGG<br>AAAGGTACCTTGGTCACCGTCTCCTCAGCGAGCACCAAAGGC<br>CCGAGCGTGTTTCCGCTGGCGCCGAGCAGCAAAAGCACCAGC<br>GGCGGCACCGCGGCGCTGGGCTGCCTGGTGAAAGATTATTTT<br>CCGGAACCGGTGACCGTGAGCTGGAACAGCGGCGCGCTGACC<br>AGCGGCGTGCATACCTTTCCGGCGGTGCTGCAGAGCAGCGGC<br>CTGTATAGCCTGAGCAGCGTGGTGACCGTGCCGAGCAGCAGC<br>CTGGGCACCCAGACCTATATTTGCAACGTGAACCATAAACCG<br>AGCAACACCAAAGTGGATAAAAAAGTGGAACCGAAAAGCTGC<br>GATAAAACCCATACCTGCCCGCCGTGCCCGGCGCCGGAACTG<br>CTGGGCGGCCCGAGCGTGTTTCTGTTTCCGCCGAAACCGAAA<br>GATACCCTGATGATTAGCCGCACCCCGGAAGTGACCTGCGTG<br>GTGGTGGATGTGAGCCATGAAGATCCGGAAGTGAAATTTAAC<br>TGGTATGTGGATGGCGTGGAAGTGCATAACGCGAAAACCAAA<br>CCGCGCGAAGAACAGTATAACAGCACCTATCGCGTGGTGAGC<br>GTGCTGACCGTGCTGCATCAGGATTGGCTGAACGGCAAAGAA<br>TATAAATGCAAAGTGAGCAACAAAGCGCTGCCGGCGCCGATT<br>GAAAAAACCATTAGCAAAGCGAAAGGCCAGCCGCGCGAACCG<br>CAGGTGTATACCCTGCCGCCGAGCCGCGATGAACTGACCAAA<br>AACCAGGTGAGCCTGACCTGCCTGGTGAAAGGCTTTTATCCG<br>AGCGATATTGCGGTGGAATGGGAAAGCAACGGCCAGCCGGAA<br>AACAACTATAAAACCACCCCGCCGGTGCTGGATAGCGATGGC<br>AGCTTTTTTCTGTATAGCAAACTGACCGTGGATAAAAGCCGC<br>TGGCAGCAGGGCAACGTGTTTAGCTGCAGCGTGATGCATGAA |

TABLE 1-continued

SEQUENCE LISTING
NT = non-traditional

|  |  |  |
|---|---|---|
|  |  | GCGCTGCATAACCATTATACCCAGAAAAGCCTGAGCCTGAGC<br>CCGGGCAAA |
| SEQ ID NO: 37 | LCDR1 (IMGT) | QSVSSN |
| SEQ ID NO: 38 | LCDR2 (IMGT) | GAS |
| SEQ ID NO: 39 | LCDR3 (IMGT) | QQHALWPLT |
| SEQ ID NO: 40 | LCDR1 (NT) | RASQSVSSNLA |
| SEQ ID NO: 41 | LCDR2 (NT) | GASTRAT |
| SEQ ID NO: 42 | LCDR3 (NT) | QQHALWPLT |
| SEQ ID NO: 43 | VL | EIVMTQSPATLSVSPGERATLSCRASQSVSSNLAWYQQKPGQ<br>APRLLIYGASTRATGIPARFSGSGSGTEFTLTISSLQSEDFA<br>VYYCQQHALWPLTFGGGTKVEIK |
| SEQ ID NO: 44 | DNA VL | GAAATAGTGATGACGCAGTCTCCAGCCACCCTGTCTGTGTCT<br>CCAGGGGAAAGAGCCACCCTCTCCTGCAGGGCCAGTCAGAGT<br>GTTAGCAGCAACTTAGCCTGGTACCAGCAGAAACCTGGCCAG<br>GCTCCCAGGCTCCTCATCTATGGTGCATCCACCAGGGCCACT<br>GGTATCCCAGCCAGGTTCAGTGGCAGTGGGTCTGGGACAGAG<br>TTCACTCTCACCATCAGCAGCCTGCAGTCTGAAGATTTTGCA<br>GTTTATTACTGTCAGCAGCACGCCCTCTGGCCTCTCACTTTT<br>GGCGGAGGGACCAAGGTTGAGATCAAA |
| SEQ ID NO: 45 | LIGHT CHAIN | EIVMTQSPATLSVSPGERATLSCRASQSVSSNLAWYQQKPGQ<br>APRLLIYGASTRATGIPARFSGSGSGTEFTLTISSLQSEDFA<br>VYYCQQHALWPLTFGGGTKVEIKRTVAAPSVFIFPPSDEQLK<br>SGTASVVCLLNNFYPREAKVQWKVDNALQSGNSQESVTEQDS<br>KDSTYSLSSILTLSKADYEKHKVYACEVTHQGLSSPVTKSFN<br>RGEC |
| SEQ ID NO: 46 | DNA LIGHT CHAIN | GAAATAGTGATGACGCAGTCTCCAGCCACCCTGTCTGTGTCT<br>CCAGGGGAAAGAGCCACCCTCTCCTGCAGGGCCAGTCAGAGT<br>GTTAGCAGCAACTTAGCCTGGTACCAGCAGAAACCTGGCCAG<br>GCTCCCAGGCTCCTCATCTATGGTGCATCCACCAGGGCCACT<br>GGTATCCCAGCCAGGTTCAGTGGCAGTGGGTCTGGGACAGAG<br>TTCACTCTCACCATCAGCAGCCTGCAGTCTGAAGATTTTGCA<br>GTTTATTACTGTCAGCAGCACGCCCTCTGGCCTCTCACTTTT<br>GGCGGAGGGACCAAGGTTGAGATCAAACGTACGGTGGCCGCT<br>CCCTCCGTGTTCATCTTCCCACCCTCCGACGAGCAGCTGAAG<br>TCCGGCACCGCCTCCGTCGTGTGCCTGCTGAACAACTTCTAC<br>CCTCGCGAGGCCAAAGTGCAGTGGAAAGTGGACAACGCCCTG<br>CAGTCCGGCAACTCCCAGGAATCCGTCACCGAGCAGGACTCC<br>AAGGACAGCACCTACTCCCTGTCCTCCACCCTGACCCTGTCC<br>AAGGCCGACTACGAGAAGCACAAAGTGTACGCCTGCGAAGTG<br>ACCCACCAGGGCCTGTCCAGCCCCGTGACCAAGTCCTTCAAC<br>CGGGGCGAGTGC |
| SRF367-D |  |  |
| SEQ ID NO: 47 | HEAVY CHAIN | QVQLVQSGAEVKKPGSSVKVSCKASGGTFSSEGISWVRQAPG<br>QGLEWMGSILPIFGTANYAQKFQGRVTITADESTSTAYMELS<br>SLRSEDTAVYYCAREAGYYRYRYFDLWGKGTLVTVSSASTKG<br>PSVFPLAPCSRSTSESTAALGCLVKDYFPEPVTVSWNSGALT<br>SGVHTFPAVLQSSGLYSLSSVVTVPSSSLGTKTYTCNVDHKP<br>SNTKVDKRVESKYGPPCPSCPAPEFLGGPSVFLFPPKPKDTL<br>MISRTPEVTCVVVDVSQEDPEVQFNWYVDGVEVHNAKTKPRE<br>EQFNSTYRVVSVLTVLHQDWLNGKEYKCKVSNKGLPSSIEKT<br>ISKAKGQPREPQVYTLPPSQEEMTKNQVSLTCLVKGFYPSDI<br>AVEWESNGQPENNYKTTPPVLDSDGSFFLYSRLTVDKSRWQE<br>GNVFSCSVMHEALHNHYTQKSLSLSLG |
| SEQ ID NO: 48 | DNA HEAVY CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCAGCGAGGGTATCAGCTGGGTGCGACAGGCCCCTGGA<br>CAAGGGCTTGAGTGGATGGGAAGTATCTTGCCTATCTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GAAGCCGGATACTACCGCTACCGATACTTCGACCTATGGGGG<br>AAAGGTACCTTGGTCACCGTCTCCTCAGCTTCCACCAAGGGC<br>CCCTCCGTGTTCCCTCTGGCCCCTTGCTCCCGGTCCACCTCC<br>GAGTCTACCGCCGCTCTGGGCTGCCTCGTGAAGGACTACTTC<br>CCCGAGCCCGTGACCGTGTCCTGGAACTCTGGCGCCCTGACC<br>TCCGGCGTGCACACCTTCCCTGCCGTGCTGCAGTCCTCCGGC<br>CTGTACTCCCTGTCCAGCGTCGTGACCGTGCCCTCCTCCAGC<br>CTGGGCACCAAGACCTACACCTGTAACGTGGACCACAAGCCC<br>TCCAACACCAAAGTGGACAAGCGGGTGGAATCTAAGTACGGC<br>CCTCCCTGCCCTTCCTGCCCTGCCCCTGAGTTCCTGGGCGGA |

TABLE 1-continued

SEQUENCE LISTING
NT = non-traditional

|  |  |  |
|---|---|---|
|  |  | CCTTCCGTGTTCCTGTTCCCTCCAAAGCCCAAGGACACCCTG<br>ATGATCTCCCGGACCCCTGAAGTGACCTGCGTGGTGGTGGAC<br>GTGTCCCAGGAAGATCCCGAAGTCCAGTTCAATTGGTACGTG<br>GACGGCGTGGAAGTGCACAACGCCAAGACCAAGCCCAGAGAG<br>GAACAGTTCAACTCCACCTACCGGGTGGTGTCCGTGCTGACC<br>GTGCTGCACCAGGACTGGCTGAACGGCAAAGAGTACAAGTGC<br>AAAGTGTCCAACAAGGGCCTGCCCTCCAGCATCGAAAAGACC<br>ATCTCCAAGGCCAAGGGCCAGCCCCGCGAGCCCAAGTGTAC<br>ACCCTGCCTCCCAGCCAGGAAGAGATGACCAAGAATCAAGTG<br>TCCCTGACTTGTCTGGTCAAGGGCTTCTACCCCTCCGATATC<br>GCCGTGGAGTGGGAGTCCAACGGCCAGCCCGAGAACAACTAC<br>AAGACCACCCCTCCCGTGCTGGACTCCGACGGCTCCTTCTTC<br>CTGTACTCTCGGCTGACCGTGGACAAGTCCCGGTGGCAGGAA<br>GGCAACGTCTTCTCCTGCTCCGTGATGCACGAGGCCCTGCAC<br>AACCACTACACCCAGAAGTCCCTGTCCCTGTCTCTGGGC |
| SRF367-A |  |  |
| SEQ ID NO: 49 | HEAVY<br>CHAIN | QVQLVQSGAEVKKPGSSVKVSCKASGGTFSSEGISWVRQAPG<br>QGLEWMGSILPIFGTANYAQKFQGRVTITADESTSTAYMELS<br>SLRSEDTAVYYCAREAGYYRYRYFDLWGKGTLVTVSSASTKG<br>PSVFPLAPCSRSTSESTAALGCLVKDYFPEPVTVSWNSGALT<br>SGVHTFPAVLQSSGLYSLSSVVTVPSSSLGTKTYTCNVDHKP<br>SNTKVDKRVESKYGPPCPPCPAPEFLGGPSVFLFPPKPKDTL<br>MISRTPEVTCVVVDVSQEDPEVQFNWYVDGVEVHNAKTKPRE<br>EQFNSTYRVVSVLTVLHQDWLNGKEYKCKVSNKGLPSSIEKT<br>ISKAKGQPREPQVYTLPPSQEEMTKNQVSLTCLVKGFYPSDI<br>AVEWESNGQPENNYKTTPPVLDSDGSFFLYSRLTVDKSRWQE<br>GNVFSCSVMHEALHNHYTQKSLSLSLG |
| SEQ ID NO: 50 | DNA<br>HEAVY<br>CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCAGCGAGGGTATCAGCTGGGTGCGACAGGCCCCTGGA<br>CAAGGGCTTGAGTGGATGGGAAGTATCTTGCCTATCTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCCGGTGTACTACTGCGCCAGA<br>GAAGCCGGATACTACCGCTACCGATACTTCGACCTATGGGGG<br>AAAGGTACCTTGGTCACCGTCTCCTCAGCTTCCACCAAGGGC<br>CCCTCCGTGTTCCCTCTGGCCCCTTGCTCCCGGTCCACCTCC<br>GAGTCTACCGCCGCTCTGGGCTGCCTCGTGAAGGACTACTTC<br>CCCGAGCCCGTGACCGTGTCCTGGAACTCTGGCGCCCTGACC<br>TCCGGCGTGCACACCTTCCCTGCCGTGCTGCAGTCCTCCGGC<br>CTGTACTCCCTGTCCAGCGTCGTGACCGTGCCCTCCTCCAGC<br>CTGGGCACCAAGACCTACACCTGTAACGTGGACCACAAGCCC<br>TCCAACACCAAAGTGGACAAGCGGGTGGAATCTAAGTACGGC<br>CCTCCCTGCCCTCCTTGCCCTGCCCCTGAGTTCCTGGGCGGA<br>CCTTCCGTGTTCCTGTTCCCTCCAAAGCCCAAGGACACCCTG<br>ATGATCTCCCGGACCCCTGAAGTGACCTGCGTGGTGGTGGAC<br>GTGTCCCAGGAAGATCCCGAAGTCCAGTTCAATTGGTACGTG<br>GACGGCGTGGAAGTGCACAACGCCAAGACCAAGCCCAGAGAG<br>GAACAGTTCAACTCCACCTACCGGGTGGTGTCCGTGCTGACC<br>GTGCTGCACCAGGACTGGCTGAACGGCAAAGAGTACAAGTGC<br>AAAGTGTCCAACAAGGGCCTGCCCTCCAGCATCGAAAAGACC<br>ATCTCCAAGGCCAAGGGCCAGCCCCGCGAGCCCAAGTGTAC<br>ACCCTGCCTCCCAGCCAGGAAGAGATGACCAAGAATCAAGTG<br>TCCCTGACTTGTCTGGTCAAGGGCTTCTACCCCTCCGATATC<br>GCCGTGGAGTGGGAGTCCAACGGCCAGCCCGAGAACAACTAC<br>AAGACCACCCCTCCCGTGCTGGACTCCGACGGCTCCTTCTTC<br>CTGTACTCTCGGCTGACCGTGGACAAGTCCCGGTGGCAGGAA<br>GGCAACGTCTTCTCCTGCTCCGTGATGCACGAGGCCCTGCAC<br>AACCACTACACCCAGAAGTCCCTGTCCCTGTCTCTGGGC |
| SRF367-B |  |  |
| SEQ ID NO: 51 | HEAVY<br>CHAIN | QVQLVQSGAEVKKPGSSVKVSCKASGGTFSSEGISWVRQAPG<br>QGLEWMGSILPIFGTANYAQKFQGRVTITADESTSTAYMELS<br>SLRSEDTAVYYCAREAGYYRYRYFDLWGKGTLVTVSSASTKG<br>PSVFPLAPCSRSTSESTAALGCLVKDYFPEPVTVSWNSGALT<br>SGVHTFPAVLQSSGLYSLSSVVTVPSSSLGTKTYTCNVDHKP<br>SNTKVDKRVESKYGPPCPPCPAPEFEGGPSVFLFPPKPKDTL<br>MISRTPEVTCVVVDVSQEDPEVQFNWYVDGVEVHNAKTKPRE<br>EQFNSTYRVVSVLTVLHQDWLNGKEYKCKVSNKGLPSSIEKT<br>ISKAKGQPREPQVYTLPPSQEEMTKNQVSLTCLVKGFYPSDI<br>AVEWESNGQPENNYKTTPPVLDSDGSFFLYSRLTVDKSRWQE<br>GNVFSCSVMHEALHNHYTQKSLSLSLG |
| SEQ ID NO: 52 | DNA<br>HEAVY<br>CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCAGCGAGGGTATCAGCTGGGTGCGACAGGCCCCTGGA<br>CAAGGGCTTGAGTGGATGGGAAGTATCTTGCCTATCTTTGGT |

TABLE 1-continued

SEQUENCE LISTING
NT = non-traditional

|  |  |  |
|---|---|---|
|  |  | ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GAAGCCGGATACTACCGCTACCGATACTTCGACCTATGGGGG<br>AAAGGTACCTTGGTCACCGTCTCCTCAGCTTCCACCAAGGGC<br>CCCTCCGTGTTCCCTCTGGCCCCTTGCTCCCGGTCCACCTCC<br>GAGTCTACCGCCGCTCTGGGCTGCCTCGTGAAGGACTACTTC<br>CCCGAGCCCGTGACCGTGTCCTGGAACTCTGGCGCCCTGACC<br>TCCGGCGTGCACACCTTCCCTGCCGTGCTGCAGTCCTCCGGC<br>CTGTACTCCCTGTCCAGCGTCGTGACCGTGCCCTCCTCCAGC<br>CTGGGCACCAAGACCTACACCTGTAACGTGGACCACAAGCCC<br>TCCAACACCAAAGTGGACAAGCGGGTGGAATCTAAGTACGGC<br>CCTCCCTGCCCTCCTTGCCCTGCCCCTGAGTTCGAGGGCGGA<br>CCTTCCGTGTTCCTGTTCCCTCCAAAGCCCAAGGACACCCTG<br>ATGATCTCCCGGACCCCTGAAGTGACCTGCGTGGTGGTGGAC<br>GTGTCCAGGAAGATCCCGAAGTCCAGTTCAATTGGTACGTG<br>GACGGCGTGGAAGTGCACAACGCCAAGACCAAGCCCAGAGAG<br>GAACAGTTCAACTCCACCTACCGGGTGGTGTCCGTGCTGACC<br>GTGCTGCACCAGGACTGGCTGAACGGCAAAGAGTACAAGTGC<br>AAAGTGTCCAACAAGGGCCTGCCCTCCAGCATCGAAAAGACC<br>ATCTCCAAGGCCAAGGGCCAGCCCCGCGAGCCCAAGTGTAC<br>ACCCTGCCTCCCAGCCAGGAAGAGATGACCAAGAATCAAGTG<br>TCCCTGACTTGTCTGGTCAAGGGCTTCTACCCCTCCGATATC<br>GCCGTGGAGTGGGAGTCCAACGGCCAGCCCGAGAACAACTAC<br>AAGACCACCCCTCCCGTGCTGGACTCCGACGGCTCCTTCTTC<br>CTGTACTCTCGGCTGACCGTGGACAAGTCCCGGTGGCAGGAA<br>GGCAACGTCTTCTCCTGCTCCGTGATGCACGAGGCCCTGCAC<br>AACCACTACACCCAGAAGTCCCTGTCCCTGTCTCTGGGC |
| SRF370-C |  |  |
| SEQ ID NO: 53 | HCDR1<br>(IMGT) | GGTFSTYA |
| SEQ ID NO: 54 | HCDR2<br>(IMGT) | IIPAFGTA |
| SEQ ID NO: 55 | HCDR3<br>(IMGT) | ARDPVRRSPFDI |
| SEQ ID NO: 56 | HCDR1<br>(NT) | GTFSTYAIG |
| SEQ ID NO: 57 | HCDR2<br>(NT) | GIIPAFGTANYAQKFQG |
| SEQ ID NO: 58 | HCDR3<br>(NT) | ARDPVRRSPFDI |
| SEQ ID NO: 59 | VH | QVQLVQSGAEVKKPGSSVKVSCKASGGTFSTYAIGWVRQAPG<br>QGLEWMGGIIPAFGTANYAQKFQGRVTITADESTSTAYMELS<br>SLRSEDTAVYYCARDPVRRSPFDIWGQGTMVTVSS |
| SEQ ID NO: 60 | DNA VH | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCACGTATGCTATCGGGTGGGTGCGACAGGCCCCTGGA<br>CAAGGGCTTGAGTGGATGGGAGGGATCATCCCTGCGTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GATCCGGTGAGAAGAAGCCCATTGACATATGGGGTCAGGGT<br>ACAATGGTCACCGTCTCCTCA |
| SEQ ID NO: 61 | HEAVY<br>CHAIN | QVQLVQSGAEVKKPGSSVKVSCKASGGTFSTYAIGWVRQAPG<br>QGLEWMGGIIPAFGTANYAQKFQGRVTITADESTSTAYMELS<br>SLRSEDTAVYYCARDPVRRSPFDIWGQGTMVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKKVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSRDELTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGK |
| SEQ ID NO: 62 | DNA<br>HEAVY<br>CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCACGTATGCTATCGGGTGGGTGCGACAGGCCCCTGGA<br>CAAGGGCTTGAGTGGATGGGAGGGATCATCCCTGCGTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GATCCGGTGAGAAGAAGCCCATTGACATATGGGGTCAGGGT<br>ACAATGGTCACCGTCTCCTCAGCGAGCACAAAGGCCCGAGC<br>GTGTTTCCGCTGGCGCCGAGCAGCAAAAGCACCAGCGGCGGC<br>ACCGCGGCGCTGGGCTGCCTGGTGAAAGATTATTTTCCGGAA<br>CCGGTGACCGTGAGCTGGAACAGCGGCGCGCTGACCAGCGGC |

TABLE 1-continued

SEQUENCE LISTING
NT = non-traditional

|  |  |  |
|---|---|---|
|  |  | GTGCATACCTTTCCGGCGGTGCTGCAGAGCAGCGGCCTGTAT<br>AGCCTGAGCAGCGTGGTGACCGTGCCGAGCAGCAGCCTGGGC<br>ACCCAGACCTATATTTGCAACGTGAACCATAAACCGAGCAAC<br>ACCAAAGTGGATAAAAAAGTGGAACCGAAAAGCTGCGATAAA<br>ACCCATACCTGCCCGCCGTGCCCGGCGCCGGAACTGCTGGGC<br>GGCCCGAGCGTGTTTCTGTTTCCGCCGAAACCGAAAGATACC<br>CTGATGATTAGCCGCACCCCGGAAGTGACCTGCGTGGTGGTG<br>GATGTGAGCCATGAAGATCCGGAAGTGAAATTTAACTGGTAT<br>GTGGATGGCGTGGAAGTGCATAACGCGAAAACCAAACCGCGC<br>GAAGAACAGTATAACAGCACCTATCGCGTGGTGAGCGTGCTG<br>ACCGTGCTGCATCAGGATTGGCTGAACGGCAAAGAATATAAA<br>TGCAAAGTGAGCAACAAAGCGCTGCCGGCGCCGATTGAAAAA<br>ACCATTAGCAAAGCGAAAGGCCAGCCGCGCGAACCGCAGGTG<br>TATACCCTGCCGCCGAGCCGCGATGAACTGACCAAAAACCAG<br>GTGAGCCTGACCTGCCTGGTGAAAGGCTTTTATCCGAGCGAT<br>ATTGCGGTGGAATGGGAAAGCAACGGCCAGCCGGAAAACAAC<br>TATAAAACCACCCCGCCGGTGCTGGATAGCGATGGCAGCTTT<br>TTTCTGTATAGCAAACTGACCGTGGATAAAAGCCGCTGGCAG<br>CAGGGCAACGTGTTTAGCTGCAGCGTGATGCATGAAGCGCTG<br>CATAACCATTATACCCAGAAAAGCCTGAGCCTGAGCCCGGGC<br>AAA |
| SEQ ID NO: 63 | LCDR1<br>(IMGT) | QSVSSY |
| SEQ ID NO: 64 | LCDR2<br>(IMGT) | DSS |
| SEQ ID NO: 65 | LCDR3<br>(IMGT) | QQSFLWPRT |
| SEQ ID NO: 66 | LCDR1<br>(NT) | RASQSVSSYLA |
| SEQ ID NO: 67 | LCDR2<br>(NT) | DSSNRAT |
| SEQ ID NO: 68 | LCDR3<br>(NT) | QQSFLWPRT |
| SEQ ID NO: 69 | VL | EIVLTQSPATLSLSPGERATLSCRASQSVSSYLAWYQQKPGQ<br>APRLLIYDSSNRATGIPARFSGSGSGTDFTLTISSLEPEDFA<br>VYYCQQSFLWPRTFGGGTKVEIK |
| SEQ ID NO: 70 | DNA VL | GAAATTGTGTTGACACAGTCTCCAGCCACCCTGTCTTTGTCT<br>CCAGGGGAAAGAGCCACCCTCTCCTGCAGGGCCAGTCAGAGT<br>GTTAGCAGCTACTTAGCCTGGTACCAACAGAAACCTGGCCAG<br>GCTCCCAGGCTCCTCATCTATGATTCATCCAACAGGGCCACT<br>GGCATCCCAGCCAGGTTCAGTGGCAGTGGGTCTGGGACAGAC<br>TTCACTCTCACCATCAGCAGCCTAGAGCCTGAAGATTTTGCA<br>GTTTATTACTGTCAGCAGTCCTTCCTCTGGCCTAGGACTTTT<br>GGCGGAGGGACCAAGGTTGAGATCAAA |
| SEQ ID NO: 71 | LIGHT<br>CHAIN | EIVLTQSPATLSLSPGERATLSCRASQSVSSYLAWYQQKPGQ<br>APRLLIYDSSNRATGIPARFSGSGSGTDFTLTISSLEPEDFA<br>VYYCQQSFLWPRTFGGGTKVEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFN<br>RGEC |
| SEQ ID NO: 72 | DNA<br>LIGHT<br>CHAIN | GAAATTGTGTTGACACAGTCTCCAGCCACCCTGTCTTTGTCT<br>CCAGGGGAAAGAGCCACCCTCTCCTGCAGGGCCAGTCAGAGT<br>GTTAGCAGCTACTTAGCCTGGTACCAACAGAAACCTGGCCAG<br>GCTCCCAGGCTCCTCATCTATGATTCATCCAACAGGGCCACT<br>GGCATCCCAGCCAGGTTCAGTGGCAGTGGGTCTGGGACAGAC<br>TTCACTCTCACCATCAGCAGCCTAGAGCCTGAAGATTTTGCA<br>GTTTATTACTGTCAGCAGTCCTTCCTCTGGCCTAGGACTTTT<br>GGCGGAGGGACCAAGGTTGAGATCAAACGTACGGTGGCCGCT<br>CCCTCCGTGTTCATCTTCCCACCCTCCGACGAGCAGCTGAAG<br>TCCGGCACCGCCTCCGTCGTGTGCCTGCTGAACAACTTCTAC<br>CCTCGCGAGGCCAAAGTGCAGTGGAAAGTGGACAACGCCCTG<br>CAGTCCGGCAACTCCCAGGAATCCGTCACCGAGCAGGACTCC<br>AAGGACAGCACCTACTCCCTGTCCTCCACCCTGACCCTGTCC<br>AAGGCCGACTACGAGAAGCACAAAGTGTACGCCTGCGAAGTG<br>ACCCACCAGGGCCTGTCCAGCCCCGTGACCAAGTCCTTCAAC<br>CGGGGCGAGTGC |
| SRF370-D |  |  |
| SEQ ID NO: 73 | HEAVY<br>CHAIN | QVQLVQSGAEVKKPGSSVKVSCKASGGTFSTYAIGWVRQAPG<br>QGLEWMGGIIPAFGTANYAQKFQGRVTITADESTSTAYMELS<br>SLRSEDTAVYYCARDPVRRSPFDIWGQGTMVTVSSASTKGPS<br>VFPLAPCSRSTSESTAALGCLVKDYFPEPVTVSWNSGALTSG<br>VHTFPAVLQSSGLYSLSSVVTVPSSSLGTKTYTCNVDHKPSN<br>TKVDKRVESKYGPPCPSCPAPEFLGGPSVFLFPPKPKDTLMI<br>SRTPEVTCVVVDVSQEDPEVQFNWYVDGVEVHNAKTKPREEQ<br>FNSTYRVVSVLTVLHQDWLNGKEYKCKVSNKGLPSSIEKTIS<br>KAKGQPREPQVYTLPPSQEEMTKNQVSLTCLVKGFYPSDIAV |

TABLE 1-continued

SEQUENCE LISTING
NT = non-traditional

| | | |
|---|---|---|
| | | EWESNGQPENNYKTTPPVLDSDGSFFLYSRLTVDKSRWQEGN<br>VFSCSVMHEALHNHYTQKSLSLSLG |
| SEQ ID NO: 74 | DNA<br>HEAVY<br>CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCACGTATGCTATCGGGTGGGTGCGACAGGCCCCTGGA<br>CAAGGGCTTGAGTGGATGGGAGGGATCATCCCTGCGTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GATCCGGTGAGAAGAAGCCCATTCGACATATGGGGTCAGGGT<br>ACAATGGTCACCGTCTCCTCAGCTTCCACCAAGGGCCCCTCC<br>GTGTTCCCTCTGGCCCCTTGCTCCCGGTCCACCTCCGAGTCT<br>ACCGCCGCTCTGGGCTGCCTCGTGAAGGACTACTTCCCCGAG<br>CCCGTGACCGTGTCCTGGAACTCTGGCGCCCTGACCTCCGGC<br>GTGCACACCTTCCCTGCCGTGCTGCAGTCCTCCGGCCTGTAC<br>TCCCTGTCCAGCGTCGTGACCGTGCCCTCCTCCAGCCTGGGC<br>ACCAAGACCTACACCTGTAACGTGGACCACAAGCCCTCCAAC<br>ACCAAAGTGGACAAGCGGGTGGAATCTAAGTACGGCCCTCCC<br>TGCCCTTCCTGCCCTGCCCCTGAGTTCCTGGGCGGACCTTCC<br>GTGTTCCTGTTCCCTCCAAAGCCCAAGGACACCCTGATGATC<br>TCCCGGACCCCTGAAGTGACCTGCGTGGTGGTGGACGTGTCC<br>CAGGAAGATCCCGAAGTCCAGTTCAATTGGTACGTGGACGGC<br>GTGGAAGTGCACAACGCCAAGACCAAGCCCAGAGAGGAACAG<br>TTCAACTCCACCTACCGGGTGGTGTCCGTGCTGACCGTGCTG<br>CACCAGGACTGGCTGAACGGCAAAGAGTACAAGTGCAAAGTG<br>TCCAACAAGGGCCTGCCCTCCAGCATCGAAAAGACCATCTCC<br>AAGGCCAAGGGCCAGCCCCGCGAGCCCAAGTGTACACCCTG<br>CCTCCCAGCCAGGAAGAGATGACCAAGAATCAAGTGTCCCTG<br>ACTTGTCTGGTCAAGGGCTTCTACCCCTCCGATATCGCCGTG<br>GAGTGGGAGTCCAACGGCCAGCCCGAGAACAACTACAAGACC<br>ACCCCTCCCGTGCTGGACTCCGACGGCTCCTTCTTCCTGTAC<br>TCTCGGCTGACCGTGGACAAGTCCCGGTGGCAGGAAGGCAAC<br>GTCTTCTCCTGCTCCGTGATGCACGAGGCCCTGCACAACCAC<br>TACACCCAGAAGTCCCTGTCCCTGTCTCTGGGC |
| SRF370-A | | |
| SEQ ID NO: 75 | HEAVY<br>CHAIN | QVQLVQSGAEVKKPGSSVKVSCKASGGTFSTYAIGWVRQAPG<br>QGLEWMGGIIPAFGTANYAQKFQGRVTITADESTSTAYMELS<br>SLRSEDTAVYYCARDPVRRSPFDIWGQGTMVTVSSASTKGPS<br>VFPLAPCSRSTSESTAALGCLVKDYFPEPVTVSWNSGALTSG<br>VHTFPAVLQSSGLYSLSSVVTVPSSSLGTKTYTCNVDHKPSN<br>TKVDKRVESKYGPPCPPCPAPEFLGGPSVFLFPPKPKDTLMI<br>SRTPEVTCVVVDVSQEDPEVQFNWYVDGVEVHNAKTKPREEQ<br>FNSTYRVVSVLTVLHQDWLNGKEYKCKVSNKGLPSSIEKTIS<br>KAKGQPREPQVYTLPPSQEEMTKNQVSLTCLVKGFYPSDIAV<br>EWESNGQPENNYKTTPPVLDSDGSFFLYSRLTVDKSRWQEGN<br>VFSCSVMHEALHNHYTQKSLSLSLG |
| SEQ ID NO: 76 | DNA<br>HEAVY<br>CHAIN | CAGGTGCAGCTGGTGCAGTCTGGGGCTGAGGTGAAGAAGCCT<br>GGGTCCTCGGTGAAGGTCTCCTGCAAGGCTTCTGGAGGCACC<br>TTCAGCACGTATGCTATCGGGTGGGTGCGACAGGCCCCTGGA<br>CAAGGGCTTGAGTGGATGGGAGGGATCATCCCTGCGTTTGGT<br>ACAGCAAACTACGCACAGAAGTTCCAGGGCAGAGTCACGATT<br>ACCGCGGACGAATCCACGAGCACAGCCTACATGGAGCTGAGC<br>AGCCTGAGATCTGAGGACACGGCGGTGTACTACTGCGCCAGA<br>GATCCGGTGAGAAGAAGCCCATTCGACATATGGGGTCAGGGT<br>ACAATGGTCACCGTCTCCTCAGCTTCCACCAAGGGCCCCTCC<br>GTGTTCCCTCTGGCCCCTTGCTCCCGGTCCACCTCCGAGTCT<br>ACCGCCGCTCTGGGCTGCCTCGTGAAGGACTACTTCCCCGAG<br>CCCGTGACCGTGTCCTGGAACTCTGGCGCCCTGACCTCCGGC<br>GTGCACACCTTCCCTGCCGTGCTGCAGTCCTCCGGCCTGTAC<br>TCCCTGTCCAGCGTCGTGACCGTGCCCTCCTCCAGCCTGGGC<br>ACCAAGACCTACACCTGTAACGTGGACCACAAGCCCTCCAAC<br>ACCAAAGTGGACAAGCGGGTGGAATCTAAGTACGGCCCTCCC<br>TGCCCTCCTTGCCCTGCCCCTGAGTTCCTGGGCGGACCTTCC<br>GTGTTCCTGTTCCCTCCAAAGCCCAAGGACACCCTGATGATC<br>TCCCGGACCCCTGAAGTGACCTGCGTGGTGGTGGACGTGTCC<br>CAGGAAGATCCCGAAGTCCAGTTCAATTGGTACGTGGACGGC<br>GTGGAAGTGCACAACGCCAAGACCAAGCCCAGAGAGGAACAG<br>TTCAACTCCACCTACCGGGTGGTGTCCGTGCTGACCGTGCTG<br>CACCAGGACTGGCTGAACGGCAAAGAGTACAAGTGCAAAGTG<br>TCCAACAAGGGCCTGCCCTCCAGCATCGAAAAGACCATCTCC<br>AAGGCCAAGGGCCAGCCCCGCGAGCCCAAGTGTACACCCTG<br>CCTCCCAGCCAGGAAGAGATGACCAAGAATCAAGTGTCCCTG<br>ACTTGTCTGGTCAAGGGCTTCTACCCCTCCGATATCGCCGTG<br>GAGTGGGAGTCCAACGGCCAGCCCGAGAACAACTACAAGACC<br>ACCCCTCCCGTGCTGGACTCCGACGGCTCCTTCTTCCTGTAC<br>TCTCGGCTGACCGTGGACAAGTCCCGGTGGCAGGAAGGCAAC |

TABLE 1-continued

SEQUENCE LISTING
NT = non-traditional

| | | |
|---|---|---|
| | | GTCTTCTCCTGCTCCGTGATGCACGAGGCCCTGCACAACCAC TACACCCAGAAGTCCCTGTCCCTGTCTCTGGGC |

SRF370-B

| | | |
|---|---|---|
| SEQ ID NO: 77 | HEAVY CHAIN | QVQLVQSGAEVKKPGSSVKVSCKASGGTFSTYAIGWVRQAPG QGLEWMGGIIPAFGTANYAQKFQGRVTITADESTSTAYMELS SLRSEDTAVYYCARDPVRRSPFDIWGQGTMVTVSSASTKGPS VFPLAPCSRSTSESTAALGCLVKDYFPEPVTVSWNSGALTSG VHTFPAVLQSSGLYSLSSVVTVPSSSLGTKTYTCNVDHKPSN TKVDKRVESKYGPPCPPCPAPEFEGGPSVFLFPPKPKDTLMI SRTPEVTCVVVDVSQEDPEVQFNWYVDGVEVHNAKTKPREEQ FNSTYRVVSVLTVLHQDWLNGKEYKCKVSNKGLPSSIEKTIS KAKGQPREPQVYTLPPSQEEMTKNQVSLTCLVKGFYPSDIAV EWESNGQPENNYKTTPPVLDSDGSFFLYSRLTVDKSRWQEGN VFSCSVMHEALHNHYTQKSLSLSLG |
| SEQ ID NO: 78 | DNA HEAVY CHAIN | CAGGTGCAGCTGGTGCAGTCTGGGGCTGAGGTGAAGAAGCCT GGGTCCTCGGTGAAGGTCTCCTGCAAGGCTTCTGGAGGCACC TTCAGCACGTATGCTATCGGGTGGGTGCGACAGGCCCCTGGA CAAGGGCTTGAGTGGATGGGAGGGATCATCCCTGCGTTTGGT ACAGCAAACTACGCACAGAAGTTCCAGGGCAGAGTCACGATT ACCGCGGACGAATCCACGAGCACAGCCTACATGGAGCTGAGC AGCCTGAGATCTGAGGACACGGCGGTGTACTACTGCGCCAGA GATCCGGTGAGAAGAAGCCCATTCGACATATGGGGTCAGGGT ACAATGGTCACCGTCTCCTCAGCTTCCACCAAGGGCCCCTCC GTGTTCCCTCTGGCCCCTTGCTCCCGGTCCACCTCCGAGTCT ACCGCCGCTCTGGGCTGCCTCGTGAAGGACTACTTCCCCGAG CCCGTGACCGTGTCCTGGAACTCTGGCGCCCTGACCTCCGGC GTGCACACCTTCCCTGCCGTGCTGCAGTCCTCCGGCCTGTAC TCCCTGTCCAGCGTCGTGACCGTGCCCTCCTCCAGCCTGGGC ACCAAGACCTACACCTGTAACGTGGACCACAAGCCCTCCAAC ACCAAAGTGGACAAGCGGGTGGAATCTAAGTACGGCCCTCCC TGCCCTCCTTGCCCTGCCCCTGAGTTCGAGGGCGGACCTTCC GTGTTCCTGTTCCCTCCAAAGCCCAAGGACACCCTGATGATC TCCCGGACCCCTGAAGTGACCTGCGTGGTGGTGGACGTGTCC CAGGAAGATCCCGAAGTCCAGTTCAATTGGTACGTGGACGGC GTGGAAGTGCACAACGCCAAGACCAAGCCCAGAGAGGAACAG TTCAACTCCACCTACCGGGTGGTGTCCGTGCTGACCGTGCTG CACCAGGACTGGCTGAACGGCAAAGAGTACAAGTGCAAAGTG TCCAACAAGGGCCTGCCCTCCAGCATCGAAAAGACCATCTCC AAGGCCAAGGGCCAGCCCCGCGAGCCCCAAGTGTACACCCTG CCTCCCAGCCAGGAAGAGATGACCAAGAATCAAGTGTCCCTG ACTTGTCTGGTCAAGGGCTTCTACCCCTCCGATATCGCCGTG GAGTGGGAGTCCAACGGCCAGCCCGAGAACAACTACAAGACC ACCCCTCCCGTGCTGGACTCCGACGGCTCCTTCTTCCTGTAC TCTCGGCTGACCGTGGACAAGTCCCGGTGGCAGGAAGGCAAC GTCTTCTCCTGCTCCGTGATGCACGAGGCCCTGCACAACCAC TACACCCAGAAGTCCCTGTCCCTGTCTCTGGGC |

SRF360-C

| | | |
|---|---|---|
| SEQ ID NO: 79 | HCDR1 (IMGT) | GFTFSSYR |
| SEQ ID NO: 80 | HCDR2 (IMGT) | ISSSSSSI |
| SEQ ID NO: 81 | HCDR3 (IMGT) | AKGPRYDSSGYRWRYGMDV |
| SEQ ID NO: 82 | HCDR1 (NT) | FTFSSYRMN |
| SEQ ID NO: 83 | HCDR2 (NT) | SISSSSSSIWYADSVKG |
| SEQ ID NO: 84 | HCDR3 (NT) | AKGPRYDSSGYRWRYGMDV |
| SEQ ID NO: 85 | VH | EVQLVESGGGLVKPGGSLRLSCAASGFTFSSYRMNWVRQAPG KGLEWVSSISSSSSSIWYADSVKGRFTISRDNAKNSLYLQMN SLRAEDTAVYYCAKGPRYDSSGYRWRYGMDVWGQGTTVTVSS |
| SEQ ID NO: 86 | DNA VH | GAGGTGCAGCTGGTGGAGTCTGGGGGAGGCCTGGTCAAGCCT GGGGGGTCCCTGAGACTCTCCTGTGCAGCCTCTGGATTCACC TTCTCTAGCTATAGGATGAACTGGGTCCGCCAGGCTCCAGGG AAGGGGCTGGAGTGGGTCTCATCCATTAGTAGTAGTAGTAGT TCGATATGGTACGCAGACTCAGTGAAGGGCCGATTCACCATC TCCAGAGACAACGCCAAGAACTCACTGTATCTGCAAATGAAC AGCCTGAGAGCCGAGGACACGGCGGTGTACTACTGCGCCAAG GGCCCCAGATACGACAGCAGCGGATACCGGTGGAGATACGGA ATGGACGTATGGGGCCAGGGAACAACTGTCACCGTCTCCTCA |
| SEQ ID NO: 87 | HEAVY CHAIN | EVQLVESGGGLVKPGGSLRLSCAASGFTFSSYRMNWVRQAPG KGLEWVSSISSSSSSIWYADSVKGRFTISRDNAKNSLYLQMN SLRAEDTAVYYCAKGPRYDSSGYRWRYGMDVWGQGTTVTVSS ASTKGPSVFPLAPSSKSTSGGTAALGCLVKDYFPEPVTVSWN |

TABLE 1-continued

SEQUENCE LISTING
NT = non-traditional

| | | |
|---|---|---|
| | | SGALTSGVHTFPAVLQSSGLYSLSSVVTVPSSSLGTQTYICN VNHKPSNTKVDKKVEPKSCDKTHTCPPCPAPELLGGPSVFLF PPKPKDTLMISRTPEVTCVVVDVSHEDPEVKFNWYVDGVEVH NAKTKPREEQYNSTYRVVSVLTVLHQDWLNGKEYKCKVSNKA LPAPIEKTISKAKGQPREPQVYTLPPSRDELTKNQVSLTCLV KGFYPSDIAVEWESNGQPENNYKTTPPVLDSDGSFFLYSKLT VDKSRWQQGNVFSCSVMHEALHNHYTQKSLSLSPGK |
| SEQ ID NO: 88 | DNA HEAVY CHAIN | GAGGTGCAGCTGGTGGAGTCTGGGGGAGGCTGGTCAAGCCT GGGGGGTCCCTGAGACTCTCCTGTGCAGCCTCTGGATTCACC TTCTCTAGCTATAGGATGAACTGGGTCCGCCAGGCTCCAGGG AAGGGGCTGGAGTGGGTCTCATCCATTAGTAGTAGTAGTAGT TCGATATGGTACGCAGACTCAGTGAAGGGCCGATTCACCATC TCCAGAGACAACGCCAAGAACTCACTGTATCTGCAAATGAAC AGCCTGAGAGCCGAGGACACGGCGGTGTACTACTGCGCCAAG GGCCCCAGATACGACAGCAGCGGATACCGATGGAGATACGGA ATGGACGTATGGGGCCAGGGAACAACTGTCACCGTCTCCTCA GCGAGCACCAAAGGCCCGAGCGTGTTTCCGCTGGCGCCGAGC AGCAAAAGCACCAGCGGCGGCACCGCGGCGCTGGGCTGCCTG GTGAAAGATTATTTTCCGGAACCGGTGACCGTGAGCTGGAAC AGCGGCGCGCTGACCAGCGGCGTGCATACCTTTCCGGCGGTG CTGCAGAGCAGCGGCCTGTATAGCCTGAGCAGCGTGGTGACC GTGCCGAGCAGCAGCCTGGGCACCCAGACCTATATTTGCAAC GTGAACCATAAACCGAGCAACACCAAAGTGGATAAAAAAGTG GAACCGAAAAGCTGCGATAAAACCCATACCTGCCCGCCGTGC CCGGCGCCGGAACTGCTGGGCGGCCCCGAGCGTGTTTCTGTTT CCGCCGAAACCGAAAGATACCCTGATGATTAGCCGCACCCCG GAAGTGACCTGCGTGGTGGTGGATGTGAGCCATGAAGATCCG GAAGTGAAATTTAACTGGTATGTGGATGGCGTGGAAGTGCAT AACGCGAAAACCAAACCGCGCGAAGAACAGTATAACAGCACC TATCGCGTGGTGAGCGTGCTGACCGTGCTGCATCAGGATTGG CTGAACGGCAAAGAATATAAATGCAAAGTGAGCAACAAAGCG CTGCCGGCGCCGATTGAAAAAACCATTAGCAAAGCGAAAGGC CAGCCGCGCGAACCGCAGGTGTATACCCTGCCGCCGAGCCGC GATGAACTGACCAAAAACCAGGTGAGCCTGACCTGCCTGGTG AAAGGCTTTTATCCGAGCGATATTGCGGTGGAATGGGAAAGC AACGGCCAGCCGGAAAACAACTATAAAACCACCCCGCCGGTG CTGGATAGCGATGGCAGCTTTTTTCTGTATAGCAAACTGACC GTGGATAAAAGCCGCTGGCAGCAGGGCAACGTGTTTAGCTGC AGCGTGATGCATGAAGCGCTGCATAACCATTATACCCAGAAA AGCCTGAGCCTGAGCCCGGGCAAA |
| SEQ ID NO: 89 | LCDR1 (IMGT) | QSISSY |
| SEQ ID NO: 90 | LCDR2 (IMGT) | AAS |
| SEQ ID NO: 91 | LCDR3 (IMGT) | QQLYVDPPWT |
| SEQ ID NO: 92 | LCDR1 (NT) | RASQSISSYLN |
| SEQ ID NO: 93 | LCDR2 (NT) | AASSLQS |
| SEQ ID NO: 94 | LCDR3 (NT) | QQLYVDPPWT |
| SEQ ID NO: 95 | VL | DIQMTQSPSSLSASVGDRVTITCRASQSISSYLNWYQQKPGK APKLLIYAASSLQSGVPSRFSGSGSGTDFTLTISSLQPEDFA TYYCQQLYVDPPWTFGGGTKVEIK |
| SEQ ID NO: 96 | DNA VL | GACATCCAGATGACCCAGTCTCCATCCTCCCTGTCTGCATCT GTAGGAGACAGAGTCACCATCACTTGCCGGGCAAGTCAGAGC ATTAGCAGCTATTTAAATTGGTATCAGCAGAAACCAGGGAAA GCCCCTAAGCTCCTGATCTATGCTGCATCCAGTTTGCAAAGT GGGGTCCCATCAAGGTTCAGTGGCAGTGGATCTGGGACAGAT TTCACTCTCACCATCAGCAGTCTGCAACCTGAAGATTTTGCA ACTTACTACTGTCAGCAACTATACGTCGACCCTCCTTGGACT TTTGGCGGAGGGACCAAGGTTGAGATCAAA |
| SEQ ID NO: 97 | LIGHT CHAIN | DIQMTQSPSSLSASVGDRVTITCRASQSISSYLNWYQQKPGK APKLLIYAASSLQSGVPSRFSGSGSGTDFTLTISSLQPEDFA TYYCQQLYVDPPWTFGGGTKVEIKRTVAAPSVFIFPPSDEQL KSGTASVVCLLNNFYPREAKVQWKVDNALQSGNSQESVTEQD SKDSTYSLSSTLTLSKADYEKHKVYACEVTHQGLSSPVTKSF NRGEC |
| SEQ ID NO: 98 | DNA LIGHT CHAIN | GACATCCAGATGACCCAGTCTCCATCCTCCCTGTCTGCATCT GTAGGAGACAGAGTCACCATCACTTGCCGGGCAAGTCAGAGC ATTAGCAGCTATTTAAATTGGTATCAGCAGAAACCAGGGAAA GCCCCTAAGCTCCTGATCTATGCTGCATCCAGTTTGCAAAGT GGGGTCCCATCAAGGTTCAGTGGCAGTGGATCTGGGACAGAT TTCACTCTCACCATCAGCAGTCTGCAACCTGAAGATTTTGCA ACTTACTACTGTCAGCAACTATACGTCGACCCTCCTTGGACT TTTGGCGGAGGGACCAAGGTTGAGATCAAACGTACGGTGGCC |

TABLE 1-continued

SEQUENCE LISTING
NT = non-traditional

|  |  |  |  |
|---|---|---|---|
|  |  |  | GCTCCCTCCGTGTTCATCTTCCCACCCTCCGACGAGCAGCTG<br>AAGTCCGGCACCGCCTCCGTCGTGTGCCTGCTGAACAACTTC<br>TACCCTCGCGAGGCCAAAGTGCAGTGGAAAGTGGACAACGCC<br>CTGCAGTCCGGCAACTCCCAGGAATCCGTCACCGAGCAGGAC<br>TCCAAGGACAGCACCTACTCCCTGTCCTCCACCCTGACCCTG<br>TCCAAGGCCGACTACGAGAAGCACAAAGTGTACGCCTGCGAA<br>GTGACCCACCAGGGCCTGTCCAGCCCCGTGACCAAGTCCTTC<br>AACCGGGGCGAGTGC |
| SRF360-D |  |  |  |
| SEQ ID NO: 99 | HEAVY<br>CHAIN |  | EVQLVESGGGLVKPGGSLRLSCAASGFTFSSYRMNWVRQAPG<br>KGLEWVSSISSSSSSIWYADSVKGRFTISRDNAKNSLYLQMN<br>SLRAEDTAVYYCAKGPRYDSSGYRWRYGMDVWGQGTTVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPSCPAPEFLGGPSVFLFPPK<br>PKDTLMISRTPEVTCVVVDVSQEDPEVQFNWYVDGVEVHNAK<br>TKPREEQFNSTYRVVSVLTVLHQDWLNGKEYKCKVSNKGLPS<br>SIEKTISKAKGQPREPQVYTLPPSQEEMTKNQVSLTCLVKGF<br>YPSDIAVEWESNGQPENNYKTTPPVLDSDGSFFLYSRLTVDK<br>SRWQEGNVFSCSVMHEALHNHYTQKSLSLSLG |
| SEQ ID NO: 100 | DNA<br>HEAVY<br>CHAIN |  | GAGGTGCAGCTGGTGGAGTCTGGGGGAGGCCTGGTCAAGCCT<br>GGGGGGTCCCTGAGACTCTCCTGTGCAGCCTCTGGATTCACC<br>TTCTCTAGCTATAGGATGAACTGGGTCCGCCAGGCTCCAGGG<br>AAGGGGCTGGAGTGGGTCTCATCCATTAGTAGTAGTAGTAGT<br>TCGATATGGTACGCAGACTCAGTGAAGGGCCGATTCACCATC<br>TCCAGAGACAACGCCAAGAACTCACTGTATCTGCAAATGAAC<br>AGCCTGAGAGCCGAGGACACGGCGGTGTACTACTGCGCCAAG<br>GGCCCCAGATACGACAGCAGCGGATACCGATGGAGATACGGA<br>ATGGACGTATGGGGCCAGGGAACAACTGTCACCGTCTCCTCA<br>GCTTCCACCAAGGGCCCCTCCGTGTTCCCTCTGGCCCCTTGC<br>TCCCGGTCCACCTCCGAGTCTACCGCCGCTCTGGGCTGCCTC<br>GTGAAGGACTACTTCCCCGAGCCCGTGACCGTGTCCTGGAAC<br>TCTGGCGCCCTGACCTCCGGCGTGCACACCTTCCCTGCCGTG<br>CTGCAGTCCTCCGGCCTGTACTCCCTGTCCAGCGTCGTGACC<br>GTGCCCTCCTCCAGCCTGGGCACCAAGACCTACACCTGTAAC<br>GTGGACCACAAGCCCTCCAACACCAAAGTGGACAAGCGGGTG<br>GAATCTAAGTACGGCCCTCCCTGCCCTTCCTGCCCTGCCCCT<br>GAGTTCCTGGGCGGACCTTCCGTGTTCCTGTTCCCTCCAAAG<br>CCCAAGGACACCCTGATGATCTCCCGGACCCCTGAAGTGACC<br>TGCGTGGTGGTGGACGTGTCCCAGGAAGATCCCGAAGTCCAG<br>TTCAATTGGTACGTGGACGGCGTGGAAGTGCACAACGCCAAG<br>ACCAAGCCCAGAGAGGAACAGTTCAACTCCACCTACCGGGTG<br>GTGTCCGTGCTGACCGTGCTGCACCAGGACTGGCTGAACGGC<br>AAAGAGTACAAGTGCAAAGTGTCCAACAAGGGCCTGCCCTCC<br>AGCATCGAAAAGACCATCTCCAAGGCCAAGGGCCAGCCCCGC<br>GAGCCCCAAGTGTACACCCTGCCTCCCAGCCAGGAAGAGATG<br>ACCAAGAATCAAGTGTCCCTGACTTGTCTGGTCAAGGGCTTC<br>TACCCCTCCGATATCGCCGTGGAGTGGGAGTCCAACGGCCAG<br>CCCGAGAACAACTACAAGACCACCCCTCCCGTGCTGGACTCC<br>GACGGCTCCTTCTTCCTGTACTCTCGGCTGACCGTGGACAAG<br>TCCCGGTGGCAGGAAGGCAACGTCTTCTCCTGCTCCGTGATG<br>CACGAGGCCCTGCACAACCACTACACCCAGAAGTCCCTGTCC<br>CTGTCTCTGGGC |
| SRF360-A |  |  |  |
| SEQ ID NO: 101 | HEAVY<br>CHAIN |  | EVQLVESGGGLVKPGGSLRLSCAASGFTFSSYRMNWVRQAPG<br>KGLEWVSSISSSSSSIWYADSVKGRFTISRDNAKNSLYLQMN<br>SLRAEDTAVYYCAKGPRYDSSGYRWRYGMDVWGQGTTVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFLGGPSVFLFPPK<br>PKDTLMISRTPEVTCVVVDVSQEDPEVQFNWYVDGVEVHNAK<br>TKPREEQFNSTYRVVSVLTVLHQDWLNGKEYKCKVSNKGLPS<br>SIEKTISKAKGQPREPQVYTLPPSQEEMTKNQVSLTCLVKGF<br>YPSDIAVEWESNGQPENNYKTTPPVLDSDGSFFLYSRLTVDK<br>SRWQEGNVFSCSVMHEALHNHYTQKSLSLSLG |
| SEQ ID NO: 102 | DNA<br>HEAVY<br>CHAIN |  | GAGGTGCAGCTGGTGGAGTCTGGGGGAGGCCTGGTCAAGCCT<br>GGGGGGTCCCTGAGACTCTCCTGTGCAGCCTCTGGATTCACC<br>TTCTCTAGCTATAGGATGAACTGGGTCCGCCAGGCTCCAGGG<br>AAGGGGCTGGAGTGGGTCTCATCCATTAGTAGTAGTAGTAGT<br>TCGATATGGTACGCAGACTCAGTGAAGGGCCGATTCACCATC<br>TCCAGAGACAACGCCAAGAACTCACTGTATCTGCAAATGAAC<br>AGCCTGAGAGCCGAGGACACGGCGGTGTACTACTGCGCCAAG<br>GGCCCCAGATACGACAGCAGCGGATACCGATGGAGATACGGA<br>ATGGACGTATGGGGCCAGGGAACAACTGTCACCGTCTCCTCA<br>GCTTCCACCAAGGGCCCCTCCGTGTTCCCTCTGGCCCCTTGC |

TABLE 1-continued

SEQUENCE LISTING
NT = non-traditional

|  |  |  |
|---|---|---|
|  |  | TCCCGGTCCACCTCCGAGTCTACCGCCGCTCTGGGCTGCCTC
GTGAAGGACTACTTCCCCGAGCCCGTGACCGTGTCCTGGAAC
TCTGGCGCCCTGACCTCCGGCGTGCACACCTTCCCTGCCGTG
CTGCAGTCCTCCGGCCTGTACTCCCTGTCCAGCGTCGTGACC
GTGCCCTCCTCCAGCCTGGGCACCAAGACCTACACCTGTAAC
GTGGACCACAAGCCCTCCAACACCAAAGTGGACAAGCGGGTG
GAATCTAAGTACGGCCCTCCCTGCCCTCCTTGCCCTGCCCCT
GAGTTCCTGGGCGGACCTTCCGTGTTCCTGTTCCCTCCAAAG
CCCAAGGACACCCTGATGATCTCCCGGACCCCTGAAGTGACC
TGCGTGGTGGTGGACGTGTCCAGGAAGATCCCGAAGTCCAG
TTCAATTGGTACGTGGACGGCGTGGAAGTGCACAACGCCAAG
ACCAAGCCCAGAGAGGAACAGTTCAACTCCACCTACCGGGTG
GTGTCCGTGCTGACCGTGCTGCACCAGGACTGGCTGAACGGC
AAAGAGTACAAGTGCAAAGTGTCCAACAAGGGCCTGCCCTCC
AGCATCGAAAAGACCATCTCCAAGGCCAAGGGCCAGCCCCGC
GAGCCCCAAGTGTACACCCTGCCTCCCAGCCAGGAAGAGATG
ACCAAGAATCAAGTGTCCCTGACTTGTCTGGTCAAGGGCTTC
TACCCCTCCGATATCGCCGTGGAGTGGGAGTCCAACGGCCAG
CCCGAGAACAACTACAAGACCACCCCTCCCGTGCTGGACTCC
GACGGCTCCTTCTTCCTGTACTCTCGGCTGACCGTGGACAAG
TCCCGGTGGCAGGAAGGCAACGTCTTCTCCTGCTCCGTGATG
CACGAGGCCCTGCACAACCACTACACCCAGAAGTCCCTGTCC
CTGTCTCTGGGC |
| SRF360-B |  |  |
| SEQ ID NO: 103 | HEAVY
CHAIN | EVQLVESGGGLVKPGGSLRLSCAASGFTFSSYRMNWVRQAPG
KGLEWVSSISSSSSSIWYADSVKGRFTISRDNAKNSLYLQMN
SLRAEDTAVYYCAKGPRYDSSGYRWRYGMDVWGQGTTVTVSS
ASTKGPSVFPLAPCSRSTSESTAALGCLVKDYFPEPVTVSWN
SGALTSGVHTFPAVLQSSGLYSLSSVVTVPSSSLGTKTYTCN
VDHKPSNTKVDKRVESKYGPPCPPCPAPEFEGGPSVFLFPPK
PKDTLMISRTPEVTCVVVDVSQEDPEVQFNWYVDGVEVHNAK
TKPREEQFNSTYRVVSVLTVLHQDWLNGKEYKCKVSNKGLPS
SIEKTISKAKGQPREPQVYTLPPSQEEMTKNQVSLTCLVKGF
YPSDIAVEWESNGQPENNYKTTPPVLDSDGSFFLYSRLTVDK
SRWQEGNVFSCSVMHEALHNHYTQKSLSLSLG |
| SEQ ID NO: 104 | DNA
HEAVY
CHAIN | GAGGTGCAGCTGGTGGAGTCTGGGGGAGGCCTGGTCAAGCCT
GGGGGGTCCCTGAGACTCTCCTGTGCAGCCTCTGGATTCACC
TTCTCTAGCTATAGGATGAACTGGGTCCGCCAGGCTCCAGGG
AAGGGGCTGGAGTGGGTCTCATCCATTAGTAGTAGTAGTAGT
TCGATATGGTACGCAGACTCAGTGAAGGGCCGATTCACCATC
TCCAGAGACAACGCCAAGAACTCACTGTATCTGCAAATGAAC
AGCCTGAGAGCCGAGGACACGGCGGTGTACTACTGCGCCAAG
GGCCCCAGATACGACAGCAGCGGATACCGATGGAGATACGGA
ATGGACGTATGGGGCCAGGGAACAACTGTCACCGTCTCCTCA
GCTTCCACCAAGGGCCCCTCCGTGTTCCCTCTGGCCCCTTGC
TCCCGGTCCACCTCCGAGTCTACCGCCGCTCTGGGCTGCCTC
GTGAAGGACTACTTCCCCGAGCCCGTGACCGTGTCCTGGAAC
TCTGGCGCCCTGACCTCCGGCGTGCACACCTTCCCTGCCGTG
CTGCAGTCCTCCGGCCTGTACTCCCTGTCCAGCGTCGTGACC
GTGCCCTCCTCCAGCCTGGGCACCAAGACCTACACCTGTAAC
GTGGACCACAAGCCCTCCAACACCAAAGTGGACAAGCGGGTG
GAATCTAAGTACGGCCCTCCCTGCCCTCCTTGCCCTGCCCCT
GAGTTCGAGGGCGGACCTTCCGTGTTCCTGTTCCCTCCAAAG
CCCAAGGACACCCTGATGATCTCCCGGACCCCTGAAGTGACC
TGCGTGGTGGTGGACGTGTCCAGGAAGATCCCGAAGTCCAG
TTCAATTGGTACGTGGACGGCGTGGAAGTGCACAACGCCAAG
ACCAAGCCCAGAGAGGAACAGTTCAACTCCACCTACCGGGTG
GTGTCCGTGCTGACCGTGCTGCACCAGGACTGGCTGAACGGC
AAAGAGTACAAGTGCAAAGTGTCCAACAAGGGCCTGCCCTCC
AGCATCGAAAAGACCATCTCCAAGGCCAAGGGCCAGCCCCGC
GAGCCCCAAGTGTACACCCTGCCTCCCAGCCAGGAAGAGATG
ACCAAGAATCAAGTGTCCCTGACTTGTCTGGTCAAGGGCTTC
TACCCCTCCGATATCGCCGTGGAGTGGGAGTCCAACGGCCAG
CCCGAGAACAACTACAAGACCACCCCTCCCGTGCTGGACTCC
GACGGCTCCTTCTTCCTGTACTCTCGGCTGACCGTGGACAAG
TCCCGGTGGCAGGAAGGCAACGTCTTCTCCTGCTCCGTGATG
CACGAGGCCCTGCACAACCACTACACCCAGAAGTCCCTGTCC
CTGTCTCTGGGC |
| SRF399-C |  |  |
| SEQ ID NO: 105 | HCDR1
(IMGT) | GYTFSSWY |
| SEQ ID NO: 106 | HCDR2
(IMGT) | INPSGGST |
| SEQ ID NO: 107 | HCDR3
(IMGT) | ARDAPFYTWDHYYGMD |

TABLE 1-continued

SEQUENCE LISTING
NT = non-traditional

| SEQ ID NO: 108 | HCDR1 (NT) | YTFSSWYMH |
|---|---|---|
| SEQ ID NO: 109 | HCDR2 (NT) | MINPSGGSTKYAQKFQG |
| SEQ ID NO: 110 | HCDR3 (NT) | ARDAPFYTWDHYYGMDV |
| SEQ ID NO: 111 | VH | QVQLVQSGAEVKKPGASVKVSCKASGYTFSSWYMHWVRQAPG QGLEWMGMINPSGGSTKYAQKFQGRVTMTRDTSTSTVYMELS SLRSEDTAVYYCARDAPFYTWDHYYGMDVWGQGTTVTVSS |
| SEQ ID NO: 112 | DNA VH | CAGGTGCAGCTGGTGCAGTCTGGGGCTGAGGTGAAGAAGCCT GGGGCCTCAGTGAAGGTTTCCTGCAAGGCATCTGGATACACC TTCAGTAGCTGGTATATGCACTGGGTGCGACAGGCCCCTGGA CAAGGGCTTGAGTGGATGGGAATGATCAACCCTAGTGGTGGT AGCACAAAGTACGCACAGAAGTTCCAGGGCAGAGTCACCATG ACCAGGGACACGTCCACGAGCACAGTCTACATGGAGCTGAGC AGCCTGAGATCTGAGGACACGGCGGTGTACTACTGCGCCAGA GATGCTCCTTTCTACACCTGGGATCACTACTACGGAATGGAC GTATGGGGCCAGGGAACAACTGTCACCGTCTCCTCA |
| SEQ ID NO: 113 | HEAVY CHAIN | QVQLVQSGAEVKKPGASVKVSCKASGYTFSSWYMHWVRQAPG QGLEWMGMINPSGGSTKYAQKFQGRVTMTRDTSTSTVYMELS SLRSEDTAVYYCARDAPFYTWDHYYGMDVWGQGTTVTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKVEPKSCDKTHTCPPCPAPELLGGPSVFLFPP KPKDTLMISRTPEVTCVVVDVSHEDPEVKFNWYVDGVEVHNA KTKPREEQYNSTYRVVSVLTVLHQDWLNGKEYKCKVSNKALP APIEKTISKAKGQPREPQVYTLPPSRDELTKNQVSLTCLVKG FYPSDIAVEWESNGQPENNYKTTPPVLDSDGSFFLYSKLTVD KSRWQQGNVFSCSVMHEALHNHYTQKSLSLSPGK |
| SEQ ID NO: 114 | DNA HEAVY CHAIN | CAGGTGCAGCTGGTGCAGTCTGGGGCTGAGGTGAAGAAGCCT GGGGCCTCAGTGAAGGTTTCCTGCAAGGCATCTGGATACACC TTCAGTAGCTGGTATATGCACTGGGTGCGACAGGCCCCTGGA CAAGGGCTTGAGTGGATGGGAATGATCAACCCTAGTGGTGGT AGCACAAAGTACGCACAGAAGTTCCAGGGCAGAGTCACCATG ACCAGGGACACGTCCACGAGCACAGTCTACATGGAGCTGAGC AGCCTGAGATCTGAGGACACGGCGGTGTACTACTGCGCCAGA GATGCTCCTTTCTACACCTGGGATCACTACTACGGAATGGAC GTATGGGGCCAGGGAACAACTGTCACCGTCTCCTCAGCGAGC ACCAAAGGCCCGAGCGTGTTTCCGCTGGCGCCGAGCAGCAAA AGCACCAGCGGCGGCACCGCGGCGCTGGGCTGCCTGGTGAAA GATTATTTTCCGGAACCGGTGACCGTGAGCTGGAACAGCGGC GCGCTGACCAGCGGCGTGCATACCTTTCCGGCGGTGCTGCAG AGCAGCGGCCTGTATAGCCTGAGCAGCGTGGTGACCGTGCCG AGCAGCAGCCTGGGCACCCAGACCTATATTTGCAACGTGAAC CATAAACCGAGCAACACCAAAGTGGATAAAAAAGTGGAACCG AAAAGCTGCGATAAAACCCATACCTGCCCGCCGTGCCCGGCG CCGGAACTGCTGGGCGGCCCGAGCGTGTTTCTGTTTCCGCCG AAACCGAAAGATACCCTGATGATTAGCCGCACCCCGGAAGTG ACCTGCGTGGTGGTGGATGTGAGCCATGAAGATCCGGAAGTG AAATTTAACTGGTATGTGGATGGCGTGGAAGTGCATAACGCG AAAACCAAACCGCGCGAAGAACAGTATAACAGCACCTATCGC GTGGTGAGCGTGCTGACCGTGCTGCATCAGGATTGGCTGAAC GGCAAAGAATATAAATGCAAAGTGAGCAACAAAGCGCTGCCG GCGCCGATTGAAAAAACCATTAGCAAAGCGAAAGGCCAGCCG CGCGAACCGCAGGTGTATACCCTGCCGCCGAGCCGCGATGAA CTGACCAAAAACCAGGTGAGCCTGACCTGCCTGGTGAAAGGC TTTTATCCGAGCGATATTGCGGTGGAATGGGAAAGCAACGGC CAGCCGGAAAACAACTATAAAACCACCCCGCCGGTGCTGGAT AGCGATGGCAGCTTTTTTCTGTATAGCAAACTGACCGTGGAT AAAAGCCGCTGGCAGCAGGGCAACGTGTTTAGCTGCAGCGTG ATGCATGAAGCGCTGCATAACCATTATACCCAGAAAAGCCTG AGCCTGAGCCCGGGCAAA |
| SEQ ID NO: 115 | LCDR1 (IMGT) | QDISNY |
| SEQ ID NO: 116 | LCDR2 (IMGT) | DAS |
| SEQ ID NO: 117 | LCDR3 (IMGT) | QQLYHLPIT |
| SEQ ID NO: 118 | LCDR1 (NT) | QASQDISNYLN |
| SEQ ID NO: 119 | LCDR2 (NT) | DASNLAT |
| SEQ ID NO: 120 | LCDR3 (NT) | QQLYHLPIT |
| SEQ ID NO: 121 | VL | DIQMTQSPSSLSASVGDRVTITCQASQDISNYLNWYQQKPGK APKLLIYDASNLATGVPSRFSGSGSGTDFTFTISSLQPEDIA TYYCQQLYHLPITFGGGTKVEIK |

TABLE 1-continued

SEQUENCE LISTING
NT = non-traditional

| SEQ ID NO: 122 | DNA VL | GACATCCAGATGACCCAGTCTCCATCCTCCCTGTCTGCATCT
GTAGGAGACAGAGTCACCATCACTTGCCAGGCGAGTCAGGAC
ATTAGCAACTATTTAAATTGGTATCAGCAGAAACCAGGGAAA
GCCCCTAAGCTCCTGATCTACGATGCATCCAATTTGGCAACA
GGGGTCCCATCAAGGTTCAGTGGAAGTGGATCTGGGACAGAT
TTTACTTTCACCATCAGCAGCCTGCAGCCTGAAGATATTGCA
ACATATTACTGTCAGCAGCTCTACCACCTCCCTATCACTTTT
GGCGGAGGGACCAAGGTTGAGATCAAA |
|---|---|---|
| SEQ ID NO: 123 | LIGHT CHAIN | DIQMTQSPSSLSASVGDRVTITCQASQDISNYLNWYQQKPGK
APKLLIYDASNLATGVPSRFSGSGSGTDFTFTISSLQPEDIA
TYYCQQLYHLPITFGGGTKVEIKRTVAAPSVFIFPPSDEQLK
SGTASVVCLLNNFYPREAKVQWKVDNALQSGNSQESVTEQDS
KDSTYSLSSILTLSKADYEKHKVYACEVTHQGLSSPVTKSFN
RGEC |
| SEQ ID NO: 124 | DNA LIGHT CHAIN | GACATCCAGATGACCCAGTCTCCATCCTCCCTGTCTGCATCT
GTAGGAGACAGAGTCACCATCACTTGCCAGGCGAGTCAGGAC
ATTAGCAACTATTTAAATTGGTATCAGCAGAAACCAGGGAAA
GCCCCTAAGCTCCTGATCTACGATGCATCCAATTTGGCAACA
GGGGTCCCATCAAGGTTCAGTGGAAGTGGATCTGGGACAGAT
TTTACTTTCACCATCAGCAGCCTGCAGCCTGAAGATATTGCA
ACATATTACTGTCAGCAGCTCTACCACCTCCCTATCACTTTT
GGCGGAGGGACCAAGGTTGAGATCAAACGTACGGTGGCCGCT
CCCTCCGTGTTCATCTTCCCACCCTCCGACGAGCAGCTGAAG
TCCGGCACCGCCTCCGTCGTGTGCCTGCTGAACAACTTCTAC
CCTCGCGAGGCCAAAGTGCAGTGGAAAGTGGACAACGCCCTG
CAGTCCGGCAACTCCCAGGAATCCGTCACCGAGCAGGACTCC
AAGGACAGCACCTACTCCCTGTCCTCCACCCTGACCCTGTCC
AAGGCCGACTACGAGAAGCACAAAGTGTACGCCTGCGAAGTG
ACCCACCAGGGCCTGTCCAGCCCCGTGACCAAGTCCTTCAAC
CGGGGCGAGTGC |

SRF399-D

| SEQ ID NO: 125 | HEAVY CHAIN | QVQLVQSGAEVKKPGASVKVSCKASGYTFSSWYMHWVRQAPG
QGLEWMGMINPSGGSTKYAQKFQGRVTMTRDTSTSTVYMELS
SLRSEDTAVYYCARDAPFYTWDHYYGMDVWGQGTTVTVSSAS
TKGPSVFPLAPCSRSTSESTAALGCLVKDYFPEPVTVSWNSG
ALTSGVHTFPAVLQSSGLYSLSSVVTVPSSSLGTKTYTCNVD
HKPSNTKVDKRVESKYGPPCPSCPAPEFLGGPSVFLFPPKPK
DTLMISRTPEVTCVVVDVSQEDPEVQFNWYVDGVEVHNAKTK
PREEQFNSTYRVVSVLTVLHQDWLNGKEYKCKVSNKGLPSSI
EKTISKAKGQPREPQVYTLPPSQEEMTKNQVSLTCLVKGFYP
SDIAVEWESNGQPENNYKTTPPVLDSDGSFFLYSRLTVDKSR
WQEGNVFSCSVMHEALHNHYTQKSLSLSLG |
|---|---|---|
| SEQ ID NO: 126 | DNA HEAVY CHAIN | CAGGTGCAGCTGGTGCAGTCTGGGGCTGAGGTGAAGAAGCCT
GGGGCCTCAGTGAAGGTTTCCTGCAAGGCATCTGGATACACC
TTCAGTAGCTGGTATATGCACTGGGTGCGACAGGCCCCTGGA
CAAGGGCTTGAGTGGATGGGAATGATCAACCCTAGTGGTGGT
AGCACAAAGTACGCACAGAAGTTCCAGGGCAGAGTCACCATG
ACCAGGGACACGTCCACGAGCACAGTCTACATGGAGCTGAGC
AGCCTGAGATCTGAGGACACGGCGGTGTACTACTGCGCCAGA
GATGCTCCTTTCTACACCTGGGATCACTACTACGGAATGGAC
GTATGGGGCCAGGGAACAACTGTCACCGTCTCCTCAGCTTCC
ACCAAGGGCCCCTCCGTGTTCCCTCTGGCCCCTTGCTCCCGG
TCCACCTCCGAGTCTACCGCCGCTCTGGGCTGCCTCGTGAAG
GACTACTTCCCCGAGCCCGTGACCGTGTCCTGGAACTCTGGC
GCCCTGACCTCCGGCGTGCACACCTTCCCTGCCGTGCTGCAG
TCCTCCGGCCTGTACTCCCTGTCCAGCGTCGTGACCGTGCCC
TCCTCCAGCCTGGGCACCAAGACCTACACCTGTAACGTGGAC
CACAAGCCCTCCAACACCAAAGTGGACAAGCGGGTGGAATCT
AAGTACGGCCCTCCCTGCCCTTCCTGCCCTGCCCCTGAGTTC
CTGGGCGGACCTTCCGTGTTCCTGTTCCCTCCAAAGCCCAAG
GACACCCTGATGATCTCCCGGACCCCTGAAGTGACCTGCGTG
GTGGTGGACGTGTCCCAGGAAGATCCCGAAGTCCAGTTCAAT
TGGTACGTGGACGGCGTGGAAGTGCACAACGCCAAGACCAAG
CCCAGAGAGGAACAGTTCAACTCCACCTACCGGGTGGTGTCC
GTGCTGACCGTGCTGCACCAGGACTGGCTGAACGGCAAAGAG
TACAAGTGCAAAGTGTCCAACAAGGGCCTGCCCTCCAGCATC
GAAAAGACCATCTCCAAGGCCAAGGGCCAGCCCCGCGAGCCC
CAAGTGTACACCCTGCCTCCCAGCCAGGAAGAGATGACCAAG
AATCAAGTGTCCCTGACTTGTCTGGTCAAGGGCTTCTACCCC
TCCGATATCGCCGTGGAGTGGGAGTCCAACGGCCAGCCCGAG
AACAACTACAAGACCACCCCTCCCGTGCTGGACTCCGACGGC
TCCTTCTTCCTGTACTCTCGGCTGACCGTGGACAAGTCCCGG
TGGCAGGAAGGCAACGTCTTCTCCTGCTCCGTGATGCACGAG
GCCCTGCACAACCACTACACCCAGAAGTCCCTGTCCCTGTCT
CTGGGC |

TABLE 1-continued

SEQUENCE LISTING
NT = non-traditional

SRF399-A

| SEQ ID NO: 127 | HEAVY CHAIN | QVQLVQSGAEVKKPGASVKVSCKASGYTFSSWYMHWVRQAPG
QGLEWMGMINPSGGSTKYAQKFQGRVTMTRDTSTSTVYMELS
SLRSEDTAVYYCARDAPFYTWDHYYGMDVWGQGTTVTVSSAS
TKGPSVFPLAPCSRSTSESTAALGCLVKDYFPEPVTVSWNSG
ALTSGVHTFPAVLQSSGLYSLSSVVTVPSSSLGTKTYTCNVD
HKPSNTKVDKRVESKYGPPCPPCPAPEFLGGPSVFLFPPKPK
DTLMISRTPEVTCVVVDVSQEDPEVQFNWYVDGVEVHNAKTK
PREEQFNSTYRVVSVLTVLHQDWLNGKEYKCKVSNKGLPSSI
EKTISKAKGQPREPQVYTLPPSQEEMTKNQVSLTCLVKGFYP
SDIAVEWESNGQPENNYKTTPPVLDSDGSFFLYSRLTVDKSR
WQEGNVFSCSVMHEALHNHYTQKSLSLSLG |
|---|---|---|
| SEQ ID NO: 128 | DNA HEAVY CHAIN | CAGGTGCAGCTGGTGCAGTCTGGGGCTGAGGTGAAGAAGCCT
GGGGCCTCAGTGAAGGTTTCCTGCAAGGCATCTGGATACACC
TTCAGTAGCTGGTATATGCACTGGGTGCGACAGGCCCCTGGA
CAAGGGCTTGAGTGGATGGGAATGATCAACCCTAGTGGTGGT
AGCACAAAGTACGCACAGAAGTTCCAGGGCAGAGTCACCATG
ACCAGGGACACGTCCACGAGCACAGTCTACATGGAGCTGAGC
AGCCTGAGATCTGAGGACACGGCGGTGTACTACTGCGCCAGA
GATGCTCCTTTCTACACCTGGGATCACTACTACGGAATGGAC
GTATGGGGCCAGGGAACAACTGTCACCGTCTCCTCAGCTTCC
ACCAAGGGCCCCTCCGTGTTCCCTCTGGCCCCTTGCTCCCGG
TCCACCTCCGAGTCTACCGCCGCTCTGGGCTGCCTCGTGAAG
GACTACTTCCCCGAGCCCGTGACCGTGTCCTGGAACTCTGGC
GCCCTGACCTCCGGCGTGCACACCTTCCCTGCCGTGCTGCAG
TCCTCCGGCCTGTACTCCCTGTCCAGCGTCGTGACCGTGCCC
TCCTCCAGCCTGGGCACCAAGACCTACACCTGTAACGTGGAC
CACAAGCCCTCCAACACCAAAGTGGACAAGCGGGTGGAATCT
AAGTACGGCCCTCCCTGCCCTCCTTGCCCTGCCCCTGAGTTC
CTGGGCGGACCTTCCGTGTTCCTGTTCCCTCCAAAGCCCAAG
GACACCCTGATGATCTCCCGGACCCCTGAAGTGACCTGCGTG
GTGGTGGACGTGTCCCAGGAAGATCCCGAAGTCCAGTTCAAT
TGGTACGTGGACGGCGTGGAAGTGCACAACGCCAAGACCAAG
CCCAGAGAGGAACAGTTCAACTCCACCTACCGGGTGGTGTCC
GTGCTGACCGTGCTGCACCAGGACTGGCTGAACGGCAAAGAG
TACAAGTGCAAAGTGTCCAACAAGGGCCTGCCCTCCAGCATC
GAAAAGACCATCTCCAAGGCCAAGGGCCAGCCCCGCGAGCCC
CAAGTGTACACCCTGCCTCCCAGCCAGGAAGAGATGACCAAG
AATCAAGTGTCCCTGACTTGTCTGGTCAAGGGCTTCTACCCC
TCCGATATCGCCGTGGAGTGGGAGTCCAACGGCCAGCCCGAG
AACAACTACAAGACCACCCCTCCCGTGCTGGACTCCGACGGC
TCCTTCTTCCTGTACTCTCGGCTGACCGTGGACAAGTCCCGG
TGGCAGGAAGGCAACGTCTTCTCCTGCTCCGTGATGCACGAG
GCCCTGCACAACCACTACACCCAGAAGTCCCTGTCCCTGTCT
CTGGGC |

SRF399-B

| SEQ ID NO: 129 | HEAVY CHAIN | QVQLVQSGAEVKKPGASVKVSCKASGYTFSSWYMHWVRQAPG
QGLEWMGMINPSGGSTKYAQKFQGRVTMTRDTSTSTVYMELS
SLRSEDTAVYYCARDAPFYTWDHYYGMDVWGQGTTVTVSSAS
TKGPSVFPLAPCSRSTSESTAALGCLVKDYFPEPVTVSWNSG
ALTSGVHTFPAVLQSSGLYSLSSVVTVPSSSLGTKTYTCNVD
HKPSNTKVDKRVESKYGPPCPPCPAPEFEGGPSVFLFPPKPK
DTLMISRTPEVTCVVVDVSQEDPEVQFNWYVDGVEVHNAKTK
PREEQFNSTYRVVSVLTVLHQDWLNGKEYKCKVSNKGLPSSI
EKTISKAKGQPREPQVYTLPPSQEEMTKNQVSLTCLVKGFYP
SDIAVEWESNGQPENNYKTTPPVLDSDGSFFLYSRLTVDKSR
WQEGNVFSCSVMHEALHNHYTQKSLSLSLG |
|---|---|---|
| SEQ ID NO: 130 | DNA HEAVY CHAIN | CAGGTGCAGCTGGTGCAGTCTGGGGCTGAGGTGAAGAAGCCT
GGGGCCTCAGTGAAGGTTTCCTGCAAGGCATCTGGATACACC
TTCAGTAGCTGGTATATGCACTGGGTGCGACAGGCCCCTGGA
CAAGGGCTTGAGTGGATGGGAATGATCAACCCTAGTGGTGGT
AGCACAAAGTACGCACAGAAGTTCCAGGGCAGAGTCACCATG
ACCAGGGACACGTCCACGAGCACAGTCTACATGGAGCTGAGC
AGCCTGAGATCTGAGGACACGGCGGTGTACTACTGCGCCAGA
GATGCTCCTTTCTACACCTGGGATCACTACTACGGAATGGAC
GTATGGGGCCAGGGAACAACTGTCACCGTCTCCTCAGCTTCC
ACCAAGGGCCCCTCCGTGTTCCCTCTGGCCCCTTGCTCCCGG
TCCACCTCCGAGTCTACCGCCGCTCTGGGCTGCCTCGTGAAG
GACTACTTCCCCGAGCCCGTGACCGTGTCCTGGAACTCTGGC
GCCCTGACCTCCGGCGTGCACACCTTCCCTGCCGTGCTGCAG
TCCTCCGGCCTGTACTCCCTGTCCAGCGTCGTGACCGTGCCC
TCCTCCAGCCTGGGCACCAAGACCTACACCTGTAACGTGGAC
CACAAGCCCTCCAACACCAAAGTGGACAAGCGGGTGGAATCT
AAGTACGGCCCTCCCTGCCCTCCTTGCCCTGCCCCTGAGTTC
GAGGGCGGACCTTCCGTGTTCCTGTTCCCTCCAAAGCCCAAG |

TABLE 1-continued

SEQUENCE LISTING
NT = non-traditional

| | | |
|---|---|---|
| | | GACACCCTGATGATCTCCCGGACCCCTGAAGTGACCTGCGTG GTGGTGGACGTGTCCCAGGAAGATCCCGAAGTCCAGTTCAAT TGGTACGTGGACGGCGTGGAAGTGCACAACGCCAAGACCAAG CCCAGAGAGGAACAGTTCAACTCCACCTACCGGGTGGTGTCC GTGCTGACCGTGCTGCACCAGGACTGGCTGAACGGCAAAGAG TACAAGTGCAAAGTGTCCAACAAGGGCCTGCCCTCCAGCATC GAAAAGACCATCTCCAAGGCCAAGGGCCAGCCCCGCGAGCCC CAAGTGTACACCCTGCCTCCCAGCCAGGAAGAGATGACCAAG AATCAAGTGTCCCTGACTTGTCTGGTCAAGGGCTTCTACCCC TCCGATATCGCCGTGGAGTGGGAGTCCAACGGCCAGCCCGAG AACAACTACAAGACCACCCCTCCCGTGCTGGACTCCGACGGC TCCTTCTTCCTGTACTCTCGGCTGACCGTGGACAAGTCCCGG TGGCAGGAAGGCAACGTCTTCTCCTGCTCCGTGATGCACGAG GCCCTGCACAACCACTACACCCAGAAGTCCCTGTCCCTGTCT CTGGGC |
| SEQ ID NO: 131 | Human IgG1 Constant Region | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPELLGGPSVFLFPPKPKDTLM ISRTPEVTCVVVDVSHEDPEVKFNWYVDGVEVHNAKTKPRE-EQYN STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEAL HNHYTQKSLSLSPGK |
| SEQ ID NO: 132 | Human IgG4 Constant Region (terminal K absent) | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPSCPAPEFLGGPSVFLFPPKPKDTLMISR TPEVTCVVVDVSQEDPEVQFNWYVDGVEVHNAKTKPREEQFN-STY RVVSVLTVLHQDWLNGKEYKCKVSNKGLPSSIEKTISKAKGQPRE PQVYTLPPSQEEMTKNQVSLTCLVKGFYPSDIAVEWESNGQPENN YKTTPPVLDSDGSFFLYSRLTVDKSRWQEGNVFSCSVMHEALHNH YTQKSLSLSLG- |
| SEQ ID NO: 133 | Human IgG4 Constant Region single mutant (S228P) (terminal K absent) | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLMISR TPEVTCVVVDVSQEDPEVQFNWYVDGVEVHNAKTKPREEQFN-STY RVVSVLTVLHQDWLNGKEYKCKVSNKGLPSSIEKTISKAKGQPRE PQVYTLPPSQEEMTKNQVSLTCLVKGFYPSDIAVEWESNGQPENN YKTTPPVLDSDGSFFLYSRLTVDKSRWQEGNVFSCSVMHEALHNH YTQKSLSLSLG- |
| SEQ ID NO: 134 | Human IgG4 Constant Region double mutant (S228P) (L235E) (terminal K absent) | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFEGGPSVFLFPPKPKDTLMISR TPEVTCVVVDVSQEDPEVQFNWYVDGVEVHNAKTKPREEQFN-STY RVVSVLTVLHQDWLNGKEYKCKVSNKGLPSSIEKTISKAKGQPRE PQVYTLPPSQEEMTKNQVSLTCLVKGFYPSDIAVEWESNGQPENN YKTTPPVLDSDGSFFLYSRLTVDKSRWQEGNVFSCSVMHEALHNH YTQKSLSLSLG- |
| SEQ ID NO: 135 | FLAG | DYKDDDDK |
| SEQ ID NO: 136 | polyhis-tidine (6-His) | HHHHHH |
| SEQ ID NO: 137 | hemag-glutinin (HA) | YPYDVPDYA |
| SEQ ID NO: 138 | CD39 (NCBI Ref Sequence: NP_0017 67.3) | MEDTKESNVKTFCSKNILAILGFSSIIAVIALLAVGLTQNKALPE NVKYGIVLDAGSSHTSLYIYKWPAEKENDTGVVHQVEECRVKGPG ISKFVQKVNEIGIYLTDCMERAREVIPRSQHQETPVYLGATAGMR LLRMESEELADRVLDVVERSLSNYPFDFQGARIITGQEEGAYGWI TINYLLGKFSQKTRWFSIVPYETNNQETFGALDLGGASTQVTFVP QNQTIESPDNALQFRLYGKDYNVYTHSFLCYGKDQALWQKLAKDI QVASNEILRDPCFHPGYKKVVNVSDLYKTPCTKRFEMTLPFQQFE IQGIGNYQQCHQSILELFNTSYCPYSQCAFNGIFLPPLQGDFGAF SAFYFVMKFLNLISEKVSQEKVTEMMKKFCAQPWEEIKTSYAGVK EKYLSEYCFSGTYILSLLLQGYHFTADSWEHIHFIGKIQGSDAGW TLGYMLNLTNMIPAEQPLSTPLSHSTYVFLMVLFSLVLFTVAIIG LLIFHKPSYFWKDMV |

The invention claimed is:

1. A method of treating a cancer associated with CD39 expression in the tumor microenvironment, the method comprising administering to a subject in need thereof a therapeutically effective amount of an isolated anti-CD39 antibody, wherein the isolated anti-CD39 antibody comprises:
   i. (a) HCDR1 comprising the amino acid sequence of SEQ ID NO: 27; (b) HCDR2 comprising the amino acid sequence of SEQ ID NO: 28; (c) HCDR3 comprising the amino acid sequence of SEQ ID NO: 29; (d) LCDR1 comprising the amino acid sequence of SEQ ID NO: 37; (e) LCDR2 comprising the amino acid sequence of SEQ ID NO: 38; and (f) LCDR3 comprising the amino acid sequence of SEQ ID NO: 39; or
   ii. (a) HCDR1 comprising the amino acid sequence of SEQ ID NO: 30; (b) HCDR2 comprising the amino acid sequence of SEQ ID NO: 31; (c) HCDR3 comprising the amino acid sequence of SEQ ID NO: 32; (d) LCDR1 comprising the amino acid sequence of SEQ ID NO: 40; (e) LCDR2 comprising the amino acid sequence of SEQ ID NO: 41; and (f) LCDR3 comprising the amino acid sequence of SEQ ID NO: 42.

2. The method of claim 1, wherein the isolated anti-CD39 antibody comprises a heavy chain variable region ($V_H$) and a light chain variable region ($V_L$), wherein the $V_H$ is at least 90% identical to the amino acid sequence of SEQ ID NO: 33 and the $V_L$ is at least 90% identical to the amino acid sequence of SEQ ID NO: 43.

3. The method of claim 1, wherein the cancer is a solid tumor.

4. The method of claim 1, wherein the cancer is selected from lung cancer, non-small cell lung cancer, ovarian cancer, kidney cancer, testicular cancer, pancreas cancer, breast cancer, triple-negative breast cancer, melanoma, head and neck cancer, squamous head and neck cancer, colorectal cancer, bladder cancer, endometrial cancer, prostate cancer, thyroid cancer, hepatocellular carcinoma, gastric cancer, brain cancer, lymphoma, and renal cancer.

5. The method of claim 1, wherein the cancer is pancreatic cancer.

6. The method of claim 1, wherein the cancer is gastric cancer.

7. The method of claim 1, wherein the cancer is prostate cancer.

8. The method of claim 1, wherein the cancer is endometrial cancer.

9. The method of claim 1, wherein the cancer is non-small cell lung cancer.

10. The method of claim 1, wherein the cancer is colorectal cancer.

11. The method of claim 1, wherein the cancer is ovarian cancer.

12. The method of claim 1, wherein the isolated anti-CD39 antibody is administered in combination with one or more additional therapeutic agents or procedure, wherein the additional therapeutic agent or procedure is selected from a chemotherapeutic agent, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, and a cellular immunotherapy, or a combination thereof.

13. The method of claim 12, wherein the one or more additional therapeutic agents is a PD-1 antagonist, an adenosine A2AR antagonist, a CD73 inhibitor, a CTLA-4 inhibitor, a TIM-3 inhibitor, a LAG-3 inhibitor, a chimeric antigen receptor (CAR) cell therapy, an anthracycline, a chemotherapeutic agent, or a combination thereof.

14. The method of claim 12, wherein the one or more additional therapeutic agents is a PD-1 antagonist.

15. The method of claim 12, wherein the one or more additional therapeutic agents is a CD73 inhibitor.

16. The method of claim 12, wherein the one or more additional therapeutic agents is an A2AR antagonist.

17. The method of claim 12, wherein the one or more additional therapeutic agents is a chemotherapeutic agent.

18. The method of claim 12, wherein the one or more additional therapeutic agents is a CD73 inhibitor and an A2AR antagonist.

19. The method of claim 12, wherein the one or more additional therapeutic agents is a PD-1 antagonist and an A2AR antagonist.

20. A method of treating a cancer associated with CD39 expression in the tumor microenvironment, the method comprising administering to a subject in need thereof a therapeutically effective amount of an isolated anti-CD39 antibody, wherein the isolated anti-CD39 antibody comprises a heavy chain variable region ($V_H$) and a light chain variable region ($V_L$), wherein the $V_H$ comprises the amino acid sequence of SEQ ID NO: 33 and the $V_L$ comprises the amino acid sequence of SEQ ID NO: 43.

* * * * *

SEQUENCE LISTING

<160> NUMBER OF SEQ ID NOS: 138

<210> SEQ ID NO 1
<211> LENGTH: 8
<212> TYPE: PRT
<213> ORGANISM: Artificial Sequence
<220> FEATURE:
<223> OTHER INFORMATION: Synthetic: HCDR1 (IMGT)

<400> SEQUENCE: 1

Gly Gly Thr Phe Ser Asp Lys Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic: HCDR2 (IMGT)

<400> SEQUENCE: 2

Ile Leu Pro Ile Phe Gly Thr Ala
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic: HCDR3 (IMGT)

<400> SEQUENCE: 3

Ala Arg Glu Ala Gly Tyr Tyr Arg Tyr Arg Tyr Phe Asp Leu
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic: HCDR1 (ADI)

<400> SEQUENCE: 4

Gly Thr Phe Ser Asp Lys Ala Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic: HCDR2 (ADI)

<400> SEQUENCE: 5

Ser Ile Leu Pro Ile Phe Gly Thr Ala Asn Tyr Ala Gln Lys Phe Gln
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: Synthetic: HCDR3 (ADI)

<400> SEQUENCE: 6

Ala Arg Glu Ala Gly Tyr Tyr Arg Tyr Arg Tyr Phe Asp Leu
1               5                   10

<210> SEQ ID NO 7
<211> LENGTH: 121
<212> TYPE: PRT
<213> ORGANISM: Artificial Sequence
<220> FEATURE:
<223> OTHER INFORMATION: Synthetic: VH

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Lys
                20                  25                  30

Ala Ile Ser Trp Val Arg Gln Ala Pro Gly Gln Gly Leu Glu Trp Met
            35                  40                  45

Gly Ser Ile Leu Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Arg Gly Thr Leu Val Thr Val Ser Ser
        115                 120

<210> SEQ ID NO 8
<211> LENGTH: 363
<212> TYPE: DNA
<213> ORGANISM: Artificial Sequence
<220> FEATURE:
<223> OTHER INFORMATION: Synthetic: DNA VH

<400> SEQUENCE: 8
caggtgcagc tggtgcagtc tggggctgag gtgaagaagc ctgggtcctc ggtgaaggtc    60
tcctgcaagg cttctggagg caccttcagc gataaggcta tcagctgggt gcgacaggcc   120
cctggacaag ggcttgagtg gatgggatcg atccttccta tctttggtac agcaaactac   180
gcacagaagt tccagggcag agtcacgatt accgcggacg aatccacgag cacagcctac   240
atggagctga gcagcctgag atctgaggac acggcggtgt actactgcgc cagagaagcc   300
ggatactacc gctaccgata cttcgaccta tgggggagag gtaccttggt caccgtctcc   360
tca                                                                 363

<210> SEQ ID NO 9
<211> LENGTH: 451
<212> TYPE: PRT
<213> ORGANISM: Artificial Sequence
<220> FEATURE:
<223> OTHER INFORMATION: Synthetic: HEAVY CHAIN

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Lys
                20                  25                  30

Ala Ile Ser Trp Val Arg Gln Ala Pro Gly Gln Gly Leu Glu Trp Met
            35                  40                  45

```
Gly Ser Ile Leu Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Gly Tyr Tyr Arg Tyr Arg Tyr Phe Asp Leu Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450
```

<210> SEQ ID NO 10
<211> LENGTH: 1353
<212> TYPE: DNA
<213> ORGANISM: Artificial Sequence
<220> FEATURE:
<223> OTHER INFORMATION: Synthetic: DNA HEAVY CHAIN

<400> SEQUENCE: 10

```
caggtgcagc tggtgcagtc tggggctgag gtgaagaagc ctgggtcctc ggtgaaggtc      60
tcctgcaagg cttctggagg caccttcagc gataaggcta tcagctgggt gcgacaggcc     120
cctggacaag gcttgagtg gatgggatcg atccttccta tctttggtac agcaaactac     180
gcacagaagt tccagggcag agtcacgatt accgcgacg aatccacgag cacagcctac     240
atggagctga gcagcctgag atctgaggac acggcggtgt actactgcgc agagaagcc     300
ggatactacc gctaccgata cttcgaccta tgggggagag gtaccttggt caccgtctcc     360
tcagcgagca ccaaaggccc gagcgtgttt ccgctggcgc cgagcagcaa aagcaccagc     420
ggcggcaccg cggcgctggg ctgcctggtg aaagattatt tccggaacc ggtgaccgtg      480
agctggaaca gcggcgcgct gaccagcggc gtgcatacct tccggcggt gctgcagagc     540
agcggcctgt atagcctgag cagcgtggtg accgtgccga gcagcagcct gggcacccag     600
acctatattt gcaacgtgaa ccataaaccg agcaacacca agtggataa aaaagtggaa      660
ccgaaaagct cgcataaaac ccatacctgc ccgccgtgcc cggcgccgga actgctgggc     720
ggcccgagcg tgtttctgtt tccgccgaaa ccgaagata ccctgatgat tagccgcacc     780
ccggaagtga cctgcgtggt ggtggatgtg agccatgaag atccggaagt gaatttaac     840
tggtatgtgg atggcgtgga agtgcataac gcgaaaacca accgcgcga agaacagtat     900
aacagcacct atcgcgtggt gagcgtgctg accgtgctgc atcaggattg gctgaacggc     960
aaagaatata atgcaaagt gagcaacaaa gcgctgccgg cgccgattga aaaaccatt     1020
agcaaagcga aggccagcc gcgcgaaccg caggtgtata ccctgccgcc gagccgcgat    1080
gaactgacca aaaccaggt gagcctgacc tgcctggtga aaggcttta tccgagcgat    1140
attgcggtgg aatgggaaag caacggccag ccggaaaaca actataaaac cacccccgcg    1200
gtgctggata gcgatggcag ctttttctg tatagcaaac tgaccgtgga taaaagccgc    1260
tggcagcagg gcaacgtgtt tagctgcagc gtgatgcatg aagcgctgca taaccattat    1320
acccagaaaa gcctgagcct gagcccgggc aaa                                 1353
```

<210> SEQ ID NO 11
<211> LENGTH: 6
<212> TYPE: PRT
<213> ORGANISM: Artificial Sequence
<220> FEATURE:
<223> OTHER INFORMATION: Synthetic: LCDR1 (IMGT)

<400> SEQUENCE: 11

Gln Ser Val Ser Ser Asn
1               5

<210> SEQ ID NO 12
<211> LENGTH: 3
<212> TYPE: PRT
<213> ORGANISM: Artificial Sequence
<220> FEATURE:
<223> OTHER INFORMATION: Synthetic: LCDR2 (IMGT)

<400> SEQUENCE: 12

```
<210> SEQ ID NO 13
<211> LENGTH: 9
<212> TYPE: PRT
<213> ORGANISM: Artificial Sequence
<220> FEATURE:
<223> OTHER INFORMATION: Synthetic: LCDR3 (IMGT)

<400> SEQUENCE: 13

Gln Gln His Ala Leu Trp Pro Leu Thr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic: LCDR1 (ADI)

<400> SEQUENCE: 14

Arg Ala Ser Gln Ser Val Ser Ser Asn Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic: LCDR2 (ADI)

<400> SEQUENCE: 15

Gly Ala Ser Thr Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic: LCDR3 (ADI)

<400> SEQUENCE: 16

Gln Gln His Ala Leu Trp Pro Leu Thr
1               5

<210> SEQ ID NO 17
<211> LENGTH: 107
<212> TYPE: PRT
<213> ORGANISM: Artificial Sequence
<220> FEATURE:
<223> OTHER INFORMATION: Synthetic: VL

<400> SEQUENCE: 17

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

(prior sequence continued:)
```
Gly Ala Ser
1
```

```
Glu Asp Phe Ala Val Tyr Tyr Cys Gln Gln His Ala Leu Trp Pro Leu
                85                  90                  95
Thr Phe Gly Gly Gly Thr Lys Val Glu Ile Lys
            100                 105
```

<210> SEQ ID NO 18
<211> LENGTH: 321
<212> TYPE: DNA
<213> ORGANISM: Artificial Sequence
<220> FEATURE:
<223> OTHER INFORMATION: Synthetic: DNA VL

<400> SEQUENCE: 18

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag cacgccctct ggcctctcac ttttggcgga   300
gggaccaagg ttgagatcaa a                                             321
```

<210> SEQ ID NO 19
<211> LENGTH: 214
<212> TYPE: PRT
<213> ORGANISM: Artificial Sequence
<220> FEATURE:
<223> OTHER INFORMATION: Synthetic: LIGHT CHAIN

<400> SEQUENCE: 19

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln His Ala Leu Trp Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
            210
```

<210> SEQ ID NO 20
<211> LENGTH: 642
<212> TYPE: DNA
<213> ORGANISM: Artificial Sequence
<220> FEATURE:
<223> OTHER INFORMATION: Synthetic: DNA LIGHT CHAIN

<400> SEQUENCE: 20

```
gaaatagtga tgacgcagtc tccagccacc ctgtctgtgt ctccagggga agagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag cacgccctct ggcctctcac ttttggcgga    300
gggaccaagg ttgagatcaa acgtacggtg gccgctccct ccgtgttcat cttcccaccc    360
tccgacgagc agctgaagtc cggcaccgcc tccgtcgtgt gcctgctgaa caacttctac    420
cctcgcgagg ccaaagtgca gtggaaagtg gacaacgccc tgcagtccgg caactcccag    480
gaatccgtca ccgagcagga ctccaaggac agcacctact ccctgtcctc caccctgacc    540
ctgtccaagg ccgactacga gaagcacaaa gtgtacgcct gcgaagtgac ccaccagggc    600
ctgtccagcc ccgtgaccaa gtccttcaac cggggcgagt gc                       642
```

<210> SEQ ID NO 21
<211> LENGTH: 447
<212> TYPE: PRT
<213> ORGANISM: Artificial Sequence
<220> FEATURE:
<223> OTHER INFORMATION: Synthetic: HEAVY CHAIN

<400> SEQUENCE: 21

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Lys
            20                  25                  30

Ala Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Ser Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
            260                 265                 270
Glu Val Gln Phe Asn Trp Tyr Val Asp Gly Val Glu Val His Asn Ala
                275                 280                 285
Lys Thr Lys Pro Arg Glu Glu Gln Phe Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly
        435                 440                 445
```

<210> SEQ ID NO 22
<211> LENGTH: 1341
<212> TYPE: DNA
<213> ORGANISM: Artificial Sequence
<220> FEATURE:
<223> OTHER INFORMATION: Synthetic: DNA HEAVY CHAIN

<400> SEQUENCE: 22

```
caggtgcagc tggtgcagtc tggggctgag gtgaagaagc ctgggtcctc ggtgaaggtc      60
tcctgcaagg cttctggagg caccttcagc gataaggcta tcagctgggt gcagaggcc     120
cctggacaag ggcttgagtg gatgggatcg atccttccta tctttggtac agcaaactac    180
gcacagaagt tccagggcag agtcacgatt accgcggacg aatccacgag cacagcctac    240
atggagctga gcagcctgag atctgaggac acggcggtgt actactgcgc cagagaagcc    300
ggatactacc gctaccgata cttcgaccta tgggggagag gtaccttggt caccgtctcc    360
tcagcttcca ccaagggccc ctccgtgttc cctctggccc cttgctcccg gtccacctcc    420
gagtctaccg ccgctctggg ctgcctcgtg aaggactact ccccgagccc gtgaccgtg     480
tcctggaact ctggcgccct gacctccggc gtgcacacct ccctgccgt gctgcagtcc    540
tccggcctgt actccctgtc cagcgtcgtg accgtgccct cctccagcct gggcaccaag    600
```

```
acctacacct gtaacgtgga ccacaagccc tccaacacca aagtggacaa gcgggtggaa    660
tctaagtacg gccctccctg cccttcctgc cctgccctg agttcctggg cggaccttcc     720
gtgttcctgt tccctccaaa gcccaaggac acctgatga tctcccggac ccctgaagtg     780
acctgcgtgg tggtggacgt gtcccaggaa gatcccgaag tccagttcaa ttggtacgtg    840
gacggcgtgg aagtgcacaa cgccaagacc aagcccagag aggaacagtt caactccacc    900
taccgggtgg tgtccgtgct gaccgtgctg caccaggact ggctgaacgg caaagagtac    960
aagtgcaaag tgtccaacaa gggcctgccc tccagcatcg aaaagaccat ctccaaggcc   1020
aagggccagc cccgcgagcc ccaagtgtac accctgcctc ccagccagga agagatgacc   1080
aagaatcaag tgtccctgac ttgtctggtc aagggcttct accctccga tatcgccgtg    1140 gagtgggagt ccaacggcca gcccgagaac aactacaaga ccaccccct cgtgctggac    1200 tccgacggct ccttcttcct gtactctcgg ctgaccgtgg acaagtcccg gtggcaggaa   1260
ggcaacgtct tctcctgctc cgtgatgcac gaggccctgc acaaccacta cacccagaag   1320
tccctgtccc tgtctctggg c                                             1341
```

<210> SEQ ID NO 23
<211> LENGTH: 447
<212> TYPE: PRT
<213> ORGANISM: Artificial Sequence
<220> FEATURE:
<223> OTHER INFORMATION: Synthetic: HEAVY CHAIN

<400> SEQUENCE: 23

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asp Lys
            20                  25                  30

Ala Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
           100                 105                 110

Arg Gly Thr Leu Val Thr Val Ser Ser Ala Ser Thr Lys Gly Pro Ser
       115                 120                 125

Val Phe Pro Leu Ala Pro Cys Ser Arg Ser Thr Ser Glu Ser Thr Ala
   130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
           180                 185                 190

Pro Ser Ser Ser Leu Gly Thr Lys Thr Tyr Thr Cys Asn Val Asp His
       195                 200                 205

Lys Pro Ser Asn Thr Lys Val Asp Lys Arg Val Glu Ser Lys Tyr Gly
   210                 215                 220

Pro Pro Cys Pro Pro Cys Pro Ala Pro Glu Phe Leu Gly Gly Pro Ser
```

```
             225                 230                 235                 240
        Val Phe Leu Phe Pro Pro Lys Pro Lys Asp Thr Leu Met Ile Ser Arg
                         245                 250                 255

Thr Pro Glu Val Thr Cys Val Val Asp Val Ser Gln Glu Asp Pro
                     260                 265                 270

Glu Val Gln Phe Asn Trp Tyr Val Asp Gly Val Glu Val His Asn Ala
                         275                 280                 285

Lys Thr Lys Pro Arg Glu Glu Gln Phe Asn Ser Thr Tyr Arg Val Val
                 290                 295                 300

Ser Val Leu Thr Val Leu His Gln Asp Trp Leu Asn Gly Lys Glu Tyr
        305                 310                 315                 320

Lys Cys Lys Val Ser Asn Lys Gly Leu Pro Ser Ser Ile Glu Lys Thr
                             325                 330                 335

Ile Ser Lys Ala Lys Gly Gln Pro Arg Glu Pro Gln Val Tyr Thr Leu
                     340                 345                 350

Pro Pro Ser Gln Glu Glu Met Thr Lys Asn Gln Val Ser Leu Thr Cys
                 355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Arg Leu Thr Val Asp Lys Ser
                         405                 410                 415

Arg Trp Gln Glu Gly Asn Val Phe Ser Cys Ser Val Met His Glu Ala
                     420                 425                 430

Leu His Asn His Tyr Thr Gln Lys Ser Leu Ser Leu Ser Leu Gly
                 435                 440                 445

<210> SEQ ID NO 24
<211> LENGTH: 1341
<212> TYPE: DNA
<213> ORGANISM: Artificial Sequence
<220> FEATURE:
<223> OTHER INFORMATION: Synthetic: DNA HEAVY CHAIN

<400> SEQUENCE: 24
caggtgcagc tggtgcagtc tggggctgag gtgaagaagc ctgggtcctc ggtgaaggtc      60
tcctgcaagg cttctggagg caccttcagc gataaggcta tcagctgggt gcgacaggcc     120
cctggacaag gcttgagtg gatgggatcg atccttccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagagaagcc     300
ggatactacc gctaccgata cttcgaccta tgggggagag gtaccttggt caccgtctcc     360
tcagcttcca ccaagggccc ctccgtgttc cctctggccc cttgctcccg gtccacctcc     420
gagtctaccg ccgctctggg ctgcctcgtg aaggactact ccccgagcc cgtgaccgtg     480 tcctggaact ctggcgccct gacctccggc gtgcacacct ccctgccgt gctgcagtcc     540 tccggcctgt actccctgtc cagcgtcgtg accgtgccct cctccagcct gggcaccaag     600
acctacacct gtaacgtgga ccacaagccc tccaacacca agtgggacaa gcgggtggaa     660
tctaagtacg gcctcccctg ccctccttgc cctgccctg agttcctggg cggaccttcc     720
gtgttcctgt ccctccaaa gcccaaggac accctgatga tctcccggac ccctgaagtg     780
acctgcgtgg tggtggacgt gtcccaggaa gatcccgaag tccagttcaa ttggtacgtg     840
```

```
gacggcgtgg aagtgcacaa cgccaagacc aagcccagag aggaacagtt caactccacc      900
taccgggtgg tgtccgtgct gaccgtgctg caccaggact ggctgaacgg caaagagtac      960
aagtgcaaag tgtccaacaa gggcctgccc tccagcatcg aaaagaccat ctccaaggcc     1020
aagggccagc ccgcgagcc ccaagtgtac accctgcctc ccagccagga agagatgacc     1080
aagaatcaag tgtccctgac ttgtctggtc aagggcttct accctccga tatcgccgtg      1140 gagtgggagt ccaacggcca gcccgagaac aactacaaga ccaccctcc cgtgctggac      1200 tccgacggct ccttcttcct gtactctcgg ctgaccgtgg acaagtcccg gtggcaggaa     1260
ggcaacgtct tctcctgctc cgtgatgcac gaggccctgc acaaccacta cacccagaag     1320
tccctgtccc tgtctctggg c                                              1341
```

<210> SEQ ID NO 25
<211> LENGTH: 447
<212> TYPE: PRT
<213> ORGANISM: Artificial Sequence
<220> FEATURE:
<223> OTHER INFORMATION: Synthetic: HEAVY CHAIN

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Lys
            20                  25                  30

Ala Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270
```

```
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 26
<211> LENGTH: 1341
<212> TYPE: DNA
<213> ORGANISM: Artificial Sequence
<220> FEATURE:
<223> OTHER INFORMATION: Synthetic: DNA HEAVY CHAIN

<400> SEQUENCE: 26
caggtgcagc tggtgcagtc tggggctgag gtgaagaagc ctgggtcctc ggtgaaggtc      60
tcctgcaagg cttctggagg caccttcagc gataaggcta tcagctgggt gcgacaggcc     120
cctggacaag gcttgagtg gatgggatcg atccttccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagagaagcc     300
ggatactacc gctaccgata cttcgaccta tgggggagag gtaccttggt caccgtctcc     360
tcagcttcca ccaagggccc ctccgtgttc cctctggccc cttgctcccg gtccacctcc     420
gagtctaccg ccgctctggg ctgcctcgtg aaggactact cccccgagcc cgtgaccgtg     480
tcctggaact ctggcgccct gacctccggc gtgcacacct ccctgccgt gctgcagtcc     540 tccggcctgt actccctgtc cagcgtcgtg accgtgccct cctccagcct gggcaccaag     600
acctacacct gtaacgtgga ccacaagccc tccaacacca agtggacaa gcgggtggaa     660 tctaagtacg gccctcctg ccctccttgc cctgccctg agttcgaggg cggaccttcc     720
gtgttcctgt ccctccaaa gcccaaggac accctgatga tctcccggac ccctgaagtg     780
acctgcgtgg tggtggacgt gtcccaggaa gatcccgaag tccagttcaa ttggtacgtg     840
gacggcgtga agtgcacaa cgccaagacc aagcccagag gaacagtt caactccacc     900 taccgggtgg tgtccgtgct gaccgtgctg caccaggact ggctgaacgg caaagagtac     960
aagtgcaaag tgtccaacaa gggcctgccc tccagcatcg aaaagaccat ctccaaggcc    1020
aagggccagc ccgcgagcc ccaagtgtac accctgcctc ccagccagga agagatgacc    1080
```

```
aagaatcaag tgtccctgac ttgtctggtc aagggcttct acccctccga tatcgccgtg    1140
gagtgggagt ccaacggcca gcccgagaac aactacaaga ccaccctcc cgtgctggac     1200 tccgacggct ccttcttcct gtactctcgg ctgaccgtgg acaagtcccg gtggcaggaa    1260
ggcaacgtct tctcctgctc cgtgatgcac gaggccctgc acaaccacta cacccagaag    1320
tccctgtccc tgtctctggg c                                              1341
```

<210> SEQ ID NO 27
<211> LENGTH: 8
<212> TYPE: PRT
<213> ORGANISM: Artificial Sequence
<220> FEATURE:
<223> OTHER INFORMATION: Synthetic: HCDR1 (IMGT)

<400> SEQUENCE: 27

```
Gly Gly Thr Phe Ser Ser Glu Gly
1               5
```

<210> SEQ ID NO 28
<211> LENGTH: 8
<212> TYPE: PRT
<213> ORGANISM: Artificial Sequence
<220> FEATURE:
<223> OTHER INFORMATION: Synthetic: HCDR2 (IMGT)

<400> SEQUENCE: 28

```
Ile Leu Pro Ile Phe Gly Thr Ala
1               5
```

<210> SEQ ID NO 29
<211> LENGTH: 14
<212> TYPE: PRT
<213> ORGANISM: Artificial Sequence
<220> FEATURE:
<223> OTHER INFORMATION: Synthetic: HCDR3 (IMGT)

<400> SEQUENCE: 29

```
Ala Arg Glu Ala Gly Tyr Tyr Arg Tyr Arg Tyr Phe Asp Leu
1               5                   10
```

<210> SEQ ID NO 30
<211> LENGTH: 9
<212> TYPE: PRT
<213> ORGANISM: Artificial Sequence
<220> FEATURE:
<223> OTHER INFORMATION: Synthetic: HCDR1 (ADI)

<400> SEQUENCE: 30

```
Gly Thr Phe Ser Ser Glu Gly Ile Ser
1               5
```

<210> SEQ ID NO 31
<211> LENGTH: 17
<212> TYPE: PRT
<213> ORGANISM: Artificial Sequence
<220> FEATURE:
<223> OTHER INFORMATION: Synthetic: HCDR2 (ADI)

<400> SEQUENCE: 31

```
Ser Ile Leu Pro Ile Phe Gly Thr Ala Asn Tyr Ala Gln Lys Phe Gln
1               5                   10                  15

Gly
```

<210> SEQ ID NO 32

```
<211> LENGTH: 14
<212> TYPE: PRT
<213> ORGANISM: Artificial Sequence
<220> FEATURE:
<223> OTHER INFORMATION: Synthetic: HCDR3 (ADI)

<400> SEQUENCE: 32

Ala Arg Glu Ala Gly Tyr Tyr Arg Tyr Arg Tyr Phe Asp Leu
1               5                   10

<210> SEQ ID NO 33
<211> LENGTH: 121
<212> TYPE: PRT
<213> ORGANISM: Artificial Sequence
<220> FEATURE:
<223> OTHER INFORMATION: Synthetic: VH

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Glu
            20                  25                  30

Gly Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Lys Gly Thr Leu Val Thr Val Ser Ser
        115                 120

<210> SEQ ID NO 34
<211> LENGTH: 363
<212> TYPE: DNA
<213> ORGANISM: Artificial Sequence
<220> FEATURE:
<223> OTHER INFORMATION: Synthetic: DNA VH

<400> SEQUENCE: 34
caggtgcagc tggtgcagtc tggggctgag gtgaagaagc ctgggtcctc ggtgaaggtc     60
tcctgcaagg cttctggagg caccttcagc agcgagggta tcagctgggt gcgacaggcc   120
cctggacaag gcttgagtg gatgggaagt atcttgccta tctttggtac agcaaactac   180
gcacagaagt tccagggcag agtcacgatt accgcggacg aatccacgag cacagcctac   240
atggagctga gcagcctgag atctgaggac acggcggtgt actactgcgc cagagaagcc   300
ggatactacc gctaccgata cttcgaccta tggggaaag gtaccttggt caccgtctcc   360
tca                                                                  363

<210> SEQ ID NO 35
<211> LENGTH: 451
<212> TYPE: PRT
<213> ORGANISM: Artificial Sequence
<220> FEATURE:
<223> OTHER INFORMATION: Synthetic: HEAVY CHAIN

<400> SEQUENCE: 35
```

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Glu
            20                  25                  30

Gly Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Lys Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
                420             425             430
His Glu Ala Leu His Asn His Tyr Thr Gln Lys Ser Leu Ser Leu Ser
        435                 440                 445

Pro Gly Lys
    450

<210> SEQ ID NO 36
<211> LENGTH: 1353
<212> TYPE: DNA
<213> ORGANISM: Artificial Sequence
<220> FEATURE:
<223> OTHER INFORMATION: Synthetic: DNA HEAVY CHAIN

<400> SEQUENCE: 36
caggtgcagc tggtgcagtc tggggctgag gtgaagaagc ctgggtcctc ggtgaaggtc      60
tcctgcaagg cttctggagg caccttcagc agcgagggta tcagctgggt gcgacaggcc     120
cctggacaag gcttgagtg gatgggaagt atcttgccta tctttggtac agcaaactac     180
gcacagaagt tccagggcag agtcacgatt accgcgacg aatccacgag cacagcctac     240
atggagctga gcagcctgag atctgaggac acggcggtgt actactgcgc cagagaagcc     300
ggatactacc gctaccgata cttcgaccta tggggaaag gtaccttggt caccgtctcc     360
tcagcgagca ccaaaggccc gagcgtgttt ccgctggcgc cgagcagcaa aagcaccagc     420
ggcggcaccg cggcgctggg ctgcctggtg aaagattatt ttccggaacc ggtgaccgtg     480
agctggaaca gcggcgcgct gaccagcggc gtgcatacct tccggcggt gctgcagagc     540 agcggcctgt atagcctgag cagcgtggtg accgtgccga gcagcagcct gggcacccag     600
acctatattt gcaacgtgaa ccataaaccg agcaacacca agtggataa aaaagtggaa     660 ccgaaaagct gcgataaaac ccatacctgc ccgccgtgcc cggcgccgga actgctgggc     720
ggcccgagcg tgttctgtt tccgccgaaa ccgaaagata ccctgatgat tagccgcacc     780
ccggaagtga cctgcgtggt ggtggatgtg agccatgaag tccggaagt gaaatttaac     840 tggtatgtgg atggcgtgga agtgcataac gcgaaaacca accgcgcga gaacagtat     900 aacagcaccct atcgcgtggt gagcgtgctg accgtgctgc atcaggattg gctgaacggc     960
aaagaatata atgcaaagt gagcaacaaa gcgctgccgg cgccgattga aaaaaccatt    1020
agcaaagcga aaggccagcc gcgcgaaccg caggtgtata ccctgccgcc gagccgcgat    1080
gaactgacca aaaaccaggt gagcctgacc tgcctggtga aaggctttta tccgagcgat    1140
attgcggtgg aatgggaaag caacggccag ccggaaaaca actataaac cacccgccg    1200 gtgctggata gcgatggcag ctttttctg tatagcaaac tgaccgtgga taaaagccgc    1260
tggcagcagg gcaacgtgtt tagctgcagc gtgatgcatg aagcgctgca taaccattat    1320
acccagaaaa gcctgagcct gagcccgggc aaa                               1353

<210> SEQ ID NO 37
<211> LENGTH: 6
<212> TYPE: PRT
<213> ORGANISM: Artificial Sequence
<220> FEATURE:
<223> OTHER INFORMATION: Synthetic: LCDR1 (IMGT)

<400> SEQUENCE: 37

Gln Ser Val Ser Ser Asn
1               5

<210> SEQ ID NO 38
```

```
<211> LENGTH: 3
<212> TYPE: PRT
<213> ORGANISM: Artificial Sequence
<220> FEATURE:
<223> OTHER INFORMATION: Synthetic: LCDR2 (IMGT)

<400> SEQUENCE: 38

Gly Ala Ser
1

<210> SEQ ID NO 39
<211> LENGTH: 9
<212> TYPE: PRT
<213> ORGANISM: Artificial Sequence
<220> FEATURE:
<223> OTHER INFORMATION: Synthetic: LCDR3 (IMGT)

<400> SEQUENCE: 39

Gln Gln His Ala Leu Trp Pro Leu Thr
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic: LCDR1 (ADI)

<400> SEQUENCE: 40

Arg Ala Ser Gln Ser Val Ser Ser Asn Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic: LCDR2 (ADI)

<400> SEQUENCE: 41

Gly Ala Ser Thr Arg Ala Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic: LCDR3 (ADI)

<400> SEQUENCE: 42

Gln Gln His Ala Leu Trp Pro Leu Thr
1               5

<210> SEQ ID NO 43
<211> LENGTH: 107
<212> TYPE: PRT
<213> ORGANISM: Artificial Sequence
<220> FEATURE:
<223> OTHER INFORMATION: Synthetic: VL

<400> SEQUENCE: 43

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30
```

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Ala Leu Trp Pro Leu
                85                  90                  95

Thr Phe Gly Gly Gly Thr Lys Val Glu Ile Lys
                100                 105

<210> SEQ ID NO 44
<211> LENGTH: 321
<212> TYPE: DNA
<213> ORGANISM: Artificial Sequence
<220> FEATURE:
<223> OTHER INFORMATION: Synthetic: DNA VL

<400> SEQUENCE: 44
gaaatagtga tgacgcagtc tccagccacc ctgtctgtgt ctccagggga agagccacc      60 ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag cacgccctct ggcctctcac ttttggcgga     300
gggaccaagg ttgagatcaa a                                                321

<210> SEQ ID NO 45
<211> LENGTH: 214
<212> TYPE: PRT
<213> ORGANISM: Artificial Sequence
<220> FEATURE:
<223> OTHER INFORMATION: Synthetic: LIGHT CHAIN

<400> SEQUENCE: 45

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Ala Leu Trp Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 642
<212> TYPE: DNA
<213> ORGANISM: Artificial Sequence
<220> FEATURE:
<223> OTHER INFORMATION: Synthetic: DNA LIGHT CHAIN

<400> SEQUENCE: 46
gaaatagtga tgacgcagtc tccagccacc ctgtctgtgt ctccagggga agagccacc      60 ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag cacgccctct ggcctctcac ttttggcgga   300
gggaccaagg ttgagatcaa acgtacggtg gccgctccct ccgtgttcat cttcccaccc   360
tccgacgagc agctgaagtc cggcaccgcc tccgtcgtgt gcctgctgaa caacttctac   420
cctcgcgagg ccaaagtgca gtggaaagtg gacaacgccc tgcagtccgg caactcccag   480
gaatccgtca ccgagcagga ctccaaggac agcacctact ccctgtcctc caccctgacc   540
ctgtccaagg ccgactacga gaagcacaaa gtgtacgcct gcgaagtgac ccaccagggc   600
ctgtccagcc ccgtgaccaa gtccttcaac cggggcgagt gc                      642

<210> SEQ ID NO 47
<211> LENGTH: 447
<212> TYPE: PRT
<213> ORGANISM: Artificial Sequence
<220> FEATURE:
<223> OTHER INFORMATION: Synthetic: HEAVY CHAIN

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Glu
            20                  25                  30

Gly Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Lys Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 48
<211> LENGTH: 1341
<212> TYPE: DNA
<213> ORGANISM: Artificial Sequence
<220> FEATURE:
<223> OTHER INFORMATION: Synthetic: DNA HEAVY CHAIN

<400> SEQUENCE: 48
caggtgcagc tggtgcagtc tggggctgag gtgaagaagc ctgggtcctc ggtgaaggtc      60
tcctgcaagg cttctggagg caccttcagc agcgagggta tcagctgggt gcgacaggcc     120
cctggacaag gcttgagtg gatgggaagt atccttgccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagagaagcc     300
ggatactacc gctaccgata cttcgaccta tggggaaag gtaccttggt caccgtctcc     360
```

```
tcagcttcca ccaagggccc ctccgtgttc cctctggccc cttgctcccg gtccacctcc    420
gagtctaccg ccgctctggg ctgcctcgtg aaggactact tccccgagcc cgtgaccgtg    480
tcctggaact ctggcgccct gacctccggc gtgcacacct ccctgccgt gctgcagtcc     540
tccggcctgt actccctgtc cagcgtcgtg accgtgccct cctccagcct gggcaccaag    600
acctacacct gtaacgtgga ccacaagccc tccaacacca aagtggacaa gcgggtggaa    660
tctaagtacg gccctcctg cccttcctgc cctgccctg agttcctggg cggaccttcc      720
gtgttcctgt ccctccaaa gcccaaggac accctgatga tctcccggac ccctgaagtg    780
acctgcgtgg tggtggacgt gtcccaggaa gatcccgaag tccagttcaa ttggtacgtg    840
gacggcgtgg aagtgcacaa cgccaagacc aagcccagag aggaacagtt caactccacc    900
taccgggtgg tgtccgtgct gaccgtgctg caccaggact ggctgaacgg caaagagtac    960
aagtgcaaag tgtccaacaa gggcctgccc tccagcatcg aaaagaccat ctccaaggcc   1020
aagggccagc cccgcgagcc ccaagtgtac accctgcctc ccagccagga agagatgacc   1080
aagaatcaag tgtccctgac ttgtctggtc aagggcttct accctccga tatcgccgtg    1140
gagtgggagt ccaacggcca gcccgagaac aactacaaga ccaccctcc cgtgctggac   1200
tccgacggct ccttcttcct gtactctcgg ctgaccgtgg acaagtcccg gtggcaggaa   1260
ggcaacgtct ctcctgctc cgtgatgcac gaggccctgc acaaccacta cacccagaag   1320
tccctgtccc tgtctctggg c                                              1341
```

<210> SEQ ID NO 49
<211> LENGTH: 447
<212> TYPE: PRT
<213> ORGANISM: Artificial Sequence
<220> FEATURE:
<223> OTHER INFORMATION: Synthetic: HEAVY CHAIN

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Glu
            20                  25                  30

Gly Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Lys Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
        260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 50
<211> LENGTH: 1341
<212> TYPE: DNA
<213> ORGANISM: Artificial Sequence
<220> FEATURE:
<223> OTHER INFORMATION: Synthetic: DNA HEAVY CHAIN

<400> SEQUENCE: 50
caggtgcagc tggtgcagtc tggggctgag gtgaagaagc ctgggtcctc ggtgaaggtc    60
tcctgcaagg cttctggagg caccttcagc agcgagggta tcagctgggt gcgacaggcc   120
cctggacaag gcttgagtg gatgggaagt atcttgccta tctttggtac agcaaactac   180
gcacagaagt tccagggcag agtcacgatt accgcggacg aatccacgag cacagcctac   240
atggagctga gcagcctgag atctgaggac acggcggtgt actactgcgc cagagaagcc   300
ggatactacc gctaccgata cttcgaccta tggggggaaag gtaccttggt caccgtctcc   360
tcagcttcca ccaagggccc ctccgtgttc cctctggccc cttgctcccg gtccacctcc   420
gagtctaccg ccgctctggg ctgcctcgtg aaggactact ccccgagcc cgtgaccgtg   480 tcctggaact ctggcgccct gacctccggc gtgcacacct ccctgccgt gctgcagtcc   540 tccggcctgt actccctgtc cagcgtcgtg accgtgccct cctccagcct gggcaccaag   600
```

```
acctacacct gtaacgtgga ccacaagccc tccaacacca aagtggacaa gcgggtggaa    660
tctaagtacg gccctccctg ccctccttgc cctgccoctg agttcctggg cggaccttcc    720
gtgttcctgt ccctccaaa gcccaaggac accctgatga tctcccggac ccctgaagtg    780
acctgcgtgg tggtggacgt gtcccaggaa gatcccgaag tccagttcaa ttggtacgtg    840
gacggcgtgg aagtgcacaa cgccaagacc aagcccagag aggaacagtt caactccacc    900
taccgggtgg tgtccgtgct gaccgtgctg caccaggact ggctgaacgg caaagagtac    960
aagtgcaaag tgtccaacaa gggcctgccc tccagcatcg aaaagaccat ctccaaggcc   1020
aagggccagc ccgcgagcc ccaagtgtac accctgcctc ccagccagga agagatgacc   1080
aagaatcaag tgtccctgac ttgtctggtc aagggcttct accctccga tatcgccgtg   1140 gagtgggagt ccaacggcca gcccgagaac aactacaaga ccaccctcc cgtgctggac   1200 tccgacggct ccttcttcct gtactctcgg ctgaccgtgg acaagtcccg gtggcaggaa   1260
ggcaacgtct tctcctgctc cgtgatgcac gaggccctgc acaaccacta cacccagaag   1320
tccctgtccc tgtctctggg c                                             1341

<210> SEQ ID NO 51
<211> LENGTH: 447
<212> TYPE: PRT
<213> ORGANISM: Artificial Sequence
<220> FEATURE:
<223> OTHER INFORMATION: Synthetic: HEAVY CHAIN

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Glu
            20                  25                  30

Gly Ile Ser Trp Val Arg Gln Ala Pro Gly Gln Gly Leu Glu Trp Met
        35                  40                  45

Gly Ser Ile Leu Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Tyr Arg Tyr Arg Tyr Phe Asp Leu Trp Gly
            100                 105                 110

Lys Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
```

```
                225                 230                 235                 240
Val Phe Leu Phe Pro Pro Lys Pro Lys Asp Thr Leu Met Ile Ser Arg
                    245                 250                 255

Thr Pro Glu Val Thr Cys Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                    405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
            435                 440                 445

<210> SEQ ID NO 52
<211> LENGTH: 1341
<212> TYPE: DNA
<213> ORGANISM: Artificial Sequence
<220> FEATURE:
<223> OTHER INFORMATION: Synthetic: DNA HEAVY CHAIN

<400> SEQUENCE: 52
caggtgcagc tggtgcagtc tggggctgag gtgaagaagc ctgggtcctc ggtgaaggtc      60
tcctgcaagg cttctggagg caccttcagc agcgagggta tcagctgggt gcgacaggcc     120
cctggacaag gcttgagtg gatgggaagt atcttgccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagagaagcc     300
ggatactacc gctaccgata cttcgaccta tggggggaaag gtaccttggt caccgtctcc     360
tcagcttcca ccaagggccc ctccgtgttc cctctggccc cttgctcccg gtccacctcc     420
gagtctaccg ccgctctggg ctgcctcgtg aaggactact ccccgagcc cgtgaccgtg     480 tcctggaact ctggcgccct gacctccggc gtgcacacct ccctgccgt gctgcagtcc     540 tccggcctgt actccctgtc cagcgtcgtg accgtgccct cctccagcct gggcaccaag     600
acctacacct gtaacgtgga ccacaagccc tccaacacca agtggacaa gcgggtggaa     660 tctaagtacg gcctcccctg ccctccttgc cctgccctg agttcgaggg cggaccttcc     720
gtgttcctgt ccctcccaaa gcccaaggac ccctgatga tctcccggac ccctgaagtg     780
acctgcgtgg tggtggacgt gtcccaggaa gatcccgaag tccagttcaa ttggtacgtg     840
```

```
gacggcgtgg aagtgcacaa cgccaagacc aagcccagag aggaacagtt caactccacc    900
taccgggtgg tgtccgtgct gaccgtgctg caccaggact ggctgaacgg caaagagtac    960
aagtgcaaag tgtccaacaa gggcctgccc tccagcatcg aaaagaccat ctccaaggcc   1020
aagggccagc ccgcgagcc ccaagtgtac accctgcctc ccagccagga agagatgacc   1080
aagaatcaag tgtccctgac ttgtctggtc aagggcttct accctccga tatcgccgtg   1140
gagtgggagt ccaacggcca gcccgagaac aactacaaga ccaccctcc cgtgctggac   1200
tccgacggct ccttcttcct gtactctcgg ctgaccgtgg acaagtcccg gtggcaggaa   1260
ggcaacgtct ctcctgctc cgtgatgcac gaggccctgc acaaccacta cacccagaag   1320
tccctgtccc tgtctctggg c                                            1341
```

<210> SEQ ID NO 53
<211> LENGTH: 8
<212> TYPE: PRT
<213> ORGANISM: Artificial Sequence
<220> FEATURE:
<223> OTHER INFORMATION: Synthetic: HCDR1 (IMGT)

<400> SEQUENCE: 53

Gly Gly Thr Phe Ser Thr Tyr Ala
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic: HCDR2 (IMGT)

<400> SEQUENCE: 54

Ile Ile Pro Ala Phe Gly Thr Ala
1               5

<210> SEQ ID NO 55
<211> LENGTH: 12
<212> TYPE: PRT
<213> ORGANISM: Artificial Sequence
<220> FEATURE:
<223> OTHER INFORMATION: Synthetic: HCDR3 (IMGT)

<400> SEQUENCE: 55

Ala Arg Asp Pro Val Arg Arg Ser Pro Phe Asp Ile
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic: HCDR1 (ADI)

<400> SEQUENCE: 56

Gly Thr Phe Ser Thr Tyr Ala Ile Gly
1               5

<210> SEQ ID NO 57
<211> LENGTH: 17
<212> TYPE: PRT
<213> ORGANISM: Artificial Sequence
<220> FEATURE:
<223> OTHER INFORMATION: Synthetic: HCDR2 (ADI)

<400> SEQUENCE: 57

Gly Ile Ile Pro Ala Phe Gly Thr Ala Asn Tyr Ala Gln Lys Phe Gln
1               5                   10                  15

Gly

<210> SEQ ID NO 58
<211> LENGTH: 12
<212> TYPE: PRT
<213> ORGANISM: Artificial Sequence
<220> FEATURE:
<223> OTHER INFORMATION: Synthetic: HCDR3 (ADI)

<400> SEQUENCE: 58

Ala Arg Asp Pro Val Arg Arg Ser Pro Phe Asp Ile
1               5                   10

<210> SEQ ID NO 59
<211> LENGTH: 119
<212> TYPE: PRT
<213> ORGANISM: Artificial Sequence
<220> FEATURE:
<223> OTHER INFORMATION: Synthetic: VH

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Gly Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Arg Arg Ser Pro Phe Asp Ile Trp Gly Gln Gly
            100                 105                 110

Thr Met Val Thr Val Ser Ser
        115

<210> SEQ ID NO 60
<211> LENGTH: 357
<212> TYPE: DNA
<213> ORGANISM: Artificial Sequence
<220> FEATURE:
<223> OTHER INFORMATION: Synthetic: DNA VH

<400> SEQUENCE: 60
caggtgcagc tggtgcagtc tggggctgag gtgaagaagc ctgggtcctc ggtgaaggtc      60
tcctgcaagg cttctggagg caccttcagc acgtatgcta tcgggtgggt gcgacaggcc     120
cctggacaag ggcttgagtg gatgggaggg atcatccctg cgtttggtac agcaaactac     180
gcacagaagt tccagggcag agtcacgatt accgcggacg aatccacgag cacagcctac     240
atggagctga gcagcctgag atctgaggac acggcggtgt actactgcgc cagagatccg     300
gtgagaagaa gcccattcga catatggggt cagggtacaa tggtcaccgt ctcctca        357

<210> SEQ ID NO 61
<211> LENGTH: 449
<212> TYPE: PRT

<213> ORGANISM: Artificial Sequence
<220> FEATURE:
<223> OTHER INFORMATION: Synthetic: HEAVY CHAIN

<400> SEQUENCE: 61

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Gly Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Arg Arg Ser Pro Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 62
<211> LENGTH: 1347
<212> TYPE: DNA
<213> ORGANISM: Artificial Sequence
<220> FEATURE:
<223> OTHER INFORMATION: Synthetic: DNA HEAVY CHAIN

<400> SEQUENCE: 62

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cttctggagg | caccttcagc | acgtatgcta | tcgggtgggt | gcgacaggcc | 120 |
| cctggacaag | gcttgagtg | gatgggaggg | atcatccctg | cgtttggtac | agcaaactac | 180 |
| gcacagaagt | tccagggcag | agtcacgatt | accgcggacg | aatccacgag | cacagcctac | 240 |
| atggagctga | gcagcctgag | atctgaggac | acggcggtgt | actactgcgc | cagagatccg | 300 |
| gtgagaagaa | gcccattcga | catatggggt | caggtacaa | tggtcaccgt | ctcctcagcg | 360 |
| agcaccaaag | gcccgagcgt | gtttccgctg | gcgccgagca | gcaaagcac | cagcggcggc | 420 |
| accgcggcgc | tgggctgcct | ggtgaaagat | tattttccgg | aaccggtgac | cgtgagctgg | 480 |
| aacagcggcg | cgctgaccag | cggcgtgcat | acctttccgg | cggtgctgca | gagcagcggc | 540 |
| ctgtatagcc | tgagcagcgt | ggtgaccgtg | ccgagcagca | gcctgggcac | ccagacctat | 600 |
| atttgcaacg | tgaaccataa | accgagcaac | accaaagtgg | ataaaaaagt | ggaaccgaaa | 660 |
| agctgcgata | aaacccatac | ctgcccgccg | tgcccggcgc | cggaactgct | gggcggcccg | 720 |
| agcgtgtttc | tgtttccgcc | gaaaccgaaa | gatacccctg | atgattagccg | caccccggaa | 780 |
| gtgacctgcg | tggtggtgga | tgtgagccat | gaagatccgg | aagtgaaatt | taactggtat | 840 |
| gtggatggcg | tggaagtgca | taacgcgaaa | accaaaccgc | gcgaagaaca | gtataacagc | 900 |
| acctatcgcg | tggtgagcgt | gctgaccgtg | ctgcatcagg | attggctgaa | cggcaaagaa | 960 |
| tataaatgca | aagtgagcaa | caaagcgctg | ccggcgccga | ttgaaaaaac | cattagcaaa | 1020 |
| gcgaaaggcc | agccgcgcga | accgcaggtg | tatacccctgc | cgccgagccg | cgatgaactg | 1080 |
| accaaaaacc | aggtgagcct | gacctgcctg | gtgaaaggct | tttatccgag | cgatattgcg | 1140 |
| gtggaatggg | aaagcaacgg | ccagccggaa | aacaactata | aaaccacccc | gccggtgctg | 1200 |
| gatagcgatg | gcagcttttt | tctgtatagc | aaactgaccg | tggataaaag | ccgctggcag | 1260 |
| cagggcaacg | tgtttagctg | cagcgtgatg | catgaagcgc | tgcataacca | ttatacccag | 1320 |
| aaaagcctga | gcctgagccc | gggcaaa | | | | 1347 |

<210> SEQ ID NO 63
<211> LENGTH: 6
<212> TYPE: PRT
<213> ORGANISM: Artificial Sequence
<220> FEATURE:
<223> OTHER INFORMATION: Synthetic: LCDR1 (IMGT)

<400> SEQUENCE: 63

```
Gln Ser Val Ser Ser Tyr
1               5

<210> SEQ ID NO 64
<211> LENGTH: 3
<212> TYPE: PRT
<213> ORGANISM: Artificial Sequence
<220> FEATURE:
<223> OTHER INFORMATION: Synthetic: LCDR2 (IMGT)

<400> SEQUENCE: 64

Asp Ser Ser
1

<210> SEQ ID NO 65
<211> LENGTH: 9
<212> TYPE: PRT
<213> ORGANISM: Artificial Sequence
<220> FEATURE:
<223> OTHER INFORMATION: Synthetic: LCDR3 (IMGT)

<400> SEQUENCE: 65

Gln Gln Ser Phe Leu Trp Pro Arg Thr
1               5

<210> SEQ ID NO 66
<211> LENGTH: 11
<212> TYPE: PRT
<213> ORGANISM: Artificial Sequence
<220> FEATURE:
<223> OTHER INFORMATION: Synthetic: LCDR1 (ADI)

<400> SEQUENCE: 66

Arg Ala Ser Gln Ser Val Ser Ser Tyr Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic: LCDR2 (ADI)

<400> SEQUENCE: 67

Asp Ser Ser Asn Arg Ala Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic: LCDR3 (ADI)

<400> SEQUENCE: 68

Gln Gln Ser Phe Leu Trp Pro Arg Thr
1               5

<210> SEQ ID NO 69
<211> LENGTH: 107
<212> TYPE: PRT
<213> ORGANISM: Artificial Sequence
<220> FEATURE:
<223> OTHER INFORMATION: Synthetic: VL

<400> SEQUENCE: 69

Glu Ile Val Leu Thr Gln Ser Pro Ala Thr Leu Ser Leu Ser Pro Gly
```

```
1               5                   10                  15
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ser Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Phe Leu Trp Pro Arg
                85                  90                  95

Thr Phe Gly Gly Gly Thr Lys Val Glu Ile Lys
            100                 105
```

<210> SEQ ID NO 70
<211> LENGTH: 321
<212> TYPE: DNA
<213> ORGANISM: Artificial Sequence
<220> FEATURE:
<223> OTHER INFORMATION: Synthetic: DNA VL

<400> SEQUENCE: 70

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat tcatccaaca gggccactgg catcccagcc   180
aggttcagtg gcagtgggtc tgggacagac ttcactctca ccatcagcag cctagagcct   240
gaagattttg cagtttatta ctgtcagcag tccttcctct ggcctaggac ttttggcgga   300
gggaccaagg ttgagatcaa a                                             321
```

<210> SEQ ID NO 71
<211> LENGTH: 214
<212> TYPE: PRT
<213> ORGANISM: Artificial Sequence
<220> FEATURE:
<223> OTHER INFORMATION: Synthetic: LIGHT CHAIN

<400> SEQUENCE: 71

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ser Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Phe Leu Trp Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 72
<211> LENGTH: 642
<212> TYPE: DNA
<213> ORGANISM: Artificial Sequence
<220> FEATURE:
<223> OTHER INFORMATION: Synthetic: DNA LIGHT CHAIN

<400> SEQUENCE: 72

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat tcatccaaca gggccactgg catcccagcc   180
aggttcagtg gcagtgggtc tgggacagac ttcactctca ccatcagcag cctagagcct   240
gaagattttg cagtttatta ctgtcagcag tccttcctct ggcctaggac ttttggcgga   300
gggaccaagg ttgagatcaa acgtacggtg gccgctccct ccgtgttcat cttcccaccc   360
tccgacgagc agctgaagtc cggcaccgcc tccgtcgtgt gcctgctgaa caacttctac   420
cctcgcgagg ccaaagtgca gtggaaagtg gacaacgccc tgcagtccgg caactcccag   480
gaatccgtca ccgagcagga ctccaaggac agcacctact ccctgtcctc caccctgacc   540
ctgtccaagg ccgactacga gaagcacaaa gtgtacgcct gcgaagtgac ccaccagggc   600
ctgtccagcc ccgtgaccaa gtccttcaac cggggcgagt gc                     642
```

<210> SEQ ID NO 73
<211> LENGTH: 445
<212> TYPE: PRT
<213> ORGANISM: Artificial Sequence
<220> FEATURE:
<223> OTHER INFORMATION: Synthetic: HEAVY CHAIN

<400> SEQUENCE: 73

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Gly Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Arg Arg Ser Pro Phe Asp Ile Trp Gly Gln Gly
            100                 105                 110

Thr Met Val Thr Val Ser Ser Ala Ser Thr Lys Gly Pro Ser Val Phe
```

```
                    115                 120                 125
Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 74
<211> LENGTH: 1335
<212> TYPE: DNA
<213> ORGANISM: Artificial Sequence
<220> FEATURE:
<223> OTHER INFORMATION: Synthetic: DNA HEAVY CHAIN

<400> SEQUENCE: 74
caggtgcagc tggtgcagtc tggggctgag gtgaagaagc ctgggtcctc ggtgaaggtc      60
tcctgcaagg cttctggagg caccttcagc acgtatgcta tcgggtgggt gcgacaggcc     120
cctggacaag ggcttgagtg gatgggaggg atcatccctg cgtttggtac agcaaactac     180
gcacagaagt tccagggcag agtcacgatt accgcggacg aatccacgag cacagcctac     240
```

```
atggagctga gcagcctgag atctgaggac acggcggtgt actactgcgc cagagatccg    300
gtgagaagaa gcccattcga catatggggt cagggtacaa tggtcaccgt ctcctcagct    360
tccaccaagg gcccctccgt gttccctctg gccccttgct cccggtccac ctccgagtct    420
accgccgctc tgggctgcct cgtgaaggac tacttccccg agcccgtgac cgtgtcctgg    480
aactctggcg ccctgacctc cggcgtgcac accttccctg ccgtgctgca gtcctccggc    540
ctgtactccc tgtccagcgt cgtgaccgtg ccctcctcca gctgggcac caagacctac    600 acctgtaacg tggaccacaa gccctccaac accaaagtgg acaagcgggt ggaatctaag    660 tacgccctc cctgcccttc ctgccctgcc cctgagttcc tgggcggacc ttccgtgttc    720
ctgttccctc caaagcccaa ggacaccctg atgatctccc ggacccctga agtgacctgc    780
gtggtggtgg acgtgtccca ggaagatccc gaagtccagt tcaattggta cgtggacggc    840
gtggaagtgc acaacgccaa gaccaagccc agagaggaac agttcaactc cacctaccgg    900
gtggtgtccg tgctgaccgt gctgcaccag gactggctga acggcaaaga gtacaagtgc    960
aaagtgtcca acaagggcct gccctccagc atcgaaaaga ccatctccaa ggccaagggc    1020
cagccccgcg agccccaagt gtacaccctg cctcccagcc aggaagagat gaccaagaat    1080
caagtgtccc tgacttgtct ggtcaagggc ttctaccccct ccgatatcgc cgtggagtgg    1140
gagtccaacg gccagcccga gaacaactac aagaccaccc ctcccgtgct ggactccgac    1200
ggctccttct tcctgtactc tcggctgacc gtggacaagt cccggtggca ggaaggcaac    1260
gtcttctcct gctccgtgat gcacgaggcc ctgcacaacc actacaccca gaagtccctg    1320
tccctgtctc tgggc                                                   1335
```

<210> SEQ ID NO 75
<211> LENGTH: 445
<212> TYPE: PRT
<213> ORGANISM: Artificial Sequence
<220> FEATURE:
<223> OTHER INFORMATION: Synthetic: HEAVY CHAIN

<400> SEQUENCE: 75

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Gly Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Arg Arg Ser Pro Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

| Asn | Ser | Gly | Ala | Leu | Thr | Ser | Gly | Val | His | Thr | Phe | Pro | Ala | Val | Leu |
| | | | | 165 | | | | | 170 | | | | | 175 | |

| Gln | Ser | Ser | Gly | Leu | Tyr | Ser | Leu | Ser | Ser | Val | Val | Thr | Val | Pro | Ser |
| | | 180 | | | | | 185 | | | | | 190 | | | |

| Ser | Ser | Leu | Gly | Thr | Lys | Thr | Tyr | Thr | Cys | Asn | Val | Asp | His | Lys | Pro |
| | 195 | | | | | 200 | | | | | 205 | | | | |

| Ser | Asn | Thr | Lys | Val | Asp | Lys | Arg | Val | Glu | Ser | Lys | Tyr | Gly | Pro | Pro |
| 210 | | | | | 215 | | | | | 220 | | | | | |

| Cys | Pro | Pro | Cys | Pro | Ala | Pro | Glu | Phe | Leu | Gly | Gly | Pro | Ser | Val | Phe |
| 225 | | | | 230 | | | | | 235 | | | | | 240 | |

| Leu | Phe | Pro | Pro | Lys | Pro | Lys | Asp | Thr | Leu | Met | Ile | Ser | Arg | Thr | Pro |
| | | | 245 | | | | | 250 | | | | | 255 | | |

| Glu | Val | Thr | Cys | Val | Val | Val | Asp | Val | Ser | Gln | Glu | Asp | Pro | Glu | Val |
| | | 260 | | | | | 265 | | | | | 270 | | | |

| Gln | Phe | Asn | Trp | Tyr | Val | Asp | Gly | Val | Glu | Val | His | Asn | Ala | Lys | Thr |
| | 275 | | | | | 280 | | | | | 285 | | | | |

| Lys | Pro | Arg | Glu | Glu | Gln | Phe | Asn | Ser | Thr | Tyr | Arg | Val | Val | Ser | Val |
| 290 | | | | | 295 | | | | | 300 | | | | | |

| Leu | Thr | Val | Leu | His | Gln | Asp | Trp | Leu | Asn | Gly | Lys | Glu | Tyr | Lys | Cys |
| 305 | | | | 310 | | | | | 315 | | | | | 320 | |

| Lys | Val | Ser | Asn | Lys | Gly | Leu | Pro | Ser | Ser | Ile | Glu | Lys | Thr | Ile | Ser |
| | | | 325 | | | | | 330 | | | | | 335 | | |

| Lys | Ala | Lys | Gly | Gln | Pro | Arg | Glu | Pro | Gln | Val | Tyr | Thr | Leu | Pro | Pro |
| | | 340 | | | | | 345 | | | | | 350 | | | |

| Ser | Gln | Glu | Glu | Met | Thr | Lys | Asn | Gln | Val | Ser | Leu | Thr | Cys | Leu | Val |
| | 355 | | | | | 360 | | | | | 365 | | | | |

| Lys | Gly | Phe | Tyr | Pro | Ser | Asp | Ile | Ala | Val | Glu | Trp | Glu | Ser | Asn | Gly |
| 370 | | | | | 375 | | | | | 380 | | | | | |

| Gln | Pro | Glu | Asn | Asn | Tyr | Lys | Thr | Thr | Pro | Pro | Val | Leu | Asp | Ser | Asp |
| 385 | | | | | 390 | | | | | 395 | | | | | 400 |

| Gly | Ser | Phe | Phe | Leu | Tyr | Ser | Arg | Leu | Thr | Val | Asp | Lys | Ser | Arg | Trp |
| | | | | 405 | | | | | 410 | | | | | 415 | |

| Gln | Glu | Gly | Asn | Val | Phe | Ser | Cys | Ser | Val | Met | His | Glu | Ala | Leu | His |
| | | | 420 | | | | | 425 | | | | | 430 | | |

| Asn | His | Tyr | Thr | Gln | Lys | Ser | Leu | Ser | Leu | Ser | Leu | Gly |
| | | 435 | | | | | 440 | | | | | 445 |

<210> SEQ ID NO 76
<211> LENGTH: 1335
<212> TYPE: DNA
<213> ORGANISM: Artificial Sequence
<220> FEATURE:
<223> OTHER INFORMATION: Synthetic: DNA HEAVY CHAIN

<400> SEQUENCE: 76

```
caggtgcagc tggtgcagtc tggggctgag gtgaagaagc ctgggtcctc ggtgaaggtc        60
tcctgcaagg cttctggagg caccttcagc acgtatgcta tcgggtgggt gcgacaggcc       120
cctggacaag gcttgagtg gatgggaggg atcatccctg cgtttggtac agcaaactac       180
gcacagaagt tccagggcag agtcacgatt accgcggacg aatccacgag cacagcctac       240
atggagctga gcagcctgag atctgaggac acggcggtgt actactgcgc cagagatccg       300
gtgagaagaa gcccattcga catatgggt cagggtacaa tggtcaccgt ctcctcagct       360
tccaccaagg gcccctccgt gttccctctg gccccttgct cccggtccac ctccgagtct       420
accgccgctc tgggctgcct cgtgaaggac tacttccccg agcccgtgac cgtgtcctgg       480
```

```
aactctggcg ccctgacctc cggcgtgcac accttccctg ccgtgctgca gtcctccggc    540
ctgtactccc tgtccagcgt cgtgaccgtg ccctcctcca gcctgggcac caagacctac    600
acctgtaacg tggaccacaa gccctccaac accaaagtgg acaagcgggt ggaatctaag    660 tacgccctc cctgccctcc ttgccctgcc cctgagttcc tgggcggacc ttccgtgttc     720
ctgttccctc caaagcccaa ggacaccctg atgatctccc ggaccccga agtgacctgc    780 gtggtggtgg acgtgtccca ggaagatccc gaagtccagt tcaattggta cgtggacggc    840
gtggaagtgc acaacgccaa gaccaagccc agagaggaac agttcaactc cacctaccgg    900
gtggtgtccg tgctgaccgt gctgcaccag gactggctga acggcaaaga gtacaagtgc    960
aaagtgtcca acaagggcct gcccccagc atcgaaaaga ccatctccaa ggccaagggc    1020
cagccccgcg agccccaagt gtacaccctg cctcccagcc aggaagagat gaccaagaat    1080
caagtgtccc tgacttgtct ggtcaagggc ttctacccct ccgatatcgc cgtggagtgg    1140
gagtccaacg ccagcccga gaacaactac aagaccaccc ctcccgtgct ggactccgac    1200
ggctccttct tcctgtactc tcggctgacc gtggacaagt cccggtggca ggaaggcaac    1260
gtcttctcct gctccgtgat gcacgaggcc ctgcacaacc actacaccca gaagtccctg    1320
tccctgtctc tgggc                                                     1335
```

<210> SEQ ID NO 77
<211> LENGTH: 445
<212> TYPE: PRT
<213> ORGANISM: Artificial Sequence
<220> FEATURE:
<223> OTHER INFORMATION: Synthetic: HEAVY CHAIN

<400> SEQUENCE: 77

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Gly Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Arg Arg Ser Pro Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205
```

```
Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 78
<211> LENGTH: 1335
<212> TYPE: DNA
<213> ORGANISM: Artificial Sequence
<220> FEATURE:
<223> OTHER INFORMATION: Synthetic: DNA HEAVY CHAIN

<400> SEQUENCE: 78
caggtgcagc tggtgcagtc tggggctgag gtgaagaagc ctgggtcctc ggtgaaggtc    60
tcctgcaagg cttctggagg caccttcagc acgtatgcta tcggtgggt gcgacaggcc   120 cctggacaag gcttgagtg gatgggaggg atcatccctg cgtttggtac agcaaactac   180
gcacagaagt tccagggcag agtcacgatt accgcggacg aatccacgag cacagcctac   240
atggagctga gcagcctgag atctgaggac acggcggtgt actactgcgc cagagatccg   300
gtgagaagaa gcccattcga catatggggt cagggtacaa tggtcaccgt ctcctcagct   360
tccaccaagg gcccctccgt gttccctctg gccccttgct ccggtccac tccgagtct   420 accgccgctc tgggctgcct cgtgaaggac tacttccccg agcccgtgac cgtgtcctgg   480
aactctggcg ccctgaccct cggcgtgcac accttccctg ccgtgctgca gtcctccggc   540
ctgtactccc tgtccagcgt cgtgaccgtg ccctcctcca gcctgggcac caagacctac   600
acctgtaacg tggaccacaa gcctccaac accaaagtgg acaagcgggt ggaatctaag   660
tacggccctc cctgccctcc ttgccctgcc ctgagttcg agggcggacc ttccgtgttc   720
```

```
ctgttccctc caaagcccaa ggacaccctg atgatctccc ggaccccctga agtgacctgc    780 gtggtggtgg acgtgtccca ggaagatccc gaagtccagt tcaattggta cgtggacggc    840
gtggaagtgc acaacgccaa gaccaagccc agagaggaac agttcaactc cacctaccgg    900
gtggtgtccg tgctgaccgt gctgcaccag gactggctga acggcaaaga gtacaagtgc    960
aaagtgtcca acaagggcct gccctccagc atcgaaaaga ccatctccaa ggccaagggc   1020
cagccccgcg agccccaagt gtacaccctg cctcccagcc aggaagagat gaccaagaat   1080
caagtgtccc tgacttgtct ggtcaagggc ttctaccccct ccgatatcgc cgtggagtgg   1140
gagtccaacg gccagcccga gaacaactac aagaccaccc tcccgtgct ggactccgac   1200 ggctccttct tcctgtactc tcggctgacc gtggacaagt cccggtggca ggaaggcaac   1260
gtcttctcct gctccgtgat gcacgaggcc ctgcacaacc actacaccca gaagtccctg   1320
tccctgtctc tgggc                                                    1335
```

```
<210> SEQ ID NO 79
<211> LENGTH: 8
<212> TYPE: PRT
<213> ORGANISM: Artificial Sequence
<220> FEATURE:
<223> OTHER INFORMATION: Synthetic: HCDR1 (IMGT)

<400> SEQUENCE: 79

Gly Phe Thr Phe Ser Ser Tyr Arg
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic: HCDR2 (IMGT)

<400> SEQUENCE: 80

Ile Ser Ser Ser Ser Ser Ser Ile
1               5

<210> SEQ ID NO 81
<211> LENGTH: 19
<212> TYPE: PRT
<213> ORGANISM: Artificial Sequence
<220> FEATURE:
<223> OTHER INFORMATION: Synthetic: HCDR3 (IMGT)

<400> SEQUENCE: 81

Ala Lys Gly Pro Arg Tyr Asp Ser Ser Gly Tyr Arg Trp Arg Tyr Gly
1               5                   10                  15

Met Asp Val

<210> SEQ ID NO 82
<211> LENGTH: 9
<212> TYPE: PRT
<213> ORGANISM: Artificial Sequence
<220> FEATURE:
<223> OTHER INFORMATION: Synthetic: HCDR1 (ADI)

<400> SEQUENCE: 82

Phe Thr Phe Ser Ser Tyr Arg Met Asn
1               5

<210> SEQ ID NO 83
```

<211> LENGTH: 17
<212> TYPE: PRT
<213> ORGANISM: Artificial Sequence
<220> FEATURE:
<223> OTHER INFORMATION: Synthetic: HCDR2 (ADI)

<400> SEQUENCE: 83

Ser Ile Ser Ser Ser Ser Ser Ser Ile Trp Tyr Ala Asp Ser Val Lys
1               5                   10                  15
Gly

<210> SEQ ID NO 84
<211> LENGTH: 19
<212> TYPE: PRT
<213> ORGANISM: Artificial Sequence
<220> FEATURE:
<223> OTHER INFORMATION: Synthetic: HCDR3 (ADI)

<400> SEQUENCE: 84

Ala Lys Gly Pro Arg Tyr Asp Ser Ser Gly Tyr Arg Trp Arg Tyr Gly
1               5                   10                  15
Met Asp Val

<210> SEQ ID NO 85
<211> LENGTH: 126
<212> TYPE: PRT
<213> ORGANISM: Artificial Sequence
<220> FEATURE:
<223> OTHER INFORMATION: Synthetic: VH

<400> SEQUENCE: 85

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Arg Met Asn Trp Val Arg Gln Ala Pro Gly Lys Gly Leu Glu Trp Val
        35                  40                  45
Ser Ser Ile Ser Ser Ser Ser Ser Ile Trp Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Gly Pro Arg Tyr Asp Ser Ser Gly Tyr Arg Trp Arg Tyr Gly
            100                 105                 110
Met Asp Val Trp Gly Gln Gly Thr Thr Val Thr Val Ser Ser
        115                 120                 125

<210> SEQ ID NO 86
<211> LENGTH: 378
<212> TYPE: DNA
<213> ORGANISM: Artificial Sequence
<220> FEATURE:
<223> OTHER INFORMATION: Synthetic: DNA VH

<400> SEQUENCE: 86
gaggtgcagc tggtggagtc tgggggaggc tggtcaagc ctggggggtc cctgagactc      60
tcctgtgcag cctctggatt caccttctct agctatagga tgaactgggt ccgccaggct    120
ccagggaagg ggctggagtg gtctcatcc attagtagta gtagtagttc gatatggtac    180
gcagactcag tgaagggccg attcaccatc tccagagaca acgccaagaa ctcactgtat    240

```
ctgcaaatga acagcctgag agccgaggac acggcggtgt actactgcgc caagggcccc    300
agatacgaca gcagcggata ccgatggaga tacggaatgg acgtatgggg ccagggaaca    360
actgtcaccg tctcctca                                                  378
```

<210> SEQ ID NO 87
<211> LENGTH: 456
<212> TYPE: PRT
<213> ORGANISM: Artificial Sequence
<220> FEATURE:
<223> OTHER INFORMATION: Synthetic: HEAVY CHAIN

<400> SEQUENCE: 87

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Ile Trp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Arg Tyr Asp Ser Ser Gly Tyr Arg Trp Arg Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335
```

```
Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 88
<211> LENGTH: 1368
<212> TYPE: DNA
<213> ORGANISM: Artificial Sequence
<220> FEATURE:
<223> OTHER INFORMATION: Synthetic: DNA HEAVY CHAIN

<400> SEQUENCE: 88
gaggtgcagc tggtggagtc tgggggaggc ctggtcaagc ctgggggtc cctgagactc          60 tcctgtgcag cctctggatt caccttctct agctatagga tgaactgggt ccgccaggct        120
ccagggaagg gctggagtg gtctcatcc attagtagta gtagtagttc gatatggtac          180
gcagactcag tgaagggccg attcaccatc tccagagaca cgccaagaa ctcactgtat         240 ctgcaaatga acagcctgag agccgaggac acggcggtgt actactgcgc aagggcccc         300 agatacgaca gcagcggata ccgatggaga tacggaatgg acgtatgggg ccagggaaca        360
actgtcaccg tctcctcagc gagcaccaaa ggcccgagcg tgtttccgct ggcgccgagc        420
agcaaaagca ccagcggcgg caccgcggcg ctgggctgcc tggtgaaaga ttatttccg         480 gaaccggtga ccgtgagctg gaacagcggc gcgctgacca gcggcgtgca tacctttccg        540
gcggtgctgc agagcagcgg cctgtatagc ctgagcagcg tggtgaccgt gccgagcagc        600
agcctgggca cccagaccta tatttgcaac gtgaaccata aaccgagcaa caccaaagtg        660
gataaaaaag tggaaccgaa aagctgcgat aaacccata cctgcccgcc gtgcccggcg         720
ccggaactgc tgggcggccc gagcgtgttt ctgtttccgc gaaaccgaa agatacccctg        780 atgattagcc gcaccccgga agtgacctgc gtggtggtgg atgtgagcca tgaagatccg        840
gaagtgaaat taactggta tgtggatggc gtggaagtgc ataacgcgaa aaccaaaccg         900
cgcgaagaac agtataacag cacctatcgc gtggtgagcg tgctgaccgt gctgcatcag        960
gattggctga acggcaaaga atataaatgc aaagtgagca caaagcgct gccggcgccg       1020 attgaaaaaa ccattagcaa agcgaaaggc cagccgcgcg aaccgcaggt gtataccctg       1080
ccgccgagcc gcgatgaact gaccaaaaac caggtgagcc tgacctgcct ggtgaaaggc       1140
ttttatccga gcgatattgc ggtggaatgg gaaagcaacg gccagccgga aaacaactat       1200
aaaaccaccc cgccggtgct ggatagcgat ggcagctttt ttctgtatag caaactgacc       1260
gtggataaaa gccgctggca gcaggcaac gtgtttagct gcagcgtgat gcatgaagcg       1320
```
ctgcataacc attataccca gaaaagcctg agcctgagcc cgggcaaa        1368

<210> SEQ ID NO 89
<211> LENGTH: 6
<212> TYPE: PRT
<213> ORGANISM: Artificial Sequence
<220> FEATURE:
<223> OTHER INFORMATION: Synthetic: LCDR1 (IMGT)

<400> SEQUENCE: 89

Gln Ser Ile Ser Ser Tyr
1               5

<210> SEQ ID NO 90
<211> LENGTH: 3
<212> TYPE: PRT
<213> ORGANISM: Artificial Sequence
<220> FEATURE:
<223> OTHER INFORMATION: Synthetic: LCDR2 (IMGT)

<400> SEQUENCE: 90

Ala Ala Ser
1

<210> SEQ ID NO 91
<211> LENGTH: 10
<212> TYPE: PRT
<213> ORGANISM: Artificial Sequence
<220> FEATURE:
<223> OTHER INFORMATION: Synthetic: LCDR3 (IMGT)

<400> SEQUENCE: 91

Gln Gln Leu Tyr Val Asp Pro Pro Trp Thr
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic: LCDR1 (ADI)

<400> SEQUENCE: 92

Arg Ala Ser Gln Ser Ile Ser Ser Tyr Leu Asn
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Synthetic: LCDR2 (ADI)

<400> SEQUENCE: 93

Ala Ala Ser Ser Leu Gln Ser
1               5

<210> SEQ ID NO 94
<211> LENGTH: 10
<212> TYPE: PRT
<213> ORGANISM: Artificial Sequence
<220> FEATURE:
<223> OTHER INFORMATION: Synthetic: LCDR3 (ADI)

<400> SEQUENCE: 94

Gln Gln Leu Tyr Val Asp Pro Pro Trp Thr
1               5                   10

<210> SEQ ID NO 95
<211> LENGTH: 108
<212> TYPE: PRT
<213> ORGANISM: Artificial Sequence
<220> FEATURE:
<223> OTHER INFORMATION: Synthetic: VL

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Val Asp Pro Pro
                85                  90                  95

Trp Thr Phe Gly Gly Gly Thr Lys Val Glu Ile Lys
            100                 105

<210> SEQ ID NO 96
<211> LENGTH: 324
<212> TYPE: DNA
<213> ORGANISM: Artificial Sequence
<220> FEATURE:
<223> OTHER INFORMATION: Synthetic: DNA VL

<400> SEQUENCE: 96
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ctatacgtcg accctccttg acttttggc      300 ggagggacca aggttgagat caaa                                            324

<210> SEQ ID NO 97
<211> LENGTH: 215
<212> TYPE: PRT
<213> ORGANISM: Artificial Sequence
<220> FEATURE:
<223> OTHER INFORMATION: Synthetic: LIGHT CHAIN

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Val Asp Pro Pro
                 85                  90                  95

Trp Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 98
<211> LENGTH: 645
<212> TYPE: DNA
<213> ORGANISM: Artificial Sequence
<220> FEATURE:
<223> OTHER INFORMATION: Synthetic: DNA LIGHT CHAIN

<400> SEQUENCE: 98
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ctatacgtcg accctccttg acttttggc      300
ggagggacca aggttgagat caaacgtacg gtggccgctc cctccgtgtt catcttccca     360
ccctccgacg agcagctgaa gtccggcacc gcctccgtcg tgtgcctgct gaacaacttc     420
taccctcgcg aggccaaagt gcagtggaaa gtggacaacg ccctgcagtc cggcaactcc     480
caggaatccg tcaccgagca ggactccaag gacagcacct actccctgtc ctccaccctg     540
accctgtcca aggccgacta cgagaagcac aaagtgtacg cctgcgaagt gacccaccag     600
ggcctgtcca gccccgtgac caagtccttc aaccggggcg agtgc                    645

<210> SEQ ID NO 99
<211> LENGTH: 452
<212> TYPE: PRT
<213> ORGANISM: Artificial Sequence
<220> FEATURE:
<223> OTHER INFORMATION: Synthetic: HEAVY CHAIN

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Ile Trp Tyr Ala Asp Ser Val

```
             50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Lys Gly Pro Arg Tyr Asp Ser Gly Tyr Arg Trp Arg Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Cys Ser Arg Ser Thr
                130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Lys Thr Tyr Thr
                195                 200                 205

Cys Asn Val Asp His Lys Pro Ser Asn Thr Lys Val Asp Lys Arg Val
210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser Gln Glu Asp Pro Glu Val Gln Phe Asn Trp Tyr Val Asp Gly Val
                275                 280                 285

Glu Val His Asn Ala Lys Thr Lys Pro Arg Glu Glu Gln Phe Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Gln Glu Glu Met Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
                420                 425                 430

Val Met His Glu Ala Leu His Asn His Tyr Thr Gln Lys Ser Leu Ser
                435                 440                 445

Leu Ser Leu Gly
            450

<210> SEQ ID NO 100
```

<211> LENGTH: 1356
<212> TYPE: DNA
<213> ORGANISM: Artificial Sequence
<220> FEATURE:
<223> OTHER INFORMATION: Synthetic: DNA HEAVY CHAIN

<400> SEQUENCE: 100

```
gaggtgcagc tggtggagtc tgggggaggc tggtcaagc ctgggggtc cctgagactc      60
tcctgtgcag cctctggatt caccttctct agctatagga tgaactgggt ccgccaggct    120
ccagggaagg gctggagtg gtctcatcc attagtagta gtagtagttc gatatggtac      180
gcagactcag tgaagggccg attcaccatc tccagagaca cgccaagaa ctcactgtat     240
ctgcaaatga acagcctgag agccgaggac acggcggtgt actactgcgc caagggcccc   300
agatacgaca gcagcggata ccgatggaga tacggaatgg acgtatgggg ccagggaaca   360
actgtcaccg tctcctcagc ttccaccaag ggcccctccg tgttccctct ggccccttgc   420
tcccggtcca cctccgagtc taccgccgct ctgggctgcc tcgtgaagga ctacttcccc   480
gagcccgtga ccgtgtcctg gaactctggc gccctgacct ccggcgtgca ccttcccct    540
gccgtgctgc agtcctccgg cctgtactcc ctgtccagcg tcgtgaccgt gccctcctcc   600
agcctgggca ccaagaccta cacctgtaac gtggaccaca agccctccaa caccaaagtg   660
gacaagcggg tggaatctaa gtacggcccc cctgcccttt cctgccctgc cctgagttc    720
ctgggcggac cttccgtgtt cctgttccct ccaaagccca aggacaccct gatgatctcc   780
cggacccctg aagtgacctg cgtggtggtg gacgtgtccc aggaagatcc cgaagtccag   840
ttcaattggt acgtggacgg cgtggaagtg cacaacgcca agaccaagcc cagagaggaa   900
cagttcaact ccacctaccg ggtggtgtcc gtgctgaccg tgctgcacca ggactggctg   960
aacggcaaag agtacaagtg caaagtgtcc aacaagggcc tgccctccag catcgaaaag  1020
accatctcca aggccaaggg ccagccccgc gagcccaag tgtacaccct gcctcccagc   1080
caggaagaga tgaccaagaa tcaagtgtcc ctgacttgtc tggtcaaggg cttctacccc  1140
tccgatatcg ccgtggagtg ggagtccaac ggccagcccg agaacaacta caagaccacc  1200
cctcccgtgc tggactccga cggctccttc ttcctgtact ctcggctgac cgtggacaag  1260
tcccggtggc aggaaggcaa cgtcttctcc tgctccgtga tgcacgaggc cctgcacaac  1320
cactacaccc agaagtccct gtccctgtct ctgggc                            1356
```

<210> SEQ ID NO 101
<211> LENGTH: 452
<212> TYPE: PRT
<213> ORGANISM: Artificial Sequence
<220> FEATURE:
<223> OTHER INFORMATION: Synthetic: HEAVY CHAIN

<400> SEQUENCE: 101

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Ile Trp Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Pro Arg Tyr Asp Ser Gly Tyr Arg Trp Arg Tyr Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly
        450

<210> SEQ ID NO 102
<211> LENGTH: 1356
<212> TYPE: DNA
<213> ORGANISM: Artificial Sequence
<220> FEATURE:
<223> OTHER INFORMATION: Synthetic: DNA HEAVY CHAIN
```

<400> SEQUENCE: 102

```
gaggtgcagc tggtggagtc tgggggaggc ctggtcaagc ctggggggtc cctgagactc      60
tcctgtgcag cctctggatt caccttctct agctatagga tgaactgggt ccgccaggct     120
ccagggaagg ggctgagtg gtctcatcc attagtagta gtagtagttc gatatggtac      180
gcagactcag tgaagggccg attcaccatc tccagagaca acgccaagaa ctcactgtat     240
ctgcaaatga acagcctgag agccgaggac acggcgtgt actactgcgc caagggcccc      300
agatacgaca gcagcggata ccgatggaga tacggaatgg acgtatgggg ccagggaaca     360
actgtcaccg tctcctcagc ttccaccaag ggcccctccg tgttccctct ggccccttgc     420
tcccggtcca cctccgagtc taccgccgct ctgggctgcc tcgtgaagga ctacttcccc     480
gagcccgtga ccgtgtcctg gaactctggc gccctgacct ccggcgtgca caccttccct     540
gccgtgctgc agtcctccgg cctgtactcc ctgtccagcg tcgtgaccgt gccctcctcc     600
agcctgggca ccaagaccta cacctgtaac gtggaccaca gcccctccaa caccaaagtg     660
gacaagcggg tggaatctaa gtacggccct cctgccctc cttgccctgc cctgagttc      720
ctgggcggac cttccgtgtt cctgttccct ccaaagccca aggacaccct gatgatctcc     780
cggacccctg aagtgacctg cgtggtggtg gacgtgtccc aggaagatcc cgaagtccag     840
ttcaattggt acgtggacgg cgtggaagtg cacaacgcca agaccaagcc agagaggaa     900
cagttcaact ccacctaccg ggtggtgtcc gtgctgaccg tgctgcacca ggactggctg     960
aacggcaaag agtacaagtg caaagtgtcc aacaagggcc tgccctccag catcgaaaag    1020
accatctcca aggccaaggg ccagccccgc gagcccaag tgtacaccct gcctcccagc     1080
caggaagaga tgaccaagaa tcaagtgtcc ctgacttgtc tggtcaaggg cttctacccc    1140
tccgatatcg ccgtggagtg ggagtccaac ggccagcccg agaacaacta caagaccacc    1200
cctcccgtgc tggactccga cggctccttc ttcctgtact ctcggctgac cgtggacaag    1260
tcccggtggc aggaaggcaa cgtcttctcc tgctccgtga tgcacgaggc cctgcacaac    1320
cactacaccc agaagtccct gtccctgtct ctgggc                              1356
```

<210> SEQ ID NO 103
<211> LENGTH: 452
<212> TYPE: PRT
<213> ORGANISM: Artificial Sequence
<220> FEATURE:
<223> OTHER INFORMATION: Synthetic: HEAVY CHAIN

<400> SEQUENCE: 103

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Ile Trp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Arg Tyr Asp Ser Ser Gly Tyr Arg Trp Arg Tyr Gly
            100                 105                 110
```

Met Asp Val Trp Gly Gln Gly Thr Thr Val Thr Val Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Glu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
                385                 390                 395                 400

Pro Pro Val Leu Asp Ser Asp Gly Ser Phe Phe Leu Tyr Ser Arg Leu
            405                 410                 415

Thr Val Asp Lys Ser Arg Trp Gln Glu Gly Asn Val Phe Ser Cys Ser
        420                 425                 430

Val Met His Glu Ala Leu His Asn His Tyr Thr Gln Lys Ser Leu Ser
    435                 440                 445

Leu Ser Leu Gly
    450

<210> SEQ ID NO 104
<211> LENGTH: 1356
<212> TYPE: DNA
<213> ORGANISM: Artificial Sequence
<220> FEATURE:
<223> OTHER INFORMATION: Synthetic: DNA HEAVY CHAIN

<400> SEQUENCE: 104
gaggtgcagc tggtggagtc tgggggaggc ctggtcaagc ctggggggtc cctgagactc      60

| | |
|---|---|
| tcctgtgcag cctctggatt caccttctct agctatagga tgaactgggt ccgccaggct | 120 |
| ccagggaagg ggctggagtg ggtctcatcc attagtagta gtagtagttc gatatggtac | 180 |
| gcagactcag tgaagggccg attcaccatc tccagagaca acgccaagaa ctcactgtat | 240 |
| ctgcaaatga acagcctgag agccgaggac acggcggtgt actactgcgc aagggccccc | 300 |
| agatacgaca gcagcggata ccgatggaga tacggaatgg acgtatgggg ccagggaaca | 360 |
| actgtcaccg tctcctcagc ttccaccaag ggcccctccg tgttccctct ggccccttgc | 420 |
| tcccggtcca cctccgagtc taccgccgct ctgggctgcc tcgtgaagga ctacttcccc | 480 |
| gagcccgtga ccgtgtcctg gaactctggc gccctgacct ccggcgtgca caccttccct | 540 |
| gccgtgctgc agtcctccgg cctgtactcc ctgtccagcg tcgtgaccgt gccctcctcc | 600 |
| agcctgggca ccaagaccta cacctgtaac gtggaccaca agccctccaa caccaaagtg | 660 |
| gacaagcggg tggaatctaa gtacggccct ccctgccctc cttgccctgc ccctgagttc | 720 |
| gagggcggac cttccgtgtt cctgttccct ccaaagccca aggacaccct gatgatctcc | 780 |
| cggacccctg aagtgacctg cgtggtggtg gacgtgtccc aggaagatcc cgaagtccag | 840 |
| ttcaattggt acgtggacgg cgtggaagtg cacaacgcca agaccaagcc cagagaggaa | 900 |
| cagttcaact ccacctaccg ggtggtgtcc gtgctgaccg tgctgcacca ggactggctg | 960 |
| aacggcaaag agtacaagtg caaagtgtcc aacaagggcc tgccctccag catcgaaaag | 1020 |
| accatctccc aggccaaggg ccagccccgc gagccccaag tgtacaccct gcctcccagc | 1080 |
| caggaagaga tgaccaagaa tcaagtgtcc ctgacttgtc tggtcaaggg cttctacccc | 1140 |
| tccgatatcg ccgtggagtg ggagtccaac ggccagcccg agaacaacta caagaccacc | 1200 |
| cctcccgtgc tggactccga cggctccttc ttcctgtact ctcggctgac cgtggacaag | 1260 |
| tcccggtggc aggaaggcaa cgtcttctcc tgctccgtga tgcacgaggc cctgcacaac | 1320 |
| cactacaccc agaagtccct gtccctgtct ctgggc | 1356 |

<210> SEQ ID NO 105
<211> LENGTH: 8
<212> TYPE: PRT
<213> ORGANISM: Artificial Sequence
<220> FEATURE:
<223> OTHER INFORMATION: Synthetic: HCDR1 (IMGT)

<400> SEQUENCE: 105

Gly Tyr Thr Phe Ser Ser Trp Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic: HCDR2 (IMGT)

<400> SEQUENCE: 106

Ile Asn Pro Ser Gly Gly Ser Thr
1               5

<210> SEQ ID NO 107
<211> LENGTH: 16
<212> TYPE: PRT
<213> ORGANISM: Artificial Sequence
<220> FEATURE:
<223> OTHER INFORMATION: Synthetic: HCDR3 (IMGT)

<400> SEQUENCE: 107

```
Ala Arg Asp Ala Pro Phe Tyr Thr Trp Asp His Tyr Tyr Gly Met Asp
1               5                   10                  15

<210> SEQ ID NO 108
<211> LENGTH: 9
<212> TYPE: PRT
<213> ORGANISM: Artificial Sequence
<220> FEATURE:
<223> OTHER INFORMATION: Synthetic: HCDR1 (ADI)

<400> SEQUENCE: 108

Tyr Thr Phe Ser Ser Trp Tyr Met His
1               5

<210> SEQ ID NO 109
<211> LENGTH: 17
<212> TYPE: PRT
<213> ORGANISM: Artificial Sequence
<220> FEATURE:
<223> OTHER INFORMATION: Synthetic: HCDR2 (ADI)

<400> SEQUENCE: 109

Met Ile Asn Pro Ser Gly Gly Ser Thr Lys Tyr Ala Gln Lys Phe Gln
1               5                   10                  15
Gly

<210> SEQ ID NO 110
<211> LENGTH: 17
<212> TYPE: PRT
<213> ORGANISM: Artificial Sequence
<220> FEATURE:
<223> OTHER INFORMATION: Synthetic: HCDR3 (ADI)

<400> SEQUENCE: 110

Ala Arg Asp Ala Pro Phe Tyr Thr Trp Asp His Tyr Tyr Gly Met Asp
1               5                   10                  15
Val

<210> SEQ ID NO 111
<211> LENGTH: 124
<212> TYPE: PRT
<213> ORGANISM: Artificial Sequence
<220> FEATURE:
<223> OTHER INFORMATION: Synthetic: VH

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Trp
            20                  25                  30

Tyr Met His Trp Val Arg Gln Ala Pro Gly Gln Gly Leu Glu Trp Met
        35                  40                  45

Gly Met Ile Asn Pro Ser Gly Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Phe Tyr Thr Trp Asp His Tyr Tyr Gly Met Asp
            100                 105                 110

Val Trp Gly Gln Gly Thr Thr Val Thr Val Ser Ser
```

<210> SEQ ID NO 112
<211> LENGTH: 372
<212> TYPE: DNA
<213> ORGANISM: Artificial Sequence
<220> FEATURE:
<223> OTHER INFORMATION: Synthetic: DNA VH

<400> SEQUENCE: 112

```
caggtgcagc tggtgcagtc tggggctgag gtgaagaagc ctggggcctc agtgaaggtt    60
tcctgcaagg catctggata caccttcagt agctggtata tgcactgggt gcgacaggcc   120
cctggacaag ggcttgagtg gatgggaatg atcaaccctc gtggtggtag cacaaagtac   180
gcacagaagt tccagggcag agtcaccatg accagggaca cgtccacgag cacagtctac   240
atggagctga gcagcctgag atctgaggac acggcggtgt actactgcgc cagagatgct   300
cctttctaca cctgggatca ctactacgga atggacgtat ggggccaggg aacaactgtc   360
accgtctcct ca                                                        372
```

<210> SEQ ID NO 113
<211> LENGTH: 454
<212> TYPE: PRT
<213> ORGANISM: Artificial Sequence
<220> FEATURE:
<223> OTHER INFORMATION: Synthetic: HEAVY CHAIN

<400> SEQUENCE: 113

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Trp
            20                  25                  30

Tyr Met His Trp Val Arg Gln Ala Pro Gly Gln Gly Leu Glu Trp Met
        35                  40                  45

Gly Met Ile Asn Pro Ser Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Phe Tyr Thr Trp Asp His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
```

```
                225                 230                 235                 240
Leu Leu Gly Gly Pro Ser Val Phe Leu Phe Pro Pro Lys Pro Lys Asp
                    245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
        450

<210> SEQ ID NO 114
<211> LENGTH: 1362
<212> TYPE: DNA
<213> ORGANISM: Artificial Sequence
<220> FEATURE:
<223> OTHER INFORMATION: Synthetic: DNA HEAVY CHAIN

<400> SEQUENCE: 114
caggtgcagc tggtgcagtc tggggctgag gtgaagaagc ctggggcctc agtgaaggtt      60
tcctgcaagg catctggata caccttcagt agctggtata tgcactgggt gcgacaggcc     120
cctggacaag gcttgagtg gatgggaatg atcaaccta gtggtggtag cacaaagtac     180
gcacagaagt tccagggcag agtcaccatg accaggggaca cgtccacgag cacagtctac     240
atggagctga gcagcctgag atctgaggac acggcggtgt actactgcgc cagagatgct     300
cctttctaca cctgggatca ctactacgga atggacgtat ggggccaggg aacaactgtc     360
accgtctcct cagcgagcac caaaggcccg agcgtgtttc cgctggcgcc gagcagcaaa     420
agcaccagcg gcggcaccgc ggcgctgggc tgcctggtga agattattt ccggaaccg     480 gtgaccgtga gctggaacag cggcgcgctg accagcggcg tgcataccct tccggcggtg     540
ctgcagagca gcggcctgta tagcctgagc agcgtggtga ccgtgccgag cagcagcctg     600
ggcacccaga cctatatttg caacgtgaac cataaaccga gcaacaccaa agtggataaa     660
aaagtggaaa cgaaaagctg cgataaaacc catacctgcc cgccgtgccc ggcgccggaa     720
ctgctgggcg gcccgagcgt gtttctgttt ccgccgaaac cgaaagatac cctgatgatt     780
```

```
agccgcaccc cggaagtgac ctgcgtggtg gtggatgtga gccatgaaga tccggaagtg    840
aaatttaact ggtatgtgga tggcgtggaa gtgcataacg cgaaaaccaa accgcgcgaa    900
gaacagtata acagcaccta tcgcgtggtg agcgtgctga ccgtgctgca tcaggattgg    960
ctgaacggca agaatataaa atgcaaagtg agcaacaaag cgctgccggc gccgattgaa    1020 aaaccatta gcaaagcgaa aggccagccg cgcgaaccgc aggtgtatac cctgccgccg    1080
agccgcgatg aactgaccaa aaaccaggtg agcctgacct gcctggtgaa aggctttat    1140 ccgagcgata ttgcggtgga atgggaaagc aacggccagc cggaaaacaa ctataaaacc    1200
accccgccgg tgctggatag cgatggcagc tttttctgt atagcaaaact gaccgtggat    1260 aaaagccgct ggcagcaggg caacgtgttt agctgcagcg tgatgcatga agcgctgcat    1320
aaccattata cccagaaaag cctgagcctg agcccgggca aa    1362
```

```
<210> SEQ ID NO 115
<211> LENGTH: 6
<212> TYPE: PRT
<213> ORGANISM: Artificial Sequence
<220> FEATURE:
<223> OTHER INFORMATION: Synthetic: LCDR1 (IMGT)

<400> SEQUENCE: 115

Gln Asp Ile Ser Asn Tyr
1               5

<210> SEQ ID NO 116
<211> LENGTH: 3
<212> TYPE: PRT
<213> ORGANISM: Artificial Sequence
<220> FEATURE:
<223> OTHER INFORMATION: Synthetic: LCDR2 (IMGT)

<400> SEQUENCE: 116

Asp Ala Ser
1

<210> SEQ ID NO 117
<211> LENGTH: 9
<212> TYPE: PRT
<213> ORGANISM: Artificial Sequence
<220> FEATURE:
<223> OTHER INFORMATION: Synthetic: LCDR3 (IMGT)

<400> SEQUENCE: 117

Gln Gln Leu Tyr His Leu Pro Ile Thr
1               5

<210> SEQ ID NO 118
<211> LENGTH: 11
<212> TYPE: PRT
<213> ORGANISM: Artificial Sequence
<220> FEATURE:
<223> OTHER INFORMATION: Synthetic: LCDR1 (ADI)

<400> SEQUENCE: 118

Gln Ala Ser Gln Asp Ile Ser Asn Tyr Leu Asn
1               5                   10

<210> SEQ ID NO 119
<211> LENGTH: 7
<212> TYPE: PRT
<213> ORGANISM: Artificial Sequence
<220> FEATURE:
```

<223> OTHER INFORMATION: Synthetic: LCDR2 (ADI)

<400> SEQUENCE: 119

Asp Ala Ser Asn Leu Ala Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic: LCDR3 (ADI)

<400> SEQUENCE: 120

Gln Gln Leu Tyr His Leu Pro Ile Thr
1               5

<210> SEQ ID NO 121
<211> LENGTH: 107
<212> TYPE: PRT
<213> ORGANISM: Artificial Sequence
<220> FEATURE:
<223> OTHER INFORMATION: Synthetic: VL

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr His Leu Pro Ile
                85                  90                  95

Thr Phe Gly Gly Gly Thr Lys Val Glu Ile Lys
            100                 105

<210> SEQ ID NO 122
<211> LENGTH: 321
<212> TYPE: DNA
<213> ORGANISM: Artificial Sequence
<220> FEATURE:
<223> OTHER INFORMATION: Synthetic: DNA VL

<400> SEQUENCE: 122
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggcaacagg ggtcccatca    180
aggttcagtg gaagtggatc tgggacagat tttactttca ccatcagcag cctgcagcct    240
gaagatattg caacatatta ctgtcagcag ctctaccacc tccctatcac ttttggcgga    300
gggaccaagg ttgagatcaa a                                              321

<210> SEQ ID NO 123
<211> LENGTH: 214
<212> TYPE: PRT
<213> ORGANISM: Artificial Sequence
<220> FEATURE:

<223> OTHER INFORMATION: Synthetic: LIGHT CHAIN

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr His Leu Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 124
<211> LENGTH: 642
<212> TYPE: DNA
<213> ORGANISM: Artificial Sequence
<220> FEATURE:
<223> OTHER INFORMATION: Synthetic: DNA LIGHT CHAIN

<400> SEQUENCE: 124

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggcaacagg gtcccatca    180
aggttcagtg gaagtggatc tgggacagat tttactttca ccatcagcag cctgcagcct    240
gaagatattg caacatatta ctgtcagcag ctctaccacc tccctatcac ttttggcgga    300
gggaccaagg ttgagatcaa acgtacggtg gccgctccct ccgtgttcat cttcccaccc    360
tccgacgagc agctgaagtc cggcaccgcc tccgtcgtgt gcctgctgaa caacttctac    420
cctcgcgagg ccaaagtgca gtggaaagtg gacaacgccc tgcagtccgg caactcccag    480
gaatccgtca ccgagcagga ctccaaggac agcacctact ccctgtcctc cacctgacc    540
ctgtccaagg ccgactacga gaagcacaaa gtgtacgcct gcgaagtgac ccaccagggc    600
ctgtccagcc ccgtgaccaa gtccttcaac cggggcgagt gc                       642
```

-continued

```
<210> SEQ ID NO 125
<211> LENGTH: 450
<212> TYPE: PRT
<213> ORGANISM: Artificial Sequence
<220> FEATURE:
<223> OTHER INFORMATION: Synthetic: HEAVY CHAIN

<400> SEQUENCE: 125
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Trp
            20                  25                  30

Tyr Met His Trp Val Arg Gln Ala Pro Gly Gln Gly Leu Glu Trp Met
        35                  40                  45

Gly Met Ile Asn Pro Ser Gly Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Phe Tyr Thr Trp Asp His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu

```
                 370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 126
<211> LENGTH: 1350
<212> TYPE: DNA
<213> ORGANISM: Artificial Sequence
<220> FEATURE:
<223> OTHER INFORMATION: Synthetic: DNA HEAVY CHAIN

<400> SEQUENCE: 126
caggtgcagc tggtgcagtc tggggctgag gtgaagaagc ctggggcctc agtgaaggtt      60
tcctgcaagg catctggata caccttcagt agctggtata tgcactgggt gcgacaggcc     120
cctggacaag gcttgagtg gatgggaatg atcaaccctaa gtggtggtag cacaaagtac     180
gcacagaagt tccagggcag agtcaccatg accagggaca cgtccacgag cacagtctac     240
atggagctga gcagcctgag atctgaggac acggcggtgt actactgcgc cagagatgct     300
cctttctaca cctgggatca ctactacgga atggacgtat ggggccaggg aacaactgtc     360
accgtctcct cagcttccac caagggcccc tccgtgttcc ctctggcccc ttgctcccgg     420
tccacctccg agtctaccgc cgctctgggc tgcctcgtga aggactactt ccccgagccc     480
gtgaccgtgt cctggaactc tggcgccctg acctccggcg tgcacacctt ccctgccgtg     540
ctgcagtcct ccggcctgta ctccctgtcc agcgtcgtga ccgtgccctc ctccagcctg     600
ggcaccaaga cctacacctg taacgtggac cacaagccct ccaacaccaa agtggacaag     660
cgggtggaat ctaagtacgg ccctccctgc ccttcctgcc ctgcccctga gttcctgggc     720
ggaccttccg tgttcctgtt ccctccaaag cccaaggaca ccctgatgat ctcccggacc     780
cctgaagtga cctgcgtggt ggtggacgtg tcccaggaag atcccgaagt ccagttcaat     840
tggtacgtgg acggcgtgga agtgcacaac gccaagacca gcccagaga ggaacagttc     900 aactccacct accgggtggt gtccgtgctg accgtgctgc accaggactg gctgaacggc     960
aaagagtaca gtgcaaagt gtccaacaag ggcctgccct ccagcatcga aagaccatc     1020 tccaaggcca agggccagcc ccgcgagccc caagtgtaca ccctgcctcc cagccaggaa    1080
gagatgacca agaatcaagt gtccctgact tgtctggtca agggcttcta ccctccgat    1140 atcgccgtgg agtgggagtc caacggccag cccgagaaca actacaagac caccctcc   1200 gtgctggact ccgacggctc cttcttcctg tactctcggc tgaccgtgga caagtcccgg    1260
tggcaggaag caacgtctt ctcctgctcc gtgatgcacg aggccctgca caaccactac    1320
acccagaagt ccctgtccct gtctctgggc                                    1350

<210> SEQ ID NO 127
<211> LENGTH: 450
<212> TYPE: PRT
<213> ORGANISM: Artificial Sequence
<220> FEATURE:
```

<223> OTHER INFORMATION: Synthetic: HEAVY CHAIN

<400> SEQUENCE: 127

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Trp
            20                  25                  30

Tyr Met His Trp Val Arg Gln Ala Pro Gly Gln Gly Leu Glu Trp Met
        35                  40                  45

Gly Met Ile Asn Pro Ser Gly Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Phe Tyr Thr Trp Asp His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Arg Leu Thr Val
            405                 410                 415

Asp Lys Ser Arg Trp Gln Glu Gly Asn Val Phe Ser Cys Ser Val Met
        420                 425                 430

His Glu Ala Leu His Asn His Tyr Thr Gln Lys Ser Leu Ser Leu Ser
    435                 440                 445

Leu Gly
    450

<210> SEQ ID NO 128
<211> LENGTH: 1350
<212> TYPE: DNA
<213> ORGANISM: Artificial Sequence
<220> FEATURE:
<223> OTHER INFORMATION: Synthetic: DNA HEAVY CHAIN

<400> SEQUENCE: 128

| | |
|---|---|
| caggtgcagc tggtgcagtc tggggctgag gtgaagaagc ctggggcctc agtgaaggtt | 60 |
| tcctgcaagg catctggata caccttcagt agctggtata tgcactgggt gcgacaggcc | 120 |
| cctggacaag gcttgagtg gatgggaatg atcaaccta gtggtggtag cacaaagtac | 180 |
| gcacagaagt tccagggcag agtcaccatg accaggaca cgtccacgag cacagtctac | 240 |
| atggagctga gcagcctgag atctgaggac acggcggtgt actactgcgc cagagatgct | 300 |
| cctttctaca cctgggatca ctactacgga atggacgtat ggggccaggg aacaactgtc | 360 |
| accgtctcct cagcttccac caagggcccc tccgtgttcc ctctggcccc ttgctcccgg | 420 |
| tccacctccg agtctaccgc cgctctgggc tgcctcgtga aggactactt ccccgagccc | 480 |
| gtgaccgtgt cctggaactc tggcgccctg acctccggcg tgcacacctt cctgccgtg | 540 |
| ctgcagtcct ccggcctgta ctccctgtcc agcgtcgtga ccgtgccctc ctccagcctg | 600 |
| ggcaccaaga cctacacctg taacgtggac cacaagccct ccaacaccaa agtggacaag | 660 |
| cgggtggaat ctaagtacgg ccctccctgc cctccttgcc ctgcccctga gttcctgggc | 720 |
| ggaccttccg tgttcctgtt ccctccaaag cccaaggaca ccctgatgat ctcccggacc | 780 |
| cctgaagtga cctgcgtggt ggtggacgtg tcccaggaag atcccgaagt ccagttcaat | 840 |
| tggtacgtgg acggcgtgga agtgcacaac gccaagacca gcccagaga ggaacagttc | 900 |
| aactccacct accgggtggt gtccgtgctg accgtgctgc accaggactg gctgaacggc | 960 |
| aaagagtaca gtgcaaagt gtccaacaag ggcctgccct ccagcatcga aaagaccatc | 1020 |
| tccaaggcca gggccagcc ccgcgagccc caagtgtaca ccctgcctcc agccaggaa | 1080 |
| gagatgacca gaatcaagt gtccctgact tgtctggtca agggcttcta cccctccgat | 1140 |
| atcgccgtgg agtgggagtc caacggccag cccgagaaca actacaagac cacccctccc | 1200 |
| gtgctggact ccgacggctc cttcttcctg tactctcggc tgaccgtgga caagtcccgg | 1260 |
| tggcaggaag caacgtctt ctcctgctcc gtgatgcacg aggccctgca caaccactac | 1320 |
| acccagaagt ccctgtccct gtctctgggc | 1350 |

<210> SEQ ID NO 129
<211> LENGTH: 450
<212> TYPE: PRT
<213> ORGANISM: Artificial Sequence
<220> FEATURE:
<223> OTHER INFORMATION: Synthetic: HEAVY CHAIN

<400> SEQUENCE: 129

Gln Val Gln Leu Val Gln Ser Gly Ala Glu Val Lys Lys Pro Gly Ala

-continued

```
                1               5                  10                 15
            Ser Val Lys Val Ser Cys Lys Ala Ser Gly Tyr Thr Phe Ser Ser Trp
                            20                  25                  30
            Tyr Met His Trp Val Arg Gln Ala Pro Gly Gln Gly Leu Glu Trp Met
                            35                  40                  45
            Gly Met Ile Asn Pro Ser Gly Gly Ser Thr Lys Tyr Ala Gln Lys Phe
                        50                  55                  60
            Gln Gly Arg Val Thr Met Thr Arg Asp Thr Ser Thr Ser Thr Val Tyr
             65                 70                  75                  80
            Met Glu Leu Ser Ser Leu Arg Ser Glu Asp Thr Ala Val Tyr Tyr Cys
                            85                  90                  95
            Ala Arg Asp Ala Pro Phe Tyr Thr Trp Asp His Tyr Tyr Gly Met Asp
                        100                 105                 110
            Val Trp Gly Gln Gly Thr Thr Val Thr Val Ser Ser Ala Ser Thr Lys
                        115                 120                 125
            Gly Pro Ser Val Phe Pro Leu Ala Pro Cys Ser Arg Ser Thr Ser Glu
                        130                 135                 140
            Ser Thr Ala Ala Leu Gly Cys Leu Val Lys Asp Tyr Phe Pro Glu Pro
            145                 150                 155                 160
            Val Thr Val Ser Trp Asn Ser Gly Ala Leu Thr Ser Gly Val His Thr
                            165                 170                 175
            Phe Pro Ala Val Leu Gln Ser Ser Gly Leu Tyr Ser Leu Ser Ser Val
                        180                 185                 190
            Val Thr Val Pro Ser Ser Ser Leu Gly Thr Lys Thr Tyr Thr Cys Asn
                        195                 200                 205
            Val Asp His Lys Pro Ser Asn Thr Lys Val Asp Lys Arg Val Glu Ser
            210                 215                 220
            Lys Tyr Gly Pro Pro Cys Pro Pro Cys Pro Ala Pro Glu Phe Glu Gly
            225                 230                 235                 240
            Gly Pro Ser Val Phe Leu Phe Pro Pro Lys Pro Lys Asp Thr Leu Met
                            245                 250                 255
            Ile Ser Arg Thr Pro Glu Val Thr Cys Val Val Val Asp Val Ser Gln
                        260                 265                 270
            Glu Asp Pro Glu Val Gln Phe Asn Trp Tyr Val Asp Gly Val Glu Val
                        275                 280                 285
            His Asn Ala Lys Thr Lys Pro Arg Glu Glu Gln Phe Asn Ser Thr Tyr
                        290                 295                 300
            Arg Val Val Ser Val Leu Thr Val Leu His Gln Asp Trp Leu Asn Gly
            305                 310                 315                 320
            Lys Glu Tyr Lys Cys Lys Val Ser Asn Lys Gly Leu Pro Ser Ser Ile
                            325                 330                 335
            Glu Lys Thr Ile Ser Lys Ala Lys Gly Gln Pro Arg Glu Pro Gln Val
                        340                 345                 350
            Tyr Thr Leu Pro Pro Ser Gln Glu Glu Met Thr Lys Asn Gln Val Ser
                        355                 360                 365
            Leu Thr Cys Leu Val Lys Gly Phe Tyr Pro Ser Asp Ile Ala Val Glu
                        370                 375                 380
            Trp Glu Ser Asn Gly Gln Pro Glu Asn Asn Tyr Lys Thr Thr Pro Pro
            385                 390                 395                 400
            Val Leu Asp Ser Asp Gly Ser Phe Phe Leu Tyr Ser Arg Leu Thr Val
                            405                 410                 415
            Asp Lys Ser Arg Trp Gln Glu Gly Asn Val Phe Ser Cys Ser Val Met
                        420                 425                 430
```

His Glu Ala Leu His Asn His Tyr Thr Gln Lys Ser Leu Ser Leu Ser
        435                 440                 445

Leu Gly
    450

<210> SEQ ID NO 130
<211> LENGTH: 1350
<212> TYPE: DNA
<213> ORGANISM: Artificial Sequence
<220> FEATURE:
<223> OTHER INFORMATION: Synthetic: DNA HEAVY CHAIN

<400> SEQUENCE: 130

```
caggtgcagc tggtgcagtc tggggctgag gtgaagaagc ctggggcctc agtgaaggtt    60
tcctgcaagg catctggata caccttcagt agctggtata tgcactgggt gcgacaggcc   120
cctggacaag gcttgagtg atgggaatg atcaaccta gtggtggtag cacaaagtac   180
gcacagaagt tccagggcag agtcaccatg accaggaca cgtccacgag cacagtctac   240
atggagctga gcagcctgag atctgaggac acggcggtgt actactgcgc cagagatgct   300
cctttctaca cctgggatca ctactacgga atggacgtat ggggccaggg aacaactgtc   360
accgtctcct cagcttccac caagggcccc tccgtgttcc ctctggcccc ttgctcccgg   420
tccacctccg agtctaccgc cgctctgggc tgcctcgtga aggactactt ccccgagccc   480
gtgaccgtgt cctggaactc tggcgccctg acctccggcg tgcacacctt ccctgccgtg   540
ctgcagtcct ccggcctgta ctccctgtcc agcgtcgtga ccgtgccctc ctccagcctg   600
ggcaccaaga cctacacctg taacgtggac cacaagccct ccaacaccaa gtggacaag   660
cgggtggaat ctaagtacgg ccctcccgc cctccttgcc ctgcccctga gttcgagggc   720
ggaccttccg tgttcctgtt ccctccaaag ccccaggaca cctgatgat ctcccggacc   780
cctgaagtga cctgcgtggt ggtggacgtg tcccaggaag atccgaagt ccagttcaat   840
tggtacgtgg acggcgtgga agtgcacaac gccaagacca gcccagaga ggaacagttc   900
aactccacct accgggtggt gtccgtgctg accgtgctgc accaggactg gctgaacggc   960
aaagagtaca gtgcaaagt gtccaacaag ggcctgccct ccagcatcga aaagaccatc  1020
tccaaggcca agggccagcc ccgcgagccc caagtgtaca ccctgcctcc cagccaggaa  1080
gagatgacca gaatcaagt gtccctgact tgtctggtca aggcttcta cccctccgat  1140
atcgccgtgg agtgggagtc caacggccag cccgagaaca actacaagac cacccctccc  1200
gtgctggact ccgacggctc cttcttcctg tactctcggc tgaccgtgga caagtcccgg  1260
tggcaggaag caacgtctt ctcctgctcc gtgatgcacg aggccctgca caaccactac  1320
acccagaagt ccctgtccct gtctctgggc                                  1350
```

<210> SEQ ID NO 131
<211> LENGTH: 330
<212> TYPE: PRT
<213> ORGANISM: Homo sapiens
<220> FEATURE:
<221> NAME/KEY: misc_feature
<223> OTHER INFORMATION: Human IgG1 Constant Region

<400> SEQUENCE: 131

Ala Ser Thr Lys Gly Pro Ser Val Phe Pro Leu Ala Pro Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 132
<211> LENGTH: 326
<212> TYPE: PRT
<213> ORGANISM: Homo sapiens
<220> FEATURE:
<221> NAME/KEY: misc_feature
<223> OTHER INFORMATION: Human IgG4 Constant Region (terminal K absent)

<400> SEQUENCE: 132

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
        50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 133
<211> LENGTH: 326
<212> TYPE: PRT
<213> ORGANISM: Homo sapiens
<220> FEATURE:
<221> NAME/KEY: misc_feature
<223> OTHER INFORMATION: Human IgG4 Constant Region single mutant
      (S228P) (terminal K absent)

<400> SEQUENCE: 133

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 134
<211> LENGTH: 326
<212> TYPE: PRT
<213> ORGANISM: Homo sapiens
<220> FEATURE:
<221> NAME/KEY: misc_feature
<223> OTHER INFORMATION: Human IgG4 Constant Region double mutant
      (S228P) (L235E) (terminal K absent)

<400> SEQUENCE: 134

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Cys Pro Ala Pro
            100                 105                 110

Glu Phe Gl

<400> SEQUENCE: 137

Tyr Pro Tyr Asp Val Pro Asp Tyr Ala
1               5

<210> SEQ ID NO 138
<211> LENGTH: 510
<212> TYPE: PRT
<213> ORGANISM: Homo sapiens
<220> FEATURE:
<221> NAME/KEY: misc_feature
<223> OTHER INFORMATION: CD39

<400> SEQUENCE: 138

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ala Val Ile Ala Leu
                20                  25                  30

Leu Ala Val Gly Leu Thr Gln Asn Lys Ala Leu Pro Glu Asn Val Lys
            35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

-continued

```
Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510
```